(12) United States Patent
Zhang et al.

(10) Patent No.: US 11,851,702 B2
(45) Date of Patent: Dec. 26, 2023

(54) RAPID DIAGNOSTICS

(71) Applicants: THE BROAD INSTITUTE, INC., Cambridge, MA (US); MASSACHUSETTS INSTITUTE OF TECHNOLOGY, Cambridge, MA (US)

(72) Inventors: Feng Zhang, Cambridge, MA (US); Jonathan Gootenberg, Cambridge, MA (US); Omar Abudayyeh, Cambridge, MA (US); Julia Joung, Cambridge, MA (US); Alim Ladha, Cambridge, MA (US); Han Altae-Tran, Cambridge, MA (US); Guilhem Faure, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 16/894,664

(22) Filed: Jun. 5, 2020

(65) Prior Publication Data
US 2021/0292823 A1    Sep. 23, 2021

Related U.S. Application Data

(60) Provisional application No. 62/993,494, filed on Mar. 23, 2020, provisional application No. 63/018,487, (Continued)

(51) Int. Cl.
*C12Q 1/68* (2018.01)
*C12Q 1/6844* (2018.01)
(Continued)

(52) U.S. Cl.
CPC ............ *C12Q 1/6844* (2013.01); *B01L 3/502* (2013.01); *B01L 3/502715* (2013.01); *B01L 7/52* (2013.01);
(Continued)

(58) Field of Classification Search
CPC ...................................................... C12Q 1/68
(Continued)

(56) References Cited

U.S. PATENT DOCUMENTS 7,312,053 B2 * 12/2007 Tada .................... C12Q 1/6806
435/6.16
9,470,699 B2 * 10/2016 Peeters ............ A61B 5/150358
(Continued)

FOREIGN PATENT DOCUMENTS

CN    101864483 A  * 10/2010
CN    102747148 A  * 10/2012
(Continued)

OTHER PUBLICATIONS

Broughton et al., A protocol for rapid detection of the 2019 novel coronavirus SARS-CoV-2 using CRISPR diagnostics: SARS-CoV-2 DETECTR, available at https://mammoth.bio/wp-content/uploads/2020/02/A-protocol-for-rapid-detection-of-the-2019-novel-coronavirus-SARS-CoV-2-using-CRISPR-diagnostics-SARS-CoV-2-DETECTR.pdf.*
(Continued)

*Primary Examiner* — Aaron A Priest
(74) *Attorney, Agent, or Firm* — Johnson, Marcou, Isaacs & Nix, LLC; F. Brent Nix, Esq.

(57) ABSTRACT

Systems and methods for rapid diagnostics related to the use of isothermal amplification reagents for detection of microbial species, including coronavirus, and methods of use, are provided.

14 Claims, 46 Drawing Sheets

Specification includes a Sequence Listing.

Related U.S. Application Data filed on Apr. 30, 2020, provisional application No. 63/019,406, filed on May 3, 2020, provisional application No. 63/032,470, filed on May 29, 2020.

(51) Int. Cl.

| | | |
|---|---|---|
| *C12N 9/22* | (2006.01) | |
| *C12Q 1/6806* | (2018.01) | |
| *C12N 9/12* | (2006.01) | |
| *C12N 9/78* | (2006.01) | |
| *B01L 3/00* | (2006.01) | |
| *B01L 7/00* | (2006.01) | |
| *C12Q 1/70* | (2006.01) | |

(52) U.S. Cl.
CPC .......... *C12N 9/1276* (2013.01); *C12N 9/22* (2013.01); *C12N 9/78* (2013.01); *C12Q 1/6806* (2013.01); *C12Q 1/701* (2013.01); *B01L 2300/0816* (2013.01); *C12N 2310/20* (2017.05); *C12Q 2600/156* (2013.01); *C12Q 2600/16* (2013.01); *C12Y 207/07049* (2013.01); *G01N 2333/165* (2013.01)

(58) Field of Classification Search
USPC ........................................................ 435/6.12
See application file for complete search history.

(56) References Cited

U.S. PATENT DOCUMENTS

| | | | |
|---|---|---|---|
| 9,556,466 B2 * | 1/2017 | Lee | C12P 19/34 |
| 10,253,365 B1 | 4/2019 | Doudna et al. | |
| 10,266,886 B2 | 4/2019 | Abudayyeh et al. | |
| 10,266,887 B2 | 4/2019 | Abudayyeh et al. | |
| 11,453,907 B2 | 9/2022 | Zhang et al. | |
| 2004/0197797 A1 | 10/2004 | Inoko et al. | |
| 2005/0100885 A1 | 5/2005 | Crooke et al. | |
| 2009/0104218 A1 | 4/2009 | Tettelin et al. | |
| 2012/0053329 A1 | 3/2012 | Yamamoto | |
| 2014/0142160 A1 | 5/2014 | Lee et al. | |
| 2015/0011430 A1 * | 1/2015 | Saxonov | C12N 15/1075 506/16 |
| 2015/0211058 A1 | 7/2015 | Carstens | |
| 2017/0081659 A1 | 3/2017 | Felgner et al. | |
| 2017/0312751 A1 | 11/2017 | Glezer et al. | |
| 2018/0274017 A1 * | 9/2018 | Abudayyeh | C12Q 1/6895 |
| 2018/0298445 A1 | 10/2018 | Abudayyeh et al. | |
| 2018/0305773 A1 | 10/2018 | Abudayyeh et al. | |
| 2018/0363026 A1 * | 12/2018 | Desharnais | C07C 309/14 |
| 2019/0218604 A1 * | 7/2019 | Liang | C12Q 1/6844 |
| 2021/0095271 A1 | 4/2021 | Li et al. | |
| 2021/0108267 A1 | 4/2021 | Zhang et al. | |
| 2021/0292824 A1 | 9/2021 | Zhang et al. | |
| 2022/0049242 A1 * | 2/2022 | Ismagilov | B01L 7/52 |

FOREIGN PATENT DOCUMENTS

| | | | | |
|---|---|---|---|---|
| CN | 106544444 A * | 3/2017 | ........... | C12Q 1/6844 |
| CN | 111187856 A | 5/2020 | | |
| CN | 112961943 A | 6/2021 | | |
| EP | 3237637 B1 * | 9/2019 | ............. | C12N 15/10 |
| EP | 3714050 A1 | 9/2020 | | |
| WO | WO-2011010740 A1 * | 1/2011 | ........... | C12Q 1/6848 |
| WO | 20110312751 A2 | 10/2011 | | |
| WO | WO-2013080154 A1 * | 6/2013 | ........... | C12Q 1/6844 |
| WO | 2014/093622 A2 | 6/2014 | | |
| WO | 2017/219027 A1 | 12/2017 | | |
| WO | 2018/107129 A1 | 6/2018 | | |
| WO | 2018/20476 A1 | 8/2018 | | |
| WO | 2018/170340 A1 | 9/2018 | | |
| WO | 2019/011022 A1 | 1/2019 | | |
| WO | 2019/051318 A1 | 3/2019 | | |
| WO | 2019/071048 A1 | 4/2019 | | |
| WO | 2019/071051 A1 | 4/2019 | | |
| WO | 2019/126577 A2 | 6/2019 | | |
| WO | 2019/126716 A1 | 6/2019 | | |
| WO | 2020087631 A1 | 5/2020 | | |
| WO | WO-2020118444 A1 * | 6/2020 | ............... | B01L 7/52 |
| WO | 2020/257356 A2 | 12/2020 | | |
| WO | 2021/087203 A1 | 5/2021 | | |
| WO | 2023039491 A2 | 3/2023 | | |

OTHER PUBLICATIONS

NCBI accession No. MW308137.1 (Nov. 30, 2020).*
Li et al., HOLMESv2: A CRISPR-Cas12b-Assisted Platform for Nucleic Acid Detection and DNA Methylation Quantitation, ACS Synth Biol. Oct. 18, 2019;8(10):2228-2237. doi: 10.1021/acssynbio. 9b00209. Epub Sep. 30, 2019.*
Gorgannezhad et al., Microfluidic-Based Nucleic Acid Amplification Systems in Microbiology, Micromachines (Basel). Jun. 2019; 10(6): 408. Published online Jun. 19, 2019.*
Sentmanat et al, One-step RNA extraction for RT-qPCR detection of 2019-nCoV, bioRxiv preprint doi: https://doi.org/10.1101/2020.04. 02.022384; this version posted Apr. 5, 2020.*
Supporting Covid-19 Research, https://www.neb.com/covid-19/ solutions-available-from-new-england-biolabs-supporting-covid-19-research, May 21, 2020, 4 pages.
Abudayyeh et al., "A Cytosine Deaminase for Programmable Single-base RNA Editing", Science, vol. 365, Issue 6451, Jul. 26, 2019, 8 pages.
Abudayyeh et al., "C2C2 is a Single-Component Programmable RNA-Guided RNA-Targeting CRISPR Effector", Science, vol. 353, No. 6299, Aug. 5, 2016, 23 pages.
Abudayyeh et al., "RNA Targeting with CRISPR-Cas13a", Nature, vol. 550, No. 7675, Oct. 4, 2017, 30 pages.
Anzalone et al., "Search-and-replace Genome Editing Without Double-Strand Breaks or Donor DNA", Nature, vol. 576, No. 7785, Dec. 5, 2019, 30 pages.
Becker et al., "Microfluidics-Enabled Diagnostic Systems: Markets, Challenges, and Examples", Methods in Molecular Biology, vol. 1547, 2017, 3-21.
Ben-Assa et al., "SARS-CoV-2 On-the-spot Virus Detection Directly from Patients", Department of Cell Biology and Cancer Science, Rappaport Faculty of Medicine, Technion, May 7, 2020, 13 pages.
Bhadra et al., "High-surety Isothermal Amplification and Detection of SARS-COV-2, including with Crude Enzymes", Department of Molecular Biosciences, College of Natural Sciences, The University of Texas at Austin, Austin, TX 78712, USA, May 7, 2020, 15 pages.
Broughton et al., "CRISPR-Cas12-Based Detection of SARS-CoV-2", Nature Biotechnology, Apr. 16, 2020, 8 pages.
Carr et al., "Genome Engineering", Nature Biotechnology, vol. 27, No. 12, Dec. 9, 2009, 1151-1162.
Chen et al., "CRISPR-Cas12 a Target Binding Unleashes Indiscriminate Single-Stranded DNase Activity", Science, vol. 360, Issue 6387, Apr. 27, 2018, 5 pages.
Cox et al., "RNA Editing with CRISPR-Cas13", Science, vol. 358, No. 6366, Nov. 24, 2017, 23 pages.
Czurratis et al., "A Novel Concept for Long-term Pre-storage and Release of Liquids for Pressure-driven Lab-on-a-chip Devices", Journal of Micromechanics and Microengineering, vol. 25, No. 4, Feb. 25, 2015, 10 pages.
Ding et al., "All-in-One Dual CRISPR-Cas12a (AIOD-CRISPR) Assay: A Case for Rapid, Ultrasensitive and Visual Detection of Novel Coronavirus SARS-CoV-2 and HIV virus", Retrieved from: bioRxiv preprint doi: https://doi.org/10.1101/2020.03.19.998724, Mar. 21, 2020, 19 pages.
Ding et al., "Efficacy and Safety of Early Prone Positioning Combined with HFNC or NIV in Moderate to Severe ARDS: A Multi-Center prospective Cohort Study", Critical Care, vol. 24, No. 28, 2020, 8 pages.
Doman et al., "Evaluation and Minimization of Cas9-Independent Off-arget DNA Editing by Cytosine Base Editors", Nature Biotechnology, vol. 38, No. 5, May 2020, 620-628.
Du et al., "Coupling Sensitive Nucleic Acid Amplification with Commercial Pregnancy Test Strips", Angewandte Chemie International Edition in English, vol. 56, No. 4, Jan. 19, 2017, 12 pages.

(56) References Cited

OTHER PUBLICATIONS

East-Seletsky et al., "Two Distinct RNase Activities of CRISPR-C2c2 Enable Guide-RNA Processing and RNA Detection", Nature, vol. 538, No. 7624, Oct. 13, 2016, 17 pages.

Gaudelli et al., "Programmable Base Editing of A•T to G•C in Genomic DNA without DNA Cleavage", Nature, vol. 551, No. 7681, Nov. 23, 2017, 37 pages.

Gootenberg et al., "Multiplexed and Portable Nucleic Acid Detection Platform with Cas13, Cas12a, and Csm6", Science, vol. 360, No. 6387, Apr. 27, 2018, 14 pages.

Gootenberg et al., "Nucleic Acid Detection with CRISPR-Cas13a/C2c2", Science, vol. 356, No. 6336, Apr. 28, 2017, 6 pages.

Goto et al., "Colorimetric Detection of Loopmediated Isothermal Amplification Reaction by using Hydroxy Naphthol Blue", BioTechniques, vol. 46, No. 3, 2009, 167-172.

Green et al., "Toehold Switches: De-Novo-Designed Regulators of Gene Expression", Cell, vol. 159, No. 4, Nov. 6, 2014, 28 pages.

Gruber et al., "The Vienna RNA Websuite", Nucleic Acids Research, vol. 36, 2008, W70-W74.

Guo et al., "SARS-CoV-2 Detection with CRISPR Diagnostics", Cell Discovery, vol. 6, No. 34, 2020, 4 pages.

Guo et al., "The Origin, Transmission and Clinical Therapies on Coronavirus Disease 2019 (COVID-19) Outbreak—an Update on the Status", Military Medical Research, vol. 7, No. 11, 2020, 10 pages.

Kashir et al., "Loop Mediated Isothermal Amplification (lamp) Assays as a Rapid Diagnostic for Covid-19", Medical Hypotheses, vol. 141, Apr. 23, 2020, 22 pages.

Kellner et al., "Sherlock: Nucleic Acid Detection with CRISPR Nucleases", Nature Protocols, vol. 14, Sep. 23, 2019, 29 pages.

Komor et al., "Programmable Editing of a Target Base in Genomic DNA without Double-Stranded DNA Cleavage", Nature, vol. 533, No. 7603, May 19, 2016, 25 pages.

Kumar et al., "Deconstructing Transcriptional Heterogeneity in Pluripotent Stem Cells", Nature. vol. 516, Dec. 4, 2014, 56-61.

Lalli et al., "Rapid and Extraction-free Detection of SARS-CoV-2 from Saliva with Colorimetric LAMP", Department of Genetics, May 11, 2020, 25 pages.

Lamb et al., "Rapid Detection of Novel Coronavirus (COVID-19) by Reverse Transcription-Loop-Mediated Isothermal Amplification", Retrieved as on Jul. 27 : https://doi.org/10.1101/2020.02.19.20025155, Feb. 24, 2020, 17 pages.

Li et al., "Design and Assessment of Engineered CRISPR-Cpf1 and its Use for Genome Editing", Nature Protocols, vol. 13, No. 5, May 2018, 48 pages.

Li et al., "Synthetic Oligonucleotides Inhibit CRISPR-Cpf1-Mediated Genome Editing", Cell Reports, vol. 25, No. 12, Dec. 18, 2018, 26 pages.

Liang et al., "Development and Characterization of Stable Anaerobic Thermophilic Methanogenic Microbiomes Fermenting Switchgrass at Decreasing Residence Times", Biotechnology for Biofuels, vol. 11, No. 243, 2018, 18 pages.

Lucia et al., "An Ultrasensitive, Rapid, and Portable Coronavirus SARS-CoV-2 Sequence Detection Method Based on CRISPR-Cas12", INPA-National Scientific and Technical Research Council (CONICET)-Argentina, Mar. 2, 2020, 10 pages.

Makarova et al., "Evolutionary Classification of CRISPR-Cas Systems: A Burst of Class 2 and Derived Variants", Nature Reviews Microbiology, vol. 18, Feb. 2020, 67-83.

Miyamoto et al., "Method for Colorimetric Detection of Double-stranded Nucleic Acid using Leuco Triphenylmethane Dyes", Analytical Biochemistry, vol. 473, Mar. 2015, 30 pages.

Myhrvold et al., "Field-deployable Viral Diagnostics using CRISPR-Cas13", Science, vol. 360, Issue 6387, Apr. 27, 2018, 6 pages.

Nagamine et al., "Accelerated Reaction by Loop-mediated Isothermal Amplification using Loop Primers", Molecular and Cellular Probes, vol. 16, Issue 3,, Jun. 2002, 223-229.

Notomi et al., "Loop-mediated Isothermal Amplification of DNA", Nucleic Acids Research, vol. 28, No. 12, Jun. 2000, 7 pages.

Osterdahl et al., "Detecting SARS-CoV-2 at Point of Care: Preliminary Data Comparing Loop-mediated Isothermal Amplification (LAMP) to PCR", Department of Ageing & Health, Guy's and St Thomas' NHS Foundation Trust, London, UK, Apr. 4, 2020, 9 pages.

Pardee et al., "Paper-Based Synthetic Gene Networks", Cell, vol. 159, No. 4, Nov. 6, 2014, 28 pages.

Pardee et al., "Rapid, Low-Cost Detection of Zika Virus Using Programmable Biomolecular Components", Cell, vol. 165, No. 5, May 19, 2016, 24 pages.

Park et al., "Development of Reverse Transcription Loop-mediated Isothermal Amplification (RT-LAMP) Assays Targeting SARS-CoV-2", Center for Convergent Research of Emerging Virus Infection, Korea Research Institute of Chemical Technology, Daejeon 34114, Republic of Korea, Mar. 24, 2020, 20 pages.

Park et al., "Development of Reverse Transcription Loop-Mediated Isothermal Amplification Assays Targeting Severe Acute Respiratory Syndrome Coronavirus 2 (SARS-CoV-2)", The Journal of Molecular Diagnostics, vol. 22, No. 6, Jun. 2020, 729-735.

Richter et al., "Phage-assisted Evolution of an Adenine Base Editor with Improved Cas Domain Compatibility and Activity", Nature Biotechnology, 2020, 18 pages.

Riddihough et al., "The CRISPR-Cas Evolutionary Mix", Science, vol. 353, Issue 6269, Aug. 5, 2016, 553-555.

Shirato et al., "Development of Fluorescent Reverse Transcription Loop-mediated Isothermal Amplification (RT-LAMP) using Quenching Probes for the Detection of the Middle East Respiratory Syndrome Coronavirus", Journal of Virological Methods, vol. 258, May 12, 2018, 41-48.

Shmakov et al., "Discovery and Functional Characterization of Diverse Class 2 CRISPR-Cas Systems", Molecular Cell, vol. 60, No. 3, Nov. 5, 2015, 385-397.

Zhang et al., "Rapid Molecular Detection of SARS-CoV-2 (COVID-19) Virus RNA Using Colorimetric LAMP", Retrieved as on Jul. 27, 2020: doi: https://doi.org/10.1101/2020.02.26.20028373., Feb. 29, 2020, 14 pages.

Shmakov et al., "Diversity and Evolution of Class 2 CRISPR-Cas Systems", Nature Reviews Microbiology, vol. 15, No. 3, Mar. 2017, 30 pages.

Smargon et al., "Cas 13B is a Type VI-B CRISPR-Associated RNA-Guided RNAse Differentially Regulated by Accessory Proteins Csx27 and Csx28", Molecular Cell, vol. 65, No. 4, Feb. 16, 2017, 30 pages.

Smith et al., "Blister Pouches for Effective Reagent Storage on Microfluidic Chips for Blood Cell Counting", Microfluidics and Nanofluidics, vol. 20, No. 163, Nov. 23, 2016, 14 pages.

Tanner et al., "Visual Detection of Isothermal Nucleic Acid Amplification using pH-sensitive Dyes", BioTechniques, vol. 58, Feb. 2015, 59-68.

Teng et al., "Repurposing CRISPR-Cas12b for Mammalian Genome Engineering", Cell Discovery, vol. 4, No. 63, Nov. 27, 2018, 15 pages.

Thi et al., "Screening for SARS-CoV-2 Infections with Colorimetric RT-Lamp and Lamp Sequencing", Schaller Research Groups, Center of Infectious Diseases, Department of Virology, Heidelberg University Hospital, Heidelberg, Germany, May 9, 2020, 28 pages.

Tian et al., "Potent Binding of 2019 Novel Coronavirus Spike Protein by a SARS Coronavirus-Specific Human Monoclonal Antibody", Emerging Microbes & Infections, vol. 9, No. 1, 2020, 382-385.

Urdea et al., "Requirements for High Impact Diagnostics in the Developing World", Nature, vol. 444, 2006, 73-79.

Wang et al., "One-pot Detection of COVID-19 with Real-time Reverse-transcription Loop-mediated Isothermal Amplification (RT-Lamp) Assay and Visual RT-Lamp Assay", Key Laboratory of Biomarker Based Rapid-detection Technology for Food Safety of Henan Province, Xuchang University, Xuchang 461000, China, Apr. 22, 2020, 7 pages.

Wang et al., "Protein Kinase D1 is Essential for Ras-induced Senescence and Tumor Suppression by Regulating Senescence-Associated Inflammation", Proceedings of the National Academy of Sciences, vol. 111, No. 21, May 27, 2014, 7683-7688.

(56) References Cited

OTHER PUBLICATIONS

Whitman et al., "Test Performance Evaluation of SARS-CoV-2 Serological Assays", Retrieved as on Jul. 27, 2020: doi: https://doi.org/10.1101/2020.04.25.20074856, May 17, 2020, 28 pages.
Wu et al., "Genome Composition and Divergence of the Novel Coronavirus (2019-nCoV) Originating in China", Cell Host and Microbe, vol. 27, Issue 3, Mar. 11, 2020, 325-328.
Wyllie et al., "Saliva is More Sensitive for SARS-CoV-2 Detection in COVID-19 Patients than Nasopharyngeal Swabs", Retrieved from-medRxiv preprint doi:https://doi.org/10.1101/2020.04.16.20067835, Apr. 22, 2020, 12 pages.
Yang et al., "Engineering and Optimizing Deaminase Fusions for Genome Editing", Nature Communication, vol. 7, Issue 13330,, Nov. 2, 2016, 11 pages.
Yang et al., "Rapid Detection of SARS-CoV-2 Using Reverse transcription RT-LAMP method", Retrieved as on Jul. 27, 2020 "https://doi.org/10.1101/2020.03.02.20030130", Mar. 3, 2020, 25 pages.
Yu et al., "Rapid Colorimetric Detection of COVID-19 Coronavirus using a Reverse Transcriptional Loop-mediated Isothermal Amplification (RT-LAMP) Diagnostic Platform: iLACO", Applied Biology Laboratory, Shenyang University of Chemical Technology, 110142, Shenyang, China, Feb. 24, 2020, 19 pages.
Yu et al., "Rapid Detection of COVID-19 Coronavirus Using a Reverse Transcriptional Loop-Mediated Isothermal Amplification (RT-LAMP) Diagnostic Platform", Clinical Chemistry, May 21, 2020, 3 pages.
Zetsche et al., "Cpf1 is a Single RNA-Guided Endonuclease of a Class 2 CRISPR-Cas System", Cell, vol. 163, No. 3, Oct. 22, 2015, 759-771.
International Application No. PCT/US2020/022795 filed Mar. 13, 2020, all enclosed pages cited.
Restriction Requirement from related U.S. Appl. No. 16/894,678 dated Jul. 22, 2020, all enclosed pages cited.
Wang, et al., "Rapid and Sensitive Detection of Severe Acute Respiratory Syndrome Coronavirus by Rolling Circle Amplification," Journal of Clinical Microbiology, May 2005, all enclosed pages cited.
Li, et al., "CRISPR-Cas12b-assisted Nucleic Acid Detection Platform," bioRxiv preprint doi: https://doi.org/10.1101/362889; Jul. 6, 2018, all enclosed pages cited.
Non-Final Office Action from corresponding U.S. Appl. No. 16/894,670 dated Dec. 31, 2020, all enclosed pages cited.
Non-Final Office Action from corresponding U.S. Appl. No. 16/894,678 dated Jan. 11, 2021, all enclosed pages cited.
Spiess, et al., "Trehalose is a Potent PCR Enhancer: Lowering of DNA Melting Temperature and Thermal Stabilization of Taq Polymerase by the Disaccharide Trehalose," 50(7) Clinical Chemistry, 1256-1259 (2004).
Final Office Action of U.S. Appl. No. 16/894,670 dated Apr. 15, 2021, all enclosed pages cited.
Final Office Action of U.S. Appl. No. 16/894,678 dated Apr. 16, 2021, all enclosed pages cited.
Invitation to Pay Additional Fees for corresponding International Application No. PCT/US2021/017985 dated May 3, 2021, all enclosed pages cited.
Non-Final Office Action of co-pending U.S. Appl. No. 16/894,670 dated Dec. 3, 2021, all enclosed pages cited.
Schermer, et al., "Rapid SARS-CoV-2 testing in primary material based on a novel multiplex RT-Lamp assay," PloS One, vol. 15, No. 11: e0238612, Nov. 2, 2020, all enclosed pages cited.
Schellenberg, et al. "Extraction-free RT-Lamp to detect SARS-CoV-2 is less sensitive but highly specific compared to standard RT-PCT in 101 samples," Journal of Clinical Virology, vol. 136: 104764, Feb. 16, 2021, all enclosed pages cited.
International Search Report and Written Opinion of corresponding International Application No. PCT/US2021/017985 dated Jul. 20, 2021, all enclosed pages cited.
Non-Final Office Action of co-pending U.S. Appl. No. 16/894,678 dated Sep. 29, 2021, all enclosed pages cited.
Notice of Allowance from corresponding U.S. Appl. No. 16/894,670 dated May 13, 2022, all enclosed pages cited.
Final Office Action of co-pending U.S. Appl. No. 16/894,670 dated Mar. 10, 2022, all enclosed pages cited.
Final Office Action of co-pending U.S. Appl. No. 16/894,678 dated Apr. 7, 2022, all enclosed pages cited.
Restriction Requirement from corresponding U.S. Appl. No. 17/731,019 dated Sep. 14, 2022, all enclosed pages cited.
Notice of Allowance from corresponding U.S. Appl. No. 16/894,678 dated Oct. 19, 2022, all enclosed pages cited.
Restriction Requirement from corresponding U.S. Appl. No. 17/731,019 dated Jan. 19, 2023, all enclosed pages cited.
Joung, "Applications to forward genetic screens to LncRNAs, cancer immunotherapy, and cellular engineering," Massachusetts Institute of Technology 2021, all enclosed pages cited.
Joung, et al., "Genome-scale CRISPR-Cas9 Knockout and transcriptional activation screening," Nat Protoc. Apr. 2017; 12(4), all enclosed pages cited.
Non-Final Office action of corresponding U.S. Appl. No. 17/731,019 dated May 11, 2023, all enclosed pages cited.
Final Office action of corresponding U.S. Appl. No. 17/731,019 dated Oct. 5, 2023, all enclosed pages cited.

* cited by examiner

| | SAR-CoV-2 infection status | | | Predictive value |
|---|---|---|---|---|
| | Pos. | Neg | Total | |
| SHERLOCK Lateral flow Pos. | 35 (True pos.) | 0 (False pos.) | 35 | PPV = 100% |
| Neg. | 1 (False neg.) | 15 (True neg.) | 16 | NPV = 94% |
| Total | 36 | 15 | | |
| | Sensitivity 97% | Specificity 100% | | |

Lysis: 10 min at 22 °C

| Patient | 1 | 2 | 3 | 4 | 5 | 6 | 7 | 8 | 9 | 10 | 11 | 12 |
|---|---|---|---|---|---|---|---|---|---|---|---|---|
| Positive NP swabs | | | | | | | | | | | | |
| Ct (CDC N1) | 31.5 | 24.5 | 20.5 | 24.6 | 24.9 | 23.1 | 20.7 | 19.5 | 26.6 | 20.4 | 25.3 | 18.3 |
| Ct (CDC N2) | 33.5 | 25.0 | 21.2 | 25.5 | 25.7 | 24.1 | 21.8 | 20.6 | 27.1 | 21.0 | 26.3 | 18.8 |

B

Lysis: 10 min at 60 °C

| Patient | 1 | 2 | 3 | 4 | 5 | 6 | 7 | 8 | 9 | 10 | 11 | 12 |
|---|---|---|---|---|---|---|---|---|---|---|---|---|
| Positive NP swabs | | | | | | | | | | | | |
| Ct (CDC N1) | 33.8 | 24.7 | 20.4 | 24.6 | 24.9 | 23.2 | 20.8 | 19.6 | 26.8 | 20.3 | 25.4 | 18.5 |
| Ct (CDC N2) | 35.1 | 25.2 | 21.3 | 25.6 | 25.7 | 24.1 | 21.7 | 20.8 | 27.3 | 20.9 | 26.4 | 19.0 |

FIG. 28

| Patient | P1 | P2 | P3 | P4 | P5 | P6 | P7 | P8 | P9 | P10 | P11 | P12 | P13 | P14 | P15 | P16 | P17 | P18 | P19 | P20 | P21 | P22 |
|---|---|---|---|---|---|---|---|---|---|---|---|---|---|---|---|---|---|---|---|---|---|---|
| Positive NP swabs | | | | | | | | | | | | | | | | | | | | | | |
| Ct (CDC N1) | 32.7 | 23.4 | 20.2 | 23.6 | 24.2 | 23.1 | 20.2 | 19.6 | 24.3 | 18.4 | 24.6 | 17.2 | 32.7 | 27.3 | 22.0 | 20.2 | 35.8 | 27.7 | 19.4 | 18.6 | 29.1 | 20.0 |
| Ct (CDC N2) | 34.3 | 24.7 | 21.7 | 24.9 | 25.3 | 24.3 | 21.2 | 20.2 | 25.3 | 19.4 | 25.8 | 18.4 | 33.7 | 28.7 | 22.6 | 21.7 | 36.2 | 28.8 | 20.3 | 19.5 | 30.1 | 20.7 |

| Patient | P23 | P24 | P25 | P26 | P27 | P28 | P29 | P30 | P31 | P32 | P33 | P34 | P35 | P36 | P37 | P38 | P39 | P40 | P41 | P42 | P43 |
|---|---|---|---|---|---|---|---|---|---|---|---|---|---|---|---|---|---|---|---|---|---|
| Positive NP swabs | | | | | | | | | | | | | | | | | | | | | |
| Ct (CDC N1) | 32.1 | 32.2 | 30.3 | 28.5 | 24.6 | 35.8 | 37.3 | 35.2 | 28.3 | 26.0 | 28.7 | 36.2 | 27.1 | 18.6 | 32.7 | 34.6 | 27.6 | 27.4 | 28.5 | 28.6 | 30.7 |
| Ct (CDC N2) | 33.4 | 32.7 | 31.1 | 29.4 | 25.6 | 38.0 | 38.4 | 36.4 | 29.2 | 27.3 | 30.3 | 39.0 | 28.0 | 19.2 | 33.9 | 35.8 | 29.0 | 28.5 | 29.3 | 29.6 | 31.7 |

| Patient | N1 | N2 | N3 | N4 | N5 | N6 | N7 | N8 | N9 | N10 | N11 | N12 | N13 | N14 | N15 |
|---|---|---|---|---|---|---|---|---|---|---|---|---|---|---|---|
| Negative NP swabs | | | | | | | | | | | | | | | |

SAR-CoV-2 infection status (3/3 replicates)

| | | Pos. | Neg. | Total | Predictive value |
|---|---|---|---|---|---|
| SHERLOCK Lateral flow | Pos. | 34 (True pos.) | 0 (False pos.) | 34 | PPV=100% |
| | Neg. | 9 (False neg.) | 15 (True neg.) | 24 | NPV=62.5% |
| | Total | 43 | 15 | | |
| | | Sensitivity 79% | Specificity 100% | | |

SAR-CoV-2 infection status (1/3 replicates)

| | | Pos. | Neg. | Total | Predictive value |
|---|---|---|---|---|---|
| SHERLOCK Lateral flow | Pos. | 39 (True pos.) | 0 (False pos.) | 39 | PPV=100% |
| | Neg. | 4 (False neg.) | 15 (True neg.) | 19 | NPV=79% |
| | Total | 43 | 15 | | |
| | | Sensitivity 91% | Specificity 100% | | |

SAR-CoV-2 infection status (filtered for CDC N1 Ct < 32)

| | | Pos. | Neg. | Total | Predictive value |
|---|---|---|---|---|---|
| SHERLOCK Lateral flow | Pos. | 34 (True pos.) | 0 (False pos.) | 34 | PPV=100% |
| | Neg. | 0 (False neg.) | 15 (True neg.) | 15 | NPV=100% |
| | Total | 34 | 15 | | |
| | | Sensitivity 100% | Specificity 100% | | |

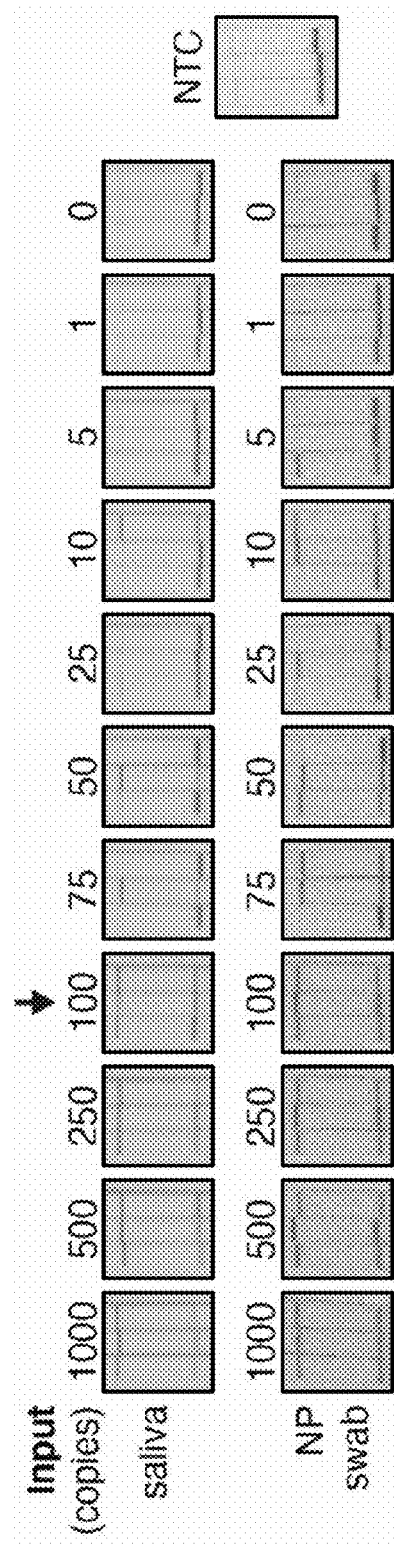
FIG. 40
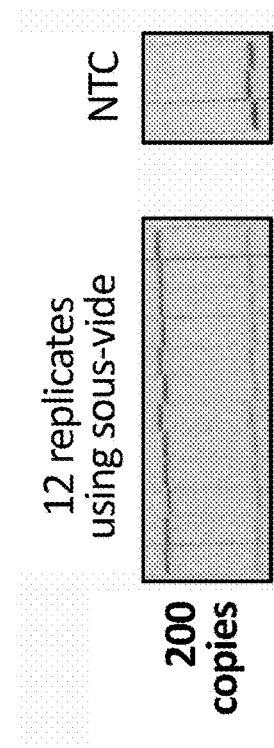
FIG. 41
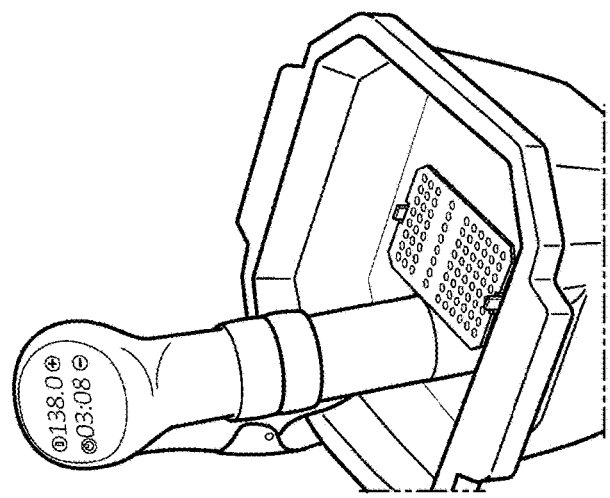

RAPID DIAGNOSTICS

CROSS REFERENCE TO RELATED APPLICATIONS

This application claims the benefit of U.S. Provisional Application Nos. 62/993,494 filed Mar. 23, 2020, 63/018,487 filed Apr. 30, 2020, 63/019,406 filed May 3, 2020 and 63/032,470 filed May 29, 2020. The entire contents of the above-identified applications are hereby fully incorporated herein by reference.

STATEMENT REGARDING FEDERALLY SPONSORED RESEARCH

This invention was made with government support under grant nos. HL141201 and MH110049 awarded by National Institutes of Health. The government has certain rights in the invention.

REFERENCE TO AN ELECTRONIC SEQUENCE LISTING

The contents of the electronic sequence listing ("BROD_5165US_ST25.txt"; Size is 13,420,004 bytes, and was created on Jun. 5, 2020) is herein incorporated by reference in its entirety.

TECHNICAL FIELD

The subject matter disclosed herein is generally directed to rapid single-reaction diagnostics, including SARS-CoV-2 diagnostics utilizing isothermal amplification reagents.

BACKGROUND

Nucleic acids are a universal signature of biological information. The ability to rapidly detect nucleic acids with high sensitivity and single-base specificity on a portable platform has the potential to revolutionize diagnosis and monitoring for many diseases, provide valuable epidemiological information, and serve as a generalizable scientific tool. Although many methods have been developed for detecting nucleic acids (Du et al., 2017; Green et al., 2014; Kumar et al., 2014; Pardee et al., 2014; Pardee et al., 2016; Urdea et al., 2006), they inevitably suffer from trade-offs among sensitivity, specificity, simplicity, and speed.

Sensitive and rapid detection of nucleic acids is important for clinical diagnostics and biotechnological applications. Particularly when responding to outbreaks, such as the novel coronavirus, which has been referred to as 2019-nCoV and SARS-CoV-2, which causes COVID 2019, time is of the essence. Sabeti, Early Detection Is Key to Combating the Spread of Coronavirus, Time (Feb. 6, 2020). The 2019-nCoV has killed hundreds in a 2-month time span, and response to the escalating outbreak, particularly where there are indications that both symptomatic and asymptomatic patients with 2019-nCov may transmit the disease. Wang, et al., A precision medicine approach to managing Wuhan Coronavirus pneumonia, Prec. Clin. Med, doi:10.1093/pcmedi/pbaa002. Current coronavirus testing kits sent to states and other countries do not work properly, according to the U.S. Centers for Disease Control and Prevention. Grady, "Coronavirus Test Kits Sent to States, 30 Countries Are Flawed, C.D.C. Says," New York Times, Feb. 12, 2020. Moreover the test being used provides results in four hours from initial sample processing to results. cdc.gov/media/releases/2020/p0206-coronavirus-diagnostic-test-kits.

Highly accurate test results at better processing speds, particularly that are field-depoloyable would aid in addressing the outbreak. Currently, the novel coronavirus SARS-CoV-2 has resulted in an international public health emergency, spreading to over 180 countries and infecting more than 300,000 individuals. Testing for the presence of the virus is of utmost importance to both reduce the basic reproductive rate of the virus (R0) and inform best clinical practices for affected patients. However, understanding the full extent of the virus outbreak has remained challenging due to bottlenecks in the diagnosis of infection.

SUMMARY

In certain example embodiments, a loop-mediated isothermal amplification (LAMP) composition is provided for detecting the presence of a target polynucleotide in a sample, comprising optimized LAMP guides and amplification reagents for single reaction amplification for amplifying the target polynucleotide in less than one hour, and an extraction-free polynucleotide isolation solution. In an aspect, the isothermal amplification reagents comprise LAMP reagents for amplification of the coronavirus target sequence, optionally comprising F3, B3, FIP, BIP, Loop Forward and Loop Reverse primers. In an aspect, the LAMP primers are selected from SEQ ID NO: 1-SEQ ID NO: 40499.

In example embodiments, the target polynucleotide is a viral polynucleotide, which may be a SARS-CoV-2 polynucleotide.

The composition may further comprise an additive. In an aspect, the additive is L-proline, L-histidine, b-alanine, L-serine, urea, acetamide, 4-aminobutyric acid, polyethylene glycol, polypropylene glycol, polyvinylpyrrolidone K, 6-O-a-D-maltosyl-b-cyclodextrin, (2-hydroxypropyl)-b-cyclodextrin, a-cyclodextrin, b-cyclodextrin, methyl-b-cyclodextrin, glycine, proline, taurine, or a combination thereof. In an aspect, the additive is glycine, taurine, and/or proline.

The composition may further comprise a set of beads for the capture of nucleic acids in the sample.

Methods of detecting a target nucleic acid in a sample are also provided, comprising steps of distributing a sample or set of samples into one or more individual discrete volumes each individual discrete volume comprising a system as disclosed herein; incubating the sample or set of samples at conditions sufficient to allow extraction of target polynucleotides from the sample, further incubating at an isothermal temperature to generate amplicons of target polynucleotides; and detecting the one or more amplicons, thereby indicated the presence of one or more target polynucleotides in the sample. In an aspect, the amplification reagents comprise LAMP primers and the isothermal incubation temperature is between 55° C. and 65° C.

A cartridge is provided, comprising at least a first and second ampoule, a lysis chamber, an amplification chamber and a sample receiving chamber, the first ampoule fluidically connected to the sample receiving chamber, the sample receiving chamber further connected to the lysis chamber, the lysis chamber connected via a metering channel to the second ampoule and the amplification chamber. The cartridge can be configured to fit in a system comprising a heating means, an optic means, a means for releasing reagents on the cartridge, and a means for readout of assay result. The cartridge may comprise wherein a first ampoule comprises extraction-free polynucleotide isolation solution, and/or the second ampoule comprises the composition as disclosed herein. The contents of the first ampoule and/or second ampoule are lyophilized.

Devices are also provided that are designed to receive one or more cartridges as provided herein, and further comprising one or more motors connected to a plunger for rupturing of the first and second ampoule of the cartridge and configured within the device to align with the first and second ampoule of the inserted cartridge, a heating element configured to align with the amplification chamber of the inserted cartridge, an optical detector configured to align with the amplification chamber of the inserted cartridge, and a display. The device may further comprise a graphical user interface for programming the device and/or readout of the results of the assay. A system is also provided comprising a docking station and two or more devices as disclosed herein, wherein the docking station is configured to receive the two or more devices.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 2B Detection of synthetic COVID-19 sequence using a two-step SHERLOCK reaction (25 min RPA followed by 30 min Cas13 reaction). Readout using lateral flow strip.

FIG. 3A—Quick Extract at a final concentration of 5% did not negatively affect the RT-qPCR reaction FIG. 3B RNA samples prepared using Quick Extract supported similarly sensitive detection of coronavirus as QIAmp Viral RNA Miniprep.

FIG. 27—POC-SHERLOCK COVID-19 detection results for patient samples tested in FIG. 19. The results yield a sensitivity of 97% and specificity of 100%.

FIG. 28—COVID-19 POC-SHERLOCK detection with SARS-CoV-2 positive patient nasopharyngeal swabs. (A) POC-SHERLOCK COVID-19 detection of 12 different SARS-CoV-2 positive patient nasopharyngeal swabs with three replicates for each sample. Prior to POC-SHERLOCK, nasopharyngeal swabs were lysed using QE for 5 minutes at 22° C. Listed below are Ct values determined by RT-PCR using the CDC N1 and N2 assays. (B) POC-SHERLOCK COVID-19 detection of 12 different SARS-CoV-2 positive patient nasopharyngeal swabs with three replicates for each sample. Prior to POC-SHERLOCK, nasopharyngeal swabs were lysed using QE for 5 minutes at 60° C. Listed below are Ct values determined by RT-PCR using the CDC N1 and N2 assays.

FIG. 31B shows three views of a quad-dock for a front loading device, showing USB port located at the back of each cavity; FIG. 31C shows stacking docs for 8 devices, on the left, a side profile, center front view, and rights, low profile feet on the botto of the dock.

FIG. 34B top loading device quad-dock, USB port located in each cavity (left), quad dock with four top loading devices in closed lid orientation (upper right), quad dock with four top loading devices with one device in open lid orientation (lower right); FIG. 34C top loading device octo-dock, rear view showing single rear power inlet (upper left), All 8 devices in octo-dock in open orientation (upper right), USB-C port located in each device cavity (lower left), and status display LED strip on octo dock with 8 devices in closed orientation (lower right).

FIG. 35A-35B—Expanded patient cohort testing from an example embodiment showing results of patient nasopharyngeal swab samples (FIG. 35A) with calculated predictive values, sensitivity and specificity (FIG. 35B)

FIG. 38A NaCl beads; FIG. 38B KCl beads.

FIG. 40—Shows data from an example embodiment demonstrating limit of detection (LOD) of 100 genomes per reaction from saliva or nasopharyngeal swabs FIG. 41—Shows results of 12 replicates (right) using sous-vide waterbath (left) for STOPCOvid reaction FIG. 42A-42B—Shows data from an example embodiment demonstrating an ability to achieve 97% sensitivity and 100% specificity on patient nasopharyngeal swab samples FIG. 43—Shows CRISPR detection may improve upon LAMP by increased specificity.

Figure 1:
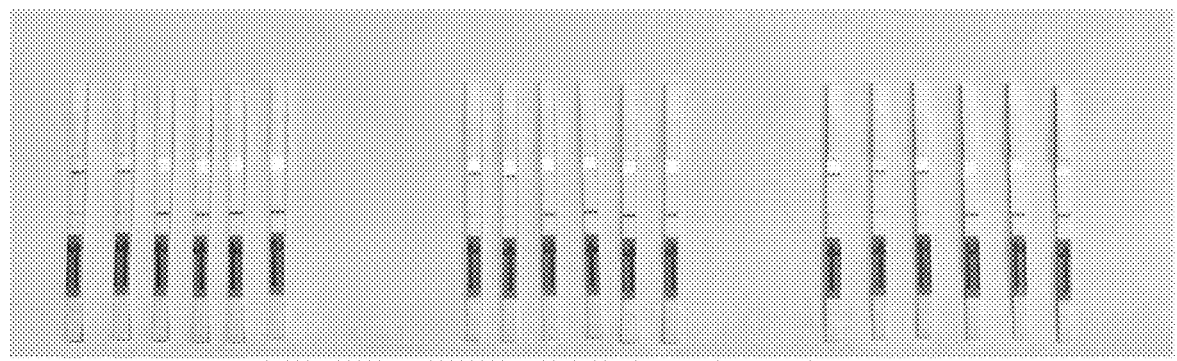
FIG. 1—includes lateral flow assay detection for three n2019-CoV targets, left, middle and right groups. Testing for each target shown with decreasing concentrations from left to right, with far right at 0 concentration S protein (left), middle, synthetic S (synthego) and right (Orflab).

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboraotry Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +1-10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments herein are directed to systems and methods of detecting the presence of a target nucleic acid in a sample. In certain example embodiments, the systems and methods provide for single reaction (one-pot) detection of target nucleic acids. In certain example embodiments, extraction, amplification, and detection may take place under a single set of reaction buffer and reagent conditions. In certain example embodiments, detection is achieved using isothermal amplification (e.g. LAMP) only. Design of reaction conditions and reagents are provided for the identification of primers and reaction conditions, including concentration and content of reagents and additives, that enhance the detection systems and methods disclosed herein. Advantageously, the systems and methods can be provided in lateral flow or self-contained cartridge devices for rapid, point-of-care diagnostics. In certain embodiments, the detection assay can be provided on a cartridge or chip. A device system can be configured to receive the cartridge and conduct an assay.

Systems and method disclosed herein include approaches to detection isothermal amplification for detection of target nucleic acids. In certain example embodiments, isothermal amplification approach is loop-mediated isothermal amplification (LAMP). Design of optimal systems, including primers, reagents and additives to be used with isothermal amplification approaches are also provided. Optionally, CRISPR-Cas systems as disclosed herein can be used with isothermal amplification approaches, including LAMP, that can enhance sensitivity and/or specificity.

Methods of designing optimal reaction conditions are also provided. As used herein, the terms optimized guides and/or optimized primers can include the optimization of reaction conditions, additives and/or reagents for use in the methods and systems herein. In an aspect, methods can comprise identifying the type of amplification reaction and designing optimal primers in accordance with the methods disclosed herein. Advantageous quick extraction approaches for the extraction of nucleic acids from a sample are also provided. Additional reaction conditions, additives and reagents can be identified to optimize the use of one-pot methodology, lyophilization of reagents, and use in the devices disclosed herein. The additives may facilitate reaction time, increase of the signal to noise ratio, enhance specificity of binding or other variables that enhance the specificity, sensitivity and/or kinetics of the reaction.

Detection of nucleic acids can optionally further utilize Cas proteins to provide improved reaction sensitivity and/or specificity, including utilization with a thermostable CRISPR-Cas protein, with the combination of thermostable protein and isothermal amplification utilized to further improve reaction conditions and times for detection and diagnostics. In certain example embodiments, the Cas protein may be a Type V CRISPR-Cas, a Type VI CRISPR-Cas, or combination thereof. In certain example embodiments, the Type V or Type VI Cas protein is a thermostable case protein with a nuclease activity above at least 50° C. In certain example embodiments, the Cas protein is a Cas12b protein. In certain other example embodiments, the Cas12b is *Alicyclobacillus acidiphilus* (AapCas12b). In certain other example embodiments, the Cas12b protein is *Brevibacillus* sp. SYSU G02855 (BrCas12b). In certain example embodiments, the Cas protein, may be paired with the novel guide designs disclosed herein.

Methods may also comprise identifying optimum CRISPR-Cas systems, including identification of the Cas protein for the reactions conditions. For example, the Cas protein may be identified based on its thermostability, cutting preferences, or other desired characteristics. Preferred guide molecules may similarly be identified. Once one or more primers and/or guides are identified, salt concentrations and other additives can be titrated and selected for further investigation.

In certain example embodiments, the system comprises a Type V CRISPR-Cas system, one or more guide polynucleotides comprising a guide sequence capable of binding a target sequence and designed to form a complex with the Type V Cas protein, and a detection construct comprising a polynucleotide component. The Type V Cas proteins of the present systems and methods exhibits collateral nuclease activity, cleaving the polynucleotide component of the detection construct once activated by the target sequence, which can generate a detectable signal.

In certain example embodiments, the system comprises a Type VI CRISPR-Cas system, one or more guide polynucleotides comprising a guide sequence capable of binding a target sequence and designed to form a complex with the Type VI Cas protein, and a detection construct comprising a polynucleotide component. The Type VI Cas proteins of the present systems and methods exhibits collateral RNase activity, cleaving the polynucleotide component of the detection construct once activated by the target sequence, which can generate a detectable signal.

Embodiments disclosed herein provide systems utilized in multiplex lateral flow devices and methods of use. In certain preferred embodiments, the guides utilized are designed to be highly active guide molecules, allowing for rapid and highly sensitive detection of coronavirus. In certain example embodiments, the systems can utilize general capture of antibody that was not bound by intact reporter RNA as described in Gootenberg et al., Science 360, 439-444 (2018).

In other embodiments, the presently disclosed system can be designed for detecting two or more targets. When utilized with a lateral flow approach, two or more separate detection lines consisting of deposited materials that capture detection construct and a molecule specific to the deposited material, allows visualization of detectable signal (e.g. gain or loss) at detection lines due to collateral activity and cleavage of corresponding reporter oligonucleotide. Utilizing guide design that allows for design of highly active guide RNAs for use with the specific Cas protein of the systems for target sequences, for example, coronavirus is also provided. In certain embodiments, the time from processing of a sample in the current methods and using the presently claimed systems, from receipt of sample to detectable signal is less than 120 minutes, 110 minutes, 100 minutes, 90 minutes, 75 minutes, 60 minutes, 45 minutes, or 30 minutes.

Single Lysis Reaction Compositions

In certain aspects, embodiments disclosed herein are directed to compositions and kits that consolidate extraction-free lysis/polynucleotide isolation and amplification of target nucleic acids into a single reaction volume. In certain example embodiments, the extraction-free polynucleotide isolation solution can be used to extract nucleic acids from cells and/or viral particles. In contrast to existing protocols, the extraction-free polynucleotide isolation solution does not require isolation of the nucleic acid prior to further amplification. The extraction-free polynucleotide isolation solution may be mixed with amplification reagents such as standard RT-PCR amplification reactions. An example extraction-free polynucleotide isolation solution is described in Example 3.

In certain example embodiments, the extraction-free polynucleotide isolation solution is combined with amplification reagents into a single volume. In certain example embodiments, the amplification reagents are isothermal amplification reagents. In certain other example embodiments, the isothermal amplification reagents are LAMP isothermal amplification reagents. In certain example embodiments, the LAMP isothermal amplification reagents may include primers for the target nucleic acids discussed in further detail below. In certain example embodiments, the LAMP amplification reagents include primer sets selected from SEQ ID Nos: 1-40499. In certain example embodiments, the LAMP amplification reagents may include primers to SARS-COV2. In certain example embodiments, the primers are SEQ ID NOS: 61983-61988 from Table 5. LAMP reagents may further comprise colorimetric and/or fluorescent detection reagents, such as hydroxy napthol blue (see, e.g. Goto, M., et al., Colorimetric detection of loop-mediated isothermal amplification reaction by using hydroxy naphthol blue. Biotechniques, 2009. 46(3): p. 167-72) leuco triphenylmethane dyes (see, e.g. Miyamoto, S., et al., Method for colorimetric detection of double-stranded nucleic acid using leuco triphenylmethane dyes. *Anal Biochem,* 2015. 473: p. 28-33) and pH-snesitive dyes (see, e.g. Tanner, N. A., Y. Zhang, and T. C. Evans, Jr., Visual detection of isothermal nucleic acid amplification using pH-sensitive dyes. Biotechniques, 2015. 58(2): p. 59-68); as well as fluorescent detection (see, e.g. Yu et al., *Clinical Chemistry,* hvaa102, doi:10.1093/clinchem/hvaa102 12 May 2020), including use of quenching probes (see, e.g. Shirato et al., *J Virol Methods.* 2018 August; 258:41-48. doi: 10.1016/j.jviromet.2018.05.006).

In certain embodiments, extraction-free polynucleotide isolation solution and isothermal amplification reagents may be lyophilized in a single reaction volume, to be reconstituted by addition of a sample to be assayed. In certain other embodiments, the extraction-free polynucleotide isolation solution and isothermal amplification reagents may be lyophilized and stored on a cartridge or lateral flow strip, as discussed in further detail below.

In certain example embodiments, the single lysis reaction compositions and kits may further comprise one or more Cas proteins possessing collateral activity and a detection construct. Pairing with one or more Cas proteins may increase sensitivity or specificity of the assay. In certain example embodiments, the one or more Cas proteins may be thermostable Cas proteins. Example Cas proteins are disclosed in further detail below.

In certain example embodiments, the single lysis amplification reaction compositions and kits may comprise optimized primers and/or one or more additives. In an aspect, the design optimizes the primers used in the amplification. In particular aspects, the isothermal amplification is used alone. In another aspect, the isothermal amplification is used with CRISPR-Cas systems. In either approach, design considerations can follow a rational design for optimization of the reactions. Optimization of the methods as disclosed herein can include first screening primers to identify one or more sets of primers that work well for a particular target, Cas protein and/or reaction. Once the primers have been screened, titration of magnesium concentration can be performed to identify an optimal magnesium concentration for higher signal to noise readout. Once an optimum magnesium concentration is identified, additional additives are screened at around 20-25% of the reaction, and once additives are identified, these additives, such as those additives identified in FIG. 17, can be evaluated and varied in concentration to identify optimal reaction kinetics for specific reaction parameters. In an example, varying additives with specific primers, target, Cas protein (when CRISPR system is used), temperature, and other additive concentrations within the reaction can be identified. Optimization can be made with the goal of reducing the number of steps and buffer exchanges that have to occur in the reaction, simplifying the reaction and reducing the risks of contamination at transfer steps. In an aspect, addition of inhibitors, such as proteinase K can be considered so that buffer exchanges can be reduced. Similarly, optimizing the salt levels as well as the type of salt utilized can further facilitate and optimize the one-pot detections disclosed herein. In an aspect, potassium chloride can be utilized rather than sodium chloride when such amplification approaches are used with bead concentration in a lysis step.

In certain embodiments, the compositions and kits may further comprise nucleic acid binding bead. The bead may be used to capture, concentrate or otherwise enrich for particular material. The bead may be magnetic, and may be provided to capture nucleic acid material. In another aspect, the bead is a silica bead. Beads may be utilized in an extraction step of the methods disclosed herein. Beads can be optionally used with the methods described herein, including with the one-pot methods that allow for concentration of viral nucleic acids from large volume samples, such as saliva or swab samples to allow for a single one-pot reaction method. Concentration of desired target molecules can be increased by about 10-fold, 50-fold, 100-fold, 200-fold, 500-fold, 800-fold, 1000-fold, 1500-fold, 2000-fold, 2500-fold, 3000-fold, or more.

Magnetic beads in a PEG and salt solution are preferred in an aspect, and in embodiments bind to viral RNA and/or DNA which allows for concentration and lysis concurrently. Silica beads can be used in another aspect. Capture moieties such as oligonucleotide functionalized beads are envisioned for use. The beads may be using with the extraction reagents, allowed to incubate with a sample and the lysis/extraction-free polynucleotide isolation solution, thereby concrrating target molecules on the beads. When used with a cartridge device detailed elsewhere herein, a magnet can be activated and the beads collected, with optional flushing of the extraction-free polynucleotide isolation solution and one or more washes performed. Advantageously, the beads can be used in the one-pot methods and systems without additional washings of the beads, allowing for a more efficient process without increased risks of contamination in multi-step processes. Beads can be utilized with the isothermal amplifications detailed herein, and the beads can flow into an amplification chamber of the cartridge or be maintained in the pot for the amplification step. Upon heating, nucleic acid can be released off the beads.

Isothermal Amplification Reagents

Isothermal amplification reagents can be utilized in accordance with the systems and methods disclosed herein. The isothermal amplification reagents can be utilized with the quick extraction solution and methods as disclosed herein to allow for one-pot detection of target polynucleotides. Further optimization of the primers and reaction conditions, including the addition of one or more additional reagents in the system can be utilized to facilitate improved/enhanced detection and/or improved signal to noise readout. The isothermal amplification may be nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). In certain example embodiments, non-isothermal amplification methods may be used which include, but are not limited to, PCR, multiple displacement amplification (MDA), rolling circle amplification (RCA), ligase chain reaction (LCR), or ramification amplification method (RAM).

Loop-Mediated Isothermal Amplification

In certain example embodiments, a loop-mediated isothermal amplification (LAMP) reaction may be used to target nucleic acids, which encompasses both LAMP and RT-LAMP reactions. LAMP can be performed with a four-primer system for isothermal nucleic acid amplification in conjunction with a polymerase. Notomi et al., Nucleic Acids Res. 2000, 28, 12, Nagamine et al., Molecular and Cellular Probes (2002) 16, 223-229, doi: 10.1006/mcpr.2002.0415. When performing LAMP with a 4-primer system, two loop-forming inner primers, denoted as FIP and BIP, are provided with two outer primers, F3 and B3. The inner primers each contain two distinct sequences, one for priming in the first stage of the amplification and the other sequence for self-priming in subsequent amplification states. The two outer primers initiate strand displacement of nucleic acid strands initiated from the FIP and BIP primers, thereby generating formation of loops and strand displacement nucleic acid synthesis utilizing the provided polymerase. LAMP can be conducted with two to six primers, ranging from only the two loop-forming primers, up to at least the addition of 2 additional primers, LF and LB along with the two outer primers and two inner primers. LAMP technologies advantageously have high specificity and can work at a variety of pH and temperature. In a preferred aspect, the LAMP is an isothermal reaction at between about 45° C. to 75° C., 55 to 70° C. or 60° C. to 65° C. Colorimetric LAMP (Y. Zhang et al., doi:10.1101/2020.92.26.20028373), RT-LAMP (Lamb et al., doi: 10.1101/2020.02.19.20025155; and Yang et al., doi:10.1101/2020.03.02.20030130) have been developed for detection of COVID-19, and are incorporated herein by reference in their entirety.

In certain embodiments, the LAMP reagents may include Bst 2.0+RTx or Bst 3.0 from New England Biolabs. In certain embodiments, the LAMP reagents may comprise colorimetric or fluorescent detection. Detection of LAMP products can be accomplished using colorimetric tools, such as hydroxy napthol blue (see, e.g. Goto, M., et al., Colorimetric detection of loop-mediated isothermal amplification reaction by using hydroxy naphthol blue. Biotechniques, 2009. 46(3): p. 167-72.) leuco triphenylmethane dyes (see, e.g. Miyamoto, S., et al., Method for colorimetric detection of double-stranded nucleic acid using leuco triphenylmethane dyes. Anal Biochem, 2015. 473: p. 28-33) and pH-snesitive dyes (see, e.g. Tanner, N. A., Y. Zhang, and T. C. Evans, Jr., Visual detection of isothermal nucleic acid amplification using pH-sensitive dyes. Biotechniques, 2015. 58(2): p. 59-68); as well as fluorescent detection (see, e.g. Yu et al., *Clinical Chemistry*, hvaa102, doi:10.1093/clinchem/hvaa102 12 May 2020), including use of quenching probes (see, e.g. Shirato et al., J Virol Methods. 2018 August; 258:41-48. doi: 10.1016/j.jviromet.2018.05.006).

In an aspect, the primer sets for LAMP are designed to amplify one or more target sequences, generating amplicons that comprise the one or more target sequences. Optionally, the primers can comprise barcodes that can be designed as described elsewhere herein. Incubating to a temperature sufficient for LAMP amplification, e.g. 50° C.-72° C., more preferably 55° C. to 65° C., using a polymerase and, optionally a reverse transcriptase (in the event RT-LAMP is utilized). Preferably the enzymes utilized in the LAMP reaction are heat-stabilized. LAMP primer sites have been designed, see, e.g. Park et al., "Development of Reverse Transcription Loop-Mediated Isothermal Amplification Assays Targeting SARS-CoV-2" J. of Mol. Diag. (2020). Optionally, a control template is further provided with the sample, which may differ from the target sequence but share primer binding sites. In an exemplary embodiment, visual read out of the detection results can be accomplished using commercially-available lateral flow substrate, e.g. a commercially available paper substrate.

In certain embodiments, the LAMP primer can be selected from SEQ ID Nos: 1-40499. In certain embodiments, the primers are designed to target one or more of the targets in Table 1, for example, *Chlamydia trachomatis* D/UW-3/CX chromosome, Hepatitis A virus, Hepatitis B virus (strain ayw) genome, Hepatitis C virus (isolate H77) genotype 1, complete cds, Hepatitis C virus genotype 1, Hepatitis C virus genotype 2, Hepatitis C virus genotype 3, genome, Hepatitis C virus genotype 4, genome, Hepatitis C virus genotype 5, genome, Hepatitis C virus genotype 6, Hepatitis C virus genotype 7, Hepatitis delta virus, Hepatitis E virus, Hepatitis E virus rat/R63/DEU/2009, Hepatitis GB virus A, Hepatitis GB virus B, Human adenovirus 54, Human adenovirus A, Human betaherpesvirus 6A, variant A DNA, complete virion genome, isolate U1102, Human coronavirus 229E, Human coronavirus HKU1, Human Coronavirus NL63, Human coronavirus OC43 strain ATCC VR-759, Human gammaherpesvirus 4, Human genital-associated circular DNA virus-1 isolate 349, Human herpesvirus 1 strain 17, Human herpesvirus 2 strain HG52, Human herpesvirus 3, Human herpesvirus 4, Human herpesvirus 5 strain Merlin, Human herpesvirus 6B, Human herpesvirus 7, Human herpesvirus 8 strain GK18, Human immunodeficiency virus 1, Human immunodeficiency virus 2, Human papillomavirus 54, Human papillomavirus 116, Human papillomavirus—1, Human papillomavirus—2, Human papillomavirus—18, Human papillomavirus—61, Human papillomavirus isolate SE379, Human papillomavirus KC5, Human papillomavirus type 4, Human papillomavirus type 6b, Human papillomavirus type 7 genomic DNA, Human papillomavirus type 9, Human papillomavirus type 10 genomic DNA, Human papillomavirus type 16, Human papillomavirus type 26, Human papillomavirus type 30 genomic DNA, Human papillomavirus type 32, Human papillomavirus type 34, Human papillomavirus type 41, Human papillomavirus type 48, Human papillomavirus type 49, Human papillomavirus type 50, Human papillomavirus type 53, Human papillomavirus type 60, Human papillomavirus type 63, Human papillomavirus type 71 DNA, Human papillomavirus type 85 isolate 114B, Human papillomavirus type 88, Human papillomavirus type 90, Human papillomavirus type 92, Human papillomavirus type 96, Human papillomavirus type 101, Human papillomavirus type 103, Human papillomavirus type 108, Human papillomavirus type 109, Human papillomavirus type 112, Human papillomavirus type 121, Human papillomavirus type 126, Human papillomavirus type 128, Human papillomavirus type 129, Human papillomavirus type 131, Human papillomavirus type 132, Human papillomavirus type 134, Human papillomavirus type 135, Human papillomavirus type 136, Human papillomavirus type 137, Human papillomavirus type 140, Human papillomavirus type 144, Human papillomavirus type 154 isolate PV77, Human papillomavirus type 156 isolate GC01, Human papillomavirus type 161 isolate KC1, Human papillomavirus type 163 isolate KC3, Human papillomavirus type 166 isolate KC9, Human papillomavirus type 167 isolate KC10, Human papillomavirus type 172, Human papillomavirus type 175 isolate SE87, Human, apillomavirus type 178, Human papillomavirus type 179 isolate SIBX16, Human papillomavirus type 184 isolate SIBX17, Human papillomavirus type 187 isolate ACS447, Human papillomavirus type 201 isolate HPV201, Human papillomavirus type 204 isolate A342, Human papillomoavirus type 5, Human parainfluenza virus 1, Human parainfluenza virus 3, Human rhinovirus 1 strain ATCC VR-1559, Human rhinovirus 3, Human rhinovirus 14, Human rhinovirus 89, Human rhinovirus C, Human rhinovirus NAT001 polyprotein gene, complete cds, Human T-lymphotropic virus 1, Influenza A virus (A/California/07/2009 (H1N1)) segment 1 polymerase PB2 (PB2) gene, complete cds, Influenza A virus (A/California/07/2009 (H1N1)) segment 2 polymerase PB1 (PB1) gene, complete cds; and nonfunctional PB1-F2 protein (PB1-F2) gene, Influenza A virus (A/California/07/2009 (H1N1)) segment 3 polymerase PA (PA) gene, complete cds, Influenza A virus (A/California/07/2009 (H1N1)) segment 4 hemagglutinin (HA) gene, complete cds, Influenza A virus (A/California/07/2009 (H1N1)) segment 5 nucleocapsid protein (NP) gene, complete cds, Influenza A virus (A/California/07/2009 (H1N1)) segment 6 neuraminidase (NA) gene, complete cds, Influenza A virus (A/California/07/2009 (H1N1)) segment 7 matrix protein 2 (M2) and matrix protein 1 (M1) genes, complete cds, Influenza A virus (A/California/07/2009 (H1N1)) segment 8 nuclear export protein (NEP) and nonstructural protein 1 (NS1) genes, complete cds, Influenza A virus (A/Goose/Guangdong/1/96 (H5N1)) neuraminidase (NA) gene, complete cds, Influenza A virus (A/Goose/Guangdong/1/96 (H5N1)) nucleocapsid protein (NP) gene, complete cds, Influenza A virus (A/Goose/Guangdong/1/96 (H5N1)) polymerase (PB2) gene, complete cds, Influenza A virus (A/goose/Guangdong/1/1996 (H5N1)) hemagglutinin (HA) gene, complete cds, Influenza A virus (A/goose/Guangdong/1/1996 (H5N1)) polymerase (PA) and PA-X protein (PA-X) genes, complete cds, Influenza A virus (A/goose/Guangdong/1/1996 (H5N1)) polymerase (PB1) and PB1-F2 protein (PB1-F2) genes, complete cds, Influenza A virus (A/goose/Guangdong/1/1996 (H5N1)) segment 7, Influenza A virus (A/goose/Guangdong/1/1996 (H5N1)) segment 8, Influenza A virus (A/Hong Kong/1073/99 (H9N2)) segment 5, Influenza A virus (A/Hong Kong/1073/99 (H9N2)) segment 7, Influenza A virus (A/Hong Kong/1073/99 (H9N2)) segment 8, Influenza A virus (A/Korea/426/1968 (H2N2)) segment 1, Influenza A virus (A/Korea/426/1968 (H2N2)) segment 2, Influenza A virus (A/Korea/426/1968 (H2N2)) segment 3, Influenza A virus (A/Korea/426/1968 (H2N2)) segment 4, Influenza A virus (A/Korea/426/1968 (H2N2)) segment 5, Influenza A virus (A/Korea/426/1968 (H2N2)) segment 6, Influenza A virus (A/Korea/426/1968 (H2N2)) segment 7, Influenza A virus (A/Korea/426/1968 (H2N2)) segment 8, Influenza A virus (A/New York/392/2004 (H3N2)) segment 1, Influenza A virus (A/New York/392/2004 (H3N2)) segment 2, Influenza A virus (A/New York/392/2004 (H3N2)) segment 3, Influenza A virus (A/New York/392/2004 (H3N2)) segment 4, Influenza A virus (A/New York/392/2004 (H3N2)) segment 5, Influenza A virus (A/New York/392/2004 (H3N2)) segment 6, Influenza A virus (A/New York/392/2004 (H3N2)) segment 7, Influenza A virus (A/New York/392/2004 (H3N2)) segment 8, Influenza A virus (A/Puerto Rico/8/1934 (H1N1)) segment 1, Influenza A virus (A/Puerto Rico/8/1934 (H1N1)) segment 2, Influenza A virus (A/Puerto Rico/8/1934 (H1N1))

segment 3, Influenza A virus (A/Puerto Rico/8/1934 (H1N1)) segment 4, Influenza A virus (A/Puerto Rico/8/1934 (H1N1)) segment 5, Influenza A virus (A/Puerto Rico/8/1934 (H1N1)) segment 6, Influenza A virus (A/Puerto Rico/8/1934 (H1N1)) segment 7, Influenza A virus (A/Puerto Rico/8/1934 (H1N1)) segment 8, Influenza A virus (A/Shanghai/02/2013 (H7N9)) segment 1 polymerase PB2 (PB2) gene, complete cds, Influenza A virus (A/Shanghai/02/2013 (H7N9)) segment 2 polymerase PB1 (PB1) and PB1-F2 protein (PB1-F2) genes, complete cds, Influenza A virus (A/Shanghai/02/2013 (H7N9)) segment 3 polymerase PA (PA) and PA-X protein (PA-X) genes, complete cds, Influenza A virus (A/Shanghai/02/2013 (H7N9)) segment 4 hemagglutinin (HA) gene, complete cds, Influenza A virus (A/Shanghai/02/2013 (H7N9)) segment 5 nucleocapsid protein (NP) gene, complete cds, Influenza A virus (A/Shanghai/02/2013 (H7N9)) segment 6 neuraminidase (NA) gene, complete cds, Influenza A virus (A/Shanghai/02/2013 (H7N9)) segment 7 matrix protein 2 (M2) and matrix protein 1 (M1) genes, complete cds, Influenza A virus (A/Shanghai/02/2013 (H7N9)) segment 8 nuclear export protein (NEP) and nonstructural protein 1 (NS1) genes, complete cds, Influenza A virus ha gene for Hemagglutinin, genomic RNA, strain A/Hong Kong/1073/99 (H9N2), Influenza A virus na gene for neuraminidase, genomic RNA, strain A/Hong Kong/1073/99 (H9N2), Influenza A virus pa gene for polymerase PA, genomic RNA, strain A/Hong Kong/1073/99 (H9N2), Influenza A virus 01 gene for polymerase Pb1, genomic RNA, strain A/Hong Kong/1073/99 (H9N2), Influenza A virus pb2 gene for polymerase Pb2, genomic RNA, strain A/Hong Kong/1073/99 (H9N2), Influenza B virus (B/Lee/1940) segment 2, Influenza B virus (B/Lee/1940) segment 3, Influenza B virus (B/Lee/1940) segment 4, Influenza B virus (B/Lee/1940) segment 5, Influenza B virus (B/Lee/1940) segment 6, Influenza B virus (B/Lee/1940) segment 7, Influenza B virus (B/Lee/1940) segment 8, Influenza B virus RNA 1, Influenza C virus (C/Ann Arbor/1/50) HEF gene for hemagglutinin-esterase-fusion, complete cds, Influenza C virus (C/Ann Arbor/1/50) M1, CM2 genes for matrix protein, CM2 protein, complete cds, Influenza C virus (C/Ann Arbor/1/50) P3 gene for polymerase 3, complete cds, Influenza C virus (C/Ann Arbor/1/50) PB1 gene for polymerase 1, complete cds, Influenza C virus (C/Ann Arbor/1/50) PB2 gene for polymerase 2, complete cds, Influenza C virus (C/Ann Arbor/1/50) segment 5, Influenza C virus (C/Ann Arbor/1/50) segment 7, *Neisseria gonorrhoeae* strain WHO F chromosome 1, Respiratory syncytial virus, SARS coronavirus, or *Streptococcus pyogenes* strain NCTC8198 chromosome 1.

TABLE 1

Exemplary target sequences

| Name | % GC | Accession | Common Name | Created | Created Date | Description |
|---|---|---|---|---|---|---|
| NC_000117 | 41.30% | NC_000117.1 | | Wed Aug. 03 00:00:00 EDT 2016 | Wed Aug. 03 00:00:00 EDT 2016 | Chlamydia trachomatis D/UW-3/CX chromosome, complete genome |
| NC_001489 | 37.90% | NC_001489.1 | | Mon Aug. 13 00:00:00 EDT 2018 | Mon Aug. 13 00:00:00 EDT 2018 | Hepatitis A virus, complete genome |
| NC_003977 | 48.50% | NC_003977.2 | | Mon Aug. 13 00:00:00 EDT 2018 | Mon Aug. 13 00:00:00 EDT 2018 | Hepatitis B virus (strain ayw) genome |
| NC_038882 | 58.40% | NC_038882.1 | isolate H77 | Tue Apr. 21 00:00:00 EDT 2020 | Tue Apr. 21 00:00:00 EDT 2020 | Hepatitis C virus (isolate H77) genotype 1, complete cds |
| NC_004102 | 58.20% | NC_004102.1 | | Thu Jul. 11 00:00:00 EDT 2019 | Thu Jul. 11 00:00:00 EDT 2019 | Hepatitis C virus genotype 1, complete genome |
| NC_009823 | 56.90% | NC_009823.1 | | Wed May 22 00:00:00 EDT 2019 | Wed May 22 00:00:00 EDT 2019 | Hepatitis C virus genotype 2, complete genome |
| NC_009824 | 55.60% | NC_009824.1 | | Wed May 22 00:00:00 EDT 2019 | Wed May 22 00:00:00 EDT 2019 | Hepatitis C virus genotype 3, genome |
| NC_009825 | 56.20% | NC_009825.1 | | Wed May 22 00:00:00 EDT 2019 | Wed May 22 00:00:00 EDT 2019 | Hepatitis C virus genotype 4, genome |
| NC_009826 | 57.10% | NC_009826.1 | | Wed May 22 00:00:00 EDT 2019 | Wed May 22 00:00:00 EDT 2019 | Hepatitis C virus genotype 5, genome |
| NC_009827 | 55.40% | NC_009827.1 | | Wed May 22 00:00:00 EDT 2019 | Wed May 22 00:00:00 EDT 2019 | Hepatitis C virus genotype 6, complete genome |
| NC_030791 | 56.80% | NC_030791.1 | | Tue May 28 00:00:00 EDT 2019 | Tue May 28 00:00:00 EDT 2019 | Hepatitis C virus genotype 7, complete genome |
| NC_001653 | 58.80% | NC_001653.2 | | Mon Aug. 13 00:00:00 EDT 2018 | Mon Aug. 13 00:00:00 EDT 2018 | Hepatitis delta virus, complete genome |
| NC_001434 | 57.90% | NC_001434.1 | | Mon Aug. 13 00:00:00 EDT 2018 | Mon Aug. 13 00:00:00 EDT 2018 | Hepatitis E virus, complete genome |
| NC_038504 | 57.60% | NC_038504.1 | | Tue Jun. 04 00:00:00 EDT 2019 | Tue Jun. 04 00:00:00 EDT 2019 | Hepatitis E virus rat/R63/DEU/2009, complete genome |
| NC_001837 | 57.90% | NC_001837.1 | | Mon Aug. 13 00:00:00 EDT 2018 | Mon Aug. 13 00:00:00 EDT 2018 | Hepatitis GB virus A, complete genome |
| NC_001655 | 50.60% | NC_001655.1 | | Thu May 23 00:00:00 EDT 2019 | Thu May 23 00:00:00 EDT 2019 | Hepatitis GB virus B, complete genome |

TABLE 1-continued

Exemplary target sequences

| Name | % GC | Accession | Common Name | Created | Created Date | Description |
|---|---|---|---|---|---|---|
| NC_012959 | 54.90% | NC_012959.1 | | Mon Aug. 13 00:00:00 EDT 2018 | Mon Aug. 13 00:00:00 EDT 2018 | Human adenovirus 54, complete genome |
| NC_001460 | 46.50% | NC_001460.1 | | Mon Aug. 13 00:00:00 EDT 2018 | Mon Aug. 13 00:00:00 EDT 2018 | Human adenovirus A, complete genome |
| NC_001664 | 42.40% | NC_001664.4 | | Fri Jan. 18 00:00:00 EST 2019 | Fri Jan. 18 00:00:00 EST 2019 | Human betaherpesvirus 6A, variant A DNA, complete virion genome, isolate U1102 |
| NC_002645 | 38.30% | NC_002645.1 | | Mon Aug. 13 00:00:00 EDT 2018 | Mon Aug. 13 00:00:00 EDT 2018 | Human coronavirus 229E, complete genome |
| NC_006577 | 32.10% | NC_006577.2 | HCoV-HKU1 | Mon Aug. 13 00:00:00 EDT 2018 | Mon Aug. 13 00:00:00 EDT 2018 | Human coronavirus HKU1, complete genome |
| NC_005831 | 34.50% | NC_005831.2 | HCoV-NL63 | Mon Aug. 13 00:00:00 EDT 2018 | Mon Aug. 13 00:00:00 EDT 2018 | Human Coronavirus NL63, complete genome |
| NC_006213 | 36.80% | NC_006213.1 | HCoV-OC43 | Thu Feb. 21 00:00:00 EST 2019 | Thu Feb. 21 00:00:00 EST 2019 | Human coronavirus OC43 strain ATCC VR-759, complete genome |
| NC_007605 | 59.50% | NC_007605.1 | Epstein-Barr virus | Mon Aug. 13 00:00:00 EDT 2018 | Mon Aug. 13 00:00:00 EDT 2018 | Human gammaherpesvirus 4, complete genome |
| NC_026817 | 54.90% | NC_026817.1 | | Mon Aug. 13 00:00:00 EDT 2018 | Mon Aug. 13 00:00:00 EDT 2018 | Human genital-associated circular DNA virus-1 isolate 349, complete genome |
| NC_001806 | 68.30% | NC_001806.2 | Herpes simplex virus 1 | Mon Aug. 13 00:00:00 EDT 2018 | Mon Aug. 13 00:00:00 EDT 2018 | Human herpesvirus 1 strain 17, complete genome |
| NC_001798 | 70.40% | NC_001798.2 | Herpes simplex virus 2 | Mon May 16 00:00:00 EDT 2016 | Mon May 16 00:00:00 EDT 2016 | Human herpesvirus 2 strain HG52, complete genome |
| NC_001348 | 46.00% | NC_001348.1 | HHV-3 | Mon Aug. 13 00:00:00 EDT 2018 | Mon Au.g 13 00:00:00 EDT 2018 | Human herpesvirus 3, complete genome |
| NC_009334 | 59.50% | NC_009334.1 | Epstein-Barr virus type 2 | Mon Aug. 13 00:00:00 EDT 2018 | Mon Aug. 13 00:00:00 EDT 2018 | Human herpesvirus 4, complete genome |
| NC_006273 | 57.50% | NC_006273.2 | HHV-5; HCMV | Mon Aug. 13 00:00:00 EDT 2018 | Mon Aug. 13 00:00:00 EDT 2018 | Human herpesvirus 5 strain Merlin, complete genome |
| NC_000898 | 42.80% | NC_000898.1 | HHV-6B | Mon Aug. 13 00:00:00 EDT 2018 | Mon Aug. 13 00:00:00 EDT 2018 | Human herpesvirus 6B, complete genome |
| NC_001716 | 36.20% | NC_001716.2 | HHV-7 | Mon Aug. 13 00:00:00 EDT 2018 | Mon Aug. 13 00:00:00 EDT 2018 | Human herpesvirus 7, complete genome |
| NC_009333 | 53.80% | NC_009333.1 | Kaposi's sarcoma-associated herpesvirus | Tue Jun. 04 00:00:00 EDT 2019 | Tue Jun. 04 00:00:00 EDT 2019 | Human herpesvirus 8 strain GK18, complete genome |
| NC_001802 | 42.10% | NC_001802.1 | HIV-1 | Mon Aug. 13 00:00:00 EDT 2018 | Mon Aug. 13 00:00:00 EDT 2018 | Human immunodeficiency virus 1, complete genome |
| NC_001722 | 45.70% | NC_001722.1 | HIV-2 | Mon Aug. 13 00:00:00 EDT 2018 | Mon Aug. 13 00:00:00 EDT 2018 | Human immunodeficiency virus 2, complete genome |
| NC_001676 | 41.90% | NC_001676.1 | | Mon Aug. 13 00:00:00 EDT 2018 | Mon Aug. 13 00:00:00 EDT 2018 | Human papillomavirus 54, complete genome |
| NC_013035 | 38.50% | NC_013035.1 | | Mon Aug. 13 00:00:00 EDT 2018 | Mon Aug. 13 00:00:00 EDT 2018 | Human papillomavirus 116, complete genome |
| NC_001356 | 40.30% | NC_001356.1 | | Mon Aug. 13 00:00:00 EDT 2018 | Mon Aug. 13 00:00:00 EDT 2018 | Human papillomavirus-1, complete genome |
| NC_001352 | 48.40% | NC_001352.1 | | Mon Aug. 13 00:00:00 EDT 2018 | Mon Aug. 13 00:00:00 EDT 2018 | Human papillomavirus-2, complete genome |
| NC_001357 | 40.40% | NC_001357.1 | | Mon Aug. 13 00:00:00 EDT 2018 | Mon Aug. 13 00:00:00 EDT 2018 | Human papillomavirus-18, complete genome |
| NC_001694 | 46.30% | NC_001694.1 | | Mon Aug. 13 00:00:00 EDT 2018 | Mon Aug. 13 00:00:00 EDT 2018 | Human papillomavirus-61, complete genome |

TABLE 1-continued

Exemplary target sequences

| Name | % GC | Accession | Common Name | Created | Created Date | Description |
|---|---|---|---|---|---|---|
| NC_027779 | 37.50% | NC_027779.1 | | Mon Aug. 13 00:00:00 EDT 2018 | Mon Aug. 13 00:00:00 EDT 2018 | Human papillomavirus isolate SE379, complete genome |
| NC_026946 | 36.80% | NC_026946.1 | | Mon Aug. 13 00:00:00 EDT 2018 | Mon Aug. 13 00:00:00 EDT 2018 | Human papillomavirus KC5, complete genome |
| NC_001457 | 38.50% | NC_001457.1 | | Mon Aug. 13 00:00:00 EDT 2018 | Mon Aug. 13 00:00:00 EDT 2018 | Human papillomavirus type 4, complete genome |
| NC_001355 | 40.90% | NC_001355.1 | | Mon Aug. 13 00:00:00 EDT 2018 | Mon Aug. 13 00:00:00 EDT 2018 | Human papillomavirus type 6b, complete genome |
| NC_001595 | 39.50% | NC_001595.1 | | Mon Aug. 13 00:00:00 EDT 2018 | Mon Aug. 13 00:00:00 EDT 2018 | Human papillomavirus type 7 genomic DNA |
| NC_001596 | 41.00% | NC_001596.1 | | Mon Aug. 13 00:00:00 EDT 2018 | Mon Aug. 13 00:00:00 EDT 2018 | Human papillomavirus type 9, complete genome |
| NC_001576 | 45.90% | NC_001576.1 | | Mon Aug. 13 00:00:00 EDT 2018 | Mon Aug. 13 00:00:00 EDT 2018 | Human papillomavirus type 10 genomic DNA |
| NC_001526 | 36.50% | NC_001526.4 | | Mon Aug. 13 00:00:00 EDT 2018 | Mon Aug. 13 00:00:00 EDT 2018 | Human papillomavirus type 16, complete genome |
| NC_001583 | 38.60% | NC_001583.1 | | Mon Aug. 13 00:00:00 EDT 2018 | Mon Aug. 13 00:00:00 EDT 2018 | Human papillomavirus type 26, complete genome |
| NC_038889 | 40.40% | NC_038889.1 | | Fri Aug. 24 00:00:00 EDT 2018 | Fri Aug. 24 00:00:00 EDT 2018 | Human papillomavirus type 30 genomic DNA |
| NC_001586 | 41.00% | NC_001586.1 | | Mon Aug. 13 00:00:00 EDT 2018 | Mon Aug. 13 00:00:00 EDT 2018 | Human papillomavirus type 32, complete genome |
| NC_001587 | 38.20% | NC_001587.1 | | Mon Aug. 13 00:00:00 EDT 2018 | Mon Aug. 13 00:00:00 EDT 2018 | Human papillomavirus type 34, complete genome |
| NC_001354 | 46.90% | NC_001354.1 | | Mon Aug. 13 00:00:00 EDT 2018 | Mon Aug. 13 00:00:00 EDT 2018 | Human papillomavirus type 41, complete genome |
| NC_001690 | 36.80% | NC_001690.1 | | Mon Aug. 13 00:00:00 EDT 2018 | Mon Aug. 13 00:00:00 EDT 2018 | Human papillomavirus type 48, complete genome |
| NC_001591 | 41.10% | NC_001591.1 | | Mon Aug. 13 00:00:00 EDT 2018 | Mon Aug. 13 00:00:00 EDT 2018 | Human papillomavirus type 49, complete genome |
| NC_001691 | 36.80% | NC_001691.1 | | Mon Aug. 13 00:00:00 EDT 2018 | Mon Aug. 13 00:00:00 EDT 2018 | Human papillomavirus type 50, complete genome |
| NC_001593 | 40.10% | NC_001593.1 | | Mon Aug. 13 00:00:00 EDT 2018 | Mon Aug. 13 00:00:00 EDT 2018 | Human papillomavirus type 53, complete genome |
| NC_001693 | 37.00% | NC_001693.1 | | Mon Aug. 13 00:00:00 EDT 2018 | Mon Aug. 13 00:00:00 EDT 2018 | Human papillomavirus type 60, complete genome |
| NC_001458 | 40.40% | NC_001458.1 | | Mon Aug. 13 00:00:00 EDT 2018 | Mon Aug. 13 00:00:00 EDT 2018 | Human papillomavirus type 63, complete genome |
| NC_039089 | 44.40% | NC_039089.1 | | Fri Aug. 24 00:00:00 EDT 2018 | Fri Aug. 24 00:00:00 EDT 2018 | Human papillomavirus type 71 DNA, complete genome |
| NC_034616 | 37.70% | NC_034616.1 | | Sat Aug. 25 00:00:00 EDT 2018 | Sat Aug. 25 00:00:00 EDT 2018 | Human papillomavirus type 85 isolate 114B, complete genome |
| NC_010329 | 40.10% | NC_010329.1 | | Mon Aug. 13 00:00:00 EDT 2018 | Mon Aug. 13 00:00:00 EDT 2018 | Human papillomavirus type 88, complete genome |
| NC_004104 | 46.70% | NC_004104.1 | candHPV90 | Mon Aug. 13 00:00:00 EDT 2018 | Mon Aug. 13 00:00:00 EDT 2018 | Human papillomavirus type 90, complete genome |
| NC_004500 | 40.00% | NC_004500.1 | | Mon Aug. 13 00:00:00 EDT 2018 | Mon Aug. 13 00:00:00 EDT 2018 | Human papillomavirus type 92, complete genome |

TABLE 1-continued

Exemplary target sequences

| Name | % GC | Accession | Common Name | Created | Created Date | Description |
|---|---|---|---|---|---|---|
| NC_005134 | 40.30% | NC_005134.2 | | Mon Aug. 13 00:00:00 EDT 2018 | Mon Aug. 13 00:00:00 EDT 2018 | Human papillomavirus type 96, complete genome |
| NC_008189 | 43.10% | NC_008189.1 | HPV101 | Mon Aug. 13 00:00:00 EDT 2018 | Mon Aug. 13 00:00:00 EDT 2018 | Human papillomavirus type 101, complete genome |
| NC_008188 | 41.60% | NC_008188.1 | HPV103 | Mon Aug. 13 00:00:00 EDT 2018 | Mon Aug. 13 00:00:00 EDT 2018 | Human papillomavirus type 103, complete genome |
| NC_012213 | 42.60% | NC_012213.1 | | Tue Jun. 04 00:00:00 EDT 2019 | Tue Jun. 04 00:00:00 EDT 2019 | Human papillomavirus type 108, complete genome |
| NC_012485 | 38.30% | NC_012485.1 | | Mon Aug. 13 00:00:00 EDT 2018 | Mon Aug. 13 00:00:00 EDT 2018 | Human papillomavirus type 109, complete genome |
| NC_012486 | 37.50% | NC_012486.1 | | Mon Aug. 13 00:00:00 EDT 2018 | Mon Aug. 13 00:00:00 EDT 2018 | Human papillomavirus type 112, complete genome |
| NC_014185 | 37.70% | NC_014185.1 | | Mon Aug. 13 00:00:00 EDT 2018 | Mon Aug. 13 00:00:00 EDT 2018 | Human papillomavirus type 121, complete genome |
| NC_016157 | 38.00% | NC_016157.1 | | Mon Aug. 13 00:00:00 EDT 2018 | Mon Aug. 13 00:00:00 EDT 2018 | Human papillomavirus type 126, complete genome |
| NC_014952 | 36.00% | NC_014952.1 | | Tue Jun. 04 00:00:00 EDT 2019 | Tue Jun. 04 00:00:00 EDT 2019 | Human papillomavirus type 128, complete genome |
| NC_014953 | 37.30% | NC_014953.1 | | Tue Jun. 04 00:00:00 EDT 2019 | Tue Jun. 04 00:00:00 EDT 2019 | Human papillomavirus type 129, complete genome |
| NC_014954 | 37.00% | NC_014954.1 | | Tue Jun. 04 00:00:00 EDT 2019 | Tue Jun. 04 00:00:00 EDT 2019 | Human papillomavirus type 131, complete genome |
| NC_014955 | 37.90% | NC_014955.1 | | Mon Aug. 13 00:00:00 EDT 2018 | Mon Aug. 13 00:00:00 EDT 2018 | Human papillomavirus type 132, complete genome |
| NC_014956 | 38.10% | NC_014956.1 | | Tue Jun. 04 00:00:00 EDT 2019 | Tue Jun. 04 00:00:00 EDT 2019 | Human papillomavirus type 134, complete genome |
| NC_017993 | 36.80% | NC_017993.1 | | Mon Aug. 13 00:00:00 EDT 2018 | Mon Aug. 13 00:00:00 EDT 2018 | Human papillomavirus type 135, complete genome |
| NC_017994 | 38.50% | NC_017994.1 | | Mon Aug. 13 00:00:00 EDT 2018 | Mon Aug. 13 00:00:00 EDT 2018 | Human papillomavirus type 136, complete genome |
| NC_017995 | 37.60% | NC_017995.1 | | Mon Aug. 13 00:00:00 EDT 2018 | Mon Aug. 13 00:00:00 EDT 2018 | Human papillomavirus type 137, complete genome |
| NC_017996 | 39.70% | NC_017996.1 | | Mon Aug. 13 00:00:00 EDT 2018 | Mon Aug. 13 00:00:00 EDT 2018 | Human papillomavirus type 140, complete genome |
| NC_017997 | 38.20% | NC_017997.1 | | Mon Aug. 13 00:00:00 EDT 2018 | Mon Aug. 13 00:00:00 EDT 2018 | Human papillomavirus type 144, complete genome |
| NC_021483 | 37.90% | NC_021483.1 | HPV154 | Mon Aug. 13 00:00:00 EDT 2018 | Mon Aug. 13 00:00:00 EDT 2018 | Human papillomavirus type 154 isolate PV77, complete genome |
| NC_033781 | 36.20% | NC_033781.1 | | Mon Aug. 13 00:00:00 EDT 2018 | Mon Aug. 13 00:00:00 EDT 2018 | Human papillomavirus type 156 isolate GC01, complete genome |
| NC_038522 | 37.70% | NC_038522.1 | | Fri Aug. 24 00:00:00 EDT 2018 | Fri Aug. 24 00:00:00 EDT 2018 | Human papillomavirus type 161 isolate KC1, complete genome |
| NC_028125 | 37.70% | NC_028125.1 | | Mon Aug. 13 00:00:00 EDT 2018 | Mon Aug. 13 00:00:00 EDT 2018 | Human papillomavirus type 163 isolate KC3, complete genome |
| NC_019023 | 38.30% | NC_019023.1 | | Mon Aug. 13 00:00:00 EDT 2018 | Mon Aug. 13 00:00:00 EDT 2018 | Human papillomavirus type 166 isolate KC9, complete genome |
| NC_022892 | 35.80% | NC_022892.1 | | Mon Aug. 13 00:00:00 EDT 2018 | Mon Aug. 13 00:00:00 EDT 2018 | Human papillomavirus type 167 isolate KC10, complete genome |
| NC_038523 | 37.80% | NC_038523.1 | HPV 172 | Fri Aug. 24 00:00:00 EDT 2018 | Fri Aug. 24 00:00:00 EDT 2018 | Human papillomavirus type 172, complete genome |

TABLE 1-continued

Exemplary target sequences

| Name | % GC | Accession | Common Name | Created | Created Date | Description |
|---|---|---|---|---|---|---|
| NC_038524 | 38.90% | NC_038524.1 | | Fri Aug. 24 00:00:00 EDT 2018 | Fri Aug. 24 00:00:00 EDT 2018 | Human papillomavirus type 175 isolate SE87, complete genome |
| NC_023891 | 38.20% | NC_023891.1 | | Mon Aug. 13 00:00:00 EDT 2018 | Mon Aug. 13 00:00:00 EDT 2018 | Human papillomavirus type 178, complete genome |
| NC_022095 | 36.80% | NC_022095.1 | | Mon Aug. 13 00:00:00 EDT 2018 | Mon Aug. 13 00:00:00 EDT 2018 | Human papillomavirus type 179 complete genome, isolate SIBX16 |
| NC_038914 | 36.90% | NC_038914.1 | | Fri Aug. 24 00:00:00 EDT 2018 | Fri Aug. 24 00:00:00 EDT 2018 | Human papillomavirus type 184 complete genome, isolate SIBX17 |
| NC_039086 | 38.90% | NC_039086.1 | | Fri Aug. 24 00:00:00 EDT 2018 | Fri Aug. 24 00:00:00 EDT 2018 | Human papillomavirus type 187 isolate ACS447, complete genome |
| NC_027528 | 37.70% | NC_027528.1 | | Mon Aug. 13 00:00:00 EDT 2018 | Mon Aug. 13 00:00:00 EDT 2018 | Human papillomavirus type 201 isolate HPV201, complete genome |
| NC_038525 | 37.80% | NC_038525.1 | | Fri Aug. 24 00:00:00 EDT 2018 | Fri Aug. 24 00:00:00 EDT 2018 | Human papillomavirus type 204 isolate A342, complete genome |
| NC_001531 | 42.40% | NC_001531.1 | | Mon Aug. 13 00:00:00 EDT 2018 | Mon Aug. 13 00:00:00 EDT 2018 | Human papillomoavirus type 5, complete genome |
| NC_003461 | 37.20% | NC_003461.1 | | Mon Aug. 13 00:00:00 EDT 2018 | Mon Aug. 13 00:00:00 EDT 2018 | Human parainfluenza virus 1, complete genome |
| NC_001796 | 34.50% | NC_001796.2 | | Mon Aug. 13 00:00:00 EDT 2018 | Mon Aug. 13 00:00:00 EDT 2018 | Human parainfluenza virus 3, complete genome |
| NC_038311 | 37.40% | NC_038311.1 | HRV-A1 | Fri Aug. 24 00:00:00 EDT 2018 | Fri Aug. 24 00:00:00 EDT 2018 | Human rhinovirus 1 strain ATCC VR-1559, complete genome |
| NC_038312 | 39.90% | NC_038312.1 | | Tue Jun. 04 00:00:00 EDT 2019 | Tue Jun. 04 00:00:00 EDT 2019 | Human rhinovirus 3, complete genome |
| NC_001490 | 40.60% | NC_001490.1 | | Mon Aug. 13 00:00:00 EDT 2018 | Mon Aug. 13 00:00:00 EDT 2018 | Human rhinovirus 14, complete genome |
| NC_001617 | 39.00% | NC_001617.1 | | Mon Aug. 13 00:00:00 EDT 2018 | Mon Aug. 13 00:00:00 EDT 2018 | Human rhinovirus 89, complete genome |
| NC_009996 | 42.80% | NC_009996.1 | | Mon Aug. 13 00:00:00 EDT 2018 | Mon Aug. 13 00:00:00 EDT 2018 | Human rhinovirus C, complete genome |
| NC_038878 | 43.40% | NC_038878.1 | | Fri Aug. 24 00:00:00 EDT 2018 | Fri Aug. 24 00:00:00 EDT 2018 | Human rhinovirus NAT001 polyprotein gene, complete cds |
| NC_001436 | 53.50% | NC_001436.1 | | Mon Aug. 13 00:00:00 EDT 2018 | Mon Aug. 13 00:00:00 EDT 2018 | Human T-lymphotropic virus 1, complete genome |
| NC_026438 | 44.80% | NC_026438.1 | A/California/07/2009(H1N1 | Mon Aug. 13 00:00:00 EDT 2018 | Mon Aug. 13 00:00:00 EDT 2018 | Influenza A virus (A/California/07/2009(H1N1)) segment 1 polymerase PB2 (PB2) gene, complete cds |
| NC_026435 | 42.00% | NC_026435.1 | A/California/07/2009(H1N1 | Mon Aug. 13 00:00:00 EDT 2018 | Mon Aug. 13 00:00:00 EDT 2018 | Influenza A virus (A/California/07/2009(H1N1)) segment 2 polymerase PB1 (PB1) gene, complete cds; and nonfunctional PB1-F2 protein (PB1-F2) gene, complete sequence |
| NC_026437 | 44.20% | NC_026437.1 | A/California/07/2009(H1N1 | Mon Aug. 13 00:00:00 EDT 2018 | Mon Aug. 13 00:00:00 EDT 2018 | Influenza A virus (A/California/07/2009(H1N1)) segment 3 polymerase PA (PA) gene, complete cds |
| NC_026433 | 40.80% | NC_026433.1 | A/California/07/2009(H1N1 | Mon Aug. 13 00:00:00 EDT 2018 | Mon Aug. 13 00:00:00 EDT 2018 | Influenza A virus (A/California/07/2009(H1N1)) segment 4 hemagglutinin (HA) gene, complete cds |
| NC_026436 | 46.30% | NC_026436.1 | A/California/07/2009(H1N1 | Mon Aug. 13 00:00:00 EDT 2018 | Mon Aug. 13 00:00:00 EDT 2018 | Influenza A virus (A/California/07/2009(H1N1)) segment 5 nucleocapsid protein (NP) gene, complete cds |
| NC_026434 | 42.10% | NC_026434.1 | A/California/07/2009(H1N1 | Mon Aug. 13 00:00:00 EDT 2018 | Mon Aug. 13 00:00:00 EDT 2018 | Influenza A virus (A/California/07/2009(H1N1)) segment 6 neuraminidase (NA) gene, complete cds |

TABLE 1-continued

Exemplary target sequences

| Name | % GC | Accession | Common Name | Created | Created Date | Description |
|---|---|---|---|---|---|---|
| NC_026431 | 47.10% | NC_026431.1 | A/California/07/2009(H1N1 | Mon Aug. 13 00:00:00 EDT 2018 | Mon Aug. 13 00:00:00 EDT 2018 | Influenza A virus (A/California/07/2009(H1N1)) segment 7 matrix protein 2 (M2) and matrix protein 1 (M1) genes, complete cds |
| NC_026432 | 43.60% | NC_026432.1 | A/California/07/2009(H1N1 | Mon Aug. 13 00:00:00 EDT 2018 | Mon Aug. 13 00:00:00 EDT 2018 | Influenza A virus (A/California/07/2009(H1N1)) segment 8 nuclear export protein (NEP) and nonstructural protein 1 (NS1) genes, complete cds |
| NC_007361 | 43.40% | NC_007361.1 | A/goose/Guangdong/1/1996(H5N1 | Mon Aug. 13 00:00:00 EDT 2018 | Mon Aug. 13 00:00:00 EDT 2018 | Influenza A virus (A/Goose/Guangdong/1/96(H5N1)) neuraminidase (NA) gene, complete cds |
| NC_007360 | 46.80% | NC_007360.1 | A/goose/Guangdong/1/1996(H5N1 | Mon Aug. 13 00:00:00 EDT 2018 | Mon Aug. 13 00:00:00 EDT 2018 | Influenza A virus (A/Goose/Guangdong/1/96(H5N1)) nucleocapsid protein (NP) gene, complete cds |
| NC_007357 | 44.30% | NC_007357.1 | A/goose/Guangdong/1/1996(H5N1 | Mon Aug. 13 00:00:00 EDT 2018 | Mon Aug. 13 00:00:00 EDT 2018 | Influenza A virus (A/Goose/Guangdong/1/96(H5N1)) polymerase (PB2) gene, complete cds |
| NC_007362 | 41.70% | NC_007362.1 | A/goose/Guangdong/1/1996(H5N1 | Mon Aug. 13 00:00:00 EDT 2018 | Mon Aug. 13 00:00:00 EDT 2018 | Influenza A virus (A/goose/Guangdong/1/1996(H5N1)) hemagglutinin (HA) gene, complete cds |
| NC_007359 | 43.80% | NC_007359.1 | A/goose/Guangdong/1/1996(H5N1 | Mon Aug. 13 00:00:00 EDT 2018 | Mon Aug. 13 00:00:00 EDT 2018 | Influenza A virus (A/goose/Guangdong/1/1996(H5N1)) polymerase (PA) and PA-X protein (PA-X) genes, complete cds |
| NC_007358 | 44.10% | NC_007358.1 | A/goose/Guangdong/1/1996(H5N1 | Mon Aug. 13 00:00:00 EDT 2018 | Mon Aug. 13 00:00:00 EDT 2018 | Influenza A virus (A/goose/Guangdong/1/1996(H5N1)) polymerase (PB1) and PB1-F2 protein (PB1-F2) genes, complete cds |
| NC_007363 | 47.90% | NC_007363.1 | A/goose/Guangdong/1/1996(H5N1 | Mon Aug. 13 00:00:00 EDT 2018 | Mon Aug. 13 00:00:00 EDT 2018 | Influenza A virus (A/goose/Guangdong/1/1996(H5N1)) segment 7, complete sequence |
| NC_007364 | 41.40% | NC_007364.1 | A/goose/Guangdong/1/1996(H5N1 | Mon Aug. 13 00:00:00 EDT 2018 | Mon Aug. 13 00:00:00 EDT 2018 | Influenza A virus (A/goose/Guangdong/1/1996(H5N1)) segment 8, complete sequence |
| NC_004905 | 47.30% | NC_004905.2 | A/Hong Kong/1073/99(H9N2 | Mon Aug. 13 00:00:00 EDT 2018 | Mon Aug. 13 00:00:00 EDT 2018 | Influenza A virus (A/Hong Kong/1073/99(H9N2)) segment 5, complete sequence |
| NC_004907 | 47.80% | NC_004907.1 | A/Hong Kong/1073/99(H9N2 | Mon Aug. 13 00:00:00 EDT 2018 | Mon Aug. 13 00:00:00 EDT 2018 | Influenza A virus (A/Hong Kong/1073/99(H9N2)) segment 7, complete sequence |
| NC_004906 | 43.30% | NC_004906.1 | A/Hong Kong/1073/99(H9N2 | Mon Aug. 13 00:00:00 EDT 2018 | Mon Aug. 13 00:00:00 EDT 2018 | Influenza A virus (A/Hong Kong/1073/99(H9N2)) segment 8, complete sequence |
| NC_007378 | 42.50% | NC_007378.1 | A/Korea/426/1968(H2N2 | Mon Aug. 13 00:00:00 EDT 2018 | Mon Aug. 13 00:00:00 EDT 2018 | Influenza A virus (A/Korea/426/1968(H2N2)) segment 1, complete sequence |
| NC_007375 | 42.70% | NC_007375.1 | A/Korea/426/1968(H2N2 | Mon Aug. 13 00:00:00 EDT 2018 | Mon Aug. 13 00:00:00 EDT 2018 | Influenza A virus (A/Korea/426/1968(H2N2)) segment 2, complete sequence |

TABLE 1-continued

Exemplary target sequences

| Name | % GC | Accession | Common Name | Created | Created Date | Description |
|---|---|---|---|---|---|---|
| NC_007376 | 42.40% | NC_007376.1 | A/Korea/426/1968(H2N2 | Mon Aug. 13 00:00:00 EDT 2018 | Mon Aug. 13 00:00:00 EDT 2018 | Influenza A virus (A/Korea/426/1968(H2N2)) segment 3, complete sequence |
| NC_007374 | 41.60% | NC_007374.1 | A/Korea/426/1968(H2N2 | Mon Aug. 13 00:00:00 EDT 2018 | Mon Aug. 13 00:00:00 EDT 2018 | Influenza A virus (A/Korea/426/1968(H2N2)) segment 4, complete sequence |
| NC_007381 | 46.40% | NC_007381.1 | A/Korea/426/1968(H2N2 | Mon Aug. 13 00:00:00 EDT 2018 | Mon Aug. 13 00:00:00 EDT 2018 | Influenza A virus (A/Korea/426/1968(H2N2)) segment 5, complete sequence |
| NC_007382 | 43.40% | NC_007382.1 | A/Korea/426/1968(H2N2 | Mon Aug. 13 00:00:00 EDT 2018 | Mon Aug. 13 00:00:00 EDT 2018 | Influenza A virus (A/Korea/426/1968(H2N2)) segment 6, complete sequence |
| NC_007377 | 47.50% | NC_007377.1 | A/Korea/426/1968(H2N2 | Mon Aug 13 00:00:00 EDT 2018 | Mon Aug. 13 00:00:00 EDT 2018 | Influenza A virus (A/Korea/426/1968(H2N2)) segment 7, complete sequence |
| NC_007380 | 43.40% | NC_007380.1 | A/Korea/426/1968(H2N2 | Mon Aug. 13 00:00:00 EDT 2018 | Mon Aug. 13 00:00:00 EDT 2018 | Influenza A virus (A/Korea/426/1968(H2N2)) segment 8, complete sequence |
| NC_007373 | 42.50% | NC_007373.1 | A/New York/392/2004(H3N2 | Mon Aug. 13 00:00:00 EDT 2018 | Mon Aug. 13 00:00:00 EDT 2018 | Influenza A virus (A/New York/392/2004(H3N2)) segment 1, complete sequence |
| NC_007372 | 42.20% | NC_007372.1 | A/New York/392/2004(H3N2 | Mon Aug. 13 00:00:00 EDT 2018 | Mon Aug. 13 00:00:00 EDT 2018 | Influenza A virus (A/New York/392/2004(H3N2)) segment 2, complete sequence |
| NC_007371 | 41.70% | NC_007371.1 | A/New York/392/2004(H3N2 | Mon Aug. 13 00:00:00 EDT 2018 | Mon Aug. 13 00:00:00 EDT 2018 | Influenza A virus (A/New York/392/2004(H3N2)) segment 3, complete sequence |
| NC_007366 | 42.00% | NC_007366.1 | A/New York/392/2004(H3N2 | Mon Aug. 13 00:00:00 EDT 2018 | Mon Aug. 13 00:00:00 EDT 2018 | Influenza A virus (A/New York/392/2004(H3N2)) segment 4, complete sequence |
| NC_007369 | 45.80% | NC_007369.1 | A/New York/392/2004(H3N2 | Mon Aug. 13 00:00:00 EDT 2018 | Mon Aug. 13 00:00:00 EDT 2018 | Influenza A virus (A/New York/392/2004(H3N2)) segment 5, complete sequence |
| NC_007368 | 42.70% | NC_007368.1 | A/New York/392/2004(H3N2 | Mon Aug. 13 00:00:00 EDT 2018 | Mon Aug. 13 00:00:00 EDT 2018 | Influenza A virus (A/New York/392/2004(H3N2)) segment 6, complete sequence |
| NC_007367 | 46.70% | NC_007367.1 | A/New York/392/2004(H3N2 | Mon Aug. 13 00:00:00 EDT 2018 | Mon Aug. 13 00:00:00 EDT 2018 | Influenza A virus (A/New York/392/2004(H3N2)) segment 7, complete sequence |
| NC_007370 | 41.70% | NC_007370.1 | A/New York/392/2004(H3N2 | Mon Aug. 13 00:00:00 EDT 2018 | Mon Aug. 13 00:00:00 EDT 2018 | Influenza A virus (A/New York/392/2004(H3N2)) segment 8, complete sequence |
| NC_002023 | 43.70% | NC_002023.1 | A/Puerto Rico/8/1934(H1N1 | Mon Aug. 13 00:00:00 EDT 2018 | Mon Aug. 13 00:00:00 EDT 2018 | Influenza A virus (A/Puerto Rico/8/1934(H1N1)) segment 1, complete sequence |
| NC_002021 | 42.10% | NC_002021.1 | A/Puerto Rico/8/1934(H1N1 | Mon Aug. 13 00:00:00 EDT 2018 | Mon Aug. 13 00:00:00 EDT 2018 | Influenza A virus (A/Puerto Rico/8/1934(H1N1)) segment 2, complete sequence |
| NC_002022 | 42.00% | NC_002022.1 | A/Puerto Rico/8/1934(H1N1 | Mon Aug. 13 00:00:00 EDT 2018 | Mon Aug. 13 00:00:00 EDT 2018 | Influenza A virus (A/Puerto Rico/8/1934(H1N1)) segment 3, complete sequence |
| NC_002017 | 41.60% | NC_002017.1 | A/Puerto Rico/8/1934(H1N1 | Mon Aug. 13 00:00:00 EDT 2018 | Mon Aug. 13 00:00:00 EDT 2018 | Influenza A virus (A/Puerto Rico/8/1934(H1N1)) segment 4, complete sequence |

TABLE 1-continued

Exemplary target sequences

| Name | % GC | Accession | Common Name | Created | Created Date | Description |
|---|---|---|---|---|---|---|
| NC_002019 | 46.40% | NC_002019.1 | A/Puerto Rico/8/1934(H1N1 | Mon Aug. 13 00:00:00 EDT 2018 | Mon Aug. 13 00:00:00 EDT 2018 | Influenza A virus (A/Puerto Rico/8/1934(H1N1)) segment 5, complete sequence |
| NC_002018 | 42.70% | NC_002018.1 | A/Puerto Rico/8/1934(H1N1 | Mon Aug. 13 00:00:00 EDT 2018 | Mon Aug. 13 00:00:00 EDT 2018 | Influenza A virus (A/Puerto Rico/8/1934(H1N1)) segment 6, complete sequence |
| NC_002016 | 47.20% | NC_002016.1 | A/Puerto Rico/8/1934(H1N1 | Mon Aug. 13 00:00:00 EDT 2018 | Mon Aug. 13 00:00:00 EDT 2018 | Influenza A virus (A/Puerto Rico/8/1934(H1N1)) segment 7, complete sequence |
| NC_002020 | 44.30% | NC_002020.1 | A/Puerto Rico/8/1934(H1N1 | Mon Aug. 13 00:00:00 EDT 2018 | Mon Aug. 13 00:00:00 EDT 2018 | Influenza A virus (A/Puerto Rico/8/1934(H1N1)) segment 8, complete sequence |
| NC_026422 | 44.90% | NC_026422.1 | A/Shanghai/02/2013(H7N9 | Mon Aug. 13 00:00:00 EDT 2018 | Mon Aug. 13 00:00:00 EDT 2018 | Influenza A virus (A/Shanghai/02/2013(H7N9)) segment 1 polymerase PB2 (PB2) gene, complete cds |
| NC_026423 | 44.20% | NC_026423.1 | A/Shanghai/02/2013(H7N9 | Mon Aug. 13 00:00:00 EDT 2018 | Mon Aug. 13 00:00:00 EDT 2018 | Influenza A virus (A/Shanghai/02/2013(H7N9)) segment 2 polymerase PB1 (PB1) and PB1-F2 protein (PB1-F2) genes, complete cds |
| NC_026424 | 44.30% | NC_026424.1 | A/Shanghai/02/2013(H7N9 | Mon Aug. 13 00:00:00 EDT 2018 | Mon Aug. 13 00:00:00 EDT 2018 | Influenza A virus (A/Shanghai/02/2013(H7N9)) segment 3 polymerase PA (PA) and PA-X protein (PA-X) genes, complete cds |
| NC_026425 | 41.80% | NC_026425.1 | A/Shanghai/02/2013(H7N9 | Mon Aug. 13 00:00:00 EDT 2018 | Mon Aug. 13 00:00:00 EDT 2018 | Influenza A virus (A/Shanghai/02/2013(H7N9)) segment 4 hemagglutinin (HA) gene, complete cds |
| NC_026426 | 46.60% | NC_026426.1 | A/Shanghai/02/2013(H7N9 | Mon Aug. 13 00:00:00 EDT 2018 | Mon Aug. 13 00:00:00 EDT 2018 | Influenza A virus (A/Shanghai/02/2013(H7N9)) segment 5 nucleocapsid protein (NP) gene, complete cds |
| NC_026429 | 43.60% | NC_026429.1 | A/Shanghai/02/2013(H7N9 | Mon Aug. 13 00:00:00 EDT 2018 | Mon Aug. 13 00:00:00 EDT 2018 | Influenza A virus (A/Shanghai/02/2013(H7N9)) segment 6 neuraminidase (NA) gene, complete cds |
| NC_026427 | 47.50% | NC_026427.1 | A/Shanghai/02/2013(H7N9 | Mon Aug. 13 00:00:00 EDT 2018 | Mon Aug. 13 00:00:00 EDT 2018 | Influenza A virus (A/Shanghai/02/2013(H7N9)) segment 7 matrix protein 2 (M2) and matrix protein 1 (M1) genes, complete cds |
| NC_026428 | 41.90% | NC_026428.1 | A/Shanghai/02/2013(H7N9 | Mon Aug. 13 00:00:00 EDT 2018 | Mon Aug. 13 00:00:00 EDT 2018 | Influenza A virus (A/Shanghai/02/2013(H7N9)) segment 8 nuclear export protein (NEP) and nonstructural protein 1 (NS1) genes, complete cds |
| NC_004908 | 42.50% | NC_004908.1 | A/Hong Kong/1073/99(H9N2 | Mon Aug. 13 00:00:00 EDT 2018 | Mon Aug. 13 00:00:00 EDT 2018 | Influenza A virus ha gene for Hemagglutinin, genomic RNA, strain A/Hong Kong/1073/99(H9N2) |
| NC_004909 | 42.60% | NC_004909.1 | A/Hong Kong/1073/99(H9N2 | Mon Aug. 13 00:00:00 EDT 2018 | Mon Aug. 13 00:00:00 EDT 2018 | Influenza A virus na gene for neuraminidase, genomic RNA, strain A/Hong Kong/1073/99(H9N2) |
| NC_004912 | 44.00% | NC_004912.1 | A/Hong Kong/1073/99(H9N2 | Mon Aug. 13 00:00:00 EDT 2018 | Mon Aug. 13 00:00:00 EDT 2018 | Influenza A virus pa gene for polymerase PA, genomic RNA, strain A/Hong Kong/1073/99(H9N2) |

TABLE 1-continued

Exemplary target sequences

| Name | % GC | Accession | Common Name | Created | Created Date | Description |
|---|---|---|---|---|---|---|
| NC_004911 | 43.50% | NC_004911.1 | A/Hong Kong/1073/99(H9N2 | Mon Aug. 13 00:00:00 EDT 2018 | Mon Aug. 13 00:00:00 EDT 2018 | Influenza A virus pb1 gene for polymerase Pb1, genomic RNA, strain A/Hong Kong/1073/99(H9N2) |
| NC_004910 | 43.20% | NC_004910.1 | A/Hong Kong/1073/99(H9N2 | Mon Aug. 13 00:00:00 EDT 2018 | Mon Aug. 13 00:00:00 EDT 2018 | Influenza A virus pb2 gene for polymerase Pb2, genomic RNA, strain A/Hong Kong/1073/99(H9N2) |
| NC_002205 | 38.50% | NC_002205.1 | B/Lee/1940 | Mon Aug. 13 00:00:00 EDT 2018 | Mon Aug. 13 00:00:00 EDT 2018 | Influenza B virus (B/Lee/1940) segment 2, complete sequence |
| NC_002206 | 39.20% | NC_002206.1 | B/Lee/1940 | Mon Aug. 13 00:00:00 EDT 2018 | Mon Aug. 13 00:00:00 EDT 2018 | Influenza B virus (B/Lee/1940) segment 3, complete sequence |
| NC_002207 | 41.80% | NC_002207.1 | B/Lee/1940 | Mon Aug. 13 00:00:00 EDT 2018 | Mon Aug. 13 00:00:00 EDT 2018 | Influenza B virus (B/Lee/1940) segment 4, complete sequence |
| NC_002208 | 42.00% | NC_002208.1 | B/Lee/1940 | Mon Aug. 13 00:00:00 EDT 2018 | Mon Aug. 13 00:00:00 EDT 2018 | Influenza B virus (B/Lee/1940) segment 5, complete sequence |
| NC_002209 | 41.60% | NC_002209.1 | B/Lee/1940 | Mon Aug. 13 00:00:00 EDT 2018 | Mon Aug. 13 00:00:00 EDT 2018 | Influenza B virus (B/Lee/1940) segment 6, complete sequence |
| NC_002210 | 38.80% | NC_002210.1 | B/Lee/1940 | Mon Aug. 13 00:00:00 EDT 2018 | Mon Aug. 13 00:00:00 EDT 2018 | Influenza B virus (B/Lee/1940) segment 7, complete sequence |
| NC_002211 | 41.30% | NC_002211.1 | B/Lee/1940 | Mon Aug. 13 00:00:00 EDT 2018 | Mon Aug. 13 00:00:00 EDT 2018 | Influenza B virus (B/Lee/1940) segment 8, complete sequence |
| NC_002204 | 39.10% | NC_002204.1 | B/Lee/1940 | Mon Aug. 13 00:00:00 EDT 2018 | Mon Aug. 13 00:00:00 EDT 2018 | Influenza B virus RNA 1, complete sequence |
| NC_006310 | 39.80% | NC_006310.2 | C/Ann Arbor/1/50 | Mon Aug. 13 00:00:00 EDT 2018 | Mon Aug. 13 00:00:00 EDT 2018 | Influenza C virus (C/Ann Arbor/1/50) HEF gene for hemagglutinin-esterase-fusion, complete cds |
| NC_006312 | 38.60% | NC_006312.2 | C/Ann Arbor/1/50 | Mon Aug. 13 00:00:00 EDT 2018 | Mon Aug. 13 00:00:00 EDT 2018 | Influenza C virus (C/Ann Arbor/1/50) M1, CM2 genes for matrix protein, CM2 protein, complete cds |
| NC_006309 | 35.60% | NC_006309.2 | C/Ann Arbor/1/50 | Mon Aug. 13 00:00:00 EDT 2018 | Mon Aug. 13 00:00:00 EDT 2018 | Influenza C virus (C/Ann Arbor/1/50) P3 gene for polymerase 3, complete cds |
| NC_006308 | 35.60% | NC_006308.2 | C/Ann Arbor/1/50 | Mon Aug. 13 00:00:00 EDT 2018 | Mon Aug. 13 00:00:00 EDT 2018 | Influenza C virus (C/Ann Arbor/1/50) PB1 gene for polymerase 1, complete cds |
| NC_006307 | 36.80% | NC_006307.2 | C/Ann Arbor/1/50 | Mon Aug. 13 00:00:00 EDT 2018 | Mon Aug. 13 00:00:00 EDT 2018 | Influenza C virus (C/Ann Arbor/1/50) PB2 gene for polymerase 2, complete cds |
| NC_006311 | 38.40% | NC_006311.1 | C/Ann Arbor/1/50 | Mon Aug. 13 00:00:00 EDT 2018 | Mon Aug. 13 00:00:00 EDT 2018 | Influenza C virus (C/Ann Arbor/1/50) segment 5, complete sequence |
| NC_006306 | 37.50% | NC_006306.2 | C/Ann Arbor/1/50 | Mon Aug. 13 00:00:00 EDT 2018 | Mon Aug. 13 00:00:00 EDT 2018 | Influenza C virus (C/Ann Arbor/1/50) segment 7, complete sequence |
| NZ_LT591897 | 52.10% | NZ_LT591897.1 | | Sat Apr. 04 00:00:00 EDT 2020 | Sat Apr. 04 00:00:00 EDT 2020 | Neisseria gonorrhoeae strain WHO F chromosome 1 |
| NC_001803 | 33.20% | NC_001803.1 | | Mon Aug. 13 00:00:00 EDT 2018 | Mon Aug. 13 00:00:00 EDT 2018 | Respiratory syncytial virus, complete genome |
| NC_004718 | 40.80% | NC_004718.3 | | Mon Aug. 13 00:00:00 EDT 2018 | Mon Aug. 13 00:00:00 EDT 2018 | SARS coronavirus, complete genome |
| NZ_LN831034 | 38.50% | NZ_LN831034.1 | | Thu Apr. 02 00:00:00 EDT 2020 | Thu Apr. 02 00:00:00 EDT 2020 | Streptococcus pyogenes strain NCTC8198 chromosome 1 |

NASBA

In certain example embodiments, the RNA or DNA amplification is NASBA, which is initiated with reverse transcription of target RNA by a sequence-specific reverse primer to create a RNA/DNA duplex. RNase H is then used to degrade the RNA template, allowing a forward primer containing a promoter, such as the T7 promoter, to bind and initiate elongation of the complementary strand, generating a double-stranded DNA product. The RNA polymerase promoter-mediated transcription of the DNA template then creates copies of the target RNA sequence. Importantly, each of the new target RNAs can be detected by the guide RNAs thus further enhancing the sensitivity of the assay. Binding of the target RNAs by the guide RNAs then leads to activation of the CRISPR effector protein and the methods proceed as outlined above. The NASBA reaction has the additional advantage of being able to proceed under moderate isothermal conditions, for example at approximately 41° C., making it suitable for systems and devices deployed for early and direct detection in the field and far from clinical laboratories.

RPA

In certain other example embodiments, a recombinase polymerase amplification (RPA) reaction may be used to amplify the target nucleic acids. RPA reactions employ recombinases which are capable of pairing sequence-specific primers with homologous sequence in duplex DNA. If target DNA is present, DNA amplification is initiated and no other sample manipulation such as thermal cycling or chemical melting is required. The entire RPA amplification system is stable as a dried formulation and can be transported safely without refrigeration. RPA reactions may also be carried out at isothermal temperatures with an optimum reaction temperature of 37-42° C. The sequence specific primers are designed to amplify a sequence comprising the target nucleic acid sequence to be detected. In certain example embodiments, a RNA polymerase promoter, such as a T7 promoter, is added to one of the primers. This results in an amplified double-stranded DNA product comprising the target sequence and a RNA polymerase promoter. After, or during, the RPA reaction, a RNA polymerase is added that will produce RNA from the double-stranded DNA templates. The amplified target RNA can then in turn be detected by the CRISPR effector system. In this way target DNA can be detected using the embodiments disclosed herein. RPA reactions can also be used to amplify target RNA. The target RNA is first converted to cDNA using a reverse transcriptase, followed by second strand DNA synthesis, at which point the RPA reaction proceeds as outlined above.

Transposase Based Amplification

Embodiments disclosed herein provide systems and methods for isothermal amplification of target nucleic acid sequences by contacting oligonucleotides containing the target nucleic acid sequence with a transposon complex. The oligonucleotides may be single stranded or double stranded RNA, DNA, or RNA/DNA hybrid oligonucleotides. The transposon complex comprises a transposase and a transposon sequence comprising one or more RNA polymerase promoters. The transposase facilitates insertion of the one or more RNA polymerase promoters into the oligonucleotide. A RNA polymerase promoter can then transcribe the target nucleic acid sequence from the inserted one or more RNA polymerase promoters. One advantage of this system is that there is no need to heat or melt double-stranded DNA templates, since RNA polymerase polymerases require a double-stranded template. Such isothermal amplification is fast and simple, obviating the need for complicated and expensive instrumentation for denaturation and cooling. In certain example embodiment the RNA polymerase promoter is a native of modified T7 RNA promoter.

The term "transposon", as used herein, refers to a nucleic acid segment, which is recognized by a transposase or an integrase enzyme and which is an essential component of a functional nucleic acid-protein complex (i.e. a transposome) capable of transposition. The term "transposase" as used herein refers to an enzyme, which is a component of a functional nucleic acid-protein complex capable of transposition and which is mediating transposition. The term "transposase" also refers to integrases from retrotransposons or of retroviral origin. Transposon complexes form between a transposase enzyme and a fragment of double stranded DNA that contains a specific binding sequence for the enzyme, termed "transposon end". The sequence of the transposon binding site can be modified with other bases, at certain positions, without affecting the ability for transposon complex to form a stable structure that can efficiently transpose into target DNA.

In embodiments provided herein, the transposon complex may comprise a transposase and a transposon sequence comprising one or more RNA polymerase promoters. The term "promoter" refers to a region of DNA involved in binding the RNA polymerase to initiate transcription. In specific embodiments, the RNA polymerase promoter may be a T7 RNA polymerase promoter. The T7 RNA promoter may be inserted into the double-stranded polynucleotide using the transposase. In some embodiments, insertion of the T7 RNA polymerase promoter into the oligonucleotide may be random.

The frequency of transposition is very low for most transposons, which use complex mechanisms to limit activity. Tn5 transposase, for example, utilizes a DNA binding sequence that is suboptimal and the C-terminus of the transposase interferes with DNA binding. Mechanisms involved in Tn5 transposition have been carefully characterized by Reznikoff and colleagues. Tn5 transposes by a cut-and-paste mechanism. The transposon has two pairs of 19 bp elements that are utilized by the transposase: outside elements (OE) and inside elements (IE). One transposase monomer binds to each of the two elements that are utilized. After a monomer is bound to each end of the transposon, the two monomers dimerize, forming a synapse. Vectors with donor backbones of at least 200 bp, but less than 1000 bp, are most functional for transposition in bacteria. Transposon cleavage occurs by trans catalysis and only when monomers bound to each DNA end are in a synaptic complex. Tn5 transposes with a relaxed target site selection and can therefore insert into target DNA with little to no target sequence specificity.

The natural downregulation of Tn5 transposition can be overcome by selection of a hyperactive transposase and by optimizing the transposase-binding elements [York et al. 1998]. A mosaic element (ME), made by modification of three bases of the wild type OE, led to a 50-fold increase in transposition events in bacteria as well as cell-free systems. The combined effect of the optimized ME and hyperactive mutant transposase is estimated to result in a 100-fold increase in transposition activity. Goryshin et al showed that preformed Tn5 transposition complexes could be functionally introduced into bacterial or yeast by electroporation [Goryshin et al. 2000]. Linearization of the DNA, to have inverted repeats precisely positioned at both ends of the transposon, allowed Goryshin and coworkers to bypass the cutting step of transposition thus enhancing transposition efficiency.

In some embodiments, the transposase may be used to tagment the oligonucleotide sequence comprising the target sequence. The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

In some embodiments, the transposase may be a Tn5 transposase. In some embodiments, the transposase may be a variant of a Tn5 transposase, or an engineered transposase. Transposases may be engineered using any method known in the art. The engineered transposase may be optimized to function at a temperature ranging from 30° C. to 45° C., 35° C. to 40° C. or any temperature in between. The engineered transposase may be optimized to release from the oligonucleotide at a faster rate compared to a wild type transposase.

In some embodiments, the transposase may be a Tn5 transposase, a Mu transposase, or a Tn7 transposase. Transposition efficiency in vitro may vary depending on the transposon system used. Generally, Tn5 and Mu transposases effect higher levels of transposition efficiency. In some embodiments, insertion may be random. In some embodiments, insertion may occur in GC rich regions of the target sequence.

In some embodiments, the transposon sequence may comprise two 19 base pair Mosaic End (ME) Tn5 transposase recognition sequences. Tn5 transposases will generally transpose any DNA sequence contained between such short 19 base pair ME Tn5 transposase recognition sequences.

In some embodiment, use of a transposase allows for separation of a double-stranded polynucleotide in the absence of heat or melting. Embodiments can be as described in PCT/US2019/039195, entitled CRISPR/Cas and Transposase Based Amplification Compositions, Systems and Methods, incorporated herein by reference.

Nickase Dependent Amplification

In an embodiment of the invention may comprise nickase-based amplification. The nicking enzyme may be a CRISPR protein. Accordingly, the introduction of nicks into dsDNA can be programmable and sequence-specific. In an embodiment of the invention, two guides can be designed to target opposite strands of a dsDNA target. According to the invention, the nickase can be Cpf1, C2c1, Cas9 or any ortholog or CRISPR protein that cleaves or is engineered to cleave a single strand of a DNA duplex. The nicked strands may then be extended by a polymerase. In an embodiment, the locations of the nicks are selected such that extension of the strands by a polymerase is towards the central portion of the target duplex DNA between the nick sites. In certain embodiments, primers are included in the reaction capable of hybridizing to the extended strands followed by further polymerase extension of the primers to regenerate two dsDNA pieces: a first dsDNA that includes the first strand Cpf1 guide site or both the first and second strand Cpf1 guide sites, and a second dsDNA that includes the second strand Cpf1 guide site or both the first and second strand Cprf guide sites. These pieces continue to be nicked and extended in a cyclic reaction that exponentially amplifies the region of the target between nicking sites.

The amplification can be isothermal and selected for temperature. In one embodiment, the amplification proceeds rapidly at 37 degrees. In other embodiments, the temperature of the isothermal amplification may be chosen by selecting a polymerase (e.g. Bsu, Bst, Phi29, klenow fragment etc.). operable at a different temperature.

Thus, whereas nicking isothermal amplification techniques use nicking enzymes with fixed sequence preference (e.g. in nicking enzyme amplification reaction or NEAR), which requires denaturing of the original dsDNA target to allow annealing and extension of primers that add the nicking substrate to the ends of the target, use of a CRISPR nickase wherein the nicking sites can be programed via guide RNAs means that no denaturing step is necessary, enabling the entire reaction to be truly isothermal. This also simplifies the reaction because these primers that add the nicking substrate are different than the primers that are used later in the reaction, meaning that NEAR requires two primer sets (i.e. 4 primers) while Cpf1 nicking amplification only requires one primer set (i.e. two primers). This makes nicking Cpf1 amplification much simpler and easier to operate without complicated instrumentation to perform the denaturation and then cooling to the isothermal temperature.

In an aspect, the isothermal amplification reagents may be utilized with a thermostable CRISPR-Cas protein. The combination of thermostable protein and isothermal amplification reagents may be utilized to further improve reaction times for detection and diagnostics.

Accordingly, in certain example embodiments the systems disclosed herein may include amplification reagents. Different components or reagents useful for amplification of nucleic acids are described herein. For example, an amplification reagent as described herein may include a buffer, such as a Tris buffer. A Tris buffer may be used at any concentration appropriate for the desired application or use, for example including, but not limited to, a concentration of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 25 mM, 50 mM, 75 mM, 1 M, or the like. One of skill in the art will be able to determine an appropriate concentration of a buffer such as Tris for use with the present invention.

A salt, such as magnesium chloride ($MgCl_2$), potassium chloride (KCl), or sodium chloride (NaCl), may be included in an amplification reaction, such as PCR, in order to improve the amplification of nucleic acid fragments. Although the salt concentration will depend on the particular reaction and application, in some embodiments, nucleic acid fragments of a particular size may produce optimum results at particular salt concentrations. Larger products may require altered salt concentrations, typically lower salt, in order to produce desired results, while amplification of smaller products may produce better results at higher salt concentrations. One of skill in the art will understand that the presence and/or concentration of a salt, along with alteration of salt concentrations, may alter the stringency of a biological or chemical reaction, and therefore any salt may be used that provides the appropriate conditions for a reaction of the present invention and as described herein.

Other components of a biological or chemical reaction may include a cell lysis component in order to break open or lyse a cell for analysis of the materials therein. A cell lysis component may include, but is not limited to, a detergent, a salt as described above, such as NaCl, KCl, ammonium sulfate [$(NH_4)_2SO_4$], or others. Detergents that may be appropriate for the invention may include Triton X-100, sodium dodecyl sulfate (SDS), CHAPS (3-[(3-cholamidopropyl)dimethylammonio]-1-propanesulfonate), ethyl trimethyl ammonium bromide, nonyl phenoxypolyethoxylethanol (NP-40). Concentrations of detergents may depend on the particular application, and may be specific to the reaction in some cases. Amplification reactions may include dNTPs and nucleic acid primers used at any concentration appropriate for the invention, such as including, but not limited to, a concentration of 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, or the like. Likewise, a polymerase useful in accordance with the invention may be any specific or general polymerase known in the art and useful or the invention, including Taq polymerase, Q5 polymerase, or the like.

In some embodiments, amplification reagents as described herein may be appropriate for use in hot-start amplification. Hot start amplification may be beneficial in some embodiments to reduce or eliminate dimerization of adaptor molecules or oligos, or to otherwise prevent unwanted amplification products or artifacts and obtain optimum amplification of the desired product. Many components described herein for use in amplification may also be used in hot-start amplification. In some embodiments, reagents or components appropriate for use with hot-start amplification may be used in place of one or more of the composition components as appropriate. For example, a polymerase or other reagent may be used that exhibits a desired activity at a particular temperature or other reaction condition. In some embodiments, reagents may be used that are designed or optimized for use in hot-start amplification, for example, a polymerase may be activated after transposition or after reaching a particular temperature. Such polymerases may be antibody-based or aptamer-based. Polymerases as described herein are known in the art. Examples of such reagents may include, but are not limited to, hot-start polymerases, hot-start dNTPs, and photo-caged dNTPs. Such reagents are known and available in the art. One of skill in the art will be able to determine the optimum temperatures as appropriate for individual reagents.

Amplification of nucleic acids may be performed using specific thermal cycle machinery or equipment, and may be performed in single reactions or in bulk, such that any desired number of reactions may be performed simultaneously. In some embodiments, amplification may be performed using microfluidic or robotic devices, or may be performed using manual alteration in temperatures to achieve the desired amplification. In some embodiments, optimization may be performed to obtain the optimum reactions conditions for the particular application or materials. One of skill in the art will understand and be able to optimize reaction conditions to obtain sufficient amplification.

In certain embodiments, detection of DNA with the methods or systems of the invention requires transcription of the (amplified) DNA into RNA prior to detection.

It will be evident that detection methods of the invention can involve nucleic acid amplification and detection procedures in various combinations. The nucleic acid to be detected can be any naturally occurring or synthetic nucleic acid, including but not limited to DNA and RNA, which may be amplified by any suitable method to provide an intermediate product that can be detected. Detection of the intermediate product can be by any suitable method including but not limited to binding and activation of a CRISPR protein which produces a detectable signal moiety by direct or collateral activity.

Helicase-Dependent Amplification

In helicase-dependent amplification, a helicase enzyme is used to unwind a double stranded nucleic acid to generate templates for primer hybridization and subsequent primer-extension. This process utilizes two oligonucleotide primers, each hybridizing to the 3'-end of either the sense strand containing the target sequence or the anti-sense strand containing the reverse-complementary target sequence. The HDA reaction is a general method for helicase-dependent nucleic acid amplification.

In combining this method with a CRISPR-SHERLOCK system, the target nucleic acid may be amplified by opening R-loops of the target nucleic acid using first and second CRISPR/Cas complexes. The first and second strand of the target nucleic acid may thus be unwound using a helicase, allowing primers and polymerase to bind and extend the DNA under isothermal conditions.

The term "helicase" refers here to any enzyme capable of unwinding a double stranded nucleic acid enzymatically. For example, helicases are enzymes that are found in all organisms and in all processes that involve nucleic acid such as replication, recombination, repair, transcription, translation and RNA splicing. (Kornberg and Baker, DNA Replication, W. H. Freeman and Company ($2^{nd}$ ed. (1992)), especially chapter 11). Any helicase that translocates along DNA or RNA in a 5' to 3' direction or in the opposite 3' to 5' direction may be used in present embodiments of the invention. This includes helicases obtained from prokaryotes, viruses, archaea, and eukaryotes or recombinant forms of naturally occurring enzymes as well as analogues or derivatives having the specified activity. Examples of naturally occurring DNA helicases, described by Kornberg and Baker in chapter 11 of their book, DNA Replication, W. H. Freeman and Company ($2^{nd}$ ed. (1992)), include *E. coli* helicase I, II, III, & IV, Rep, DnaB, PriA, PcrA, T4 Gp41helicase, T4 Dda helicase, T7 Gp4 helicases, SV40 Large T antigen, yeast RAD. Additional helicases that may be useful in HDA include RecQ helicase (Harmon and Kowalczykowski, *J. Biol. Chem.* 276:232-243 (2001)), thermostable UvrD helicases from *T. tengcongensis* (disclosed in this invention, Example XII) and *T. thermophilus* (Collins and McCarthy, Extremophiles. 7:35-41. (2003)), thermostable DnaB helicase from *T. aquaticus* (Kaplan and Steitz, *J. Biol. Chem.* 274:6889-6897 (1999)), and MCM helicase from archaeal and eukaryotic organisms ((Grainge et al., *Nucleic Acids Res.* 31:4888-4898 (2003)).

A traditional definition of a helicase is an enzyme that catalyzes the reaction of separating/unzipping/unwinding the helical structure of nucleic acid duplexes (DNA, RNA or hybrids) into single-stranded components, using nucleoside triphosphate (NTP) hydrolysis as the energy source (such as ATP). However, it should be noted that not all helicases fit this definition anymore. A more general definition is that they are motor proteins that move along the single-stranded or double stranded nucleic acids (usually in a certain direction, 3' to 5' or 5 to 3, or both), i.e. translocases, that can or cannot unwind the duplexed nucleic acid encountered. In addition, some helicases simply bind and "melt" the duplexed nucleic acid structure without an apparent translocase activity.

Helicases exist in all living organisms and function in all aspects of nucleic acid metabolism. Helicases are classified based on the amino acid sequences, directionality, oligomerization state and nucleic-acid type and structure preferences. The most common classification method was developed based on the presence of certain amino acid sequences, called motifs. According to this classification helicases are divided into 6 super families: SF1, SF2, SF3, SF4, SF5 and SF6. SF1 and SF2 helicases do not form a ring structure around the nucleic acid, whereas SF3 to SF6 do. Superfamily classification is not dependent on the classical taxonomy.

DNA helicases are responsible for catalyzing the unwinding of double-stranded DNA (dsDNA) molecules to their respective single-stranded nucleic acid (ssDNA) forms. Although structural and biochemical studies have shown how various helicases can translocate on ssDNA directionally, consuming one ATP per nucleotide, the mechanism of nucleic acid unwinding and how the unwinding activity is regulated remains unclear and controversial (T. M. Lohman, E. J. Tomko, C. G. Wu, "Non-hexameric DNA helicases and translocases: mechanisms and regulation," Nat Rev Mol Cell Biol 9:391-401 (2008)). Since helicases can potentially unwind all nucleic acids encountered, understanding how their unwinding activities are regulated can lead to harnessing helicase functions for biotechnology applications.

The term "HDA" refers to Helicase Dependent Amplification, which is an in vitro method for amplifying nucleic acids by using a helicase preparation for unwinding a double stranded nucleic acid to generate templates for primer hybridization and subsequent primer-extension. This process utilizes two oligonucleotide primers, each hybridizing to the 3'-end of either the sense strand containing the target sequence or the anti-sense strand containing the reverse-complementary target sequence. The HDA reaction is a general method for helicase-dependent nucleic acid amplification.

The invention comprises use of any suitable helicase known in the art. These include, but are not necessarily limited to, UvrD helicase, CRISPR-Cas3 helicase, *E. coli* helicase I, *E. coli* helicase II, *E. coli* helicase III, *E. coli* helicase IV, Rep helicase, DnaB helicase, PriA helicase, PcrA helicase, T4 Gp41 helicase, T4 Dda helicase, SV40 Large T antigen, yeast RAD helicase, RecD helicase, RecQ helicase, thermostable *T. tengcongensis* UvrD helicase, thermostable *T. thermophilus* UvrD helicase, thermostable *T. aquaticus* DnaB helicase, Dda helicase, papilloma virus E1 helicase, archaeal MCM helicase, eukaryotic MCM helicase, and T7 Gp4 helicase.

In particularly preferred embodiments, the helicase comprises a super mutation. In particular embodiments, Although the *E. coli* mutation has been described, the mutations were generated by sequence alignment (e.g. D409A/D410A for TteUvrd) and result in thermophilic enzymes working at lower temperatures like 37° C., which is advantageous for amplification methods and systems described herein. In some embodiments, the super mutations is an aspartate to alanine mutation, with position based on sequence alignment. In some embodiments, the super mutant helicase is selected from WP 003870487.1 *Thermoanaerobacter ethanolicus* 403/404, WP_049660019.1 *Bacillus* sp. FJAT-27231 407/408, WP_034654680.1 *Bacillus megaterium* 415/416, WP_095390358.1 *Bacillus simplex* 407/408, and WP_055343022.1 *Paeniclostridium sordellii* 402/403.

Example CRISPR-Cas Systems

In certain embodiments, the single lysis reaction with isothermal amplification reagents can be optionally utilized with CRISPR-Cas systems. CRISPR Cas for use in the embodiments disclosed herein may comprise a Type V Cas protein, a Type VI Cas protein, or a combination thereof. In certain embodiments, the Cas proteins are thermostable Cas proteins. Example thermostable Cas proteins can be selected from Table 2A or Table 2B, comprising Cas12 thermostable Cas proteins; other representative Cas12 and Cas13 proteins can be identified from Cas systems isolated from organisms that inhabit similar microenvironments. In certain example embodiments, the Cas is AapCas12b. In other example embodiments, the Cas is BrCas12b. In an aspect, two or more CRISPR effector systems are provided which may be RNA-targeting effector proteins, DNA-targeting effector proteins, or a combination thereof. The RNA-targeting effector proteins may be a Type VI Cas protein, such as Cas13 protein, including Cas13b, Cas13c, or Cas13d. The DNA-targeting effector protein may be a Type V Cas protein, such as Cas12a (Cpf1), Cas12b (C2c2), or Cas12c (C2c3).

Thermostable Proteins

In certain example embodiments, the protein selected may be more thermostable at higher temperatures. Exemplary proteins may comprise any Cas protein with collateral effect when used with particular methodologies disclosed herein. In an aspect, the Cas protein is a thermostable protein. The thermostable Cas protein may be a Type V or a Type VI protein, for example, a Cas12 or Cas13 protein. In embodiments, the thermostable protein, upon activation, comprises collateral cleavage. A thermostable protein as used herein comprises a protein that retains catalytic activity at a temperature at or above 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C. In certain example embodiments, the protein is thermostable at or above 55° C.

Methods for identification of thermostable proteins are detailed herein, and may comprise identifying Cas proteins from thermophilic bacterial species. Upon identification of a particular Cas protein from a species, Cas proteins form similar species may be identified.

In certain embodiments, the thermostable CRISPR-Cas protein is a Cas 12 protein from Table 2A or 2B, or at least 80% identity to a polypeptide from Table 2A or 2B, at least 90%, 85%, 90%, 95%, 96%, 97%, 98%, 99% identify to one of SEQ ID Nos: 61644-61990.

In an embodiment, the thermostable Cas protein is a Cas12 protein selected from a protein in Table 2A, more preferably from Table 2B.

TABLE 2A

Cas 12 proteins
Cas 12 proteins (65C) Ga0209381_1004188 | GENOME_ACCESSION
(66C)_a0212093_1 | Ga0212093_1006934 | GENOME_ACCESSION
3300022548 | Ga0212092_1000015 | GENOME_ACCESSION
a0117933_1071983 | Ga0117933_1071983 | GENOME_ACCESSION
a0212092_1024084 | Ga0212092 _024084 | GENOME_ACCESSION
a0212093_1001507 | Ga0212093_1001507 | GENOME_ACCESSION
a0212120_1000874 | Ga0212120_1000874 | GENOME_ACCESSION
a0212125_1004414 | Ga0212125_1004414 | GENOME_ACCESSION
a0212125_1006348 | Ga0212125_1006348 | GENOME_ACCESSION
ABHJ01000011.1_o | Hydrogenivirga sp. 128-5-R1-1 1102927038514
AGIV01000002.1_o | Rhodothermus marinus SG0.5JP17-171 Rhoma_Contig848_C
BDSM01000053.1_o | Microcystis sp. 0824 DNA
BFBB01000008.1_o | Leptospira sp. YH101 DNA
BHZK01000001.1_o | Parageobacillus thermoglucosidasius TG4 DNA TABLE 2A-continued

| Cas 12 proteins |
| --- |
| Cas 12 proteins |

CP000240.1_organ | Synechococcus sp. JA-2-3B'a(2-13)
CP001229.1_organ | Sulfurihydrogenibium azorense Az-Fu1
CP011339.1_organ | Microcystis panniformis FACHB-1757
CP020382.1_organ | Rhodothermaceae bacterium RA chromosome
CP040694.1 organ | Elizabethkingia sp. JS20170427COW chromosome
DCUT01000059.1_o | TPA asm
DHGN01000237.1_o | TPA_asm
FQUK01000003.1_o | Thermomonas hydrothermalis strain DSM 14834 genome assembly
Ga0063162_1014580 | GENOME_ACCESSION
Ga0065719_107896 | GENOME_ACCESSION
Ga0065719_116807 | GENOME_ACCESSION
Ga0067045_1002454 | GENOME_ACCESSION
Ga0067045_1004962 | GENOME_ACCESSION]
Ga0068669_1023596 | GENOME_ACCESSION
Ga0068707_1002163 | GENOME_ACCESSION
Ga0068707_1009867 | GENOME_ACCESSION
Ga0068707_1024093 | GENOME_ACCESSION
Ga0071330_1110381 | GENOME_ACCESSION
Ga0072682_101461 | GENOME_ACCESSION
Ga0073928_10004924 | GENOME_ACCESSION
Ga0073932_1022770 | GENOME_ACCESSION
Ga0079044_1002244 | GENOME_ACCESSION
Ga0079639_1009487 | GENOME_ACCESSION
Ga0099914_10727 | GENOME_ACCESSION
Ga0101790_149349 | GENOME_ACCESSION
Ga0102924_1013089 | GENOME_ACCESSION
Ga0103818_10095 | GENOME_ACCESSION
Ga0 105154_1006902 | GENOME_ACCESSION
Ga0105158_1004615 | GENOME_ACCESSION
Ga0114945_10008792 | GENOME_ACCESSION
Ga0116141_10037070 | GENOME_ACCESSION
Ga0116143_10029534 | GENOME_ACCESSION
Ga0116146_1004071 | GENOME_ACCESSION
Ga0116159_1001590 | GENOME_ACCESSION
Ga0116160_1008286 | GENOME_ACCESSION
Ga0116161_1004008 | GENOME_ACCESSION
Ga0116167_1006930 | GENOME_ACCESSION
Ga0116184_10002336 | GENOME_ACCESSION
Ga0116185_1015740 | GENOME_ACCESSION
Ga0116188_1022712 | GENOME_ACCESSION
Ga0116210_1003377 | GENOME_ACCESSION
Ga0123519_10000481 | GENOME_ACCESSION
Ga0123519_10002165 | GENOME_ACCESSION
Ga0123519_10002912 | GENOME_ACCESSION
Ga0123519_10003344 | GENOME_ACCESSION
Ga0123519_10003852 | GENOME_ACCESSION
Ga0123519_10021143 | GENOME_ACCESSION
Ga0123519_10027137 | GENOME_ACCESSION
Ga0123519_10057643 | GENOME_ACCESSION
Ga0123519_10064432 | GENOME_ACCESSION
Ga0124943_1106748 | GENOME_ACCESSION
Ga0124945_1030784 | GENOME_ACCESSION
Ga0133944_1001807 | GENOME_ACCESSION
Ga0134095_1000962 | GENOME_ACCESSION
Ga0137716_10003017 | GENOME_ACCESSION
Ga0137716_10003038 | GENOME_ACCESSION
Ga0137716_10003531 | GENOME_ACCESSION
Ga0137716_10006890 | GENOME_ACCESSION
Ga0137716_10009026 | GENOME_ACCESSION
Ga0137716_10009341 | GENOME_ACCESSION
Ga0137716_10027208 | GENOME_ACCESSION
Ga0137716_10032400 | GENOME_ACCESSION
Ga0137716_10033855 | GENOME_ACCESSION
Ga0137716_10038387 | GENOME_ACCESSION
Ga0137716_10042212 | GENOME_ACCESSION
Ga0137716_10061480 | GENOME_ACCESSION
Ga0172363_10016551 | GENOME_ACCESSION
Ga0172365_10006450 | GENOME_ACCESSION
Ga0172382_10012866 | GENOME_ACCESSION
Ga0180300_10000403 | GENOME_ACCESSION
Ga0180301_10011215 | GENOME_ACCESSION
Ga0180435_10008691 | GENOME_ACCESSION
Ga0180446_1198 | GENOME_ACCESSION
Ga0181613_1004254 | GENOME_ACCESSION
Ga0181613_1005053 | GENOME_ACCESSION
Ga0181858_1004277 | GENOME_ACCESSION
Ga0182014_10001887 | GENOME_ACCESSION TABLE 2A-continued Cas 12 proteins
Cas 12 proteins Ga0186994_110 | GENOME_ACCESSION
Ga0187028_105 | GENOME_ACCESSION
Ga0187073_104 | GENOME_ACCESSION
Ga0187107_1033 | GENOME_ACCESSION
Ga0187121_108 | GENOME_ACCESSION
Ga0187143_105 | GENOME_ACCESSION
Ga0187864_10009485 | GENOME_ACCESSION
Ga0190309_1003062 | GENOME_ACCESSION
Ga0190334_1000016 | GENOME_ACCESSION
Ga0190361_1000443 | GENOME_ACCESSION
Ga0190361_1001609 | GENOME_ACCESSION
Ga0190361_1003780 | GENOME_ACCESSION 27
Ga0190361_1003780 | GENOME_ACCESSION 31
Ga0190363_1000125 | GENOME_ACCESSION
Ga0194111_10067953 | GENOME_ACCESSION
Ga0207429_10023 | GENOME_ACCESSION
Ga0207433_10006213 | GENOME_ACCESSION
Ga0207433_10011113 | GENOME_ACCESSION
Ga0207433_10012523 | GENOME_ACCESSION
Ga0207433_10020534 | GENOME_ACCESSION
Ga0207433_10021674 | GENOME_ACCESSION
Ga0207433_10022806 | GENOME_ACCESSION
Ga0207433_10030792 | GENOME_ACCESSION
Ga0207433_10045901 | GENOME_ACCESSION
Ga0207433_10075234 | GENOME_ACCESSION
Ga0207433_10075916 | GENOME_ACCESSION
Ga0207433_10082276 | GENOME_ACCESSION
Ga0207747_1007959 | GENOME_ACCESSION
Ga0207868_1000002 | GENOME_ACCESSION
Ga0208151_102415 | GENOME_ACCESSION
Ga0208195_1004385 | GENOME_ACCESSION
Ga0208357_1002034 | GENOME_ACCESSION
Ga0208429_100128 | GENOME_ACCESSION
Ga0208429_100584 | GENOME_ACCESSION
Ga0208429_100770 | GENOME_ACCESSION
Ga0208461_1008711 | GENOME_ACCESSION
Ga0208609_100002 | GENOME_ACCESSION
Ga0208683_103187 | GENOME_ACCESSION
Ga0208683_103849 | GENOME_ACCESSION
Ga0208683_104403 | GENOME_ACCESSION
Ga0208940_1001448 | GENOME_ACCESSION
Ga0209012_1000842 | GENOME_ACCESSION
Ga0209012_1001252 | GENOME_ACCESSION
Ga0209012_1015334 | GENOME_ACCESSION
Ga0209018_1000172 | GENOME_ACCESSION
Ga0209101_1000507 | GENOME_ACCESSION
Ga0209101_1006392 | GENOME_ACCESSION
Ga0209102_1000334 | GENOME_ACCESSION
Ga0209102_1003688 | GENOME_ACCESSION
Ga0209143_1000788 | GENOME_ACCESSION
Ga0209143_1002248 | GENOME_ACCESSION
Ga0209143_1006289 | GENOME_ACCESSION
Ga0209162_1014546 | GENOME_ACCESSION
Ga0209171_10000726 | GENOME_ACCESSION
Ga0209172_10015399 | GENOME_ACCESSION
Ga0209201_1007464 | GENOME_ACCESSION
Ga0209207_1001084 | GENOME_ACCESSION
Ga0209207_1006579 | GENOME_ACCESSION
Ga0209224_1000001 | GENOME_ACCESSION
Ga0209225_1002268 | GENOME_ACCESSION
Ga0209399_10016114 | GENOME_ACCESSION
Ga0209410_1010848 | GENOME_ACCESSION
Ga0209467_1000554 | GENOME_ACCESSION
Ga0209507_1000982 | GENOME_ACCESSION
Ga0209513_1002134 | GENOME_ACCESSION
Ga0209542_10001012 | GENOME_ACCESSION
Ga0209542_10007289 | GENOME_ACCESSION
Ga0209669_100016 | GENOME_ACCESSION
Ga0209669_101200 | GENOME_ACCESSION
Ga0209750_1000252 | GENOME_ACCESSION
Ga0209827_10659006 | GENOME_ACCESSION
Ga0209980_10011112 | GENOME_ACCESSION
Ga0210049_1040060 | GENOME_ACCESSION
Ga0210051_1028938 | GENOME_ACCESSION
Ga0210057_1032582 | GENOME_ACCESSION
Ga0214474_1011027 | GENOME_ACCESSION
Ga0255343_1026926 | GENOME_ACCESSION TABLE 2A-continued

| Cas 12 proteins |
| --- |
| Cas 12 proteins |

| | |
|---|---|
| Ga0255346_1002844 \| GENOME_ACCESSION | |
| Ga0255355_1000451 \| GENOME_ACCESSION | |
| Ga0255811_11272827 \| GENOME_ACCESSION | |
| Ga0255812_10127107 \| GENOME_ACCESSION | |
| Ga0272445_1000517 \| GENOME_ACCESSION | |
| Ga0272446_1000057 \| GENOME_ACCESSION | |
| Ga0272446_1000164 \| GENOME_ACCESSION | |
| Ga0272446_1001728 \| GENOME_ACCESSION | 137 |
| Ga0272446_1001728 \| GENOME_ACCESSION | 249 |
| Ga0272446_1001929 \| GENOME_ACCESSION | |
| Ga0272446_1017314 \| GENOME_ACCESSION | |
| Ga0272447_1003507 \| GENOME_ACCESSION | |
| Ga0272448_1000001 \| GENOME_ACCESSION | |
| Ga0272448_1000002 \| GENOME_ACCESSION | |
| Ga0272448_1000009 \| GENOME_ACCESSION | |
| Ga0272448_1000011 \| GENOME_ACCESSION | |
| Ga0272448_1000062 \| GENOME_ACCESSION | |
| Ga0272448_1000167 \| GENOME_ACCESSION | |
| Ga0272448_1002516 \| GENOME_ACCESSION | |
| Ga0272448_1011735 \| GENOME_ACCESSION | |
| Ga0272448_1059621 \| GENOME_ACCESSION | |
| Ga0272448_1067731 \| GENOME_ACCESSION | |
| Ga0272449_1002236 \| GENOME_ACCESSION | |
| Ga0272449_1004365 \| GENOME_ACCESSION | |
| Ga0272449_1006528 \| GENOME_ACCESSION | |
| Ga0272449_1019852 \| GENOME_ACCESSION | |
| Ga0302046_10000852 \| GENOME_ACCESSION | |
| Ga0302192_10026063 \| GENOME_ACCESSION | |
| Ga0302246_1000265 \| GENOME_ACCESSION | |
| Ga0302251_1001844 \| GENOME_ACCESSION | |
| Ga0302253_1002416 \| GENOME_ACCESSION | |
| Ga0307340_100872 \| GENOME_ACCESSION | |
| Ga0308310_1004946 \| GENOME_ACCESSION | |
| Ga0308310_1013800 \| GENOME_ACCESSION | |
| Ga0308411_10001123 \| GENOME_ACCESSION | |
| Ga0308411_10021369 \| GENOME_ACCESSION | |
| Ga0308414_1002480 \| GENOME_ACCESSION | |
| Ga0308414_1007395 \| GENOME_ACCESSION | |
| Ga0308414_1018540 \| GENOME_ACCESSION | |
| Ga0308415_1006042 \| GENOME_ACCESSION | |
| Ga0308419_1006240 \| GENOME_ACCESSION | |
| Ga0308419_1011938 \| GENOME_ACCESSION | |
| Ga0310136_000087 \| GENOME_ACCESSION | |
| Ga0310138_009337 \| GENOME_ACCESSION | |
| Ga0310146_00181 \| GENOME_ACCESSION | |
| Ga0310828_1006812 \| GENOME_ACCESSION | |
| Ga0311022_13670299 \| GENOME_ACCESSION | |
| Ga0315269_0011078 \| GENOME_ACCESSION | |
| Ga0315269_0014929 \| GENOME_ACCESSION | |
| Ga0315269_0030078 \| GENOME_ACCESSION | |
| Ga0315277_10001015 \| GENOME_ACCESSION | |
| Ga0315280_10009663 \| GENOME_ACCESSION | |
| Ga0315280_10032046 \| GENOME_ACCESSION | |
| Ga0315282_10006339 \| GENOME_ACCESSION | |
| Ga0315282_10053614 \| GENOME_ACCESSION | |
| Ga0315285_10079970 \| GENOME_ACCESSION | |
| Ga0315288_10142264 \| GENOME_ACCESSION | |
| Ga0315298_1000517 \| GENOME_ACCESSION | |
| Ga0315298_1001941 \| GENOME_ACCESSION | |
| Ga0315298_1005332 \| GENOME_ACCESSION | |
| Ga0315298_1007399 \| GENOME_ACCESSION | |
| Ga0315298_1007594 \| GENOME_ACCESSION | |
| Ga0315298_1015991 \| GENOME_ACCESSION | |
| Ga0315903_10087816 \| GENOME_ACCESSION | |
| Ga0334883_1024988 \| GENOME_ACCESSION | |
| Ga0334884_1015165 \| GENOME_ACCESSION | |
| Ga0370516_000963 \| GENOME_ACCESSION | |
| Ga0370516_004838 \| GENOME_ACCESSION | |
| Ga0370516_008232 \| GENOME_ACCESSION | |
| Ga0370516_009639 \| GENOME_ACCESSION | |
| Ga0370516_018229 \| GENOME_ACCESSION | |
| Ga0370516_020865 \| GENOME_ACCESSION | |
| Ga0373397_000168 \| GENOME_ACCESSION | |
| Ga0373621_000479 \| GENOME_ACCESSION | |
| Ga0373621_007959 \| GENOME_ACCESSION | |
| Ga0373621_010685 \| GENOME_ACCESSION | |
| Ga0373621_017562 \| GENOME_ACCESSION | |

TABLE 2A-continued

| Cas 12 proteins |
| --- |
| Cas 12 proteins |

Ga0373621_020135 | GENOME_ACCESSION
Ga0373621_023545 | GENOME_ACCESSION
Ga0373621_050562 | GENOME_ACCESSION
Ga0373637_0010996 | GENOME_ACCESSION
Ga0373637_0021496 | GENOME_ACCESSION
Ga0373637_0024972 | GENOME_ACCESSION
Ga0373637_0031827 | GENOME_ACCESSION
Ga0373637_0034837 | GENOME_ACCESSION
Ga0373637_0065620 | GENOME_ACCESSION
Ga0374803_055 | GENOME_ACCESSION
GCA_000092125.1 | Meiothermus silvanus DSM 9946 plasmid pMESIL02
GCA_000444055.1 | Alicyclobacillus acidoterrestris ATCC 49025 contig_23
GCA_000444055.1 | Alicyclobacillus acidoterrestris ATCC 49025 contig_26
GCA_000832185.1_ASM83218v1 | Bacillus thermoamylovorans strain B4167 NODE_88
GCA_002951815.1_ASM295181v1 | Sulfobacillus thermotolerans strain Kr chromosome
GCA_004343255.1_ASM434325v1 | Laceyella sacchari strain DSM 43356 Ga0244645_102
GCA_006503695.1 | Tepidiphilus succinatimandens strain DSM 15512 Scaffold2
GCA_006503695.1_ASM650369v1 | Tepidiphilus succinatimandens strain DSM 15512 Scaffold2
GCA_900116805.1 | Alicyclobacillus macrosporangiidus strain DSM 17980 genome assembly
GCA_900129915.1 | Tepidibacter thalassicus DSM 15285 genome assembly
JGI12383J13903_1002647 | GENOME_ACCESSION
JGI24108J20142_1001595 | GENOME_ACCESSION
JGI24721J44947_10029740 | GENOME_ACCESSION
JGI24721J44947_10039167 | GENOME_ACCESSION
JGI26463J51803_1000081 | GENOME_ACCESSION
KE386988.1_organ | Desulfatirhabdium butyrativorans DSM 18734 genomic scaffold G492DRAFT_scaffold00017.17
KE387196.1_organ | Tuberibacillus calidus DSM 17572 genomic scaffold H532DRAFT_scaffold00011.11
LGRA01000008.1_o | Azospirillum sp. TSO35-2 Contig02
LNAA02000020.1_o | Oscillatoriales cyanobacterium MTP1 Contig_26
mgm4742482.3 | NODE_1674_length_13888_cov_4.96582_ID_49155357 | GENOME_ACCESSION
MHOL01000010.1_o | Candidatus Staskawiczbacteria bacterium RIFCSPHIGHO2_01_FULL_34_27 rifcsphigho2_01_scaffold_2126
MHPA01000001.1_o | Candidatus Staskawiczbacteria bacterium RIFCSPLOWO2_01_FULL_ 38_12b
rifcsplowo2_01_scaffold_12327
MTKY01071110.1_o | Anaerobic digester metagenome soeholt_digester_71110
MVGR01000004.1_o | Microcystis aeruginosa KW Contig4
NICF_comb_assmDRAFT_10010420 | GENOME_ACCESSION
NJDI01000010.1_o | Archaeoglobales archaeon ex4484_92 ex4484_82_scaffold_1630_length_14867__count_1478
OGCG01005283.1_o | hot springs metagenome genome assembly
OGCG01007631.1 o | hot springs metagenome genome assembly
OKRQ01000045.1_o | freshwater metagenome genome assembly
OQOO01000421.1_o | human oral metagenome genome assembly
OQUW01.1 | hot springs metagenome genome assembly
OQUW01000094.1_o | hot springs metagenome genome assembly
OQUW01000235.1_o | hot springs metagenome genome assembly
OQUW01001775.1_o | hot springs metagenome genome assembly
ORXB01007227.1_o | sediment metagenome genome assembly
OVXJ01001238.1_o | sediment metagenome genome assembly
QNAW01000106.1_o | Thermodesulfobacteria bacterium isolate B8_G2 B8_Guay2_scaffold_12966
UOVV01006324.1_o | compost metagenome genome assembly
UPSJ01002360.1_o | activated sludge metagenome genome assembly
YNPsite07_CeleraDRAF_scfl119010704098 | GENOME_ACCESSION
Ga0065721_10050166 | GENOME_ACCESSION: BioRi_2199352012_$F_3300005286 GENOME ID: 23829 CONTIG_ID: 14524
Ga0255812_10583625 | GENOME_ACESSION: IMG_3300023203_$F_3300023203 GENOME_ID: 30040 CONTIG_ID: 32030
Ga0265297_10015673 | GENOME_ACESSION: Munlanlwell13791_2_$F_3300029288 GENOME_ID: 280701 CONTIG_ID: 15672
Ga0315280_10014676 | GENOME_ACESSION: YL17G06_40_MG_2_$F_3300031862 GENOME_ID: 281631 CONTIG_ID: 14675
Ga0206102_1000160 | GENOME_ACESSION: 1B1Ametagenome_2_$F_3300020149 GENOME_ID: 20785 CONTIG_ID: 159
Ga0207869_1001742 | GENOME_ACESSION: Higso1AR5DSPAdes_$F_3300025517 GENOME_ID: 27181 CONTIG_ID: 1741
Ga0209347_1001125 | GENOME_ACESSION: AutmicBR23SPAdes $F_3300027640 GENOME_ID: 23478 CONTIG_ID: 1124
Alicyclobacillus kakegawensis NBRC 103104 DNA, contig: AK2_CON0027_0001, whole genome shotgun sequence |
GENOME_ACESSION: GCA_001552655.1_ASM155265v1_genomic GENOME_ID: 98642 CONTIG_ID: 26
FNOJ01000000035.1
Alicyclobacillus hesperidum strain DSM 12489 genome assembly, contig: Ga0074806_135, whole genome shotgun sequence |
GENOME_ACESSION: GCA_900107035.1_IMG-taxon_2634166329_annotated_assembly_genomic GENOME_ID: 184129
CONTIG_ID: 49
OQO001000421.1
human oral metagenome genome assembly, contig: NODE_421_length_10358_cov_14.800155, whole genome shotgun sequence |
GENOME_ACESSION: OQO001.1 GENOME_ID: 9995 CONTIG_ID: 420
bioreactor metagenome genome assembly, contig: NODE_247_length_93349_cov_7.384563, whole genome shotgun sequence |
GENOME_ACCESSION: OWPA01.1 GENOME_ID: 12159 CONTIG_ID: 246
PGUZ01000040.1
Bacillus sp. V3-13 contig 40, whole genome shotgun sequence | GENOME_ACCESSION: GCA_002860165.1
ASM286016v1_genomic
GENOME_ID: 150146 CONTIG_ID: 56
RHHN01000007.1
Brevibacillus agri strain NRRL NRS 1219 contig_7, whole genome shotgun sequence | GENOME_ACCESSION:
GCA_003710885.1_ASM371088v1_genomic GENOME_ID: 202321 CONTIG_ID: 115
RHHS01000035.1

TABLE 2A-continued

Cas 12 proteins
Cas 12 proteins

Brevibacillus gelatini strain DSM 100115 contig_35, whole genome shotgun sequence | GENOME_ACESSION: GCA_003710935.1_ASM371093v1_genomic GENOME_ID: 202324 CONTIG_ID: 28
AacCas12b
AapCas12b
BrCas12b

TABLE 2B

Cas12 proteins
Cas 12 proteins (65C) Ga0209381_1004188 | GENOME_ACCESSION
a0212093_1001507 | Ga0212093_1001507 | GENOME_ACCESSION
DCUT01000059.1_o | TPA_asm: Syntrophaceae bacterium UBA2207 UBA2207_contig_83649, whole genome shotgun sequence | GENOME_ACESSION: GCA_002328545.1_ASM232854v1_genomic GENOME_ID: 131523 CONTIG ID: 133
FQUK01000003.1_o | Thermomonas hydrothermalis strain DSM 14834 genome assembly
Ga0067045_1002454 | GENOME_ACCESSION
Ga0067045_1004962 | GENOME_ACCESSION]
Ga0116159_1001590 | GENOME_ACCESSION
Ga0116160|_1008286 | GENOME_ACCESSION
Ga0116161_1004008 | GENOME_ACCESSION
Ga0116167_1006930 | GENOME_ACCESSION
Ga0116184_10002336 | GENOME_ACCESSION
Ga0123519_10002912 | GENOME_ACCESSION
Ga0123519_10003852 | GENOME_ACCESSION
Ga0137716_10027208 | GENOME_ACCESSION
Ga0172382_10012866 | GENOME_ACCESSION
Ga0180435_10008691 | GENOME_ACCESSION
Ga0182014_10001887 | GENOME_ACCESSION
Ga0187107_1033 | GENOME_ACCESSION
Ga0187864_10009485 | GENOME_ACCESSION
Ga0208195_1004385 | GENOME_ACCESSION
Ga0208357_1002034 | GENOME_ACCESSION
Ga0208609_100002 | GENOME_ACCESSION
Ga0209012_1001252 | GENOME_ACCESSION
Ga0209018_1000172 | GENOME_ACCESSION
Ga0209507_1000982 | GENOME_ACCESSION
Ga0209513_1002134 | GENOME_ACCESSION
Ga0255346_1002844 | GENOME_ACCESSION
Ga0255812_10127107 | GENOME_ACCESSION
Ga0272448_1000001 | GENOME_ACCESSION
Ga0272448_1000009 | GENOME_ACCESSION
Ga0272448_1000167 | GENOME_ACCESSION
Ga0272448_1002516 | GENOME_ACCESSION
Ga0302246_1000265 | GENOME_ACCESSION
Ga0302251_1001844 | GENOME_ACCESSION
Ga0302253_1002416 | GENOME_ACCESSION
Ga0310136_000087 | GENOME_ACCESSION
Ga0315298_1005332 | GENOME_ACCESSION
Ga0315298_1015991 | GENOME_ACCESSION
Ga0334884_1015165 | GENOME_ACCESSION
Ga0373637_0010996 | GENOME_ACCESSION
Ga0373637_0024972 | GENOME_ACCESSION
Ga0373637_0031827 | GENOME_ACCESSION
GCA_000444055.1 | Alicyclobacillus acidoterrestris ATCC 49025 contig 26
GCA_000832185.1_ASM83218v1 | Bacillus thermoamylovorans strain B4167 NODE_88
GCA_002951815.1_ASM295181v1 | Sulfobacillus thermotolerans strain Kr chromosome
GCA_004343255.1_ASM434325v1 | Laceyella sacchari strain DSM 43356 Ga0244645_102
GCA_900116805.1 | Alicyclobacillus macrosporangiidus strain DSM 17980 genome assembly
KE386988.1_organ | Desulfatirhabdium butyrativorans DSM 18734 genomic scaffold G492DRAFT_scaffold00017.17
KE387196.1_organ | Tuberibacillus calidus DSM 17572 genomic scaffold H532DRAFT_scaffold00011.11
LNAA02000020.1_o | Oscillatoriales cyanobacterium MTP1 Contig_26
OQUW01000094.1_o | hot springs metagenome genome assembly
OQUW01001775.1_o | hot springs metagenome genome assembly
Ga0255812_10583625 | GENOME_ACESSION: IMG_3300023203_$F_3300023203 GENOME_ID: 30040 CONTIG_ID: 32030
Ga0065721_10050166 | GENOME_ ACCESSION: BioRi_2199352012_$F_3300005286 GENOME_ID: 23829 CONTIG_ID: 14524
Ga0265297_10015673 | GENOME_ACCESSION: Munlanlwell13791_2_$F_3300029288 GENOME_ ID: 280701 CONTIG_ID: 15672
Ga0315280_10014676 | GENOME_ACESSION: YL17G06 40 MG 2 $F_3300031862 GENOME_ID: 281631 CONTIG_ID: 14675

TABLE 2B-continued

Cas12 proteins
Cas 12 proteins

Ga0206102_1000160 | GENOME_ACESSION: 1B1Ametagenome_2_$F_3300020149 GENOME_ID: 20785 CONTIG_ID: 159
Ga0207869_1001742 | GENOME_ACESSION: HigsolAR5DSPAdes_$F_3300025517 GENOME_ID: 27181 CONTIG_ID: 1741
Ga0209347_1001125 | GENOME ACESSION: AutmicBR23SPAdes_$F_3300027640 GENOME_ID: 23478 CONTIG_ID: 1124
Alicyclobacillus kakegawensis NBRC 103104 DNA, contig: AK2_CON0027_0001, whole genome shotgun
sequence | GENOME_ACESSION: GCA_001552655.1_ASM155265v1_genomic GENOME_ID: 98642 CONTIG_ID: 26
FNOJ0100000035.1
Alicyclobacillus hesperidum strain DSM 12489 genome assembly, contig: Ga0074806_135, whole genome
shotgun sequence | GENOME_ACESSION: GCA_900107035.1 IMG-
taxon_2634166329_annotated_assembly_genomic GENOME_ID: 184129 CONTIG_ID: 49
OQOO010000421.1
human oral metagenome genome assembly, contig: NODE_421_length_10358_cov_14.800155, whole genome shotgun sequence | GENOME_ACESSION: OQO001.1 GENOME_ID: 9995 CONTIG_ID: 420
bioreactor metagenome genome assembly, contig: NODE_247_length_93349_cov_7.384563, whole genome shotgun sequence | GENOME_ACCESSION: OWPA01.1 GENOME_ID: 12159 CONTIG_ID: 246
PGUZ01000040.1
Bacillus sp. V3-13 contig_40, whole genome shotgun sequence | GENOME_ACCESSION: GCA_002860165.1_ASM286016v1_genomic GENOME_ID: 150146 CONTIG_ID: 56
RHHN01000007.1
Brevibacillus agri strain NRRL NRS 1219 contig_7, whole genome shotgun sequence | GENOME_ACCESSION: GCA_003710885.1_ASM371088v1_genomic GENOME_ID: 202321 CONTIG_ID: 115
RHHS01000035.1
Brevibacillus gelatini strain DSM 100115 contig_35, whole genome shotgun sequence | GENOME_ACESSION: GCA_003710935.1_ASM371093v1_genomic GENOME_ID: 202324 CONTIG_ID: 28
AacCas12b
AapCas12b
BrCas12b In certain embodiments, the CRISPR-Cas protein is a Cas12b from a thermostable species, for example *Alicyclobacillus acidiphilus* (Aap). Cas 12a proteins can be identified from similar organisms as identified in any of Table 2A or 2B. In certain embodiments, the thermostable CRISPR-Cas protein is a Cas13a. In an aspect, the Cas13a thermostable protein is from FIG. 1A of U.S. Provisional Application 62/967,408, filed Jan. 29, 2020, entitled "Novel CRISPR Enzymes and Systems" which were identified from stable anaerobic thermophilic methanogenic microbiomes fermenting switchgrass, supporting their thermostability. See, Liang et al., Biotechnol Biofuels 2018; 11: 243 doi: 10.1186/s13068-018-1238-1. Similarly, the 0J26742_10014101 clusters with the verified thermophilic sourced Cas13a sequences detailed in FIG. 1A of U.S. Provisional Application 62/967,408, filed Jan. 29, 2020, entitled "Novel CRISPR Enzymes and Systems". The nucleic acid identified at loci 123519_10037894 was identified from a study focusing on 70° C. organism. In certain example embodiments, the Cas13 orthologue has at least two HEPN domains and at least 80% identity to a polypeptide encoded by the nucleic acid sequence 0123519_10037894 or 0J26742_10014101.

Figure 4:
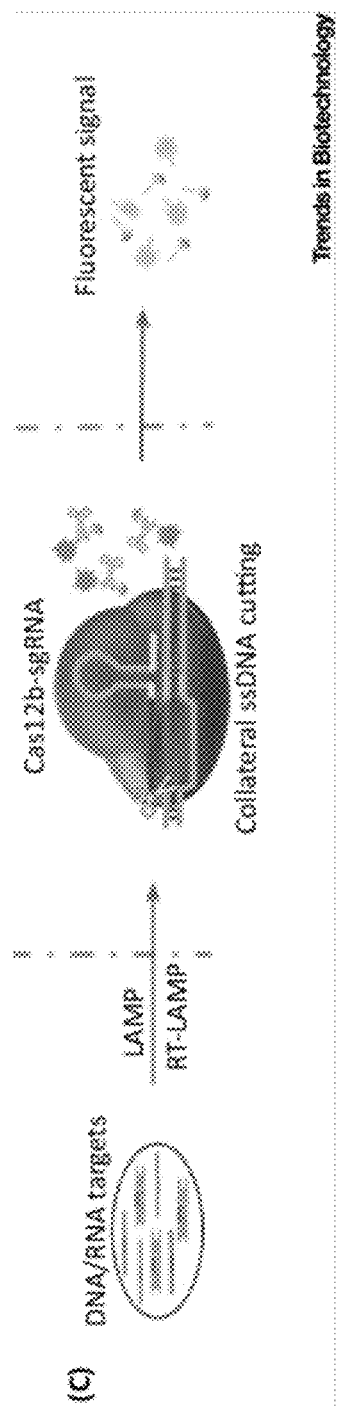
FIG. 4—Schematic for developing a one pot RT-LAMP Cas12b SHERLOCK reaction.
Figure 5:
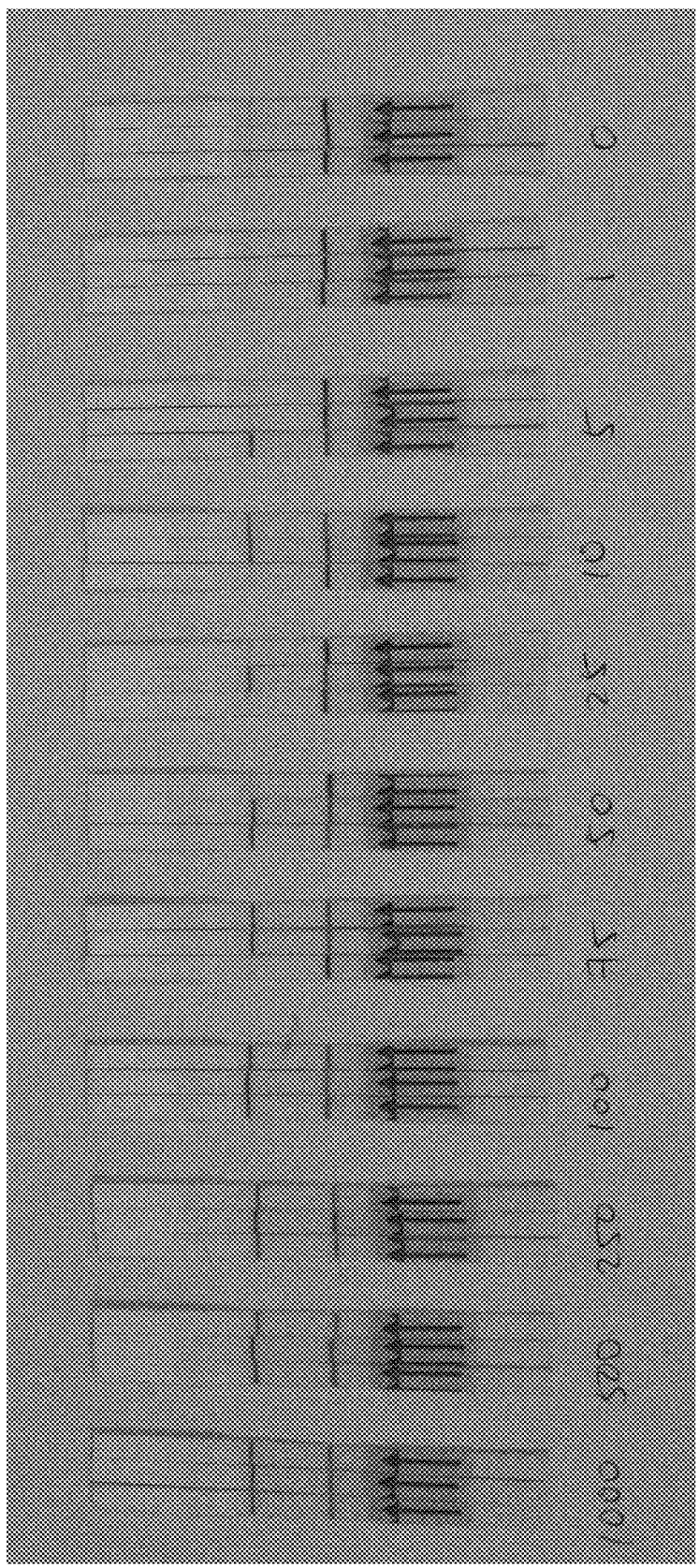
FIG. 5—Figure shows results obtained for assessing limit of detection by lateral flow assay at 60° C. for 60 minutes. The limit of detection was 100 molecules per reaction.

Certain example embodiments disclosed herein provide are based on low-cost CRISPR-based diagnostic that enables single-molecule detection of DNA or RNA with single-nucleotide specificity (Gootenberg, 2018; Gootenberg, et al, Science. 2017 Apr. 28; 356(6336):438-442 (2017); Myhrvold, et al., Science 360, 444-448 (2018)). Nucleic acid detection with SHERLOCK relies on the collateral activity of Type VI and Type V Cas proteins, such as Cas13 and Cas12, which unleashes promiscuous cleavage of reporters upon target detection (Gooteneberg et al., 2018) (Abudayyeh, et al., Science. 353(6299) (2016); East-Seletsky et al. Nature 538:270-273 (2016); Smargon et al. *Mol Cell* 65(4):618-630 (2017)). Certain embodiments disclosed herein, are capable of single-molecule detection in less than an hour and can be used for multiplexed target detection when using CRISPR enzymes with orthogonal cleavage preference, such as Cas13a from *Leptotrichia wadei* (LwaCas13a), Cas13b from *Capnocytophaga canimorsus* Cc5 (CcaCas13b), and Cas12a from *Acidaminococcus* sp. BV3L6 (AsCas12a); *Alicyclobacillus acidiphilus* (Aap) Cas 12b and *Brevibacillus* sp. SYSU G02855 (BrCas12b); (Gootenberg, 2018; Myhrvold et al. Science 360(6387):444-448 (2018); Gootenberg, 2017; Chen et al. *Science* 360(6387): 436-439 (2018); Li et al. *Cell Rep* 25(12):3262-3272 (2018); Li et al. *Nat Protoc* 13(5):899-914 (2018)). Guide molecules used herein are designed using a model for high activity-based Cas guide selection for coronavirus would facilitate design of optimal diagnostic assays, especially in applications requiring high-activity guides like lateral flow detection, and enable guide RNA design for in vivo RNA targeting applications with Cas13 has also been detailed in U.S. Provisional Applications 62/818,702 filed Mar. 14, 2019, now PCT/US20/22795 and 62/890,555, filed Aug. 22, 2019, now PCT/US20/22795, both entitled CRISPR Effector System Based Multiplex Diagnostics, incorporated herein by reference in their entirety, and, in particular, Examples 1-4, Tables 1-8 and FIG. 4A of U.S. Provisional Application 62/890,555.

Embodiments disclosed herein utilize Cas proteins possessing non-specific nuclease collateral activity to cleave detectable reporters upon target recognition, providing sensitive and specific diagnostics, including single nucleotide variants, detection based on rRNA sequences, screening for drug resistance, monitoring microbe outbreaks, genetic perturbations, and screening of environmental samples, as described, for example, in PCT/US18/054472 filed Oct. 22, 2018 at [0183]-[0327], incorporated herein by reference. Reference is made to WO 2017/219027, WO2018/107129, US20180298445, US 2018-0274017, US 2018-0305773, WO 2018/170340, U.S. application Ser. No. 15/922,837, filed Mar. 15, 2018 entitled "Devices for CRISPR Effector System Based Diagnostics", PCT/US18/50091, filed Sep. 7, 2018 "Multi-Effector CRISPR Based Diagnostic Systems", PCT/US18/66940 filed Dec. 20, 2018 entitled "CRISPR Effector System Based Multiplex Diagnostics", PCT/US18/054472 filed Oct. 4, 2018 entitled "CRISPR Effector System Based Diagnostic", U.S. Provisional 62/740,728 filed Oct. 3, 2018 entitled "CRISPR Effector System Based Diagnostics for Hemorrhagic Fever Detection", U.S. Provisional 62/690,278 filed Jun. 26, 2018 and U.S. Provisional 62/767,059 filed Nov. 14, 2018 both entitled "CRISPR Double Nickase Based Amplification, Compositions, Systems and Methods", U.S. Provisional 62/690,160 filed Jun. 26, 2018 and 62/767,077 filed Nov. 14, 2018, both entitled "CRISPR/CAS and Transposase Based Amplification Compositions, Systems, And Methods", U.S. Provisional 62/690,257 filed Jun. 26, 2018 and 62/767,052 filed Nov. 14, 2018 both entitled "CRISPR Effector System Based Amplification Methods, Systems, And Diagnostics", U.S. Provisional 62/767,076 filed Nov. 14, 2018 entitled "Multiplexing Highly Evolving Viral Variants With SHERLOCK" and 62/767,070 filed Nov. 14, 2018 entitled "Droplet SHERLOCK." Reference is further made to WO2017/127807, WO2017/184786, WO 2017/184768, WO 2017/189308, WO 2018/035388, WO 2018/170333, WO 2018/191388, WO 2018/213708, WO 2019/005866, PCT/US18/67328 filed Dec. 21, 2018 entitled "Novel CRISPR Enzymes and Systems", PCT/US18/67225 filed Dec. 21, 2018 entitled "Novel CRISPR Enzymes and Systems" and PCT/US18/67307 filed Dec. 21, 2018 entitled "Novel CRISPR Enzymes and Systems", U.S. 62/712,809 filed Jul. 31, 2018 entitled "Novel CRISPR Enzymes and Systems", U.S. 62/744,080 filed Oct. 10, 2018 entitled "Novel Cas12b Enzymes and Systems" and U.S. 62/751,196 filed Oct. 26, 2018 entitled "Novel Cas12b Enzymes and Systems", U.S. 715,640 filed August 7, 2-18 entitled "Novel CRISPR Enzymes and Systems", WO 2016/205711, U.S. Pat. No. 9,790,490, WO 2016/205749, WO 2016/205764, WO 2017/070605, WO 2017/106657, and WO 2016/149661, WO2018/035387, WO2018/194963, Cox DBT, et al., RNA editing with CRISPR-Cas13, Science. 2017 Nov. 24; 358(6366):1019-1027; Gootenberg J S, et al., Multiplexed and portable nucleic acid detection platform with Cas13, Cas12a, and Csm6, Science. 2018 Apr. 27; 360 (6387):439-444; Gootenberg J S, et al., Nucleic acid detection with CRISPR-Cas13a/C2c2, Science. 2017 Apr. 28; 356(6336):438-442; Abudayyeh 00, et al., RNA targeting with CRISPR-Cas13, Nature. 2017 Oct. 12; 550(7675):280-284; Smargon A A, et al., Cas13b Is a Type VI-B CRISPR-Associated RNA-Guided RNase Differentially Regulated by Accessory Proteins Csx27 and Csx28. Mol Cell. 2017 Feb. 16; 65(4):618-630.e7; Abudayyeh 00, et al., C2c2 is a single-component programmable RNA-guided RNA-targeting CRISPR effector, Science. 2016 Aug. 5; 353(6299): aaf5573; Yang L, et al., Engineering and optimising deaminase fusions for genome editing. Nat Commun. 2016 Nov. 2; 7:13330, Myhrvold et al., Field deployable viral diagnostics using CRISPR-Cas13, Science 2018 360, 444-448, Shmakov et al. "Diversity and evolution of class 2 CRISPR-Cas systems," Nat Rev Microbiol. 2017 15(3):169-182, each of which is incorporated herein by reference in its entirety.

In general, a CRISPR-Cas or CRISPR system as used herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). When the CRISPR protein is a Cas13 protein, a tracrRNA is not required. Cas13 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molce1.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molce1.2016.12.023, which is incorporated herein in its entirety by reference.

In certain embodiments, protospacer flanking site, or protospacer flanking sequence (PFS) directs binding of the effector proteins (e.g Type VI) as disclosed herein to the target locus of interest. A PFS is a region that can affect the efficacy of Cas13a mediated targeting, and may be adjacent to the protospacer target in certain Cas13a proteins, while other orthologs do not require a specific PFS. In a preferred embodiment, the CRISPR effector protein may recognize a 3' PFS. In certain embodiments, the CRISPR effector protein may recognize a 3' PFS which is 5'H, wherein H is A, C or U. See, e.g. Abudayyeh, 2016. In certain embodiments, the effector protein may be *Leptotrichia shahii* Cas13p, more preferably *Leptotrichia shahii* DSM 19757 Cas13, and the 3' PFS is a 5' H.

In the context of formation of a CRISPR complex, "target molecule" or "target sequence" or "target nucleic acid" refers to a molecule harboring a sequence, or a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell. A target sequence may comprise DNA polynucleotides.

As such, a CRISPR system may comprise RNA-targeting effector proteins. A CRISPR system may comprise DNA-targeting effector proteins. In some embodiments, a CRISPR system may comprise a combination of RNA- and DNA-targeting effector proteins, or effector proteins that target both RNA and DNA.

Other Example Type VI Cas Proteins

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of Cas13a or Cas13b orthologs provided herein. In certain example embodiments, the effector protein comprises a single HEPN domain. In certain other example embodiments, the effector protein comprises two HEPN domains.

In one example embodiment, the effector protein comprises one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application 62/484,786 entitled "Novel Type VI CRISPR Orthologs and Systems," filed on Apr. 12, 2017.

In an embodiment of the invention, a HEPN domain comprises at least one RxxxxH motif comprising the sequence of R(N/H/K)X1X2X3H. In an embodiment of the invention, a HEPN domain comprises a RxxxxH motif comprising the sequence of R(N/H)X1X2X3H. In an embodiment of the invention, a HEPN domain comprises the sequence of R(N/K)X1X2X3H. In certain embodiments, X1 is R, S, D, E, Q, N, G, Y, or H. In certain embodiments, X2 is I, S, T, V, or L. In certain embodiments, X3 is L, F, N, Y, V, I, S, D, E, or A.

In particular embodiments, the Type VI RNA-targeting Cas enzyme is Cas13a. In other example embodiments, the Type VI RNA-targeting Cas enzyme is Cas13b. In certain embodiments, the Cas13b protein is from an organism of a genus selected from the group consisting of: *Bergeyella, Prevotella, Porphyromonas, Bacterioides, Alistipes, Riemerella, Myroides, Capnocytophaga, Porphyromonas, Flavobacterium, Porphyromonas, Chryseobacterium, Paludibacter, Psychroflexus, Riemerella, Phaeodactylibacter, Sinomicrobium, Reichenbachiella*.

In particular embodiments, the homologue or orthologue of a Type VI protein such as Cas13a as referred to herein has a sequence homology or identity of at least 30%, or at least 40%, or at least 50%, or at least 60%, or at least 70%, or at least 80%, more preferably at least 85%, even more preferably at least 90%, such as for instance at least 95% with a Type VI protein such as Cas13a (e.g., based on the wild-type sequence of any of *Leptotrichia shahii* Cas13a, Lachnospiraceae bacterium MA2020 Cas13a, Lachnospiraceae bacterium NK4A179 Cas13a, *Clostridium aminophilum* (DSM 10710) Cas13a, *Carnobacterium gallinarum* (DSM 4847) Cas13, *Paludibacter propionicigenes* (WB4) Cas13, *Listeria weihenstephanensis* (FSL R9-0317) Cas13, Listeriaceae bacterium (FSL M6-0635) Cas13, *Listeria newyorkensis* (FSL M6-0635) Cas13, *Leptotrichia wadei* (F0279) Cas13, *Rhodobacter capsulatus* (SB 1003) Cas13, *Rhodobacter capsulatus* (R121) Cas13, *Rhodobacter capsulatus* (DE442) Cas13, *Leptotrichia wadei* (Lw2) Cas13, or *Listeria seeligeri* Cas13). In further embodiments, the homologue or orthologue of a Type VI protein such as Cas13 as referred to herein has a sequence identity of at least 30%, or at least 40%, or at least 50%, or at least 60%, or at least 70%, or at least 80%, more preferably at least 85%, even more preferably at least 90%, such as for instance at least 95% with the wild type Cas13 (e.g., based on the wild-type sequence of any of *Leptotrichia shahii* Cas13, Lachnospiraceae bacterium MA2020 Cas13, Lachnospiraceae bacterium NK4A179 Cas13, *Clostridium aminophilum* (DSM 10710) Cas13, *Carnobacterium gallinarum* (DSM 4847) Cas13, *Paludibacter propionicigenes* (WB4) Cas13, *Listeria weihenstephanensis* (FSL R9-0317) Cas13, Listeriaceae bacterium (FSL M6-0635) Cas13, *Listeria newyorkensis* (FSL M6-0635) Cas13, *Leptotrichia wadei* (F0279) Cas13, *Rhodobacter capsulatus* (SB 1003) Cas13, *Rhodobacter capsulatus* (R121) Cas13, *Rhodobacter capsulatus* (DE442) Cas13, *Leptotrichia wadei* (Lw2) Cas13, or *Listeria seeligeri* Cas13).

In certain other example embodiments, the CRISPR system the effector protein is a Cas13 nuclease. The activity of Cas13 may depend on the presence of two HEPN domains. These have been shown to be RNase domains, i.e. nuclease (in particular an endonuclease) cutting RNA. Cas13a HEPN may also target DNA, or potentially DNA and/or RNA. On the basis that the HEPN domains of Cas13a are at least capable of binding to and, in their wild-type form, cutting RNA, then it is preferred that the Cas13a effector protein has RNase function. Regarding Cas13a CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional 62/432,240 entitled "Novel Crispr Enzymes and Systems" filed Dec. 9, 2016. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi: 10.1101/054742.

RNase function in CRISPR systems is known, for example mRNA targeting has been reported for certain type III CRISPR-Cas systems (Hale et al., 2014, Genes Dev, vol. 28, 2432-2443; Hale et al., 2009, Cell, vol. 139, 945-956; Peng et al., 2015, Nucleic acids research, vol. 43, 406-417) and provides significant advantages. In the *Staphylococcus epidermis* type III-A system, transcription across targets results in cleavage of the target DNA and its transcripts, mediated by independent active sites within the Cas10-Csm ribonucleoprotein effector protein complex (see, Samai et al., 2015, Cell, vol. 151, 1164-1174). A CRISPR-Cas system, composition or method targeting RNA via the present effector proteins is thus provided.

In an embodiment, the Cas protein may be a Cas13a ortholog of an organism of a genus which includes but is not limited to *Leptotrichia, Listeria*, Corynebacter, *Sutterella, Legionella, Treponema, Filifactor, Eubacterium, Streptococcus, Lactobacillus, Mycoplasma, Bacteroides, Flaviivola*,

*Flavobacterium, Sphaerochaeta, Azospirillum, Gluconacetobacter, Neisseria, Roseburia, Parvibaculum, Staphylococcus, Nitratifractor, Mycoplasma* and *Campylobacter*. Species of organism of such a genus can be as otherwise herein discussed.

It will be appreciated that any of the functionalities described herein may be engineered into CRISPR enzymes from other orthologs, including chimeric enzymes comprising fragments from multiple orthologs. Examples of such orthologs are described elsewhere herein. Thus, chimeric enzymes may comprise fragments of CRISPR enzyme orthologs of an organism which includes but is not limited to *Leptotrichia, Listeria,* Corynebacter, *Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter*. A chimeric enzyme can comprise a first fragment and a second fragment, and the fragments can be of CRISPR enzyme orthologs of organisms of genera herein mentioned or of species herein mentioned; advantageously the fragments are from CRISPR enzyme orthologs of different species.

In embodiments, the Cas13a protein as referred to herein also encompasses a functional variant of Cas13a or a homologue or an orthologue thereof. A "functional variant" of a protein as used herein refers to a variant of such protein which retains at least partially the activity of that protein. Functional variants may include mutants (which may be insertion, deletion, or replacement mutants), including polymorphs, etc. Also included within functional variants are fusion products of such protein with another, usually unrelated, nucleic acid, protein, polypeptide or peptide. Functional variants may be naturally occurring or may be manmade. Advantageous embodiments can involve engineered or non-naturally occurring Type VI RNA-targeting effector protein.

In an embodiment, nucleic acid molecule(s) encoding the Cas13 or an ortholog or homolog thereof, may be codon-optimized for expression in a eukaryotic cell. A eukaryote can be as herein discussed. Nucleic acid molecule(s) can be engineered or non-naturally occurring.

In an embodiment, the Cas13a or an ortholog or homolog thereof, may comprise one or more mutations (and hence nucleic acid molecule(s) coding for same may have mutation (s). The mutations may be artificially introduced mutations and may include but are not limited to one or more mutations in a catalytic domain. Examples of catalytic domains with reference to a Cas9 enzyme may include but are not limited to RuvC I, RuvC II, RuvC III and HNH domains.

In an embodiment, the Cas13a or an ortholog or homolog thereof, may comprise one or more mutations. The mutations may be artificially introduced mutations and may include but are not limited to one or more mutations in a catalytic domain. Examples of catalytic domains with reference to a Cas enzyme may include but are not limited to HEPN domains.

In an embodiment, the Cas1a3 or an ortholog or homolog thereof, may be used as a generic nucleic acid binding protein with fusion to or being operably linked to a functional domain. Exemplary functional domains may include but are not limited to translational initiator, translational activator, translational repressor, nucleases, in particular ribonucleases, a spliceosome, beads, a light inducible/controllable domain or a chemically inducible/controllable domain.

In certain example embodiments, the Cas13a effector protein may be from an organism selected from the group consisting of; *Leptotrichia, Listeria,* Corynebacter, *Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma,* and *Campylobacter*.

In certain embodiments, the effector protein may be a *Listeria* sp. Cas13p, preferably *Listeria seeligeria* Cas13p, more preferably *Listeria seeligeria* serovar 1/2b str. SLCC3954 Cas13p and the crRNA sequence may be 44 to 47 nucleotides in length, with a 5' 29-nt direct repeat (DR) and a 15-nt to 18-nt spacer.

In certain embodiments, the effector protein may be a *Leptotrichia* sp. Cas13p, preferably *Leptotrichia shahii* Cas13p, more preferably *Leptotrichia shahii* DSM 19757 Cas13p and the crRNA sequence may be 42 to 58 nucleotides in length, with a 5' direct repeat of at least 24 nt, such as a 5' 24-28-nt direct repeat (DR) and a spacer of at least 14 nt, such as a 14-nt to 28-nt spacer, or a spacer of at least 18 nt, such as 19, 20, 21, 22, or more nt, such as 18-28, 19-28, 20-28, 21-28, or 22-28 nt.

In certain example embodiments, the effector protein may be a *Leptotrichia* sp., *Leptotrichia wadei* F0279, or a *Listeria* sp., preferably *Listeria newyorkensis* FSL M6-0635.

In certain example embodiments, the Cas13 effector proteins of the invention include, without limitation, the following 21 ortholog species (including multiple CRISPR loci: *Leptotrichia shahii; Leptotrichia wadei* (Lw2); *Listeria seeligeri*; Lachnospiraceae bacterium MA2020; Lachnospiraceae bacterium NK4A179; *[Clostridium] aminophilum* DSM 10710; *Carnobacterium gallinarum* DSM 4847; *Carnobacterium gallinarum* DSM 4847 (second CRISPR Loci); *Paludibacter propionicigenes* WB4; *Listeria weihenstephanensis* F SL R9-0317; Listeriaceae bacterium F SLM6-0635; *Leptotrichia wadei* F0279; *Rhodobacter capsulatus* SB 1003; *Rhodobacter capsulatus* R121; *Rhodobacter capsulatus* DE442; *Leptotrichia buccalis* C-1013-b; Herbinix hemicellulosilytica; *[Eubacterium] rectale*; Eubacteriaceae bacterium CHKCI004; *Blautia* sp. Marseille-P2398; and *Leptotrichia* sp. oral taxon 879 str. F0557. Twelve (12) further non-limiting examples are: Lachnospiraceae bacterium NK4A144; *Chloroflexus aggregans; Demequina aurantiaca; Thalassospira* sp. TSLS-1; *Pseudobutyrivibrio* sp. OR37; *Butyrivibrio* sp. YAB3001; *Blautia* sp. Marseille-P2398; *Leptotrichia* sp. Marseille-P3007; *Bacteroides ihuae*; Porphyromonadaceae bacterium KH3CP3RA; *Listeria riparia*; and *Insolitispirillum peregrinum*.

In certain embodiments, the Cas13 protein according to the invention is or is derived from one of the orthologues as described, or is a chimeric protein of two or more of the orthologues as described below, or is a mutant or variant of one of the orthologues as described (or a chimeric mutant or variant), including dead Cas13, split Cas13, destabilized Cas13, etc. as defined herein elsewhere, with or without fusion with a heterologous/functional domain.

In certain example embodiments, the Cas13a effector protein is from an organism of a genus selected from the group consisting of: *Leptotrichia, Listeria,* Corynebacter, *Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter,* and *Lachnospira*.

In an embodiment of the invention, there is provided an effector protein which comprises an amino acid sequence having at least 80% sequence homology to the wild-type sequence of any of *Leptotrichia shahii* Cas13, *Lachnospiraceae bacterium MA2020* Cas13, *Lachnospiraceae bacterium NK4A179* Cas13, *Clostridium aminophilum* (DSM 10710) Cas13, *Carnobacterium gallinarum* (DSM 4847) Cas13, *Paludibacter propionicigenes* (WB4) Cas13, *Listeria weihenstephanensis* (FSL R9-0317) Cas13, Listeriaceae bacterium (FSL M6-0635) Cas13, *Listeria newyorkensis* (FSL M6-0635) Cas13, *Leptotrichia wadei* (F0279) Cas13, *Rhodobacter capsulatus* (SB 1003) Cas13, *Rhodobacter capsulatus* (R121) Cas13, *Rhodobacter capsulatus* (DE442) Cas13, *Leptotrichia wadei* (Lw2) Cas13, or *Listeria seeligeri* Cas13. According to the invention, a consensus sequence can be generated from multiple Cas13 orthologs, which can assist in locating conserved amino acid residues, and motifs, including but not limited to catalytic residues and HEPN motifs in Cas13 orthologs that mediate Cas13 function. One such consensus sequence, generated from selected orthologs.

In an embodiment of the invention, the effector protein comprises an amino acid sequence having at least 80% sequence homology to a Type VI effector protein consensus sequence including but not limited to a consensus sequence described herein.

In another non-limiting example, a sequence alignment tool to assist generation of a consensus sequence and identification of conserved residues is the MUSCLE alignment tool (www.ebi.ac.uk/Tools/msa/muscle/). For example, using MUSCLE, the following amino acid locations conserved among Cas13a orthologs can be identified in *Leptotrichia wadei* Cas13a:K2; K5; V6; E301; L331; I335; N341; G351; K352; E375; L392; L396; D403; F446; I466; I470; R474 (HEPN); H475; H479 (HEPN), E508; P556; L561; I595; Y596; F600; Y669; I673; F681; L685; Y761; L676; L779; Y782; L836; D847; Y863; L869; I872; K879; I933; L954; I958; R961; Y965; E970; R971; D972; R1046 (HEPN), H1051 (HEPN), Y1075; D1076; K1078; K1080; I1083; I1090.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023. In certain example embodiments, the Cas13b effector protein is, or comprises an amino acid sequence having at least 80% sequence homology to any of the sequences of Table 1 of International Patent Application No. PCT/US2016/058302. Further reference is made to example Type VI-B effector proteins of U.S. Provisional Application Nos. 62/471,710, 62/566,829 and International Patent Publication No. WO2018/1703333, entitled "Novel Cas13b Orthologues CRISPR Enzymes and System". In particular embodiments, the Cas13b enzyme is derived from *Bergeyella zoohelcum*. In certain other example embodiments, the effector protein is, or comprises an amino acid sequence having at least 80% sequence homology to any of the sequences listed in Tables 1A or 1B of International Patent Publication No. WO2018/1703333, specifically incorporated herein by reference. In certain embodiments, the Cas 13b effector protein is, or comprises an amino acid sequence having at least 80% sequence homology to any of the polypeptides in U.S. Provisional Applications 62/484,791, 62/561,662, 62/568,129 or International Patent Publication WO2018/191388, all entitled "Novel Type VI CRISPR Orthologs and Systems," incorporated herein by reference. In certain embodiments, the Cas13b effector protein is, or comprises an amino acid sequence having at least 80% sequence homology to a polypeptide as set forth in FIG. 1 of International Patent Publication WO2018/191388, specifically incorporated herein by reference. In an aspect, the Cas13b protein is selected from the group consisting of *Porphyromonas gulae* Cas13b (accession number WP 039434803), *Prevotella* sp. P5-125 Cas 13b (accession number WP 044065294), *Porphyromonas gingivalis* Cas 13b (accession number WP 053444417), *Porphyromonas* sp. COT-052 OH4946 Cas 13b (accession number WP 039428968), *Bacteroides pyogenes* Cas 13b (accession number WP 034542281), *Riemerella anatipestifer* Cas13b (accession number WP 004919755).

In certain example embodiments, the RNA-targeting effector protein is a Cas13c effector protein as disclosed in U.S. Provisional Patent Application No. 62/525,165 filed Jun. 26, 2017, and International Patent Publication No. WO2018/035250 filed Aug. 16, 2017. In certain example embodiments, the Cas13c protein may be from an organism of a genus such as *Fusobacterium* or *Anaerosalibacter*. Example wildtype orthologue sequences of Cas13c are: EHO19081, WP_094899336, WP_040490876, WP_047396607, WP_035935671, WP_035906563, WP_042678931, WP_062627846, WP_005959231, WP_027128616, WP_062624740, WP_096402050.

In certain example embodiments, the Cas13 protein may be selected from any of the following: Cas13a: *Leptotrichia shahii*, *Leptotrichia wadei* (Lw2), *Listeria seeligeri*, Lachnospiraceae bacterium MA2020, Lachnospiraceae bacterium NK4A179, [*Clostridium*] *aminophilum* DSM 10710, *Carnobacterium gallinarum* DSM 4847, *Carnobacterium gallinarum* DSM 4847, *Paludibacter propionicigenes* WB4, *Listeria weihenstephanensis* FSL R9-0317, Listeriaceae bacterium FSL M6-0635, *Leptotrichia wadei* F0279, *Rhodobacter capsulatus* SB 1003, *Rhodobacter capsulatus* R121, *Rhodobacter capsulatus* DE442, *Leptotrichia buccalis* C-1013-b, *Herbinix hemicellulosilytica*, [*Eubacterium*] *rectale*, Eubacteriaceae bacterium CHKCI004, *Blautia* sp. Marseille-P2398, *Leptotrichia* sp. oral taxon 879 str. F0557; Cas 13b: *Bergeyella zoohelcum*, *Prevotella intermedia*, *Prevotella buccae*, *Alistipes* sp. ZOR0009, *Prevotella* sp. MA2016, *Riemerella anatipestifer*, *Prevotella aurantiaca*, *Prevotella saccharolytica*, *Prevotella intermedia*, *Capnocytophaga canimorsus*, *Porphyromonas gulae*, *Prevotella* sp. P5-125, *Flavobacterium branchiophilum*, *Porphyromonas gingivalis*, *Prevotella intermedia*; Cas13c: *Fusobacterium necrophorum* subsp. *funduliforme* ATCC 51357 contig00003, *Fusobacterium necrophorum* DJ-2 contig0065, whole genome shotgun sequence, *Fusobacterium necrophorum* BFTR-1 contig0068, *Fusobacterium necrophorum* subsp. *funduliforme* 1_1_36S cont1.14, *Fusobacterium perfoetens* ATCC 29250 T364DRAFT_scaffold00009.9_C,

*Fusobacterium ulcerans* ATCC 49185 cont2.38, *Anaerosalibacter* sp. ND1 genome assembly *Anaerosalibacter massiliensis* ND1.

In certain example embodiments the orthologue is a Cas13a, Cas13b, Cas13c, or Cas13d. In certain example embodiments the orthologue is a Cas13 orthologue. In certain example embodiments, the Cas13a orthologues is derived from Herbinix hemicellulosilytica. In certain example embodiments, the Cas13a orthologue is derived from Herbinix hemicellulosilytica DSM 29228. In certain example embodiments, the Cas 13 orthologue is defined by SEQ ID NO: 75 of International Publication No. WO 2017/219027. In certain example embodiments, the Cas 13 orthologue is defined by a sequence from FIG. 1A of U.S. Provisional Application 62/967,408, filed Jan. 29, 2020, entitled "Novel CRISPR Enzymes and Systems" (loci QNRW01000010.1, OWPA01000389.1, 0153798_10014618, 0153978_10005171, and 0153798_10004687). In certain example embodiments, the Cas 13a orthologue is encoded by the nucleic acid sequence 0123519_10037894 or 0J26742_10014101. In certain other example embodiments, the Cas13 orthologue has at least 80% sequence identity to SEQ ID NO: 75 of International Publication No. WO 2017/219027. In certain other example embodiments, the Cas13 orthologue has at least 80% sequence identity to sequence from FIG. 1A of U.S. Provisional Application 62/967,408, filed Jan. 29, 2020, entitled "Novel CRISPR Enzymes and Systems" (loci QNRW01000010.1, OWPA01000389.1, 0153798_10014618, 0153978_10005171, and 0153798_10004687), incorporated herein by reference. In certain other example embodiments, the Cas13 orthologue has at least 80% sequence identity to a polypeptide encoded by the nucleic acid sequence 0123519_10037894 or 0J26742_10014101. In certain example embodiments, the Cas13 orthologue has at least one HEPN domain and at least 80% identity to SEQ ID NO: 75 of International Publication No. WO 2017/219027. In certain example embodiments, the Cas13 orthologue has at least one HEPN domain and at least 80% identity to sequence from loci QNRW01000010.1, OWPA01000389.1, 0153798_10014618, 0153978_10005171, and 0153798_10004687. In certain example embodiments, the Cas13 orthologue has at least one HEPN domain and at least 80% identity to a polypeptide encoded by the nucleic acid sequence of 0123519_10037894 or 0J26742_10014101 in BROD-4880P2 Cas13a sequences-.txt. In another example embodiment, the Cas13 orthologue has at least two HEPN domains and at least 80% identity to SEQ ID NO: 75 of International Publication No. WO 2017/219027. In another example embodiment, the Cas13 orthologue has at least two HEPN domains and at least 80% identity to sequence from FIG. 1A of U.S. Provisional Application 62/967,408, filed Jan. 29, 2020, entitled "Novel CRISPR Enzymes and Systems" loci QNRW01000010.1, OWPA01000389.1, 0153798_10014618, 0153978_10005171, and 0153798_10004687. The Cas13a thermostable proteins of FIG. 1A of U.S. Provisional Application 62/967,408, filed Jan. 29, 2020, entitled "Novel CRISPR Enzymes and Systems" were identified from stable anaerobic thermophilic methanogenic microbiomes fermenting switchgrass, supporting their thermostability. See, Liang et al., Biotechnol Biofuels 2018; 11: 243 doi: 10.1186/s13068-018-1238-1. Similarly, the 0J26742_10014101 clusters with the verified thermophilic sourced Cas13a sequences detailed in FIG. 1A of U.S. Provisional Application 62/967,408, filed Jan. 29, 2020, entitled "Novel CRISPR Enzymes and Systems". The nucleic acid identified at loci 123519_10037894 was identified from a study focusing on 70° C. organism. In certain example embodiments, the Cas13 orthologue has at least two HEPN domains and at least 80% identity to a polypeptide encoded by the nucleic acid sequence 0123519_10037894 or 0J26742_10014101. Accordingly, a person of ordinary skill in the art may use characteristics of the above identified orthologs to select other suitable thermostable orthologues from those disclosed herein.

Other Example Type V Cas Proteins

In certain example embodiments, the assays may comprise a DNA-targeting effector protein. In certain example embodiments, the assays may comprise multiple DNA-targeting effectors or one or more orthologs in combination with one or more RNA-targeting effectors. In certain example embodiments, the DNA targeting are Type V Cas proteins, such as Cas12 proteins. In certain other example embodiments, the Cas12 proteins are Cas12a, Cas12b, Cas12c, Cas12d, Cas12e, Cas12g, or a combination thereof.

Cpf1 Orthologs

The present invention encompasses the use of a Cpf1 effector protein, derived from a Cpf1 locus denoted as subtype V-A. Herein such effector proteins are also referred to as "Cpf1p", e.g., a Cpf1 protein (and such effector protein or Cpf1 protein or protein derived from a Cpf1 locus is also called "CRISPR enzyme"). Presently, the subtype V-A loci encompasses cas1, cas2, a distinct gene denoted cpf1 and a CRISPR array. Cpf1 (CRISPR-associated protein Cpf1, subtype PREFRAN) is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in all Cas9 proteins, and the RuvC-like domain is contiguous in the Cpf1 sequence, in contrast to Cas9 where it contains long inserts including the HNH domain. Accordingly, in particular embodiments, the CRISPR-Cas enzyme comprises only a RuvC-like nuclease domain.

The programmability, specificity, and collateral activity of the RNA-guided Cpf1 also make it an ideal switchable nuclease for non-specific cleavage of nucleic acids. In one embodiment, a Cpf1 system is engineered to provide and take advantage of collateral non-specific cleavage of RNA. In another embodiment, a Cpf1 system is engineered to provide and take advantage of collateral non-specific cleavage of ssDNA. Accordingly, engineered Cpf1 systems provide platforms for nucleic acid detection and transcriptome manipulation. Cpf1 is developed for use as a mammalian transcript knockdown and binding tool. Cpf1 is capable of robust collateral cleavage of RNA and ssDNA when activated by sequence-specific targeted DNA binding.

Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. doi: 10.1002/pro.2225). See also Shmakov et al. (2015) for application in the field of CRISPR-Cas loci. Homologous proteins may but need not be structurally related, or are only partially structurally related. The Cpf1 gene is found in several diverse bacterial genomes, typically in the same locus with cas1, cas2, and cas4 genes and a CRISPR cassette (for example, FNFX1_1431-FNFX1_1428 of *Francisella cf. novicida* Fx1). In particular embodiments, the effector protein is a Cpf1 effector protein from an organism from a genus comprising *Streptococcus, Campylobacter, Nitrati-* fractor, *Staphylococcus, Parvibaculum, Roseburia, Neisseria, Gluconacetobacter, Azospirillum, Sphaerochaeta, Lactobacillus, Eubacterium,* Corynebacter, *Carnobacterium, Rhodobacter, Listeria, Paludibacter, Clostridium,* Lachnospiraceae, Clostridiaridium, *Leptotrichia, Francisella, Legionella, Alicyclobacillus, Methanomethyophilus, Porphyromonas, Prevotella,* Bacteroidetes, *Helcococcus,* Letospira, *Desulfovibrio, Desulfonatronum,* Opitutaceae, *Tuberibacillus, Bacillus, Brevibacilus, Methylobacterium* or *Acidaminococcus.*

In further particular embodiments, the Cpf1 effector protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii.*

The effector protein may comprise a chimeric effector protein comprising a first fragment from a first effector protein (e.g., a Cpf1) ortholog and a second fragment from a second effector (e.g., a Cpf1) protein ortholog, and wherein the first and second effector protein orthologs are different. At least one of the first and second effector protein (e.g., a Cpf1) orthologs may comprise an effector protein (e.g., a Cpf1) from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium,* Corynebacter, *Carnobacterium, Rhodobacter, Listeria, Paludibacter, Clostridium,* Lachnospiraceae, Clostridiaridium, *Leptotrichia, Francisella, Legionella, Alicyclobacillus, Methanomethyophilus, Porphyromonas, Prevotella,* Bacteroidetes, *Helcococcus,* Letospira, *Desulfovibrio, Desulfonatronum,* Opitutaceae, *Tuberibacillus, Bacillus, Brevibacilus, Methylobacterium* or *Acidaminococcus*; e.g., a chimeric effector protein comprising a first fragment and a second fragment wherein each of the first and second fragments is selected from a Cpf1 of an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium,* Corynebacter, *Carnobacterium, Rhodobacter, Listeria, Paludibacter, Clostridium,* Lachnospiraceae, Clostridiaridium, *Leptotrichia, Francisella, Legionella, Alicyclobacillus, Methanomethyophilus, Porphyromonas, Prevotella,* Bacteroidetes, *Helcococcus,* Letospira, *Desulfovibrio, Desulfonatronum,* Opitutaceae, *Tuberibacillus, Bacillus, Brevibacilus, Methylobacterium* or *Acidaminococcus* wherein the first and second fragments are not from the same bacteria; for instance a chimeric effector protein comprising a first fragment and a second fragment wherein each of the first and second fragments is selected from a Cpf1 of *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis,* Lachnospiraceae bacterium MC2017 1, *Butyrivibrio proteoclasticus,* Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai,* Lachnospiraceae bacterium ND2006, *Porphyromonas crevioricanis* 3, *Prevotella disiens* and *Porphyromonas macacae,* wherein the first and second fragments are not from the same bacteria. In a more preferred embodiment, the Cpf1p is derived from a bacterial species selected from *Francisella tularensis* 1, *Prevotella albensis,* Lachnospiraceae bacterium MC2017 1, *Butyrivibrio proteoclasticus,* Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai,* Lachnospiraceae bacterium ND2006, *Porphyromonas crevioricanis* 3, *Prevotella disiens* and *Porphyromonas macacae.* In certain embodiments, the Cpf1p is derived from a bacterial species selected from *Acidaminococcus* sp. BV3L6, Lachnospiraceae bacterium MA2020. In certain embodiments, the effector protein is derived from a subspecies of *Francisella tularensis* 1, including but not limited to *Francisella tularensis* subsp. *Novicida.*

In some embodiments, the Cpf1p is derived from an organism from the genus of *Eubacterium.* In some embodiments, the CRISPR effector protein is a Cpf1 protein derived from an organism from the bacterial species of *Eubacterium rectale.* In some embodiments, the amino acid sequence of the Cpf1 effector protein corresponds to NCBI Reference Sequence WP_055225123.1, NCBI Reference Sequence WP_055237260.1, NCBI Reference Sequence WP_055272206.1, or GenBank ID OLA16049.1. In some embodiments, the Cpf1 effector protein has a sequence homology or sequence identity of at least 60%, more particularly at least 70, such as at least 80%, more preferably at least 85%, even more preferably at least 90%, such as for instance at least 95%, with NCBI Reference Sequence WP_055225123.1, NCBI Reference Sequence WP_055237260.1, NCBI Reference Sequence WP_055272206.1, or GenBank ID OLA16049.1. The skilled person will understand that this includes truncated forms of the Cpf1 protein whereby the sequence identity is determined over the length of the truncated form. In some embodiments, the Cpf1 effector recognizes the PAM sequence of TTTN or CTTN.

In particular embodiments, the homologue or orthologue of Cpf1 as referred to herein has a sequence homology or identity of at least 80%, more preferably at least 85%, even more preferably at least 90%, such as for instance at least 95% with Cpf1. In further embodiments, the homologue or orthologue of Cpf1 as referred to herein has a sequence identity of at least 80%, more preferably at least 85%, even more preferably at least 90%, such as for instance at least 95% with the wild type Cpf1. Where the Cpf1 has one or more mutations (mutated), the homologue or orthologue of said Cpf1 as referred to herein has a sequence identity of at least 80%, more preferably at least 85%, even more preferably at least 90%, such as for instance at least 95% with the mutated Cpf1.

In an embodiment, the Cpf1 protein may be an ortholog of an organism of a genus which includes, but is not limited to *Acidaminococcus* sp, Lachnospiraceae bacterium or *Moraxella bovoculi*; in particular embodiments, the type V Cas protein may be an ortholog of an organism of a species which includes, but is not limited to *Acidaminococcus* sp. BV3L6; Lachnospiraceae bacterium ND2006 (LbCpf1) or *Moraxella bovoculi* 237. In particular embodiments, the homologue or orthologue of Cpf1 as referred to herein has a sequence homology or identity of at least 80%, more preferably at least 85%, even more preferably at least 90%, such as for instance at least 95% with one or more of the Cpf1 sequences disclosed herein. In further embodiments, the homologue or orthologue of Cpf as referred to herein has a sequence identity of at least 80%, more preferably at least 85%, even more preferably at least 90%, such as for instance at least 95% with the wild type FnCpf1, AsCpf1 or LbCpf1. The skilled person will understand that this includes truncated forms of the Cpf1 protein whereby the sequence identity is determined over the length of the truncated form. In certain of the following, Cpf1 amino acids are followed by nuclear localization signals (NLS) (italics), a glycine-serine (GS) linker, and 3×HA tag. Further Cpf1 orthologs include NCBI WP_055225123.1, NCBI WP_055237260.1, NCBI WP_055272206.1, and GenBank OLA16049.1.

C2c1 Orthologs

The present invention encompasses the use of a C2c1 effector proteins, derived from a C2c1 locus denoted as subtype V-B. Herein such effector proteins are also referred to as "C2c1p", e.g., a C2c1 protein (and such effector protein or C2c1 protein or protein derived from a C2c1 locus is also called "CRISPR enzyme"). Presently, the subtype V-B loci encompasses cas1-Cas4 fusion, cas2, a distinct gene denoted C2c1 and a CRISPR array. C2c1 (CRISPR-associated protein C2c1) is a large protein (about 1100-1300 amino acids) that contains a RuvC-like nuclease domain homologous to the corresponding domain of Cas9 along with a counterpart to the characteristic arginine-rich cluster of Cas9. However, C2c1 lacks the HNH nuclease domain that is present in all Cas9 proteins, and the RuvC-like domain is contiguous in the C2c1 sequence, in contrast to Cas9 where it contains long inserts including the HNH domain. Accordingly, in particular embodiments, the CRISPR-Cas enzyme comprises only a RuvC-like nuclease domain.

The programmability, specificity, and collateral activity of the RNA-guided C2c1 also make it an ideal switchable nuclease for non-specific cleavage of nucleic acids. In one embodiment, a C2c1 system is engineered to provide and take advantage of collateral non-specific cleavage of RNA. In another embodiment, a C2c1 system is engineered to provide and take advantage of collateral non-specific cleavage of ssDNA. Accordingly, engineered C2c1 systems provide platforms for nucleic acid detection and transcriptome manipulation, and inducing cell death. C2c1 is developed for use as a mammalian transcript knockdown and binding tool. C2c1 is capable of robust collateral cleavage of RNA and ssDNA when activated by sequence-specific targeted DNA binding.

In certain embodiments, C2c1 is provided or expressed in an in vitro system or in a cell, transiently or stably, and targeted or triggered to non-specifically cleave cellular nucleic acids. In one embodiment, C2c1 is engineered to knock down ssDNA, for example viral ssDNA. In another embodiment, C2c1 is engineered to knock down RNA. The system can be devised such that the knockdown is dependent on a target DNA present in the cell or in vitro system, or triggered by the addition of a target nucleic acid to the system or cell.

C2c1 (also known as Cas12b) proteins are RNA guided nucleases. In certain embodiments, the Cas protein may comprise at least 80% sequence identity to a polypeptide as described in International Patent Publication WO 2016/205749 at FIG. 17-21, FIG. 41A-41M, 44A-44E, incorporated herein by reference. Its cleavage relies on a tracr RNA to recruit a guide RNA comprising a guide sequence and a direct repeat, where the guide sequence hybridizes with the target nucleotide sequence to form a DNA/RNA heteroduplex. Based on current studies, C2c1 nuclease activity also requires relies on recognition of PAM sequence. C2c1 PAM sequences are T-rich sequences. In some embodiments, the PAM sequence is 5' TTN 3' or 5' ATTN 3', wherein N is any nucleotide. In a particular embodiment, the PAM sequence is 5' TTC 3'. In a particular embodiment, the PAM is in the sequence of *Plasmodium falciparum*.

In particular embodiments, the effector protein is a C2c1 effector protein from an organism from a genus comprising *Alicyclobacillus, Desulfovibrio, Desulfonatronum,* Opitutaceae, *Tuberibacillus, Bacillus, Brevibacillus, Candidatus, Desulfatirhabdium, Citrobacter,* Elusimicrobia, *Methylobacterium,* Omnitrophica, Phycisphaerae, Planctomycetes, Spirochaetes, and Verrucomicrobiaceae.

In further particular embodiments, the C2c1 effector protein is from a species selected from *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus* Lindowbacteria bacterium RIFCSPLOWO2, *Desulfovibrio inopinatus* (e.g., DSM 10711), *Desulfonatronum thiodismutans* (e.g., strain MLF-1), Elusimicrobia bacterium RIFOXYA12, Omnitrophica WOR_2 bacterium RIFCSPHIGHO2, Opitutaceae bacterium TAV5, Phycisphaerae bacterium ST-NAGAB-D1, Planctomycetes bacterium RBG_13_46_10, Spirochaetes bacterium GWB1_27_13, Verrucomicrobiaceae bacterium UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060).

In one aspect, the CRISPR-Cas protein is a Cas12b from Table 2A or Table 2B. In certain embodiments, the CRISPR-Cas protein is a Cas12b from a thermostable species, for example *Alicyclobacillus acidiphilus* (AapCas12b). When the Aap protein is utilized, a related guide can be used, for example from the same or another *Alicyclobacillus* species, e.g. *Alicyclobacillus* acidoterrestrus (AacCas12b). In an aspect, the guide comprises at least 95%, 96%, 97% or more sequence identity to the DR and/or the tracr sequence from Aac. In certain embodiments, the AapCas12b protein comprises a sequence with 80%, 85%, 90%, 95% identity to, or consisting of the sequence:

```
MAVKSMKVKLRLDNMPEIRAGLWKLHTEVNAGVRYYTEWLSLLRQENLY

RRSPNGDGEQECYKTAEECKAELLERLRARQVENGHCGPAGSDDELLQL

ARQLYELLVPQAIGAKGDAQQIARKFLSPLADKDAVGGLGIAKAGNKPR

WVRMREAGEPGWEEEKAKAEARKSTDRTADVLRALADFGLKPLMRVYTD

SDMSSVQWKPLRKGQAVRTWDRDMFQQAIERMMSWESWNORVGEAYAKL

VEQKSRFEQKNFVGQEHLVQLVNQLQQDMKEASHGLESKEQTAHYLTGR

ALRGSDKVFEKWEKLDPDAPFDLYDTEIKNVQRRNTRRFGSHDLFAKLA

EPKYQALWREDASFLTRYAVYNSIVRKLNHAKMFATFTLPDATAHPIWT

RFDKLGGNLHQYTFLFNEFGEGRHAIRFQKLLTVEDGVAKEVDDVTVPI

SMSAQLDDLLPRDPHELVALYFQDYGAEQHLAGEFGGAKIQYRRDQLNH

LHARRGARDVYLNLSVRVQSQSEARGERRPPYAAVFRLVGDNHRAFVHF

DKLSDYLAEHPDDGKLGSEGLLSGLRVMSVDLGLRTSASISVFRVARKD

ELKPNSEGRVPFCFPIEGNENLVAVHERSQLLKLPGETESKDLRAIREE

RQRTLRQLRTQLAYLRLLVRCGSEDVGRRERSWAKLIEQPMDANQMTPD
```

-continued

```
WREAFEDELQKLKSLYGICGDREWTEAVYESVRRVWRHMGKQVRDWRKD

VRSGERPKIRGYQKDVVGGNSIEQIEYLERQYKFLKSWSFFGKVSGQVI

RAEKGSRFAITLREHIDHAKEDRLKKLADRIIMEALGYVYALDDERGKG

KWVAKYPPCQLILLEELSEYQFNNDRPPSENNQLMQWSHRGVFQELLNQ

AQVHDLLVGTMYAAFSSRFDARTGAPGIRCRRVPARCAREQNPEPFPWW

LNKFVAEHKLDGCPLRADDLIPTGEGEFFVSPFSAEEGDFHQIHADLNA

AQNLQRRLWSDFDISQIRLRCDWGEVDGEPVLIPRTTGKRTADSYGNKV

FYTKTGVTYYERERGKKRRKVFAQEELSEEEAELLVEADEAREKSVVLM

RDPSGIINRGDWTRQKEFWSMVNQRIEGYLVKQIRSRVRLQESACENTG

DI*.
```

The guide may be derived from a different species than the Cas protein. In certain embodiments, the CRISPR-Cas protein is a Cas12b from a thermostable species, for example *Alicyclobacillus acidiphilus* (Aap). When the Aap Cas protein is utilized, a related guide can be used, for example from the same or another *Alicyclobacillus* species, e.g. *Alicyclobacillus* acidoterrestrus (Aac). In an aspect, the guide comprises at least 95%, 96%, 97% or more sequence similarity to the DR and/or the tracr sequence from Aac Cas12b. The guide can be designed similarly for other Cas proteins, deriving the guide from a different species than the Cas protein species.

In an aspect, the CRISPR-Cas protein is a Cas12b from Aap, and the guide molecule is derived from Aac, or an *Alicyclobacillus* CRISPR Cas system direct repeat and tracrRNA. In certain embodiments, the guide is designed with a spacer sequence to target a molecule of interest, for example, SARS-CoV-2. While any portion of the SARS-CoV-2 can be targeted, as described elsewhere herein, in an aspect, the spacer is designed to target the Nucleocapsid protein of the SARS-CoV-2. In certain embodiments, the Aac guide has 90%, 91%, 92%, 93%, 94%, 95%, 96%, 97%, 98%, 99% sequence similarity to any one of Type 1 to Type 5 guide sequence below.

In an aspect, the guide comprises:
Type 1:
GTCTAGAGGACAGAATTTTTCAACGGGTGTGC-CAATGGCCACTTTCCAGGTGGCAAAGCCCGTT-GAGCTTCTCAAATCTGAGAAGTGGCAC (SEQ ID NO: 61,957),
Type 2:
GTCTAAAGGACAGAATTTTTCAACGGGTGTGC-CAATGGCCACTTTCCAGGTGGCAAAGCCCGTT-GAACTTCTCAAATCTGAGAAGTGGCAC (SEQ ID NO: 61,958)
Type 3:
GTCTAGAGGACAGAATTTTTCAACGGGTGTGC-CAATGGCCACTTTCCAGGTGGCAAAGCCCGTT-GAACTTCTCAAATCTGAGAAGTGGCAC (SEQ ID NO: 61,959)
Type 4:
GTCTAAAGGACAGAATTTTTCAACGGGTGTGC-CAATGGCCACTTTCCAGGTGGCAAAGCCCGTT-GAGCTTCTCAAATCTGAGAAGTGGCAC (SEQ ID NO:61,960) or
Type 5:
GTCTAGAGGACAGAATTTTTCAACGGGTGTGC-CAATGGCCACTTTCCAGGTGGCAAAGCCCGTT-GAACTTCTCAAATCTGCGAAGTGGCAC (SEQ ID NO: 61,961).

In certain embodiments, preservation of the underlined portions of the following guide sequence are maintained:
GTCTAGAGGACAGAATTTTTCAACGGGTGTGC-CAATGGCCACTTTCCAGGTGGCAAAGCCCGTT-GAGCTTCTCAAATCTGAGAAGTGGCAC (SEQ ID NO: 61962).

Figure 45:
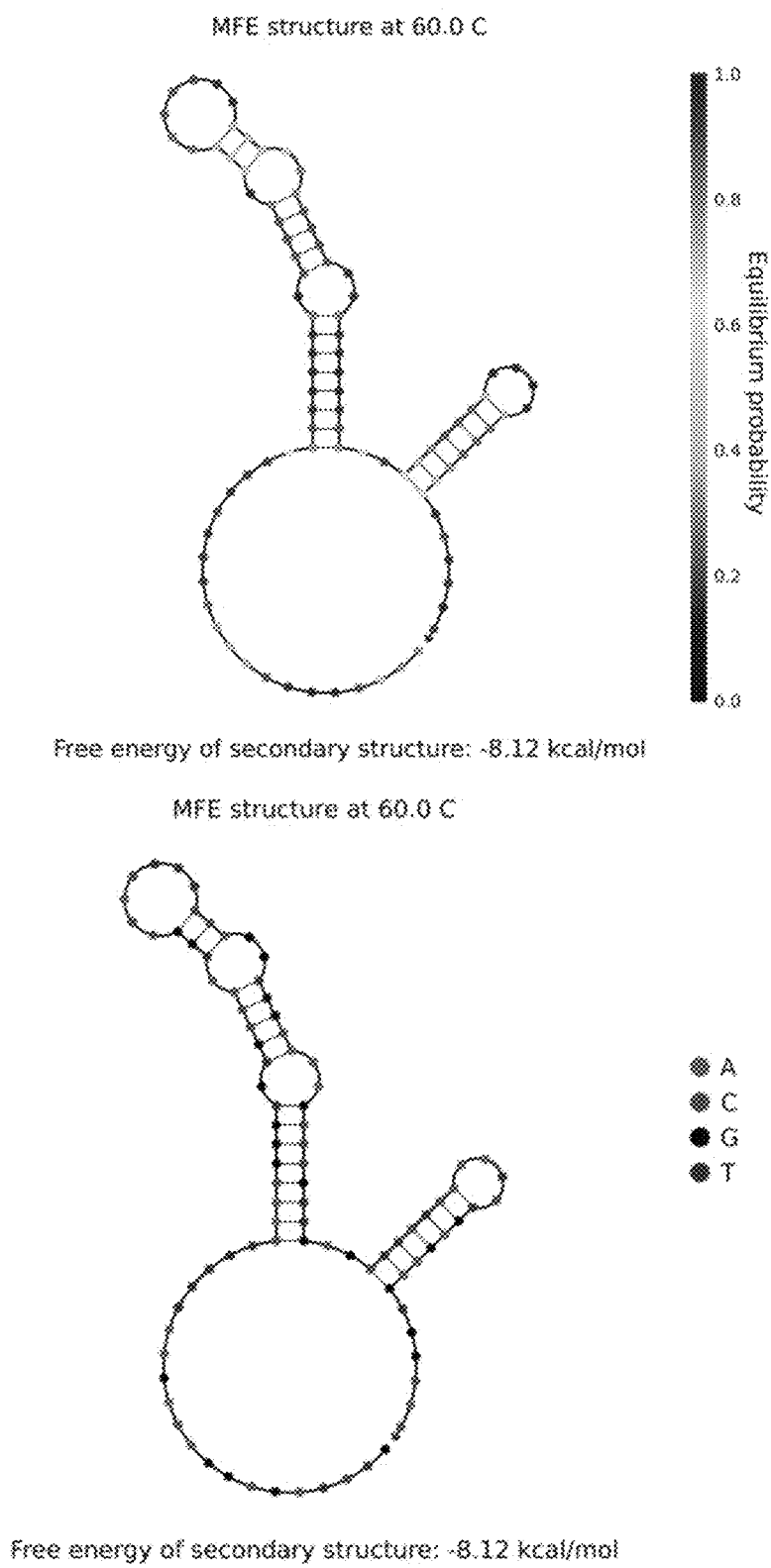
FIG. 45—Shows secondary structure of guide of *Alicyclobacillus acidoterrestris* (Aac) that is used with *Alicyclobacillus acidiphilus* (Aap) Cas12b in exemplary CRISPR Systems.

However, importance of particular bases of the guide sequence are not limited to the underlined areas in SEQ ID NO: 61962, and mutations of these bases can be performed when structure and activity of the guide sequence can be maintained. Such mutations can be tested and optimized in accordance with the guide optimization methods detailed elsewhere herein. In an aspect, the guide preserves the secondary structure as detailed in FIG. 45. In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In an aspect, the CRISPR-Cas protein is a Cas12b from Aap, and the guide molecule is derived from Aac, or an *Alicyclobacillus* CRISPR Cas system direct repeat and tracrRNA. In certain embodiments, the guide is designed with a spacer sequence to target SARS-CoV-2. While any portion of the SARS-CoV-2 can be targeted, as described elsewhere herein, in an aspect, the spacer is designed to target the Nucleocapsid protein of the SARS-CoV-2.

In an aspect, the CRISPR-Cas protein is a BrCas12b. In certain embodiments, the BrCas12b protein comprises a sequence with 80%, 85%, 90%, 95% identity to, or consisting of the sequence:

```
                                    (SEQ ID NO: 61963)
MPVRSFKVKLVTRSGDAEHMLQLRRGLWKTHEIVNQGIAYYMNKLALMR

QEPYAGKSREVVRLELLHSLRAQQKRNNWTGDAGTDDEILNLSRRLYEL

LVPSAIGEKGDAQMLSRKFLSPLVDPNSEGGKGTAKSGRKPRWMKMREE

GHPDWEAEREKDRAKKAADPTASILNDLEAFGLRPLFPLFTDEQKGIQW

LPKQKRQFVRTFDRDMFQQALERMLSWESWNRRVAEEYQKLQAQRDELY

AKYLADGGAWLEALQSFEKQREVELAEESFAAKSEYLITRRQIRGWKQV

YEKWSQLPEHAAQEQFWQVVADVQTSLPGAFGDPKVYQFLSQPEHHHIW

RGYPNRLFHYSDYNGVRKKLQRARHDATFTLPDPVEHPLWIRFDARGGN

IHDYEISQNGKQYQVTFSRLLWPENETWVERENVTVAIGASQQLKRQIR

LDGYADKKQKVRYRDYSSGIELTGVLGGAKIQFDRRHLRKASNRLADGE

TGPVYLNVVVDIEPFLAMRNGRLQTPIGQVLQVNTKDWPKVTGYKPAEL

ISWIQNSPLAVGTGVNTIEAGMRVMSVDLGQRSAAAVSIFEVMRQKPAE
```

```
-continued
QETKLFYPIAVTGLYAVHRRSLLLRLPGEKISDEIEQQRKIRAHARSLV

RYQIRLLADVLRLHTRGTAEQRRAKLDELLATLQTKQELDQKLWQTELE

KLFDYIHEPAERWQQALVAAHRTLEPVIGQAVRHWRKSLRIDRKGLAGM

SMWNIEELEETRKLLIAWSKHSRVPGEPNRLDKEETFAPQQLQHIQNVK

DDRLKQMANLLVMTALGYKYDEAEKQWKEAYPACQMILFEDLSRYRFAL

DRPRRENNRLMKWAHRSIPRLVYLQGELFGIQVGDVYSAYTSRFHAKTG

APGIRCHALKEEDLQPNSYVVKQLIKDGFIREDQTGSLKPGQIVPWSGG

ELFVTLADRSGSRLAVIHADINAAQNLQKRFWQQNTEIFRVPCKVTTSG

LIPAYDKMKKLFGKGYFAKINQTDTSEVYVWEHSAKMKGKTTPADPAEE

GVFDESLTDEMEELEDSQEGYKTLFRDPSGFFWSSDRWLPQKEFWFWVK

RRIEKKLREQLQ.
```

In an aspect, when the CRISPR-Cas protein is a BrCas12b, the tracrRNA can be selected from one of tracrRNA design 1-tracrRNA design 6 as detailed below:
tracrRdesign
  1: TGCAGGTTAGTGGAAATATAGA-TAGCCGTTGTGACTGAGTGACGTGTTAGGT-CAC CGTAGCA-CATGACACAACTGCACTGGTCAGCCTGTAGCTAAC-CACCTTCATTATATC TAGTTTTTCCAAC (SEQ ID NO: 61964) tracrRNA design
  2: GTTGTGACTGAGTGACGTGTTAGGT-CACCGTAGCACATGACACAACTGCACTGGT CAGCCTGTAGCTAACCACCTTCAT-TATATCTAGTTTTTCCAAC (SEQ ID NO: 61965) tracrRNA design
  3: TGACACAACTGCACTGGTCAGCCTGTAGCTAAC-CACCTTCATTATATCTAGTTTTT CCAAC (SEQ ID NO: 61966) tracrRNA design
  4: GAAGGTGGTTAGCTA-CAGGCTGACCAGTGCAGTTGTGTCATGTGC-TACGGTGACC TAACACGTCACTCAGT-CACAACGGCTATCTATATTTCCACTAAC (SEQ ID NO: 61967) tracrRNA design
  5: GTTGGAAAAACTAGATATAATGAAGGTGGT-TAGCTACAGGCTGACCAGTGCAGTT GTGT-CATGTGCTACGGTGACCTAACACGT-CACTCAGTCACAACGGCTATCTATATTT CCACTAAC (SEQ ID NO: 61968) tracrRNA design
  6: GTGCAGTTGTGTCATGTGC-TACGGTGACCTAACACGTCACTCAGT-CACAACGGCT ATCTATATTCCACTAAC (SEQ ID NO: 61969)

In an aspect, when BrCas12b is utilized, the crNA design can be selected from one of crRNAdesign 1 to crRNA design 3, wherein N represents the spacer design:
  crRNA design 1: GTCCGTTTCGTTAGTG-GAAATGTAGATGGT-TAGCACNNNNNNNNNNNNNNNNNNNN NNNNNNN (SEQ ID NO: 61970)
  crRNA design 2: TAGTGGAAATGTAGATGGT-TAGCACNNNNNNNNNNNNNNNNNNNNNNN-NNNN (SEQ ID NO: 61971)
  crRNA design 3: GTTAGTGGAAATCTAGATGGT-TAGCACNNNNNNNNNNNNNNNNNNNNNNN-NNNN (SEQ ID NO: 61972)

In certain example embodiments, the guide sequence is selected from SEQ ID Nos:40500-61643.

The effector protein may comprise a chimeric effector protein comprising a first fragment from a first effector protein (e.g., a C2c1) ortholog and a second fragment from a second effector (e.g., a C2c1) protein ortholog, and wherein the first and second effector protein orthologs are different. At least one of the first and second effector protein (e.g., a C2c1) orthologs may comprise an effector protein (e.g., a C2c1) from an organism comprising *Alicyclobacillus, Desulfovibrio, Desulfonatronum,* Opitutaceae, *Tuberibacillus, Bacillus, Brevibacillus, Candidatus, Desulfatirhabdium,* Elusimicrobia, *Citrobacter, Methylobacterium,* Omnitrophicai, Phycisphaerae, Planctomycetes, Spirochaetes, and Verrucomicrobiaceae; e.g., a chimeric effector protein comprising a first fragment and a second fragment wherein each of the first and second fragments is selected from a C2c1 of an organism comprising *Alicyclobacillus, Desulfovibrio, Desulfonatronum,* Opitutaceae, *Tuberibacillus, Bacillus, Brevibacillus, Candidatus, Desulfatirhabdium,* Elusimicrobia, *Citrobacter, Methylobacterium,* Omnitrophicai, Phycisphaerae, Planctomycetes, Spirochaetes, and Verrucomicrobiaceae wherein the first and second fragments are not from the same bacteria; for instance a chimeric effector protein comprising a first fragment and a second fragment wherein each of the first and second fragments is selected from a C2c1 of *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus* Lindowbacteria bacterium RIFCSPLOWO2, *Desulfovibrio inopinatus* (e.g., DSM 10711), *Desulfonatronum thiodismutans* (e.g., strain MLF-1), Elusimicrobia bacterium RIFOXYA12, Omnitrophica WOR 2 bacterium RIFCSPHIGHO2, Opitutaceae bacterium TAV5, Phycisphaerae bacterium ST-NAGAB-D1, Planctomycetes bacterium RBG_13_46_10, Spirochaetes bacterium GWB1_27_13, Verrucomicrobiaceae bacterium UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060), wherein the first and second fragments are not from the same bacteria.

In a more preferred embodiment, the C2c1p is derived from a bacterial species selected from *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus* Lindowbacteria bacterium RIFCSPLOWO2, *Desulfovibrio inopinatus* (e.g., DSM 10711), *Desulfonatronum thiodismutans* (e.g., strain MLF-1), Elusimicrobia bacterium RIFOXYA12, Omnitrophica WOR_2 bacterium RIFCSPHIGHO2, Opitutaceae bacterium TAV5, Phycisphaerae bacterium ST-NAGAB-D1, Planctomycetes bacterium RBG_13_46_10, Spirochaetes bacterium GWB1_27_13, Verrucomicrobiaceae bacterium UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060). In certain embodiments, the C2c1p is derived from a bacterial species selected from *Alicyclobacillus acidoterrestris* (e.g., ATCC 49025), *Alicyclobacillus contaminans* (e.g., DSM 17975).

In particular embodiments, the homologue or orthologue of C2c1 as referred to herein has a sequence homology or identity of at least 80%, more preferably at least 85%, even more preferably at least 90%, such as for instance at least 95% with C2c1. In further embodiments, the homologue or orthologue of C2c1 as referred to herein has a sequence identity of at least 80%, more preferably at least 85%, even more preferably at least 90%, such as for instance at least 95% with the wild type C2c1. Where the C2c1 has one or more mutations (mutated), the homologue or orthologue of said C2c1 as referred to herein has a sequence identity of at least 80%, more preferably at least 85%, even more preferably at least 90%, such as for instance at least 95% with the mutated C2c1.

In an embodiment, the C2c1 protein may be an ortholog of an organism of a genus which includes, but is not limited to *Alicyclobacillus, Desulfovibrio, Desulfonatronum,* Opitutaceae, *Tuberibacillus, Bacillus, Brevibacillus, Candidatus, Desulfatirhabdium,* Elusimicrobia, *Citrobacter, Methylobacterium,* Omnitrophicai, Phycisphaerae, Planctomycetes, Spirochaetes, and Verrucomicrobiaceae; in particular embodiments, the type V Cas protein may be an ortholog of an organism of a species which includes, but is not limited to *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus* Lindowbacteria bacterium RIFCSPLOWO2, *Desulfovibrio inopinatus* (e.g., DSM 10711), *Desulfonatronum thiodismutans* (e.g., strain MLF-1), Elusimicrobia bacterium RIFOXYA12, Omnitrophica WOR_2 bacterium RIFCSPHIGHO2, Opitutaceae bacterium TAV5, Phycisphaerae bacterium ST-NAGAB-D1, Planctomycetes bacterium RBG_13_46_10, Spirochaetes bacterium GWB1_27_13, Verrucomicrobiaceae bacterium UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060). In particular embodiments, the homologue or orthologue of C2c1 as referred to herein has a sequence homology or identity of at least 80%, more preferably at least 85%, even more preferably at least 90%, such as for instance at least 95% with one or more of the C2c1 sequences disclosed herein. In further embodiments, the homologue or orthologue of C2c1 as referred to herein has a sequence identity of at least 80%, more preferably at least 85%, even more preferably at least 90%, such as for instance at least 95% with the wild type AacC2c1 or BthC2c1.

In particular embodiments, the C2c1 protein of the invention has a sequence homology or identity of at least 60%, more particularly at least 70, such as at least 80%, more preferably at least 85%, even more preferably at least 90%, such as for instance at least 95% with AacC2c1 or BthC2c1. In further embodiments, the C2c1 protein as referred to herein has a sequence identity of at least 60%, such as at least 70%, more particularly at least 80%, more preferably at least 85%, even more preferably at least 90%, such as for instance at least 95% with the wild type AacC2c1. In particular embodiments, the C2c1 protein of the present invention has less than 60% sequence identity with AacC2c1. The skilled person will understand that this includes truncated forms of the C2c1 protein whereby the sequence identity is determined over the length of the truncated form.

In certain methods according to the present invention, the CRISPR-Cas protein is preferably mutated with respect to a corresponding wild-type enzyme such that the mutated CRISPR-Cas protein lacks the ability to cleave one or both DNA strands of a target locus containing a target sequence. In particular embodiments, one or more catalytic domains of the C2c1 protein are mutated to produce a mutated Cas protein which cleaves only one DNA strand of a target sequence.

In particular embodiments, the CRISPR-Cas protein may be mutated with respect to a corresponding wild-type enzyme such that the mutated CRISPR-Cas protein lacks substantially all DNA cleavage activity. In some embodiments, a CRISPR-Cas protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form.

In certain embodiments of the methods provided herein the CRISPR-Cas protein is a mutated CRISPR-Cas protein which cleaves only one DNA strand, i.e. a nickase. More particularly, in the context of the present invention, the nickase ensures cleavage within the non-target sequence, i.e. the sequence which is on the opposite DNA strand of the target sequence and which is 3' of the PAM sequence. By means of further guidance, and without limitation, an arginine-to-alanine substitution (R911A) in the Nuc domain of C2c1 from *Alicyclobacillus acidoterrestris* converts C2c1 from a nuclease that cleaves both strands to a nickase (cleaves a single strand). It will be understood by the skilled person that where the enzyme is not AacC2c1, a mutation may be made at a residue in a corresponding position.

Cas 12c Orthologs

Figure 43:
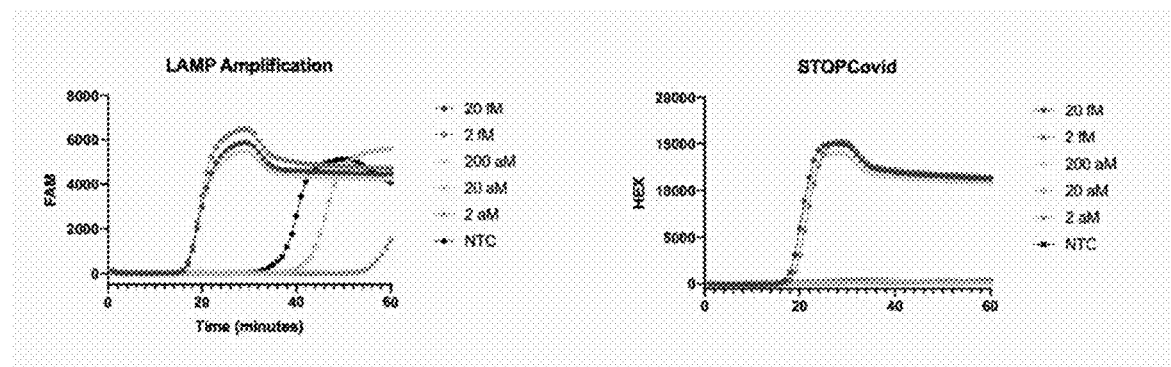
Figure 44:
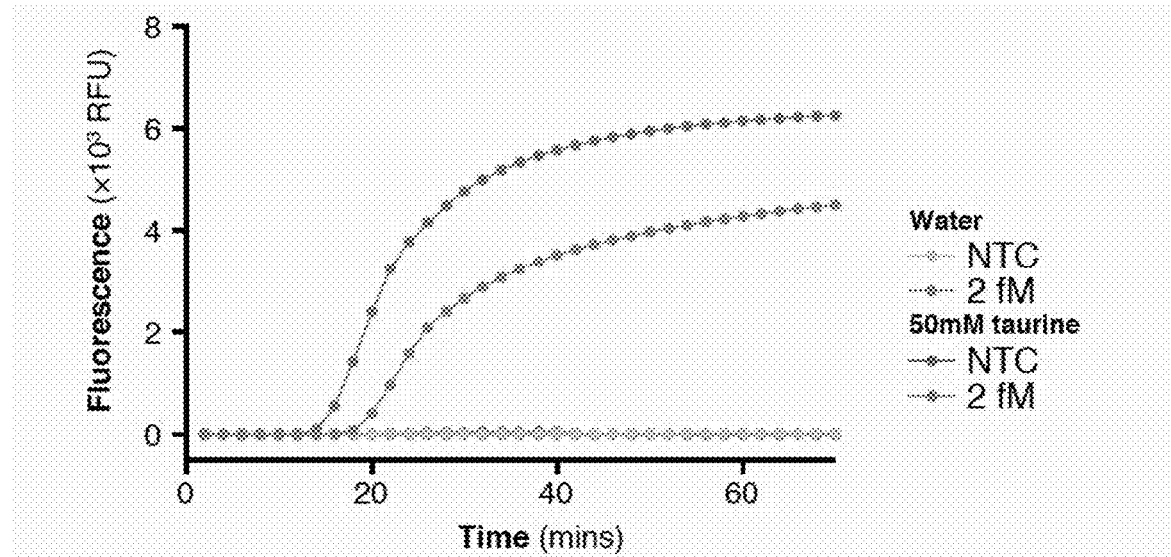
FIG. 44—Provides data showing an ability to detect target in 20 to 30 minutes

In certain embodiments, the effector protein, particularly a Type V loci effector protein, more particularly a Type V-C loci effector protein, even more particularly a C2c3p, may originate, may be isolated or may be derived from a bacterial metagenome selected from the group consisting of the bacterial metagenomes listed in the Table in FIG. 43A-43B of PCT/US2016/038238, specifically incorporated by reference, which presents analysis of the Type-V-C Cas12c loci.

In certain embodiments, the effector protein, particularly a Type V loci effector protein, more particularly a Type V-C loci effector protein, even more particularly a C2c3p, may comprise, consist essentially of or consist of an amino acid sequence selected from the group consisting of amino acid sequences shown in the multiple sequence alignment in FIG. 131 of PCT/US2016/038238, specifically incorporated by reference.

Figure 14:
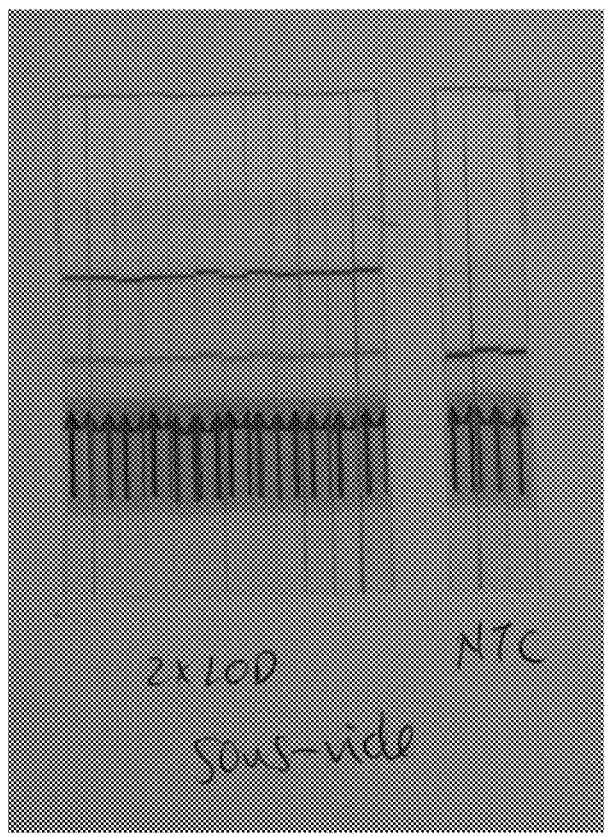
FIG. 14—The SHERLOCK assay can be run with a <$40 using conventional heating devices such as a sous vide heater FIG. 15—Shows SHERLOCK assays strips for 9 different patients using a nasopharyngeal swab sample. The results were compared to qPCR tests.
Figure 15:
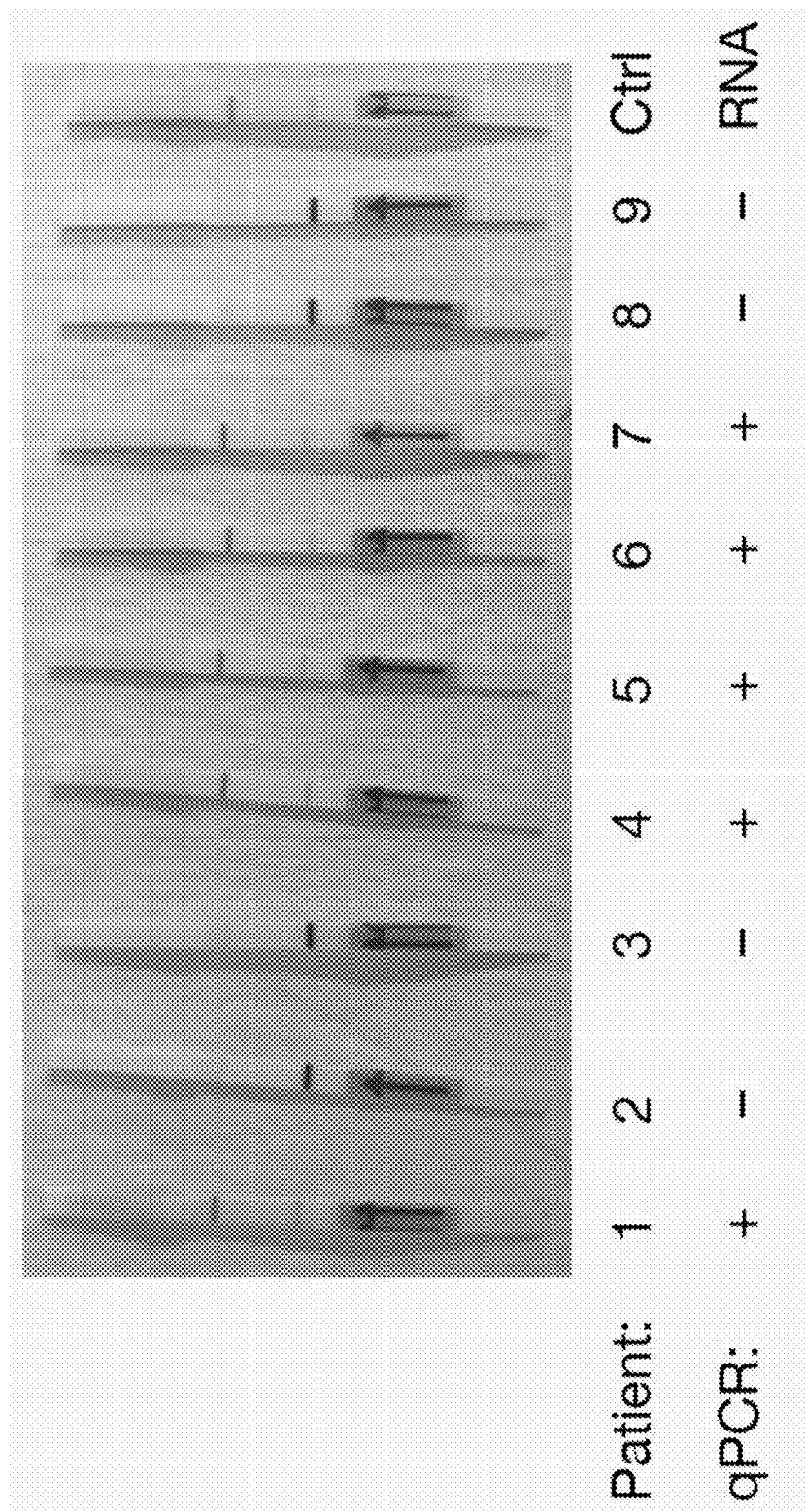

In certain embodiments, a Type V-C locus as intended herein may encode Cas1 and the C2c3p effector protein. See FIG. 14 of PCT/US2016/038238, specifically incorporated by reference, depicting the genomic architecture of the Cas12c CRISPR-Cas loci. In certain embodiments, a Cas1 protein encoded by a Type V-C locus as intended herein may cluster with Type I-B system. See FIG. 10A and 10B and FIG. 10C-V of PCT/US2016/038238, specifically incorporated by reference, illustrating a Cas1 tree including Cas1 encoded by representative Type V-C loci.

In certain embodiments, the effector protein, particularly a Type V loci effector protein, more particularly a Type V-C loci effector protein, even more particularly a C2c3p, such as a native C2c3p, may be about 1100 to about 1500 amino acids long, e.g., about 1100 to about 1200 amino acids long, or about 1200 to about 1300 amino acids long, or about 1300 to about 1400 amino acids long, or about 1400 to about 1500 amino acids long, e.g., about 1100, about 1200, about 1300, about 1400 or about 1500 amino acids long, or at least about 1100, at least about 1200, at least about 1300, at least about 1400 or at least about 1500 amino acids long.

Figure 13:
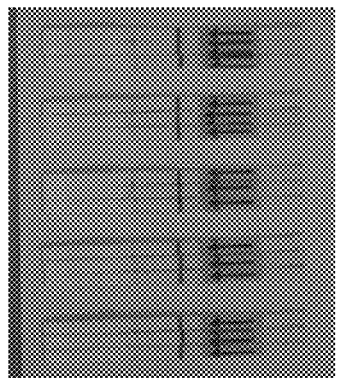
FIG. 13—Shows positive detection of COVID in 12 patients using the SHERLOCK assay.
Figure 13:
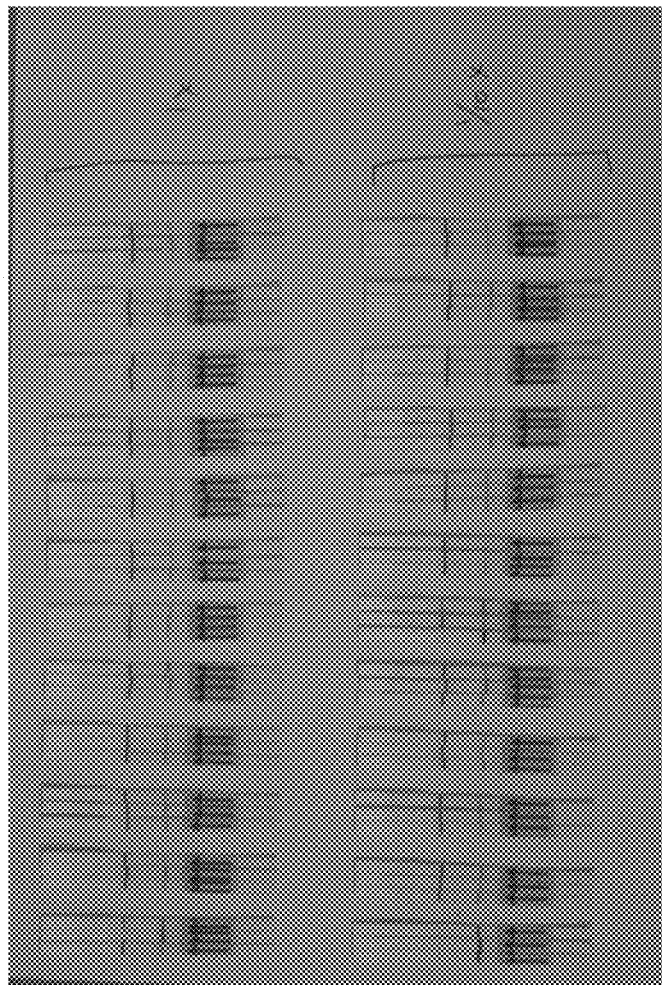

In certain embodiments, the effector protein, particularly a Type V loci effector protein, more particularly a Type V-C loci effector protein, even more particularly a C2c3p, and preferably the C-terminal portion of said effector protein, comprises the three catalytic motifs of the RuvC-like nuclease (i.e., RuvCI, RuvCII and RuvCIII). In certain embodiments, said effector protein, and preferably the C-terminal portion of said effector protein, may further comprise a region corresponding to the bridge helix (also known as arginine-rich cluster) that in Cas9 protein is involved in crRNA-binding. In certain embodiments, said effector protein, and preferably the C-terminal portion of said effector protein, may further comprise a Zn finger region. Preferably, the Zn-binding cysteine residue(s) may be conserved in C2c3p. In certain embodiments, said effector protein, and preferably the C-terminal portion of said effector protein, may comprise the three catalytic motifs of the RuvC-like nuclease (i.e., RuvCI, RuvCII and RuvCIII), the region corresponding to the bridge helix, and the Zn finger region, preferably in the following order, from N to C terminus: RuvCI-bridge helix-RuvCII-Zinc finger-RuvCIII. See FIG. 13A and 13C of PCT/US2016/038238, specifically incorporated by reference, for illustration of representative Type V-C effector proteins domain architecture.

In certain embodiments, Type V-C loci as intended herein may comprise CRISPR repeats between 20 and 30 bp long, more typically between 22 and 27 bp long, yet more typically 25 bp long, e.g., 20, 21, 22, 23, 24, 25, 26, 27, 28, 29, or 30 bp long.

Orthologous proteins may but need not be structurally related, or are only partially structurally related. In particular embodiments, the homologue or orthologue of a Type V protein such as Cas12c as referred to herein has a sequence homology or identity of at least 80%, more preferably at least 85%, even more preferably at least 90%, such as for instance at least 95% with a Cas12c. In further embodiments, the homologue or orthologue of a Type V Cas12c as referred to herein has a sequence identity of at least 80%, more preferably at least 85%, even more preferably at least 90%, such as for instance at least 95% with the wild type Cas12c.

In an embodiment, the Type V RNA-targeting Cas protein may be a Cas12c ortholog of an organism of a genus which includes but is not limited to Corynebacter, *Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter*.

In an embodiment, the Cas12c or an ortholog or homolog thereof, may comprise one or more mutations (and hence nucleic acid molecule(s) coding for same may have mutation(s). The mutations may be artificially introduced mutations and may include but are not limited to one or more mutations in a catalytic domain. Examples of catalytic domains with reference to a Cas9 enzyme may include but are not limited to RuvC I, RuvC II, RuvC III and HNH domains. In an embodiment, the Cas12c or an ortholog or homolog thereof, may comprise one or more mutations. The mutations may be artificially introduced mutations and may include but are not limited to one or more mutations in a catalytic domain. Examples of catalytic domains with reference to a Cas enzyme may include but are not limited to RuvC I, RuvC II, RuvC III, HNH domains, and HEPN domains.

Guide Sequences

As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

As used herein, the term "guide sequence," "crRNA," "guide RNA," or "single guide RNA," or "gRNA" refers to a polynucleotide comprising any polynucleotide sequence having sufficient complementarity with a target nucleic acid sequence to hybridize with the target nucleic acid sequence and to direct sequence-specific binding of a RNA-targeting complex comprising the guide sequence and a CRISPR effector protein to the target nucleic acid sequence. In some example embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'phosphorothioate (MS), S-constrained ethyl(cEt), or 2'-O-methyl 3'thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., Med Chem Comm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In some embodiments, a nucleic acid-targeting guide is designed or selected to modulate intermolecular interactions among guide molecules, such as among stem-loop regions of different guide molecules. It will be appreciated that nucleotides within a guide that base-pair to form a stem-loop are also capable of base-pairing to form an intermolecular duplex with a second guide and that such an intermolecular duplex would not have a secondary structure compatible with CRISPR complex formation. Accordingly, is useful to select or design DR sequences in order to modulate stem-loop formation and CRISPR complex formation. In some embodiments, about or less than about 75%, 50%, 40%, 30%, 25%, 20%, 15%, 10%, 5%, 1%, or fewer of nucleic acid-targeting guides are in intermolecular duplexes. It will be appreciated that stem-loop variation will often be within limits imposed by DR-CRISPR effector interactions. One way to modulate stem-loop formation or change the equilibrium between stem-loop and intermolecular duplex is to vary nucleotide pairs in the stem of the stem-loop of a DR. For example, in one embodiment, a G-C pair is replaced by an A-U or U-A pair. In another embodiment, an A-U pair is substituted for a G-C or a C-G pair. In another embodiment, a naturally occurring nucleotide is replaced by a nucleotide analog. Another way to modulate stem-loop formation or change the equilibrium between stem-loop and intermolecular duplex is to modify the loop of the stem-loop of a DR. Without be bound by theory, the loop can be viewed as an intervening sequence flanked by two sequences that are complementary to each other. When that intervening sequence is not self-complementary, its effect will be to destabilize intermolecular duplex formation. The same principle applies when guides are multiplexed: while the targeting sequences may differ, it may be advantageous to modify the stem-loop region in the DRs of the different guides. Moreover, when guides are multiplexed, the relative activities of the different guides can be modulated by balancing the activity of each individual guide. In certain embodiments, the equilibrium between intermolecular stem-loops vs. intermolecular duplexes is determined. The determination may be made by physical or biochemical means and can be in the presence or absence of a CRISPR effector.

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

In general, the CRISPR-Cas, CRISPR-Cas9 or CRISPR system may be as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, in particular a Cas9 gene in the case of CRISPR-Cas9, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

Multiplexing Polynucleotides

Provided herein are engineered polynucleotide sequences that can direct the activity of a CRISPR protein to multiple targets using a single crRNA. The engineered polynucleotide sequences, also referred to as a multiplexing polynucleotides, can include two or more direct repeats interspersed with two or more guide sequences. More specifically, the engineered polynucleotide sequences can include a direct repeat sequence having one or more mutations relative to the corresponding wild type direct repeat sequence. The engineered polynucleotide can be configured, for example, as: 5' DR1-G1-DR2-G2 3'. In some embodiments, the engineered polynucleotide can be configured to include three, four, five, or more additional direct repeat and guide sequences, for example: 5' DR1-G1-DR2-G2-DR3-G3 3', 5" DR1-G1-DR2-G2-DR3-G3-DR4-G4 3', or 5' DR1-G1-DR2-G2-DR3-G3-DR4-G4-DR5-G5 3'.

Regardless of the number of direct repeat sequences, the direct repeat sequences differ from one another. Thus, DR1 can be a wild type sequence and DR2 can include one or more mutations relative to the wild type sequence in accordance with the disclosure provided herein regarding direct repeats for Cas orthologs. The guide sequences can also be the same or different. In some embodiments, the guide sequences can bind to different nucleic acid targets, for example, nucleic acids encoding different polypeptides. The multiplexing polynucleotides can be as described, for example, at [0039]-[0072] in U.S. Application 62/780,748 entitled "CRISPR Cpf1 Direct Repeat Variants" and filed Dec. 17, 2018, incorporated herein in its entirety by reference.

Multiplex design of guide molecules for the detection of coronaviruses and/or other respiratory viruses in a sample to identify the cause of a respiratory infection is envisioned, and design can be according to the methods disclosed herein. Briefly, the design of guide molecules can encompass utilization of training models described herein using a variety of input features, which may include the particular Cas protein used for targeting of the sequences of interest. See U.S. Provisional Application 62/818,702 FIG. 4A, incorporated specifically by reference. Guide molecules can be designed as detailed elsewhere herein. Regarding detection of coronavirus, guide design can be predicated on genome sequences disclosed in Tian et al, "Potent binding of 2019 novel coronavirus spike protein by a SARS coronavirus-specific human monoclonal antibody"; doi: 10.1101/2020.01.28.923011, incorporated by reference, which details human monoclonal antibody, CR3022 binding of the 2019-nCoV RBD (KD of 6.3 nM) or Sequences of the 2019-nCoV are available at GISAID accession no. EPI_ISL_402124 and EPI_ISL_402127-402130, and described in doi:10.1101/2020.01.22.914952, or EP_ISL_402119-402121 and EP_ISL_402123-402124; see also GenBank Accession No. MN908947.3. Guide design can target unique viral genomic regions of SARS-CoV-2 or conserved genomic regions across one or more viruses of the coronavirus family.

Guide Modifications

In certain embodiments, guides of the invention comprise non-naturally occurring nucleic acids and/or non-naturally occurring nucleotides and/or nucleotide analogs, and/or chemical modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, 2-thiouridine analogs, N6-methyladenosine analogs, or 2'-fluoro analogs. Further examples of modified bases include, but are not limited to, 2-aminopurine, 5-bromo-uridine, pseudouridine (Ψ), N1-methylpseudouridine (me1Ψ), 5-methoxyuridine (5moU), inosine, 7-methylguanosine. Examples of guide RNA chemical modifications include, without limitation, incorporation of 2'-O-methyl (M), 2'-O-methyl-3'-phosphorothioate (MS), phosphorothioate (PS), S-constrained ethyl(cEt), or 2'-O-methyl-3'-thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015; Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., Med Chem Comm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target DNA and one or more deoxyribonucleotides and/or nucleotide analogs in a region that binds to Cas9, Cpf1, or C2c1. In an embodiment of the invention, deoxyribonucleotides and/or nucleotide analogs are incorporated in engineered guide structures, such as, without limitation, 5' and/or 3' end, stem-loop regions, and the seed region. In certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl-3'-phosphorothioate (MS), S-constrained ethyl(cEt), or 2'-O-methyl-3'-thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles.

Such chemically modified guide can be used to identify or enrich cells generically edited by a CRISPR system (see Lee et al., eLife, 2017, 6:e25312, DOI:10.7554).

In certain embodiments, the CRISPR system as provided herein can make use of a crRNA or analogous polynucleotide comprising a guide sequence, wherein the polynucleotide is an RNA, a DNA or a mixture of RNA and DNA, and/or wherein the polynucleotide comprises one or more nucleotide analogs. The sequence can comprise any structure, including but not limited to a structure of a native crRNA, such as a bulge, a hairpin or a stem loop structure. In certain embodiments, the polynucleotide comprising the guide sequence forms a duplex with a second polynucleotide sequence which can be an RNA or a DNA sequence.

In certain embodiments, use is made of chemically modified guide RNAs. Examples of guide RNA chemical modifications include, without limitation, incorporation of 2'-O-methyl (M), 2'-O-methyl 3'phosphorothioate (MS), or 2'-O-methyl 3'thioPACE (MSP) at one or more terminal nucleotides. Such chemically modified guide RNAs can comprise increased stability and increased activity as compared to unmodified guide RNAs, though on-target vs. off-target specificity is not predictable. (See, Hendel, 2015, Nat Biotechnol. 33(9):985-9, doi: 10.1038/nbt.3290, published online 29 Jun. 2015). Chemically modified guide RNAs further include, without limitation, RNAs with phosphorothioate linkages and locked nucleic acid (LNA) nucleotides comprising a methylene bridge between the 2' and 4' carbons of the ribose ring.

In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 to 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target RNA may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5moU), inosine, 7-methylguanosine, 2'-O-methyl-3'-phosphorothioate (MS), S-constrained ethyl(cEt), phosphorothioate (PS), or 2'-O-methyl-3'-thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 or 10 nucleotides in the 3'-terminus are chemically modified. Such chemical modifications at the 3'-terminus of the Cpf1 CrRNA improve gene cutting efficiency (see Li, et al., Nature Biomedical Engineering, 2017, 1:0066). In a specific embodiment, 5 nucleotides in the 3'-terminus are replaced with 2'-fluoro analogues. In a specific embodiment, 10 nucleotides in the 3'-terminus are replaced with 2'-fluoro analogues. In a specific embodiment, 5 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the loop comprises 3, 4, or 5 nucleotides. In certain embodiments, the loop comprises the sequence of UCUU, UUUU, UAUU, or UGUU.

A guide sequence, and hence a nucleic acid-targeting guide RNA may be selected to target any target nucleic acid sequence. In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nuclear RNA (snoRNA), double stranded RNA (dsRNA), non coding RNA (ncRNA), long non-coding RNA (lncRNA), and small cytoplasmic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In certain embodiments, the spacer length of the guide RNA is less than 28 nucleotides. In certain embodiments, the spacer length of the guide RNA is at least 18 nucleotides and less than 28 nucleotides. In certain embodiments, the spacer length of the guide RNA is between 19 and 28 nucleotides. In certain embodiments, the spacer length of the guide RNA is between 19 and 25 nucleotides. In certain embodiments, the spacer length of the guide RNA is 20 nucleotides. In certain embodiments, the spacer length of the guide RNA is 23 nucleotides. In certain embodiments, the spacer length of the guide RNA is 25 nucleotides.

In certain embodiments, modulations of cleavage efficiency can be exploited by introduction of mismatches, e.g. 1 or more mismatches, such as 1 or 2 mismatches between spacer sequence and target sequence, including the position of the mismatch along the spacer/target. The more central (i.e. not 3' or 5') for instance a double mismatch is, the more cleavage efficiency is affected. Accordingly, by choosing mismatch position along the spacer, cleavage efficiency can be modulated. By means of example, if less than 100% cleavage of targets is desired (e.g. in a cell population), 1 or more, such as preferably 2 mismatches between spacer and target sequence may be introduced in the spacer sequences. The more central along the spacer of the mismatch position, the lower the cleavage percentage.

In certain example embodiments, the cleavage efficiency may be exploited to design single guides that can distinguish two or more targets that vary by a single nucleotide, such as a single nucleotide polymorphism (SNP), variation, or (point) mutation. The CRISPR effector may have reduced sensitivity to SNPs (or other single nucleotide variations) and continue to cleave SNP targets with a certain level of efficiency. Thus, for two targets, or a set of targets, a guide RNA may be designed with a nucleotide sequence that is complementary to one of the targets i.e. the on-target SNP. The guide RNA is further designed to have a synthetic mismatch. As used herein a "synthetic mismatch" refers to a non-naturally occurring mismatch that is introduced upstream or downstream of the naturally occurring SNP, such as at most 5 nucleotides upstream or downstream, for instance 4, 3, 2, or 1 nucleotide upstream or downstream, preferably at most 3 nucleotides upstream or downstream, more preferably at most 2 nucleotides upstream or downstream, most preferably 1 nucleotide upstream or downstream (i.e. adjacent the SNP). When the CRISPR effector binds to the on-target SNP, only a single mismatch will be formed with the synthetic mismatch and the CRISPR effector will continue to be activated and a detectable signal produced. When the guide RNA hybridizes to an off-target SNP, two mismatches will be formed, the mismatch from the SNP and the synthetic mismatch, and no detectable signal generated. Thus, the systems disclosed herein may be designed to distinguish SNPs within a population. For, example the systems may be used to distinguish pathogenic strains that differ by a single SNP or detect certain disease specific SNPs, such as but not limited to, disease associated SNPs, such as without limitation cancer associated SNPs.

In certain embodiments, the guide RNA is designed such that the SNP is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the SNP is located on position 1, 2, 3, 4, 5, 6, 7, 8, or 9 of the spacer sequence (starting at the 5' end). In certain embodiments, the guide RNA is designed such that the SNP is located on position 2, 3, 4, 5, 6, or 7 of the spacer sequence (starting at the 5' end). In certain embodiments, the guide RNA is designed such that the SNP is located on position 3, 4, 5, or 6 of the spacer sequence (starting at the 5' end). In certain embodiments, the guide RNA is designed such that the SNP is located on position 3 of the spacer sequence (starting at the 5' end).

In certain embodiments, the guide RNA is designed such that the mismatch (e.g. the synthetic mismatch, i.e. an additional mutation besides a SNP) is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the mismatch is located on position 1, 2, 3, 4, 5, 6, 7, 8, or 9 of the spacer sequence (starting at the 5' end). In certain embodiments, the guide RNA is designed such that the mismatch is located on position 4, 5, 6, or 7 of the spacer sequence (starting at the 5' end. In certain embodiments, the guide RNA is designed such that the mismatch is located at position 3, 4, 5, or 6 of the spacer, preferably position 3. In certain embodiments, the guide RNA is designed such that the mismatch is located on position 5 of the spacer sequence (starting at the 5' end).

In certain embodiments, said mismatch is 1, 2, 3, 4, or 5 nucleotides upstream or downstream, preferably 2 nucleotides, preferably downstream of said SNP or other single nucleotide variation in said guide RNA.

In certain embodiments, the guide RNA is designed such that the mismatch is located 2 nucleotides upstream of the SNP (i.e. one intervening nucleotide).

In certain embodiments, the guide RNA is designed such that the mismatch is located 2 nucleotides downstream of the SNP (i.e. one intervening nucleotide).

In certain embodiments, the guide RNA is designed such that the mismatch is located on position 5 of the spacer sequence (starting at the 5' end) and the SNP is located on position 3 of the spacer sequence (starting at the 5' end).

In certain embodiments, the guide RNA comprises a spacer which is truncated relative to a wild type spacer. In certain embodiments, the guide RNA comprises a spacer which comprises less than 28 nucleotides, preferably between and including 20 to 27 nucleotides.

In certain embodiments, the guide RNA comprises a spacer which consists of 20-25 nucleotides or 20-23 nucleotides, such as preferably 20 or 23 nucleotides.

In certain embodiments, the one or more guide RNAs are designed to detect a single nucleotide polymorphism in a target RNA or DNA, or a splice variant of an RNA transcript.

In certain embodiments, the one or more guide RNAs may be designed to bind to one or more target molecules that are diagnostic for a disease state. In some embodiments, the disease may be cancer. In some embodiments, the disease state may be an autoimmune disease. In some embodiments, the disease state may be an infection. In some embodiments, the infection may be caused by a virus, a bacterium, a fungus, a protozoa, or a parasite. In specific embodiments, the infection is a viral infection. In specific embodiments, the viral infection is caused by a DNA virus.

The embodiments described herein comprehend inducing one or more nucleotide modifications in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s). The mutations can include the introduction, deletion, or substitution of 1-75 nucleotides at each target sequence of said cell(s) via the guide(s) RNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 40, 45, 50, 75, 100, 200, 300, 400 or 500 nucleotides at each target sequence of said cell(s) via the guide(s) RNA(s).

Typically, in the context of an endogenous CRISPR system, formation of a CRISPR complex (comprising a guide sequence hybridized to a target sequence and complexed with one or more Cas proteins) results in cleavage in or near (e.g. within 1, 2, 3, 4, 5, 6, 7, 8, 9, 10, 20, 50, or more base pairs from) the target sequence, but may depend on for instance secondary structure, in particular in the case of RNA targets.

Methods for Designing Highly Active Guides

A method for designing highly active guide molecules, e.g., guide RNAs, for use in the detection systems may comprise the steps of designing putative guide RNAs tiled across a target molecule of interest; creating a training model based on results of incubating guide RNAs with a Cas13 protein and the target molecule; predicting highly active guide RNAs for the target molecule, wherein the predicting comprises optimizing the nucleotide at each base position in the guide RNA based on the training model; and validating the predicted highly active guide RNAs by incubating the guide RNAs with the Cas13 protein and the target molecule. The method can be as described in U.S. Provisional Application Nos. 62/818,702 and 62/890,555 incorporated by reference in their entirety. Guide RNAs generate by the design methods can be used with the systems for detecting coronavirus as described elsewhere herein.

In some embodiments, the invention provides a method for designing guide RNAs for use in the detection systems described herein. The method may comprise designing putative guide RNAs tiled across a target molecule of interest, such as a coronavirus, viruses that cause respiratory illness, including coronavirus, including 2019-nCov (Covid-19). The method may further comprise creating a training model based on results of incubating guide RNAs with a Cas13 protein and the target molecule. The method may further comprise predicting highly active guide RNAs for the target molecule. Predicting may comprise optimizing the nucleotide at each base position in the guide RNA based on the training model. The method may further comprise validating the predicted highly active guide RNAs by incubating the guide RNAs with the Cas13 protein and the target molecule.

In certain instances, the optimized guide for the target molecule is generated by pooling a set of guides, the guides produced by tiling guides across the target molecule; incubating the set of guides with a Cas polypeptide and the target molecule and measuring cleavage activity of each guide in the set; creating a training model based on the cleavage activity of the set of guides in the incubating step. Steps of predicting highly active guides for the target molecule and identifying the optimized guides by incubating the predicted highly active guides with the Cas polypeptide and the target molecule and selecting optimized guides may also be utilized in generating optimized guides. In embodiments, the training model comprises one or more input features selected from guide sequence, flanking target sequence, normalized positions of the guide in the target and guide GC content. In certain instances, the guide sequence and/or flanking sequence input comprises one hit encoding mononucleotide and/or dinucleotide In an embodiments, the training model comprises applying logistic regression model on the activity of the guides across the one or more input features.

In an aspect, the predicting highly active guides for the target molecule comprises selecting guides with an increase in activity of a guide relative to the median activity, or selecting guides with highest guide activity. In certain instances, the increase in activity is measured by an increase in fluorescence. Guides may be selected based on a particular cutoff, in certain instances based on activity relative to a median or above a particular cutoff-, for instance, are selected with a 1.5, 2, 2.5 or 3-fold activity relative to median, or are in the top quartile or quintile for each target tested.

The optimized guides may be generated for a Cas13 ortholog, in some instances, the optimized guide is generated for an LwaCas13a or a Cca13b ortholog.

In some embodiments, the invention provides a method for designing guide RNAs for use in the detection systems described herein. The method may comprise designing putative guide RNAs tiled across a target molecule of interest. The method may further comprise creating a training model based on results of incubating guide RNAs with a Cas13 protein and the target molecule. The method may further comprise predicting highly active guide RNAs for the target molecule. Predicting may comprise optimizing the nucleotide at each base position in the guide RNA based on the training model. The method may further comprise validating the predicted highly active guide RNAs by incubating the guide RNAs with the Cas13 protein and the target molecule.

Guides may be screened for on-target and off-target effects. When using LAMP amplification, the products of LAMP can help identify those guides with more minimal off-target effects relative to on-target products.

The design of putative guide RNAs for target molecules of interest is described elsewhere herein.

The creation of training models is known in the art. Machine learning can be generalized as the ability of a learning machine to perform accurately on new, unseen examples/tasks after having experienced a learning data set. Machine learning may include the following concepts and methods. Supervised learning concepts may include AODE; Artificial neural network, such as Backpropagation, Autoencoders, Hopfield networks, Boltzmann machines, Restricted Boltzmann Machines, and Spiking neural networks; Bayesian statistics, such as Bayesian network and Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor Algorithm and Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, Support vector machines; Quadratic classifiers; k-nearest neighbor; Boosting; Decision trees, such as C4.5, Random forests, ID3, CART, SLIQ, SPRINT; Bayesian networks, such as Naive Bayes; and Hidden Markov models. Unsupervised learning concepts may include; Expectation-maximization algorithm; Vector Quantization; Generative topographic map; Information bottleneck method; Artificial neural network, such as Self-organizing map; Association rule learning, such as, Apriori algorithm, Eclat algorithm, and FP-growth algorithm; Hierarchical clustering, such as Single-linkage clustering and Conceptual clustering; Cluster analysis, such as, K-means algorithm, Fuzzy clustering, DBSCAN, and OPTICS algorithm; and Outlier Detection, such as Local Outlier Factor. Semi-supervised learning concepts may include; Generative models; Low-density separation; Graph-based methods; and Co-training. Reinforcement learning concepts may include; Temporal difference learning; Q-learning; Learning Automata; and SARSA. Deep learning concepts may include; Deep belief networks; Deep Boltzmann machines; Deep Convolutional neural networks; Deep Recurrent neural networks; and Hierarchical temporal memory.

The methods as disclosed herein designing putative guide RNAs may comprise design based on one or more variables, including guide sequence, flanking target sequence, guide position and guide GC content as input features. In certain embodiments, the length of the flanking target region can be considered a free parameter and can be further selected during cross-validation. Additionally, mono-nucleotide and/or dinucleotide based identities across a guide length and flanking sequence in the target, varying one or more of flanking sequence length, normalized positions of the guide in the target, and GC content of the guide, or a combination thereof.

In embodiments, the training model for the guide design of highly active guides is Cas protein specific. In embodiments, the Cas protein is a Cas13a, Cas13b, a Cas12a and/or a Cas12b protein. In certain embodiments, the protein is LwaCas13a or CcaCas13b. Selection for the best guides can be dependent on each enzyme. In particular embodiments, where majority of guides have activity above background on a per-target basis, selection of guides may be based on 1.5 fold, 2, 2.5, 3 or more fold activity over the median activity. In other instances, the best performing guides may be at or near background fluorescence. In this instance, the guide selection may be based on a top percentile, e.g. quartile or quintile, of performing guides.

Codon optimization is described elsewhere herein. In specific embodiments, the nucleotide at each base position in the guide RNA may be optimized based on the training model, thus allowing for prediction of highly active guide RNAs for the target molecule.

The predicted highly active guide RNAs may then be validated or verified by incubating the guide RNAs with a Cas effector protein, such as Cas13 protein and the target molecule(s) for coronavirus, for example coronavirus sequence that is immunostimulatory to a host immune system, or a target sequence unique to the 2019-nCov, as described elsewhere herein.

In certain embodiments, optimization comprises validation of best performing models for a particular Cas polypeptide across multiple guides may comprise comparing the predicted score of each guide versus actual collateral activity upon target recognition. In embodiments, kinetic data of the best and worst predicted guides are evaluated. In embodiments, lateral flow performance of the predicted guides is evaluated for a target sequence.

In an aspect, the guide sequence is selected from SEQ ID NO: 40,500-61,643.

Detection Construct

The systems and methods described herein comprise a detection construct. As used herein, a "detection construct" refers to a molecule that can be cleaved or otherwise deactivated by an activated CRISPR system effector protein described herein. The term "detection construct" may also be referred to in the alternative as a "masking construct." Depending on the nuclease activity of the CRISPR effector protein, the masking construct may be an RNA-based masking construct or a DNA-based masking construct. The Nucleic Acid-based masking constructs comprises a nucleic acid element that is cleavable by a CRISPR effector protein. Cleavage of the nucleic acid element releases agents or produces conformational changes that allow a detectable signal to be produced. Example constructs demonstrating how the nucleic acid element may be used to prevent or mask generation of detectable signal are described below and embodiments of the invention comprise variants of the same. Prior to cleavage, or when the masking construct is in an 'active' state, the masking construct blocks the generation or detection of a positive detectable signal. In certain embodiments, detection constructs are designed for cutting motifs of particular Cas proteins. See, International Publication WO 2019/126577, incorporated herein by reference in its entirety, specifically, paragraphs [00314]-[00356], Table 25, and Examples 8-10, for teaching of design of detection constructs for Cas proteins with preferred cutting motifs. For example, when AapCas12b is used, a reporter designed with A and T bases can be utilized because of preferred cleavage specificity. In an aspect, a reporter comprising sequence TTTTTTT is utilized with AapCas12b systems.

It will be understood that in certain example embodiments a minimal background signal may be produced in the presence of an active masking construct. A positive detectable signal may be any signal that can be detected using optical, fluorescent, chemiluminescent, electrochemical or other detection methods known in the art. The term "positive detectable signal" is used to differentiate from other detectable signals that may be detectable in the presence of the masking construct. For example, in certain embodiments a first signal may be detected when the masking agent is present or when a CRISPR system has not been activated (i.e. a negative detectable signal), which then converts to a second signal (e.g. the positive detectable signal) upon detection of the target molecules and cleavage or deactivation of the masking agent, or upon activation of the CRISPR effector protein. The positive detectable signal, then, is a signal detected upon activation of the CRISPR effector protein, and may be, in a colorimetric or fluorescent assay, a decrease in fluorescence or color relative to a control or an increase in fluorescence or color relative to a control, depending on the configuration of the lateral flow substrate, and as described further herein.

In certain example embodiments, the masking construct may comprise a HCR initiator sequence and a cutting motif, or a cleavable structural element, such as a loop or hairpin, that prevents the initiator from initiating the HCR reaction. The cutting motif may be preferentially cut by one of the activated CRISPR effector proteins. Upon cleavage of the cutting motif or structure element by an activated CRISPR effector protein, the initiator is then released to trigger the HCR reaction, detection thereof indicating the presence of one or more targets in the sample. In certain example embodiments, the masking construct comprises a hairpin with a RNA loop. When an activated CRISPR effector protein cuts the RNA loop, the initiator can be released to trigger the HCR reaction.

In certain example embodiments, the masking construct may suppress generation of a gene product. The gene product may be encoded by a reporter construct that is added to the sample. The masking construct may be an interfering RNA involved in a RNA interference pathway, such as a short hairpin RNA (shRNA) or small interfering RNA (siRNA). The masking construct may also comprise microRNA (miRNA). While present, the masking construct suppresses expression of the gene product. The gene product may be a fluorescent protein or other RNA transcript or proteins that would otherwise be detectable by a labeled probe, aptamer, or antibody but for the presence of the masking construct. Upon activation of the effector protein the masking construct is cleaved or otherwise silenced allowing for expression and detection of the gene product as the positive detectable signal. In preferred embodiments, the masking constructs comprise two or more detectable signals, for example, fluorescent signals, that can be read on different channels of a fluorimeter.

In specific embodiments, the masking construct comprises a silencing RNA that suppresses generation of a gene product encoded by a reporting construct, wherein the gene product generates the detectable positive signal when expressed.

In certain example embodiments, the masking construct may sequester one or more reagents needed to generate a detectable positive signal such that release of the one or more reagents from the masking construct results in generation of the detectable positive signal. The one or more reagents may combine to produce a colorimetric signal, a chemiluminescent signal, a fluorescent signal, or any other detectable signal and may comprise any reagents known to be suitable for such purposes. In certain example embodiments, the one or more reagents are sequestered by RNA aptamers that bind the one or more reagents. The one or more reagents are released when the effector protein is activated upon detection of a target molecule and the RNA or DNA aptamers are degraded.

In certain example embodiments, the masking construct may be immobilized on a solid substrate in an individual discrete volume (defined further below) and sequesters a single reagent. For example, the reagent may be a bead comprising a dye. When sequestered by the immobilized reagent, the individual beads are too diffuse to generate a detectable signal, but upon release from the masking construct are able to generate a detectable signal, for example by aggregation or simple increase in solution concentration. In certain example embodiments, the immobilized masking agent is a RNA- or DNA-based aptamer that can be cleaved by the activated effector protein upon detection of a target molecule.

In certain other example embodiments, the masking construct binds to an immobilized reagent in solution thereby blocking the ability of the reagent to bind to a separate labeled binding partner that is free in solution. Thus, upon application of a washing step to a sample, the labeled binding partner can be washed out of the sample in the absence of a target molecule. However, if the effector protein is activated, the masking construct is cleaved to a degree sufficient to interfere with the ability of the masking construct to bind the reagent thereby allowing the labeled binding partner to bind to the immobilized reagent. Thus, the labeled binding partner remains after the wash step indicating the presence of the target molecule in the sample. In certain aspects, the masking construct that binds the immobilized reagent is a DNA or RNA aptamer. The immobilized reagent may be a protein and the labeled binding partner may be a labeled antibody. Alternatively, the immobilized reagent may be streptavidin and the labeled binding partner may be labeled biotin. The label on the binding partner used in the above embodiments may be any detectable label known in the art. In addition, other known binding partners may be used in accordance with the overall design described herein.

In certain example embodiments, the masking construct may comprise a ribozyme. Ribozymes are RNA molecules having catalytic properties. Ribozymes, both naturally and engineered, comprise or consist of RNA that may be targeted by the effector proteins disclosed herein. The ribozyme may be selected or engineered to catalyze a reaction that either generates a negative detectable signal or prevents generation of a positive control signal. Upon deactivation of the ribozyme by the activated effector protein the reaction generating a negative control signal, or preventing generation of a positive detectable signal, is removed thereby allowing a positive detectable signal to be generated. In one example embodiment, the ribozyme may catalyze a colorimetric reaction causing a solution to appear as a first color. When the ribozyme is deactivated the solution then turns to a second color, the second color being the detectable positive signal. An example of how ribozymes can be used to catalyze a colorimetric reaction are described in Zhao et al. "Signal amplification of glucosamine-6-phosphate based on ribozyme glmS," Biosens Bioelectron. 2014; 16:337-42, and provide an example of how such a system could be modified to work in the context of the embodiments disclosed herein. Alternatively, ribozymes, when present can generate cleavage products of, for example, RNA transcripts. Thus, detection of a positive detectable signal may comprise detection of non-cleaved RNA transcripts that are only generated in the absence of the ribozyme.

In some embodiments, the masking construct may be a ribozyme that generates a negative detectable signal, and wherein a positive detectable signal is generated when the ribozyme is deactivated.

In certain example embodiments, the one or more reagents is a protein, such as an enzyme, capable of facilitating generation of a detectable signal, such as a colorimetric, chemiluminescent, or fluorescent signal, that is inhibited or sequestered such that the protein cannot generate the detectable signal by the binding of one or more DNA or RNA aptamers to the protein. Upon activation of the effector proteins disclosed herein, the DNA or RNA aptamers are cleaved or degraded to an extent that they no longer inhibit the protein's ability to generate the detectable signal. In certain example embodiments, the aptamer is a thrombin inhibitor aptamer. In certain example embodiments the thrombin inhibitor aptamer has a sequence of GGGAACAAAGCUGAAGUACUUACCC (SEQ ID NO:XX). When this aptamer is cleaved, thrombin will become active and will cleave a peptide colorimetric or fluorescent substrate. In certain example embodiments, the colorimetric substrate is para-nitroanilide (pNA) covalently linked to the peptide substrate for thrombin. Upon cleavage by thrombin, pNA is released and becomes yellow in color and easily visible to the eye. In certain example embodiments, the fluorescent substrate is 7-amino-4-methylcoumarin a blue fluorophore that can be detected using a fluorescence detector. Inhibitory aptamers may also be used for horseradish peroxidase (HRP), beta-galactosidase, or calf alkaline phosphatase (CAP) and within the general principals laid out above.

In certain embodiments, RNAse or DNAse activity is detected colorimetrically via cleavage of enzyme-inhibiting aptamers. One potential mode of converting DNAse or RNAse activity into a colorimetric signal is to couple the cleavage of a DNA or RNA aptamer with the re-activation of an enzyme that is capable of producing a colorimetric output. In the absence of RNA or DNA cleavage, the intact aptamer will bind to the enzyme target and inhibit its activity. The advantage of this readout system is that the enzyme provides an additional amplification step: once liberated from an aptamer via collateral activity (e.g. Cpf1 collateral activity), the colorimetric enzyme will continue to produce colorimetric product, leading to a multiplication of signal.

In certain embodiments, an existing aptamer that inhibits an enzyme with a colorimetric readout is used. Several aptamer/enzyme pairs with colorimetric readouts exist, such as thrombin, protein C, neutrophil elastase, and subtilisin. These proteases have colorimetric substrates based upon pNA and are commercially available. In certain embodiments, a novel aptamer targeting a common colorimetric enzyme is used. Common and robust enzymes, such as beta-galactosidase, horseradish peroxidase, or calf intestinal alkaline phosphatase, could be targeted by engineered aptamers designed by selection strategies such as SELEX. Such strategies allow for quick selection of aptamers with nanomolar binding efficiencies and could be used for the development of additional enzyme/aptamer pairs for colorimetric readout.

In certain embodiments, the masking construct may be a DNA or RNA aptamer and/or may comprise a DNA or RNA-tethered inhibitor.

In certain embodiments, the masking construct may comprise a DNA or RNA oligonucleotide to which a detectable ligand and a masking component are attached.

In certain embodiments, RNAse or DNase activity is detected colorimetrically via cleavage of RNA-tethered inhibitors. Many common colorimetric enzymes have competitive, reversible inhibitors: for example, beta-galactosidase can be inhibited by galactose. Many of these inhibitors are weak, but their effect can be increased by increases in local concentration. By linking local concentration of inhibitors to DNase RNAse activity, colorimetric enzyme and inhibitor pairs can be engineered into DNase and RNAse sensors. The colorimetric DNase or RNAse sensor based upon small-molecule inhibitors involves three components: the colorimetric enzyme, the inhibitor, and a bridging RNA or DNA that is covalently linked to both the inhibitor and enzyme, tethering the inhibitor to the enzyme. In the uncleaved configuration, the enzyme is inhibited by the increased local concentration of the small molecule; when the DNA or RNA is cleaved (e.g. by Cas13 or Cas12 collateral cleavage), the inhibitor will be released and the colorimetric enzyme will be activated.

In certain embodiments, the aptamer or DNA- or RNA-tethered inhibitor may sequester an enzyme, wherein the enzyme generates a detectable signal upon release from the aptamer or DNA or RNA tethered inhibitor by acting upon a substrate. In some embodiments, the aptamer may be an inhibitor aptamer that inhibits an enzyme and prevents the enzyme from catalyzing generation of a detectable signal from a substance. In some embodiments, the DNA- or RNA-tethered inhibitor may inhibit an enzyme and may prevent the enzyme from catalyzing generation of a detectable signal from a substrate.

In certain embodiments, RNAse activity is detected colorimetrically via formation and/or activation of G-quadruplexes. G quadruplexes in DNA can complex with heme (iron (III)-protoporphyrin IX) to form a DNAzyme with peroxidase activity. When supplied with a peroxidase substrate (e.g. ABTS: (2,2'-Azinobis [3-ethylbenzothiazoline-6-sulfonic acid]-diammonium salt)), the G-quadruplex-heme complex in the presence of hydrogen peroxide causes oxidation of the substrate, which then forms a green color in solution. An example G-quadruplex forming DNA sequence is: GGGTAGGGCGGGTTGGGA (SEQ ID NO:311). By hybridizing an additional DNA or RNA sequence, referred to herein as a "staple," to this DNA aptamer, formation of the G-quadraplex structure will be limited. Upon collateral activation, the staple will be cleaved allowing the G quadraplex to form and heme to bind. This strategy is particularly appealing because color formation is enzymatic, meaning there is additional amplification beyond collateral activation.

In certain embodiments, the masking construct may comprise an RNA oligonucleotide designed to bind a G-quadruplex forming sequence, wherein a G-quadruplex structure is formed by the G-quadruplex forming sequence upon cleavage of the masking construct, and wherein the G-quadruplex structure generates a detectable positive signal.

In certain example embodiments, the masking construct may be immobilized on a solid substrate in an individual discrete volume (defined further below) and sequesters a single reagent. For example, the reagent may be a bead comprising a dye. When sequestered by the immobilized reagent, the individual beads are too diffuse to generate a detectable signal, but upon release from the masking construct are able to generate a detectable signal, for example by aggregation or simple increase in solution concentration. In certain example embodiments, the immobilized masking agent is a DNA- or RNA-based aptamer that can be cleaved by the activated effector protein upon detection of a target molecule.

In one example embodiment, the masking construct comprises a detection agent that changes color depending on whether the detection agent is aggregated or dispersed in solution. For example, certain nanoparticles, such as colloidal gold, undergo a visible purple to red color shift as they move from aggregates to dispersed particles. Accordingly, in certain example embodiments, such detection agents may be held in aggregate by one or more bridge molecules. At least a portion of the bridge molecule comprises RNA or DNA. Upon activation of the effector proteins disclosed herein, the RNA or DNA portion of the bridge molecule is cleaved allowing the detection agent to disperse and resulting in the corresponding change in color. In certain example embodiments, the detection agent is a colloidal metal. The colloidal metal material may include water-insoluble metal particles or metallic compounds dispersed in a liquid, a hydrosol, or a metal sol. The colloidal metal may be selected from the metals in groups IA, IB, IIB and IIIB of the periodic table, as well as the transition metals, especially those of group VIII. Preferred metals include gold, silver, aluminum, ruthenium, zinc, iron, nickel and calcium. Other suitable metals also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form, derived from an appropriate metal compound, for example the Al3+, Ru3+, Zn2+, Fe3+, Ni2+ and Ca2+ ions.

When the RNA or DNA bridge is cut by the activated CRISPR effector, the aforementioned color shift is observed. In certain example embodiments the particles are colloidal metals. In certain other example embodiments, the colloidal metal is a colloidal gold. In certain example embodiments, the colloidal nanoparticles are 15 nm gold nanoparticles (AuNPs). Due to the unique surface properties of colloidal gold nanoparticles, maximal absorbance is observed at 520 nm when fully dispersed in solution and appear red in color to the naked eye. Upon aggregation of AuNPs, they exhibit a red-shift in maximal absorbance and appear darker in color, eventually precipitating from solution as a dark purple aggregate. In certain example embodiments the nanoparticles are modified to include DNA linkers extending from the surface of the nanoparticle. Individual particles are linked together by single-stranded RNA (ssRNA) or single-stranded DNA bridges that hybridize on each end to at least a portion of the DNA linkers. Thus, the nanoparticles will form a web of linked particles and aggregate, appearing as a dark precipitate. Upon activation of the CRISPR effectors disclosed herein, the ssRNA or ssDNA bridge will be cleaved, releasing the AU NPS from the linked mesh and producing a visible red color. Example DNA linkers and bridge sequences are listed below. Thiol linkers on the end of the DNA linkers may be used for surface conjugation to the AuNPS. Other forms of conjugation may be used. In certain example embodiments, two populations of AuNPs may be generated, one for each DNA linker. This will help facilitate proper binding of the ssRNA bridge with proper orientation. In certain example embodiments, a first DNA linker is conjugated by the 3' end while a second DNA linker is conjugated by the 5' end.

In certain other example embodiments, the masking construct may comprise an RNA or DNA oligonucleotide to which are attached a detectable label and a masking agent of that detectable label. An example of such a detectable label/masking agent pair is a fluorophore and a quencher of the fluorophore. Quenching of the fluorophore can occur as a result of the formation of a non-fluorescent complex between the fluorophore and another fluorophore or non-fluorescent molecule. This mechanism is known as ground-state complex formation, static quenching, or contact quenching. Accordingly, the RNA or DNA oligonucleotide may be designed so that the fluorophore and quencher are in sufficient proximity for contact quenching to occur. Fluorophores and their cognate quenchers are known in the art and can be selected for this purpose by one having ordinary skill in the art. The particular fluorophore/quencher pair is not critical in the context of this invention, only that selection of the fluorophore/quencher pairs ensures masking of the fluorophore. Upon activation of the effector proteins disclosed herein, the RNA or DNA oligonucleotide is cleaved thereby severing the proximity between the fluorophore and quencher needed to maintain the contact quenching effect. Accordingly, detection of the fluorophore may be used to determine the presence of a target molecule in a sample.

In certain other example embodiments, the masking construct may comprise one or more RNA oligonucleotides to which are attached one or more metal nanoparticles, such as gold nanoparticles. In some embodiments, the masking construct comprises a plurality of metal nanoparticles cross-linked by a plurality of RNA or DNA oligonucleotides forming a closed loop. In one embodiment, the masking construct comprises three gold nanoparticles crosslinked by three RNA or DNA oligonucleotides forming a closed loop. In some embodiments, the cleavage of the RNA or DNA oligonucleotides by the CRISPR effector protein leads to a detectable signal produced by the metal nanoparticles.

In certain other example embodiments, the masking construct may comprise one or more RNA or DNA oligonucleotides to which are attached one or more quantum dots. In some embodiments, the cleavage of the RNA or DNA oligonucleotides by the CRISPR effector protein leads to a detectable signal produced by the quantum dots.

In one example embodiment, the masking construct may comprise a quantum dot. The quantum dot may have multiple linker molecules attached to the surface. At least a portion of the linker molecule comprises RNA or DNA. The linker molecule is attached to the quantum dot at one end and to one or more quenchers along the length or at terminal ends of the linker such that the quenchers are maintained in sufficient proximity for quenching of the quantum dot to occur. The linker may be branched. As above, the quantum dot/quencher pair is not critical, only that selection of the quantum dot/quencher pair ensures masking of the fluorophore. Quantum dots and their cognate quenchers are known in the art and can be selected for this purpose by one having ordinary skill in the art. Upon activation of the effector proteins disclosed herein, the RNA or DNA portion of the linker molecule is cleaved thereby eliminating the proximity between the quantum dot and one or more quenchers needed to maintain the quenching effect. In certain example embodiments the quantum dot is streptavidin conjugated. RNA or DNA are attached via biotin linkers and recruit quenching molecules with the sequences /5Biosg/UCUCGUACGUUC/3IAbRQSp/ (SEQ ID NO:XX) or /5Biosg/UCUCGUACGUUCUCUCGUACGUUC/3IAbRQSp/ (SEQ ID NO:XX) where /5Biosg/ is a biotin tag and /3IAbRQSp/ is an Iowa black quencher (Iowa Black FQ). Upon cleavage, by the activated effectors disclosed herein the quantum dot will fluoresce visibly.

In specific embodiments, the detectable ligand may be a fluorophore and the masking component may be a quencher molecule.

In a similar fashion, fluorescence energy transfer (FRET) may be used to generate a detectable positive signal. FRET is a non-radiative process by which a photon from an energetically excited fluorophore (i.e. "donor fluorophore") raises the energy state of an electron in another molecule (i.e. "the acceptor") to higher vibrational levels of the excited singlet state. The donor fluorophore returns to the ground state without emitting a fluoresce characteristic of that fluorophore. The acceptor can be another fluorophore or non-fluorescent molecule. If the acceptor is a fluorophore, the transferred energy is emitted as fluorescence characteristic of that fluorophore. If the acceptor is a non-fluorescent molecule the absorbed energy is loss as heat. Thus, in the context of the embodiments disclosed herein, the fluorophore/quencher pair is replaced with a donor fluorophore/acceptor pair attached to the oligonucleotide molecule. When intact, the masking construct generates a first signal (negative detectable signal) as detected by the fluorescence or heat emitted from the acceptor. Upon activation of the effector proteins disclosed herein the RNA oligonucleotide is cleaved and FRET is disrupted such that fluorescence of the donor fluorophore is now detected (positive detectable signal).

In certain example embodiments, the masking construct comprises the use of intercalating dyes which change their absorbance in response to cleavage of long RNAs or DNAs to short nucleotides. Several such dyes exist. For example, pyronine-Y will complex with RNA and form a complex that has an absorbance at 572 nm. Cleavage of the RNA results in loss of absorbance and a color change. Methylene blue may be used in a similar fashion, with changes in absorbance at 688 nm upon RNA cleavage. Accordingly, in certain example embodiments the masking construct comprises a RNA and intercalating dye complex that changes absorbance upon the cleavage of RNA by the effector proteins disclosed herein.

In certain example embodiments, the masking construct may comprise an initiator for an HCR reaction. See e.g. Dirks and Pierce. PNAS 101, 15275-15728 (2004). HCR reactions utilize the potential energy in two hairpin species. When a single-stranded initiator having a portion of complementary to a corresponding region on one of the hairpins is released into the previously stable mixture, it opens a hairpin of one species. This process, in turn, exposes a single-stranded region that opens a hairpin of the other species. This process, in turn, exposes a single stranded region identical to the original initiator. The resulting chain reaction may lead to the formation of a nicked double helix that grows until the hairpin supply is exhausted. Detection of the resulting products may be done on a gel or colorimetrically. Example colorimetric detection methods include, for example, those disclosed in Lu et al. "Ultra-sensitive colorimetric assay system based on the hybridization chain reaction-triggered enzyme cascade amplification ACS Appl Mater Interfaces, 2017, 9(1):167-175, Wang et al. "An enzyme-free colorimetric assay using hybridization chain reaction amplification and split aptamers" Analyst 2015, 150, 7657-7662, and Song et al. "Non-covalent fluorescent labeling of hairpin DNA probe coupled with hybridization chain reaction for sensitive DNA detection." Applied Spectroscopy, 70(4): 686-694 (2016).

In certain example embodiments, the masking construct suppresses generation of a detectable positive signal until cleaved, or modified by an activated CRISPR effector protein. In some embodiments, the masking construct may suppress generation of a detectable positive signal by masking the detectable positive signal, or generating a detectable negative signal instead.

Devices for Detection Assays

In certain embodiments, the detection assay can be provided on a cartridge or chip. In an aspect, the cartridge can comprise one or more ampoules and one or more wells that are communicatively coupled, allowing for the transfer, exchange or movement of reagents and sample with or without the use of beads through the chambers of the cartridge and facilitating detection assays utilizing systems/devices for facilitating the detection assay on the cartridge.

Cartridge

The cartridge, also referred to herein as a chip, according to the present invention comprises a series of components of ampoules and chambers that are communicatively coupled with one or more other components on the cartridge. The coupling is typically a fluidic communication, for example, via channels. The cartridge may comprise a membrane that seals one or more of the chambers and/or ampoules. In an aspect, the membrane allows for storage of reagents, buffers and other solid or fluid components which cover and seal the cartridge. The membrane can be configured to be punctured, pierced or otherwise released from sealing or covering one or more components of the cartridge by a means for releasing reagents.

As noted above, certain embodiments enable the use of nucleic acid binding beads to concentrate target nucleic acid but that do not require elution of the isolated nucleic acid. Thus, in certain example embodiments, the cartridge may further comprise an activatable magnet, such as an electromagnet. A means for activating the magnet may be located on the device, or the means for supplying the magnet or activating the magnet on the cartridge may be provided by a second device, such as those disclosed in further detail below.

Figure 30A:
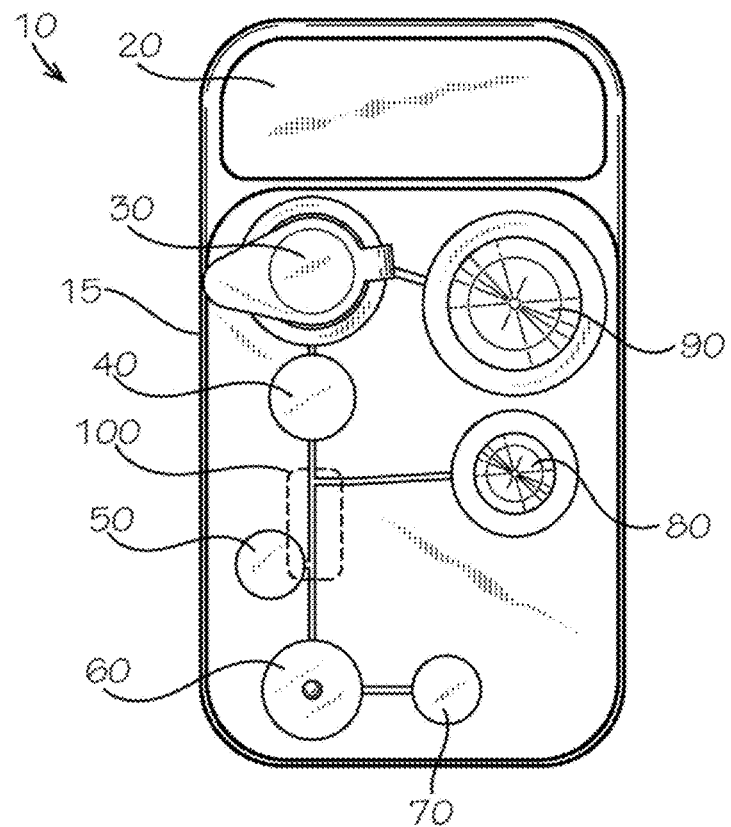
FIG. 30A-30B—shows the top view (FIG. 30A) and side view (FIG. 30B) of an exemplary cartridge (10) according to the invention.
Figure 30B:
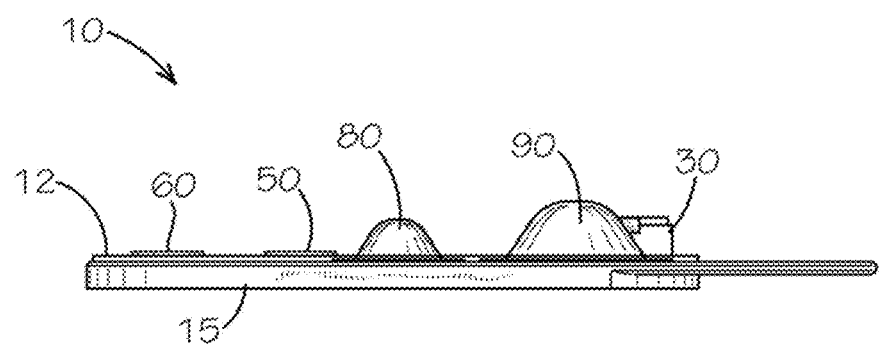
Figure 31A:
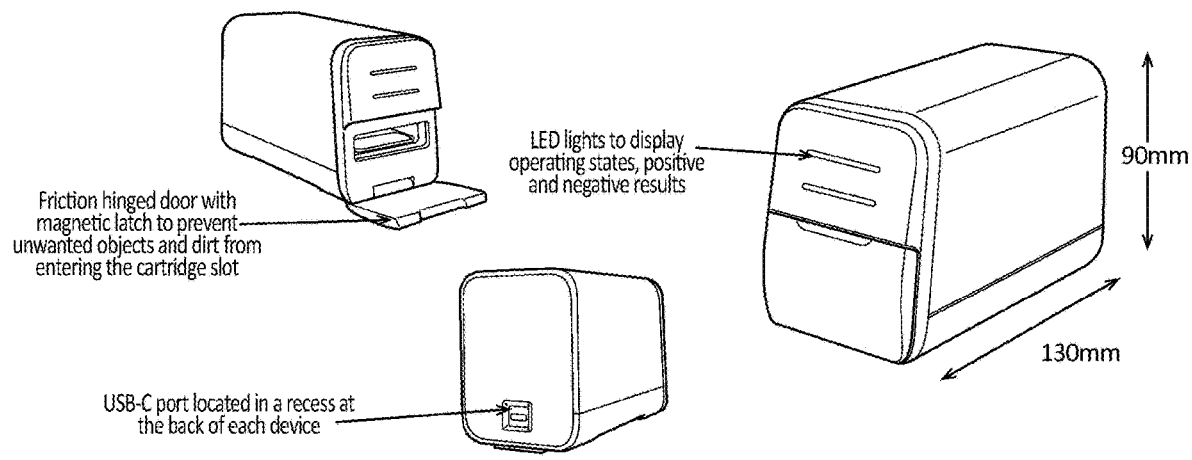
FIG. 31A-31C—FIG. 31A provides an exemplary front loading device, upper left shows a friction hinged door with magnetic latch to prevent unwanted objects and dirt from entering the cartridge slot, upper right, device showing use of LED lights to display operating states, positive and negative results; lower image depicts rear of device with USB-C port located in a recess.
Figure 31B:
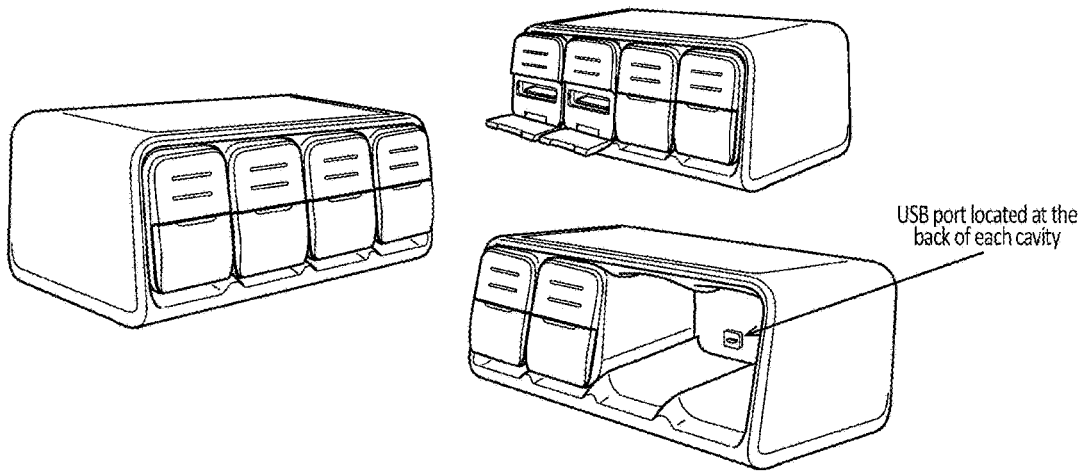
Figure 31C:
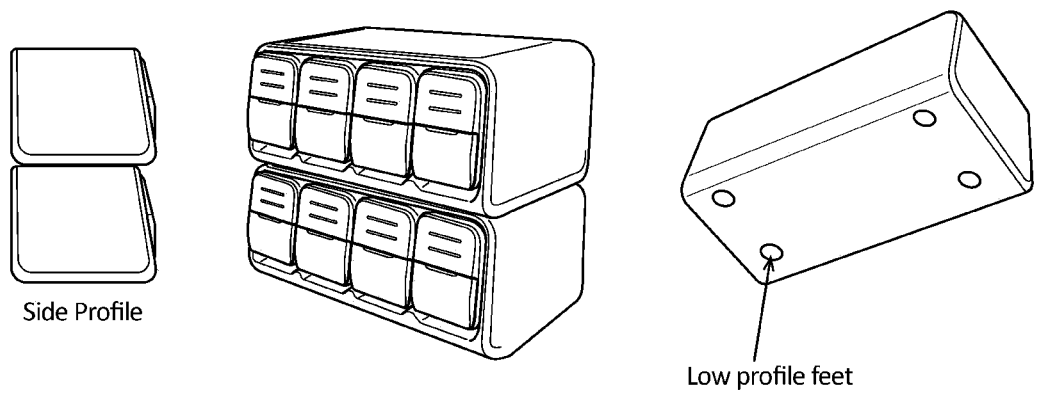
Figure 32:
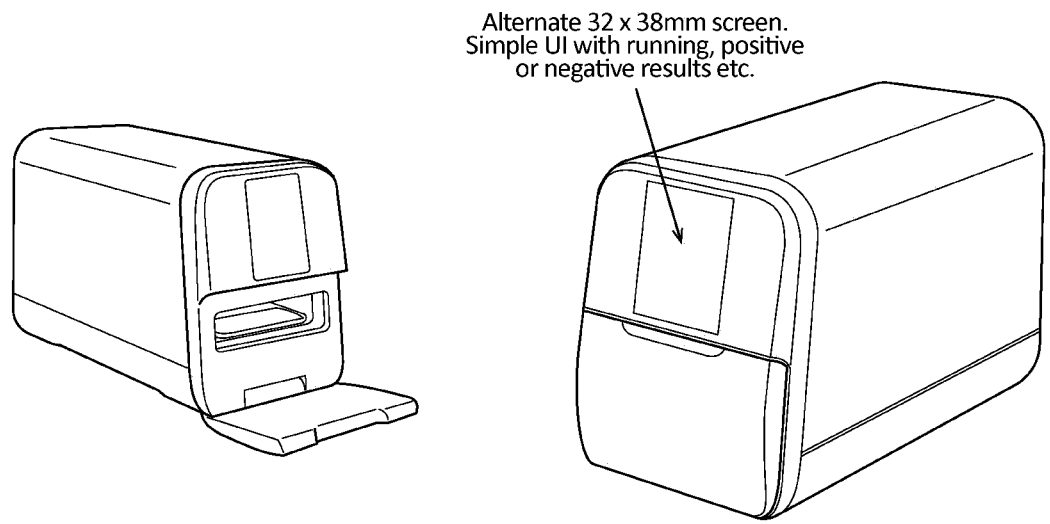
FIG. 32—shows alternate front-loading device with screen, left with front hinge open; right, with front hinge closed with alternate screen and simple user interface with running, positive, negative results r other display information FIG. 33—depicts front loading internal details, tope view (left) shows geared otor, optics and USB-C port; profile view (right) shows cartridge detection sensor, cam wheel, main PCBA, heater and plunger.
Figure 33:
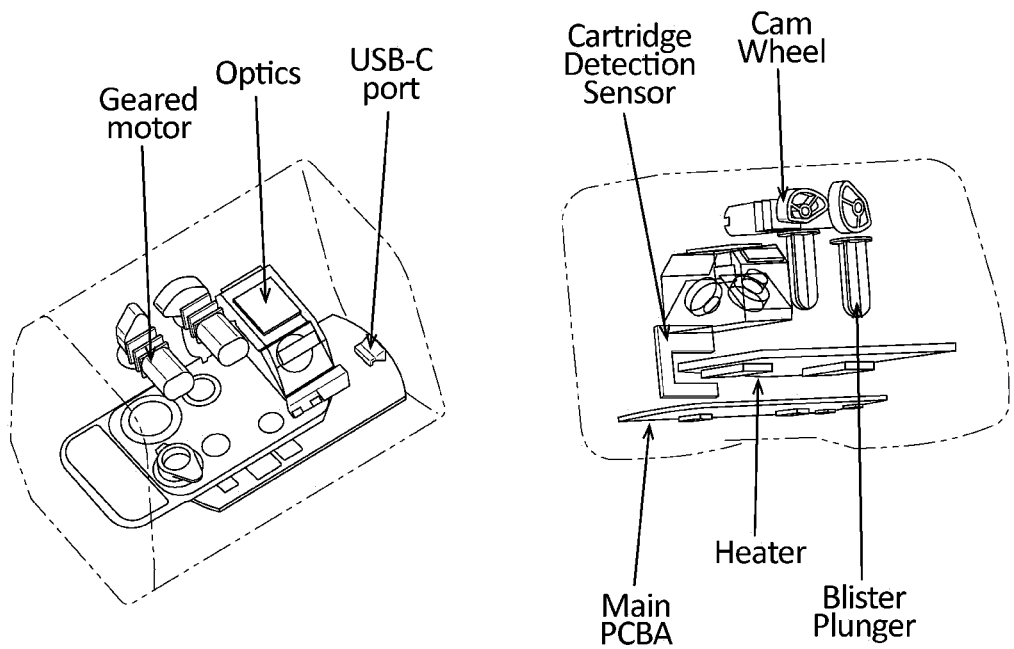
Figure 34A:
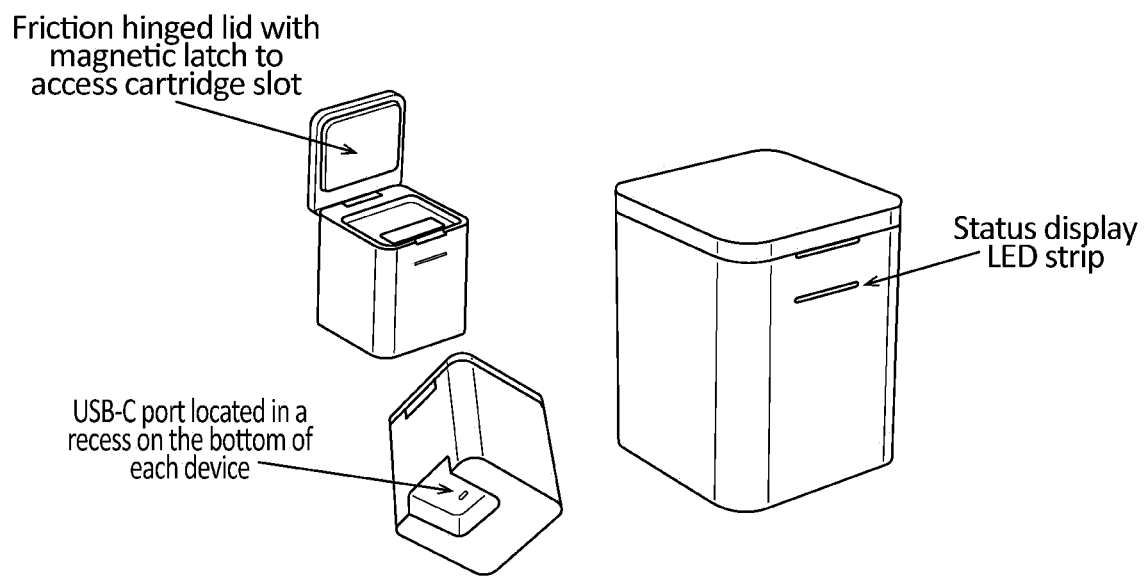
FIG. 34A-34C—FIG. 34A shows top loading device detains, friction hinged lid with magnetic latch to access cartridge slot (upper left), USB-C port in recess on the bottom of each device (lower left), front view of a top loading details (right) shows status display LED strip.
Figure 34B:
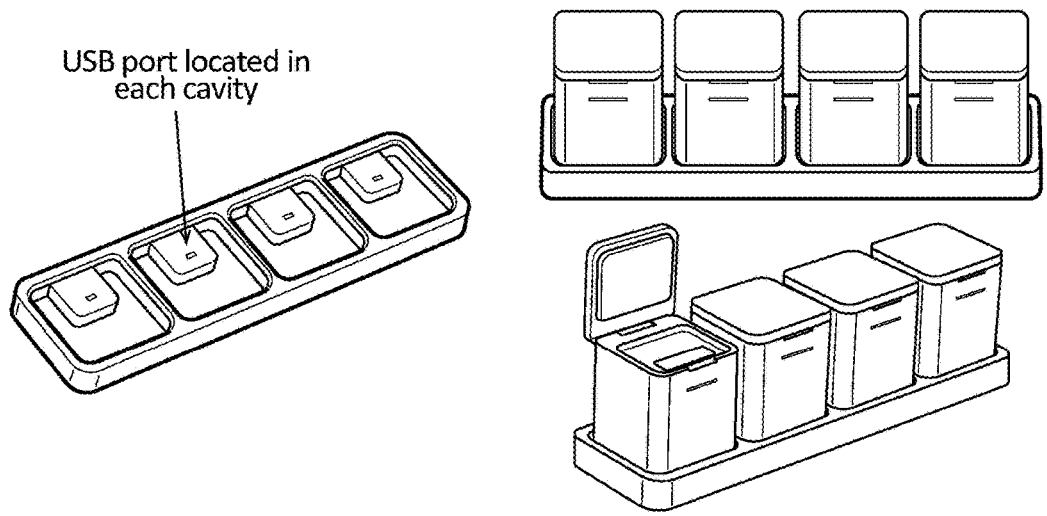
Figure 34C:
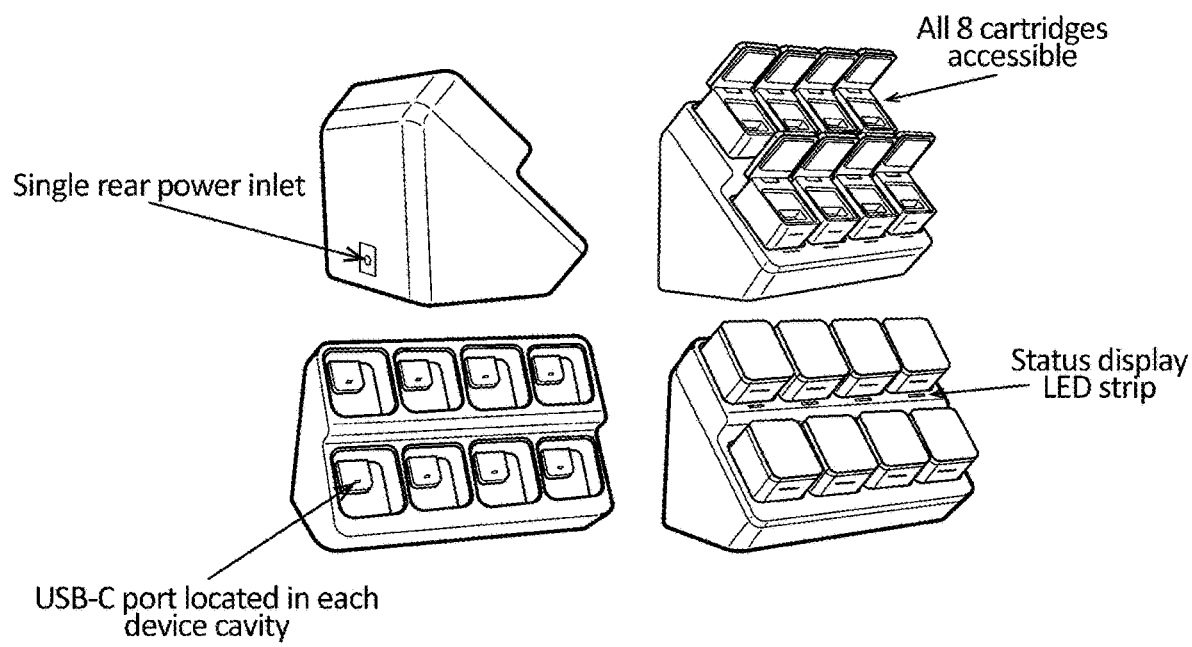
Figure 36:
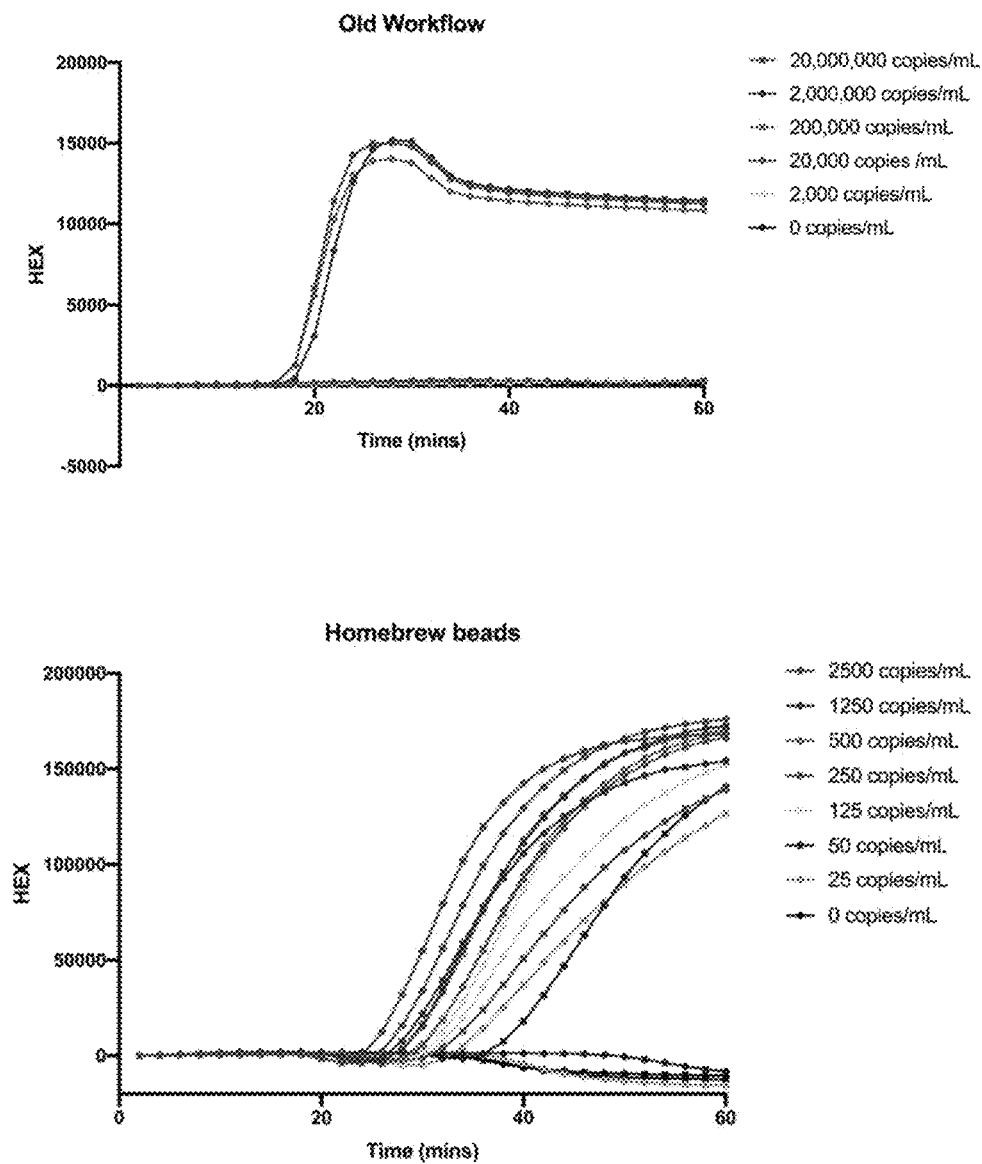
FIG. 36—Concentration with magnetic beads. Upper panel shows old workflow, lower panel with homebrew beads FIG. 37A-37C—Simplifying bead purification for POC application shows no mixing is required after addition of STOPCovid Master Mix FIG. 37A Free Beads, FIG. 37B beads on magnet (Elution only), FIG. 37C beads on magnet (binding and elution)
Figure 37A:
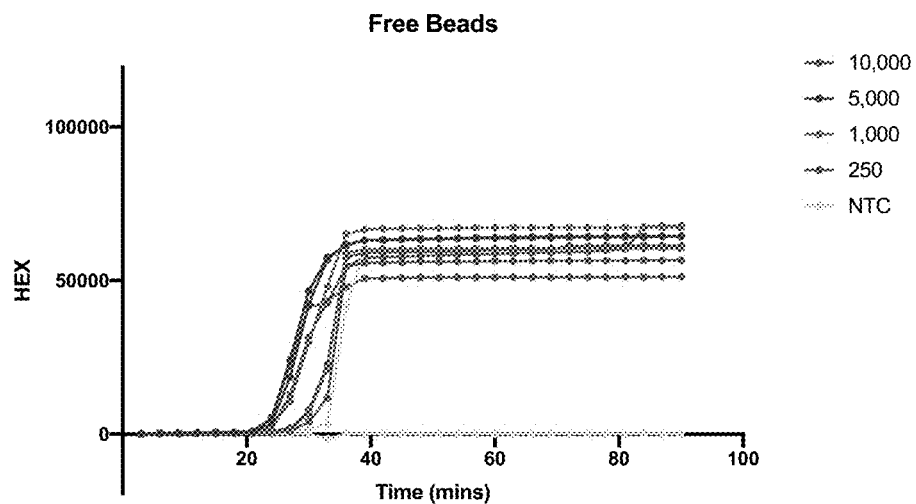
Figure 37B:
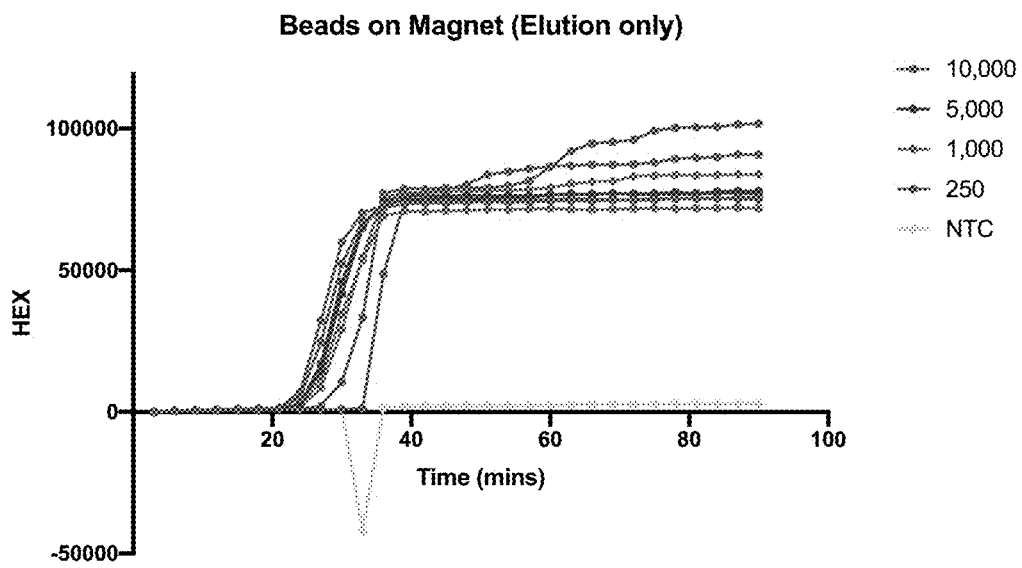
Figure 37C:
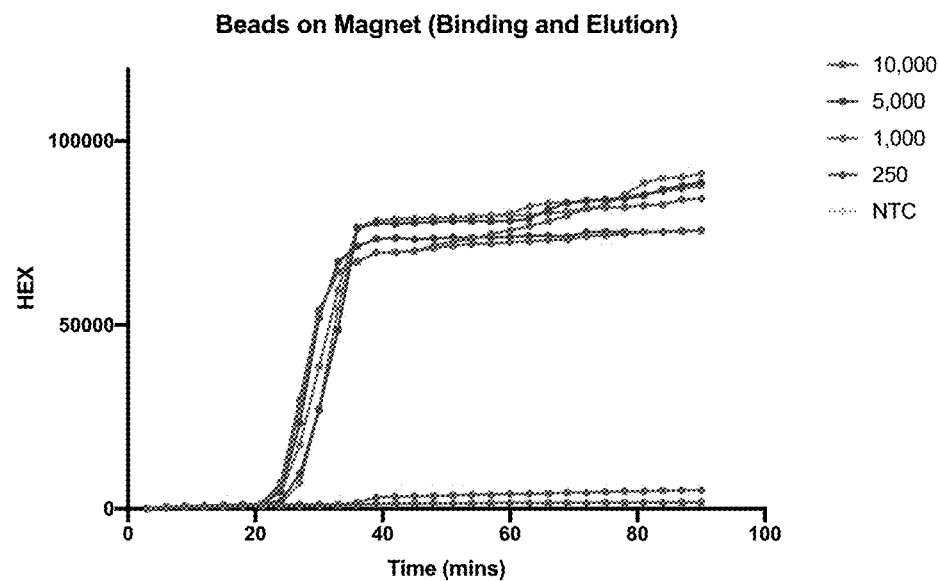
Figure 38A:
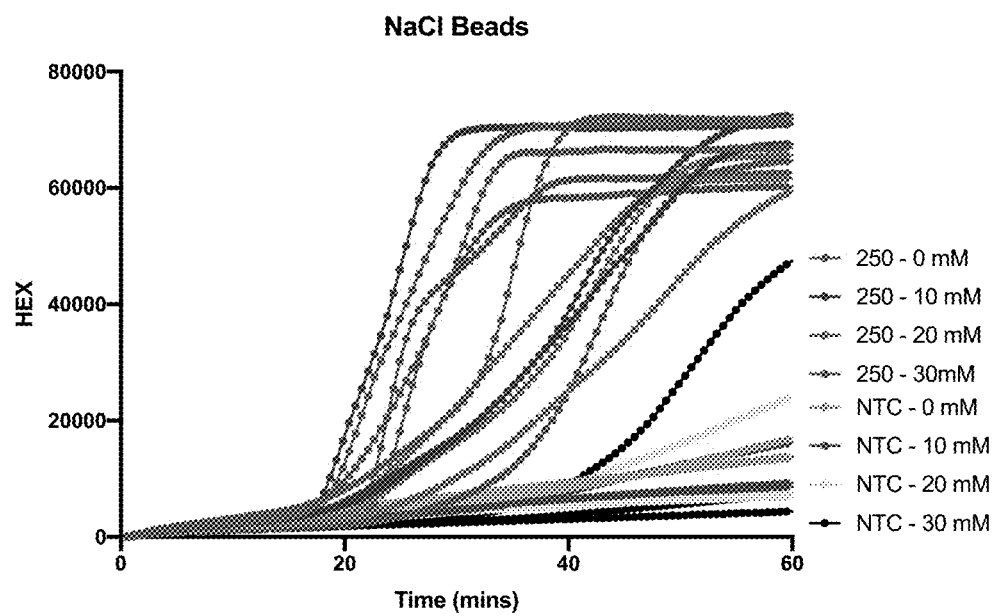
FIG. 38A-38B—Simplifying Bead purification for POC application shows removing the wash step requires significant reduction in salt concentration in the reaction buffer.
Figure 38B:
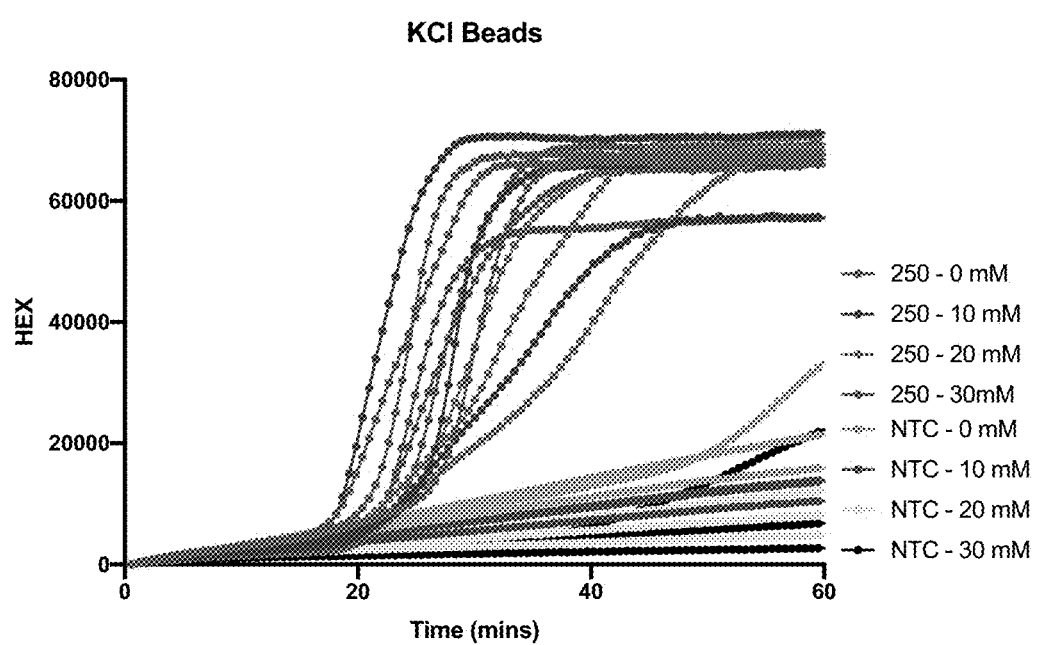
Figure 39:
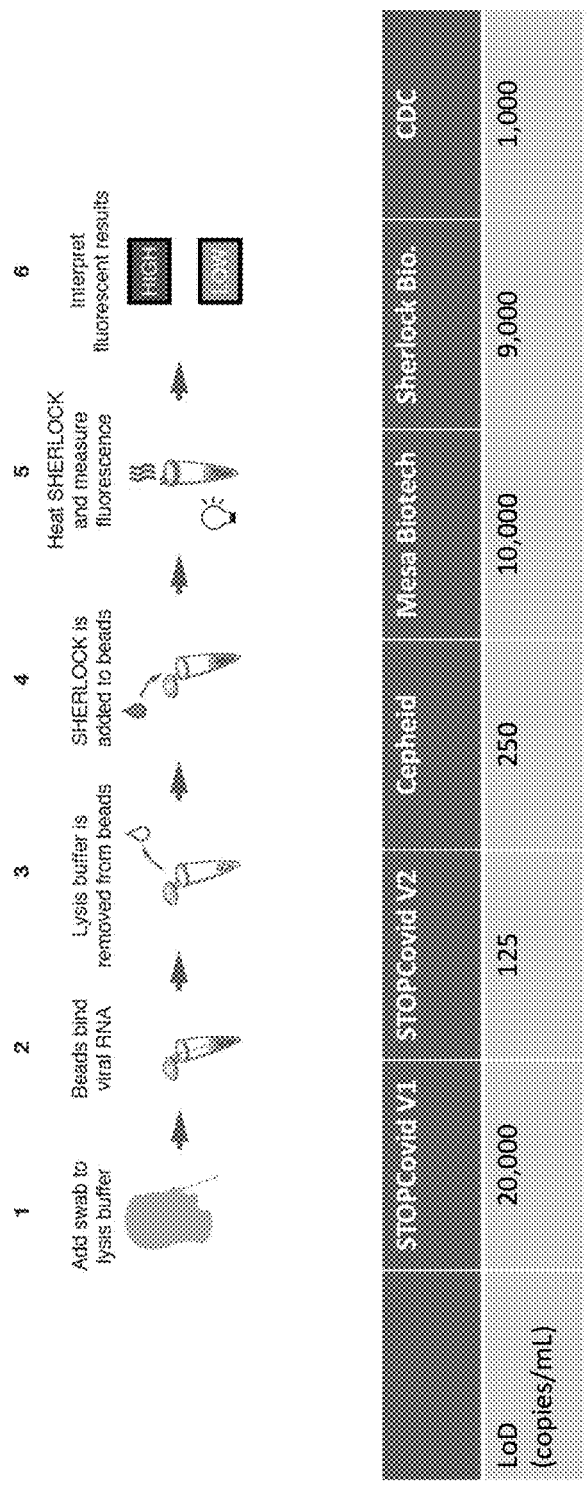
FIG. 39—An example workflow demonstrating increased sensitivity while minimizing complexity.

An exemplary cartridge is depicted in FIG. 30A-30B. This embodiment is by way of example only, and it should be understood that other configurations of individual components on the cartridge are also envisioned without departing from the overall scope and function of the invention. The cartridge (10) can comprise two or more ampoules (80,90). A first chamber for receiving a sample (30) is also provided and can be communicatively connected to an ampoule (90) and a second chamber (40). The second chamber (40) may be a lysis chamber. The lysis chamber can in turn be communicatively connected to a channel (100). The channel (100) may be a metering channel that is communicatively coupled to an ampoule (90) and a third chamber (60). The third chamber (60) may be an amplification chamber. Hydrophobic vents can be disposed on the cartridge (50, 70). FIG. 30B shows the cartridge body (15) with a membrane cover or laminate film (12).

The overall size of the device may be between 10, 15, 20, 25, 30, 35, 40, 45, 55, 60, 65, 70, 75, 80, 85, 90, 95, or 100 mm in width, and 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mm. The sizing of ampoules, chambers, and channels can be selected to be in line with the reaction volumes discussed herein and to fit within the general size parameters of the overall cartridge.

Ampoules

The ampoules, also referred to as blisters, allow for storage and release of reagents throughout the cartridge. Ampoules can include liquid or solid reagents, for example, lysis reagents in one ampoule and reaction reagents in another ampoule. The reagents can be as described elsewhere herein, and can be adapted for the use in the cartridge. The ampoule may be sealed by a film that allows for the bursting, puncture or other release of the contents of the ampoules. See, e.g. Becker, H. & Gärtner, C. Microfluidics-enabled diagnostic systems: markets, challenges, and examples. In Microchip Diagnostics: Methods and Protocols (eds Taly, V. et al.) (Springer, New York, 2017); Czurratis et al., doi: 10.1088/0960-1317/25/4/045002. Considerations for ampoules can include as discussed in, for example, Smith, S., et al., Blister pouches for effective reagent storage on microfluidic chips for blood cell counting. Microfluid Nanofluid 20, 163 (2016). DOI:10.1007/s10404-016-1830-2. In an aspect, the seal is a frangible seal formed of a composite-layer film that is assembled to the cartridge main body. While referred to herein as an ampoule, the ampoule may comprise a cavity on a chip which comprises a sealed film that is opened by the release means.

Chambers

The chambers on the chip may located and sized for fluidic communication via channels or other communication means with ampoules and/or other chambers on the chip, see, e.g. FIG. 30A. A chamber for receiving a sample can be provided. The sample can be injected, placed in a receptacle into the chamber for receiving a sample, or otherwise transferred to the chamber. A lysis chamber may comprise, for example, capture beads, that may be used for concentration and/or extraction of the desired target material from the sample. Alternatively, the beads may be comprised in an ampoule comprising lysis reagents that are in fluidic communication with the lysis chamber. An amplification chamber may also be provided with, for example, one or more lyophilized components of the system in the amplification chamber and/or communicatively connected to an ampoule comprising one or more components of the amplification reaction.

When the cartridge comprises a magnet, it may be configured near one or more of the chambers. In an aspect, the magnet is near the lysis well, and may be configured such that the device has a means for activating the magnet. Embodiments comprising a magnet in the cartridge may be utilized with methodologies using magnetic beads for extraction of particular target molecules.

System for Detection Assays

A system configured for use with the cartridge and to perform an assay, also referred to as a sample analysis apparatus, detection system or detection device, is configured system to receive the cartridge and conduct an assay comprising isothermal amplification of nucleic acids and detection of target nucleic acids on the cartridge. The system may comprise: a body; a door housing which may be provided in an opened state or a closed state, and configured to be coupled to the body of the sample analysis apparatus by a hinge or other closure means; a cartridge accommodating unit included in the detection system and configured to accommodate the cartridge. The system may further comprise one or more means for releasing reagents for extractions, amplification and/or detection; one or more heating means for extractions, amplification and/or detection, a means for mixing reagents for extraction, amplification, and/or detections, and/or a means for reading the results of the assay. The device may further comprise a user interface for programming the device and/or readout of the results of the assay.

Means for Release of Reagents

The system may comprise means for releasing reagents for extraction, amplification and/or detection. Release of reagents can be performed by a crushing, puncturing, applying heat or pressure until burst, cutting, or other means for the opening of the ampoule and release of contents. e.g. Becker, H. & Gärtner, C. Microfluidics-enabled diagnostic systems: markets, challenges, and examples. In Microchip Diagnostics: Methods and Protocols (eds Taly, V. et al.) (Springer, New York, 2017); Czurratis et al., doi: 10.1088/0960-1317/25/4/045002. Mechanical actuators Heating Means The heating means or heating element can be provided, for example, by electrical or chemical elements. One or more heating means can be utilized, or circuits providing regulation of temperature to one or more locations within the detection device can be utilized. In one preferred embodiment the device is configured to comprise a heating means for heating the lysis (extraction) chamber and at the amplification chamber of the cartridge. In an aspect, the heating element is disposed under the extraction well. The system can be designed with one or more heating means for extraction, amplification and/or detection.

Mixing Means

A means for mixing reagents for extraction, amplification and/or detection can be provided. A means for mixing reagents may comprise a means for mixing one or more fluids, or a fluid with a solid or lyophilized reaction mixture can also be provided. Means for mixing that disturb the laminar flow can be provided. In an aspect, the mixing means is a passive mixer, in another aspect, the mixing means is an active mixer. See, e.g. Nam-Trung Nguyen and Zhigang Wu 2005 J. Micromech. Microeng. 15 R1, doi: 10.1088/0960-1317/15/2/R01 for discussion of mixing approaches. In an aspect, the active mixer can be based on external sources such as pressure, temperature, hydrodynamics (with electrical or magnetic forces), dielectrophoresis, electrokinetics, or acoustics. Examples of passive mixing means can be provided by use of geometric approaches, such as a curved path or channel, see, e.g. U.S. Pat. No. 7,160,025, or an expansion/contraction of a channel cross section or diameter. When the cartridge is utilized with beads, channels and wells are configured and sized for the flow of beads.

Means for Reading the Results of the Assay

A means for reading the results of the assay can be provided in the system. The means for reading the results of the assay will depend in part on the type of detectable signal generated by the assay. In particular embodiments, the assay generates a detectable fluorescent or color readaout. In these instances, the means for reading the results of the assay will be an optic means, for example a single channel or multi-channel optical means such as a fluorimeter, colorimeter or other spectroscopic sensor.

A combination of means for reading the results of the assay can be utilized, and may include readings such as turbidity, temperature, magnetic, radio, or electrical properties and/or optical properties, including scattering, polarization effects, etc.

The system may further comprise a user interface for programming the device and/or readout of the results of the assay. The user interface may comprise an LED screen. The system can be further configured for a USB port that can allow for docking of four or more devices.

In an aspect, the system comprises a means for activating a magnet that is disposed within or on the cartridge.

Lateral Flow Devices

In certain embodiments, the detection assay can be provided on a lateral flow device, as described in International Publication WO 2019/071051, incorporated herein by reference. The lateral flow device can be adapted to detect one or more coronaviruses and/or other viruses in combination of the coronavirus. The lateral flow device may comprise a flexible substrate, such as a paper substrate or a flexible polymer-based substrate, which can include freeze-dried reagents for detection assays with a visual readout of the assay results. See, WO 2019/071051 at [0145]-[0151] and Example 2, specifically incorporated herein by reference. In an aspect, lyophilized reagents can include preferred excipients that aid in rate of reaction, specificity, or other variables. The excipients may comprise trehalose, histidine, and/or glycine. In certain embodiments, the coronavirus assay can be utilized with isothermal amplification reagents, allowing amplification without complex instrumentation that may be unavailable in the field, as described in WO 2019/071051. Accordingly, the assay can be adapted for field diagnostics, including use of visual readout on a lateral flow device, rapid, sensitive detection and can be deployed for early and direct detection. Colorimetric detection can be utilized and may be particularly suited for field deployable applications, as described in International Application PCT/US2019/015726, published as WO2019/148206. In particular, colorimetric detection can be as described in WO2019/148206 at FIGS. 102, 105, 107-111 and [00306]-[00324], incorporated herein by reference.

In one embodiment, the invention provides a lateral flow device comprising a substrate comprising a first end and a second end. The first end may comprise a sample loading portion, a first region comprising a detectable ligand, two or more CRISPR effector systems, two or more detection constructs, and one or more first capture regions, each comprising a first binding agent. The substrate may also comprise two or more second capture regions between the first region of the first end and the second end, each second capture region comprising a different binding agent. Each of the two or more CRISPR effector systems may comprise a CRISPR effector protein and one or more guide sequences, each guide sequence configured to bind one or more target molecules.

The embodiments disclosed herein are directed to lateral flow detection devices that comprise SHERLOCK systems.

The device may comprise a lateral flow substrate for detecting a SHERLOCK reaction. Substrates suitable for use in lateral flow assays are known in the art. These may include, but are not necessarily limited to membranes or pads made of cellulose and/or glass fiber, polyesters, nitrocellulose, or absorbent pads (J Saudi Chem Soc 19(6):689-705; 2015), and other embodiments further described herein. The SHERLOCK system, i.e. one or more CRISPR systems and corresponding reporter constructs are added to the lateral flow substrate at a defined reagent portion of the lateral flow substrate, typically on one end of the lateral flow substrate. Reporting constructs used within the context of the present invention can comprise a first molecule and a second molecule linked by an RNA or DNA linker. The lateral flow substrate further comprises a sample portion. The sample portion may be equivalent to, continuous with, or adjacent to the reagent portion. In an aspect, the lateral flow substrate can be contained within a further device (see, e.g. FIG. 21). In an aspect, the lateral flow substrate can be utilized for visual readout of a detectable signal in one-pot reactions, e.g. wherein steps of extracting, amplifying and detecting are performed in an individual discrete volume.

Lateral Flow Substrate

In certain example embodiments, a lateral flow device comprises a lateral flow substrate on which detection can be performed. Substrates suitable for use in lateral flow assays are known in the art. These may include, but are not necessarily limited to, membranes or pads made of cellulose and/or glass fiber, polyesters, nitrocellulose, or absorbent pads (J Saudi Chem Soc 19(6):689-705; 2015).

Lateral support substrates comprise a first and second end, and one or more capture regions that each comprise binding agents. The first end may comprise a sample loading portion, a first region comprising a detectable ligand, two or more CRISPR effector systems, two or more detection constructs, and one or more first capture regions, each comprising a first binding agent. The substrate may also comprise two or more second capture regions between the first region of the first end and the second end, each second capture region comprising a different binding agent. Each of the two or more CRISPR effector systems may comprise a CRISPR effector protein and one or more guide sequences, each guide sequence configured to bind one or more target molecules. The lateral flow substrates may be configured to detect a SHERLOCK reaction.

Lateral support substrates may be located within a housing (see for example, "Rapid Lateral Flow Test Strips" Merck Millipore 2013). The housing may comprise at least one opening for loading samples and a second single opening or separate openings that allow for reading of detectable signal generated at the first and second capture regions.

The embodiments disclosed herein can be prepared in freeze-dried format for convenient distribution and point-of-care (POC) applications. Such embodiments are useful in multiple scenarios in human health including, for example, viral detection, bacterial strain typing, sensitive genotyping, and detection of disease-associated cell free DNA. Accordingly, the lateral substrate comprising one or more of the elements of the system, including detectable ligands, CRISPR effector systems, detection constructs and binding agents may be freeze-dried to the lateral flow substrate and packaged as a ready to use device. Alternatively, all or a portion of the elements of the system may be added to the reagent portion of the lateral flow substrate at the time of using the device.

First End and Second End of the Substrate

The substrate of the lateral flow device comprises a first and second end. The SHERLOCK system, i.e. one or more CRISPR systems and corresponding reporter constructs are added to the lateral flow substrate at a defined reagent portion of the lateral flow substrate, typically on a first end of the lateral flow substrate. Reporting constructs used within the context of the present invention comprise a first molecule and a second molecule linked by an RNA or DNA linker. The lateral flow substrate further comprises a sample portion. The sample portion may be equivalent to, continuous with, or adjacent to the reagent portion.

In certain example embodiments, the first end comprises a first region. The first region comprises a detectable ligand, two or more CRISPR effector systems, two or more detection constructs, and one or more first capture regions, each comprising a first binding agent.

Capture Regions

The lateral flow substrate can comprise one or more capture regions. In embodiments the first end of the lateral flow substrate comprises one or more first capture regions, with two or more second capture regions between the first region of the first end of the substrate and the second end of the substrate. The capture regions may be provided as a capture line, typically a horizontal line running across the device, but other configurations are possible. The first capture region is proximate to and on the same end of the lateral flow substrate as the sample loading portion.

Binding Agents

Specific binding-integrating molecules comprise any members of binding pairs that can be used in the present invention. Such binding pairs are known to those skilled in the art and include, but are not limited to, antibody-antigen pairs, enzyme-substrate pairs, receptor-ligand pairs, and streptavidin-biotin. In addition to such known binding pairs, novel binding pairs may be specifically designed. A characteristic of binding pairs is the binding between the two members of the binding pair.

A first binding agent that specifically binds the first molecule of the reporter construct is fixed or otherwise immobilized to the first capture region. The second capture region is located towards the opposite end of the lateral flow substrate from the first capture region. A second binding agent is fixed or otherwise immobilized at the second capture region. The second binding agent specifically binds the second molecule of the reporter construct, or the second binding agent may bind a detectable ligand. For example, the detectable ligand may be a particle, such as a colloidal particle, that when it aggregates can be detected visually, and generates a detectable positive signal. The particle may be modified with an antibody that specifically binds the second molecule on the reporter construct. If the reporter construct is not cleaved it will facilitate accumulation of the detectable ligand at the first binding region. If the reporter construct is cleaved the detectable ligand is released to flow to the second binding region. In such an embodiment, the second binding region comprises a second binding agent capable of specifically or non-specifically binding the detectable ligand on the antibody of the detectable ligand. Binding agents can be, for example, antibodies, that recognize a particular affinity tag. Such binding agents can further contain, for example, detectable labels, such as isotope labels and/or nucleic acid barcodes. A barcode is a short sequence of nucleotides (for example, DNA, RNA, or combinations thereof) that is used as an identifier. A nucleic acid barcode may have a length of 4-100 nucleotides and be either single or double-stranded. Methods for identifying cells with barcodes are known in the art. Accordingly, guide RNAs of the CRISPR effector systems described herein may be used to detect the barcode.

Detectable Ligands

The first region is loaded with a detectable ligand, such as those disclosed herein, for example a gold nanoparticle. The detectable ligand may be a particle, such as a colloidal particle, that when it aggregates can be detected visually. The particle may be modified with an antibody that specifically binds the second molecule on the reporter construct. If the reporter construct is not cleaved it will facilitate accumulation of the detectable ligand at the first binding region. If the reporter construct is cleaved the detectable ligand is released to flow to the second binding region. In such an embodiment, the second binding agent is an agent capable of specifically or non-specifically binding the detectable ligand on the antibody on the detectable ligand. Examples of suitable binding agents for such an embodiment include, but are not limited to, protein A and protein G. In some examples, the detectable ligand is a gold nanoparticle, which may be modified with a first antibody, such as an anti-FITC antibody.

Lateral Flow Detection Constructs

The first region also comprises a detection construct. In one example embodiment, a RNA detection construct and a CRISPR effector system (a CRISPR effector protein and one or more guide sequences configured to bind to one or more target sequences) as disclosed herein. In one example embodiment, and for purposes of further illustration, the RNA construct may comprise a FAM molecule on a first end of the detection construction and a biotin on a second end of the detection construct. Upstream of the flow of solution from the first end of the lateral flow substrate is a first test band. The test band may comprise a biotin ligand. Accordingly, when the RNA detection construct is present in its initial state, i.e. in the absence of target, the FAM molecule on the first end will bind the anti-FITC antibody on the gold nanoparticle, and the biotin on the second end of the RNA construct will bind the biotin ligand allowing for the detectable ligand to accumulate at the first test, generating a detectable signal. Generation of a detectable signal at the first band indicates the absence of the target ligand. In the presence of target, the CRISPR effector complex forms and the CRISPR effector protein is activated resulting in cleavage of the RND detection construct. In the absence of intact RNA detection construct the colloidal gold will flow past the second strip. The lateral flow device may comprise a second band, upstream of the first band. The second band may comprise a molecule capable of binding the antibody-labeled colloidal gold molecule, for example an anti-rabbit antibody capable of binding a rabbit anti-FITC antibody on the colloidal gold. Therefore, in the presence of one or more targets, the detectable ligand will accumulate at the second band, indicating the presence of the one or more targets in the sample.

In some embodiments, the first end of the lateral flow device comprises two detection constructs and each of the two detection constructs comprises an RNA or DNA oligonucleotide, comprising a first molecule on a first end and a second molecule on a second end. The first molecule and the second molecule may be linked by an RNA or DNA linker.

In some embodiments, the first molecule on the first end of the first detection construct may be FAM and the second molecule on the second end of the first detection construct may be biotin, or vice versa. In some embodiments, the first molecule on the first end of the second detection construct may be FAM and the second molecule on the second end of the second detection construct may be Digoxigenin (DIG), or vice versa.

In some embodiments, the first end may comprise three detection constructs, wherein each of the three detection constructs comprises an RNA or DNA oligonucleotide, comprising a first molecule on a first end and a second molecule on a second end. In specific embodiments, the first and second molecules on the detection constructs comprise Tye 665 and Alexa 488; Tye 665 and FAM, and Tye 665 and Digoxigenin (DIG), respectively.

In some embodiments, the first end of the lateral flow device comprises two or more CRISPR effector systems, also referred to as a CRISPR-Cas or CRISPR system. In some embodiments, such a CRISPR effector system may include a CRISPR effector protein and one or more guide sequences configured to bind to one or more target sequences.

Samples

When utilizing the detection systems with a lateral flow substrate, samples to be screened are loaded at the sample loading portion of the lateral flow substrate. The samples must be liquid samples or samples dissolved in an appropriate solvent, usually aqueous. The liquid sample reconstitutes the SHERLOCK reagents such that a SHERLOCK reaction can occur. The liquid sample begins to flow from the sample portion of the substrate towards the first and second capture regions.

A sample for use with the invention may be a biological or environmental sample, such as a surface sample, a fluid sample, or a food sample (fresh fruits or vegetables, meats). Food samples may include a beverage sample, a paper surface, a fabric surface, a metal surface, a wood surface, a plastic surface, a soil sample, a freshwater sample, a wastewater sample, a saline water sample, exposure to atmospheric air or other gas sample, or a combination thereof. For example, household/commercial/industrial surfaces made of any materials including, but not limited to, metal, wood, plastic, rubber, or the like, may be swabbed and tested for contaminants. Soil samples may be tested for the presence of pathogenic bacteria or parasites, or other microbes, both for environmental purposes and/or for human, animal, or plant disease testing. Water samples such as freshwater samples, wastewater samples, or saline water samples can be evaluated for cleanliness and safety, and/or potability, to detect the presence of, for example, *Cryptosporidium parvum, Giardia lamblia*, or other microbial contamination. In further embodiments, a biological sample may be obtained from a source including, but not limited to, a tissue sample, saliva, blood, plasma, sera, stool, urine, sputum, mucous, lymph, synovial fluid, spinal fluid, cerebrospinal fluid, ascites, pleural effusion, seroma, pus, bile, aqueous or vitreous humor, transudate, exudate, or swab of skin or a mucosal membrane surface. In some particular embodiments, an environmental sample or biological samples may be crude samples and/or the one or more target molecules may not be purified or amplified from the sample prior to application of the method. Identification of microbes may be useful and/or needed for any number of applications, and thus any type of sample from any source deemed appropriate by one of skill in the art may be used in accordance with the invention.

In particular embodiments, the methods and systems can be utilized for direct detection from patient samples. In an aspect, the methods and systems can further allow for direct detection from patient samples with a visual readout to further facilitate field-deployability. In an aspect, a field depoloyable version can include, for example the lateral flow devices and systems as described herein, and/or colorimetric detection. The methods and systems can be utilized to distinguish multipe viral species and strains and identify clinically relevant mutations, important with viral outbreaks such as the coronavirus outbreak in Wuhan (2019-nCoV). In an aspect, the sample is from a nasophyringeal swab or a saliva sample. See, e.g. FIG. 40, see also, Wyllie et al., "Saliva is more sensitive for SARS-CoV-2 detection in COVID-19 patients than nasopharyngeal swabs," DOI: 10.1101/2020.04.16.20067835.

Methods for Detecting and/or Quantifying Target Nucleic Acids

In some embodiments, the invention provides methods for detecting target nucleic acids in a sample. Such methods may comprise contacting a sample with the first end of a lateral flow device as described herein. The first end of the lateral flow device may comprise a sample loading portion, wherein the sample flows from the sample loading portion of the substrate towards the first and second capture regions and generates a detectable signal.

A positive detectable signal may be any signal that can be detected using optical, fluorescent, chemiluminescent, electrochemical or other detection methods known in the art, as described elsewhere herein.

In some embodiments, the lateral flow device may be capable of detecting two different target nucleic acid sequences. In some embodiments, this detection of two different target nucleic acid sequences may occur simultaneously.

In some embodiments, the absence of target nucleic acid sequences in a sample elicits a detectable fluorescent signal at each capture region. In such instances, the absence of any target nucleic acid sequences in a sample may cause a detectable signal to appear at the first and second capture regions.

In some embodiments, the lateral flow device as described herein is capable of detecting three different target nucleic acid sequences. In specific embodiments, when the target nucleic acid sequences are absent from the sample, a fluorescent signal may be generated at each of the three capture regions. In such exemplary embodiments, a fluorescent signal may be absent at the capture region for the corresponding target nucleic acid sequence when the sample contains one or more target nucleic acid sequences.

Samples to be screened are loaded at the sample loading portion of the lateral flow substrate. The samples must be liquid samples or samples dissolved in an appropriate solvent, usually aqueous. The liquid sample reconstitutes the system reagents such that a SHERLOCK reaction can occur. Intact reporter construct is bound at the first capture region by binding between the first binding agent and the first molecule. Likewise, the detection agent will begin to collect at the first binding region by binding to the second molecule on the intact reporter construct. If target molecule(s) are present in the sample, the CRISPR effector protein collateral effect is activated. As activated CRISPR effector protein comes into contact with the bound reporter construct, the reporter constructs are cleaved, releasing the second molecule to flow further down the lateral flow substrate towards the second binding region. The released second molecule is then captured at the second capture region by binding to the second binding agent, where additional detection agent may also accumulate by binding to the second molecule. Accordingly, if the target molecule(s) is not present in the sample, a detectable signal will appear at the first capture region, and if the target molecule(s) is present in the sample, a detectable signal will appear at the location of the second capture region.

In some embodiments, the invention provides a method for quantifying target nucleic acids in samples comprising distributing a sample or set of samples into one or more individual discrete volumes comprising two or more CRISPR systems as described herein. The method may comprise using HDA to amplify one or more target molecules in the sample or set of samples, as described herein. The method may further comprise incubating the sample or set of samples under conditions sufficient to allow binding of the guide RNAs to one or more target molecules. The method may further comprise activating the CRISPR effector protein via binding of the guide RNAs to the one or more target molecules. Activating the CRISPR effector protein may result in modification of the detection construct such that a detectable positive signal is generated. The method may further comprise detecting the one or more detectable positive signals, wherein detection indicates the presence of one or more target molecules in the sample. The method may further comprise comparing the intensity of the one or more signals to a control to quantify the nucleic acid in the sample. The steps of amplifying, incubating, activating, and detecting may all be performed in the same individual discrete volume.

An "individual discrete volume" is a discrete volume or discrete space, such as a container, receptacle, or other defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electro-magnetic, or light illumination, or any combination thereof. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electromagnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents may be passed in Applicants' through the discrete volume, while other material, such as target molecules, may be maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are the wells of a microplate. In certain example embodiments, the microplate is a 96 well, a 384 well, or a 1536 well microplate.

Incubating the sample at either the amplification step or the extraction steps as described herein can be performed using heat sources known in the art. Advantageously, the heat source can be readily commercially available heating sources that do not require complicated instrumentation. Exemplary heating systems can include heating blocks, incubators, and/or water baths with temperatures maintained by commercially available sous-vide cookers. In this way, sample diagnostics can be performed without the requirement of expensive and proprietary equipment found primarily in diagnostic laboratory and hospital settings.

In certain example embodiments, paper-based microfluidics may be used for transfer of samples or reagents. For example, paper strips having wax barrier printed at a defined distance from the end of a paper dipstick may be used to define a volume of reagent or sample to be transferred. For example, a wax barrier may be printed across a paper dipstick to define a microliter volume such that when the dipstick is transferred into a volume of a reagent or sample only a microliter of said reagent or sample is absorbed onto the dipstick. The dipstick may be place in a second regant mix, where the reagent or sample will diffuse into the reaction mixture. Such components allow for preparation and use of the assay without specialized equipment such as pipettors.

Amplifying Target Molecules

The step of amplifying one or more target molecules can comprise amplification systems known in the art. In some embodiments, amplification is isothermal and can utilize amplification reagents as described elsewhere herein. In certain example embodiments, target RNAs and/or DNAs may be amplified prior to the optional step of use and activating the CRISPR effector protein. Any suitable RNA or DNA amplification technique may be used. In certain embodiments, the amplifying step may take less than about 1 hour, 50 minutes, 40 minutes, 30 minutes, 25 minutes, 20 minutes or 15 minutes, which may depend on the sample, starting concentrations and nature of amplification used.

In certain embodiments, the amplifying of the target molecules and the detection of the target molecules can be performed in a single reaction, for example, a 'one-pot' method. Guidance for use of a single-pot approach can be as described in Gootenberg, et al., Science 2018 Apr. 27: 360(6387) 439-444 (using Cas13, Cas12a and Csm6 generally, detecting multiple targets in a single reaction, and specifically performing DNA extraction in a sample and using as input for direct detection at Figure S33); and Ding et al., "All-in-One Dual CRISPR-Cas12a (AIOD-CRISPR) Assay: A Case for Rapid, Ultrasensitive and Visual Detection of Novel Coronavirus SARS-CoV-2 and HIV Virus," doi:10.1101/2020.03.19.998724, biorxiv preprint (utilizing a pair of crRNAs with dual CRISPR-Cas12a detection for a one-pot approach to target-specific nucleic acid detection); and International Patent Application PCT/US2020/022795, filed Mar. 13, 2020, incorporated herein by reference in its entirety.

In certain example embodiments, the RNA or DNA amplification is an isothermal amplification. In certain example embodiments, the isothermal amplification may be nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). In certain example embodiments, non-isothermal amplification methods may be used which include, but are not limited to, PCR, multiple displacement amplification (MDA), rolling circle amplification (RCA), ligase chain reaction (LCR), or ramification amplification method (RAM).

The amplifying of target molecules can be optimized by methods as detailed herein. In an aspect, the design optimizes the primers used in the amplification, In particular aspects, the isothermal amplification is used alone. In another aspect, the iotheraml amplification is used with CRISPR-Cas systems. In either approach, design considerations can follow a rational design for optimization of the reactions. Optimization of the methods as disclosed herein can include first screening primers to identify one or more sets of primers that work well for a particular target, Cas protein and/or reaction. Once the primers have been screened, titration of magnesium concentration can be performed to identify an optimal magnesium concentration for higher signal to noise readout. Once an optimum magnesium concentration is identified, additional additives are screened at around 20-25% of the reaction, and once additives are identified, these additives, such as those additives identified in FIG. 17, can be evaluated and varied in concentration to identify optimal reaction kinetics for specific reaction parameters. In an example, varying additives with specific primers, target, Cas protein (when CRISPR system is used), temperature, and other additive concentrations within the reaction can be identified. Optimization can be made with the goal of reducing the number of steps and buffer exchanges that have to occur in the reaction, simplifying the reaction and reducing the risks of contamination at transfer steps. In an aspect, addition of inhibitors, such as proteinase K can be considered so that buffer exchanges can be reduced. Similarly, optimizing the salt levels as well as the type of salt utilized can further facilitate and optimize the one-pot detections disclosed herein. In an aspect, potassium chloride can be utilized rather than sodium chloride when such amplification approaches are used with bead concentration in a lysis step.

Incubating

Methods of detection and/or extraction using the systems disclosed herein can comprise incubating the sample or set of samples under conditions sufficient to allow binding of the guide RNAs to one or more target molecules. Extraction can comprise incubating the sample under conditions sufficient to allow release of viral RNA present in the sample, which may comprise incubating at 22° C. to 60° C. for 30 to 70 minutes or at 90° C.-100° C. for about 10 minutes.

In certain example embodiments, the incubation time of the amplifying and detecting in the present invention may be shortened. The assay may be performed in a period of time required for an enzymatic reaction to occur. One skilled in the art can perform biochemical reactions in 5 minutes (e.g., 5 minute ligation). Incubating may occur at one or more temperatures over timeframes between about 10 minutes and 90 minutes, preferably less than 90 minutes, 75 minutes, 60 minutes, 45 minutes, 30 minutes, 25 minutes, 20 minutes, 15 minutes, or 10 minutes depending on sample, reagents and components of the system. In some embodiments, incubating for the amplification is performed at one or more temperatures between about 20° C. and 80° C., in some embodiments, about 37° C. In some embodiments, incubating for the amplification is performed at one or more temperatures between about 55° C. and 65° C., between about 59° C. and 61° C., in some embodiments, about 60° C.

Activating

In certain example embodiment, activating of the Cas protein occurs via binding of the CRISPR-Cas complex via the guide molecule to the one or more target molecules, wherein activating the CRISPR effector protein results in modification of the detection construct such that a detectable positive signal is generated.

Detecting a Signal

Detecting may comprise visual observance of a positive signal relative to a control. Detecting may comprise a loss of signal or presence of signal at one or more capture regions, for example colorimetric detection, or fluorescent detection. In certain example embodiments, further modifications may be introduced that further amplify the detectable positive signal. For example, when utilizing isothermal amplification methods as disclosed herein, colorimetric and/or fluorescent detection reagents, including use of pH sensitive dyes and quenching probes can be utilized, as described herein for LAMP reagents. The discussion herein is of exemplary LAMP reagents, but can be applied equally to the isothermal amplification reagents and approaches detailed elsewhere herein.

For example, activated CRISPR effector protein collateral activation may be used to generate a secondary target or additional guide sequence, or both. In one example embodiment, the reaction solution would contain a secondary target that is spiked in at high concentration. The secondary target may be distinct from the primary target (i.e. the target for which the assay is designed to detect) and in certain instances may be common across all reaction volumes. A secondary guide sequence for the secondary target may be protected, e.g. by a secondary structural feature such as a hairpin with an RNA loop, and unable to bind the second target or the CRISPR effector protein. Cleavage of the protecting group by an activated CRISPR effector protein (i.e. after activation by formation of complex with the primary target(s) in solution) and formation of a complex with free CRISPR effector protein in solution and activation from the spiked in secondary target. In certain other example embodiments, a similar concept is used with free guide sequence to a secondary target and protected secondary target. Cleavage of a protecting group off the secondary target would allow additional CRISPR effector protein, guide sequence, secondary target sequence to form. In yet another example embodiment, activation of CRISPR effector protein by the primary target(s) may be used to cleave a protected or circularized primer, which would then be released to perform an isothermal amplification reaction, such as those disclosed herein, on a template for either secondary guide sequence, secondary target, or both. Subsequent transcription of this amplified template would produce more secondary guide sequence and/or secondary target sequence, followed by additional CRISPR effector protein collateral activation.

Quantifying

In particular methods, comparing the intensity of the one or more signals to a control is performed to quantify the nucleic acid in the sample. The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be stored sample or previous sample measurement) with a known outcome; normal tissue, fluid, or cells isolated from a subject, such as a normal patient or the patient having a condition of interest.

The intensity of a signal is "significantly" higher or lower than the normal intensity if the signal is greater or less, respectively, than the normal or control level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the signal can be considered "significantly" higher or lower than the normal and/or control signal if the amount is at least about two, and preferably at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, two times, three times, four times, five times, or more, or any range in between, such as 5%-100%, higher or lower, respectively, than the normal and/or control signal. Such significant modulation values can be applied to any metric described herein, such as altered level of expression, altered activity, changes in biomarker inhibition, changes in test agent binding, and the like.

In some embodiments, the detectable positive signal may be a loss of fluorescent signal or colorimetric relative to a control, as described herein. In some embodiments, the detectable positive signal may be detected on a lateral flow device, as described herein.

Applications of Detection Methods

Systems and methods can be designed for the detection and diagnosis of microbes, including bacterial, fungi and viral microbes. In an aspect, the systems may comprise multiplex detection of multiple variants of viral infections, including coronavirus, different viruses which may be related coronaviruses or respiratory viruses, or a combination thereof. In embodiments, assays can be performed for a variety of viruses and viral infections, including acute respiratory infections using the disclosure detailed herein. The systems comprise isothermal amplification approaches, and can optionally comprise two or more CRISPR Cas systems to multiplex, as described elsewhere herein, to detect a plurality of respiratory infections or viral infections, including coronavirus. The coronavirus is a positive-sense single stranded RNA family of viruses, infecting a variety of animals and humans. SARS-CoV is one type of coronavirus infection, as well as MERS-CoV Detection of one or more coronaviruses are envisioned, including the 2019-nCoV detected in Wuhan City. Sequences of the SARS-CoV-2 are available at GISAID accession no. EPI_ISL_402124 and EPI_ISL_402127-402130, and described in DOI: 10.1101/2020.01.22.914952. Further deposits of the SARS-CoV-2 deposited in the GISAID platform include EP_ISL_402119-402121 and EP_ISL_402123-402124; see also GenBank Accession No. MN908947.3.

Target molecule detection can comprise two or more detection systems utilizing RNA targeting Cas effector proteins; DNA targeting Cas effector proteins, or a combination thereof. The RNA-targeting effector proteins may be a Cas13 protein, such as Cas13a, Cas13b, or Cas13c, including one of the thermostable Cas13a proteins described herein. The DNA-targeting effector protein may be a Type V protein, e.g. Cas12 protein such as Cpf1 and C2c1. The Cas protein may preferably be thermostable, such as BrCas12b or Aap Cas12b. Multiplexing systems can be designed such that different Cas proteins with different sequence specificities or other motif cutting preferences can be used, including, in certain embodiments, at least one Cas. thermostable protein described herein. See International Publication WO 2019/126577. Type VI and Type V Cas proteins are known to possess different cutting motif preferences. See Gootenberg et al. "Multiplexed and portable nucleic acid detection platform with Cas13b, Cas12a, and Csm6." Science. Apr. 27, 2018, 360:439-444; International Publication WO 2019/051318. Thus, embodiments disclosed herein may further comprise multiplex embodiments comprising two or more Type VI Cas proteins with different cutting preferences, or one or more Type VI Cas proteins and one or more Type V Cas proteins.

Multiplex approaches and selection of Cas effector proteins can be as described in International Publication WO 2019/126577 at [0415]-[0416] and Examples 1-10, incorporated herein by reference. In certain example embodiments, the coronavirus assay comprises a Type VI Cas protein disclosed herein and guide molecule comprising a guide sequence configured to directed binding of the CRISPR-Cas complex to a target molecule and a labeled detection molecule ("RNA-based masking construct"). A multiplex embodiment can be designed to track one or more variants of coronavirus or one or more variants of coronavirus, including SARS-CoV-2, in combination with other viruses, for example, Human respiratory syncytial virus, Middle East respiratory syndrome (MERS) coronavirus, Severe acute respiratory syndrome-related (SARS) coronavirus, and influenza. In embodiments, assays can be done in multiplex to detect multiple variants of coronavirus, different viruses which may be related coronaviruses or respiratory viruses, or a combination thereof. In an aspect, each assay can take place in an individual discrete volume. An "individual discrete volume" is a discrete volume or discrete space, such as a container, receptacle, or other defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electro-magnetic, or light illumination, or any combination thereof. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents may be passed in Applicants' through the discrete volume, while other material, such as target molecules, may be maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are the wells of a microplate. In certain example embodiments, the microplate is a 96 well, a 384 well, or a 1536 well microplate.

In certain example embodiments, the systems, devices, and methods, disclosed herein are directed to detecting the presence of one or more microbial agents in a sample, such as a biological sample obtained from a subject. In certain example embodiments, the microbe may be a bacterium, a fungus, a yeast, a protozoan, a parasite, or a virus. Accordingly, the methods disclosed herein can be adapted for use in other methods (or in combination) with other methods that require quick identification of microbe species, monitoring the presence of microbial proteins (antigens), antibodies, antibody genes, detection of certain phenotypes (e.g. bacterial resistance), monitoring of disease progression and/or outbreak, and antibiotic screening. Because of the rapid and sensitive diagnostic capabilities of the embodiments disclosed here, detection of microbe species type, down to a single nucleotide difference, and the ability to be deployed as a POC device, the embodiments disclosed herein may be used as guide therapeutic regimens, such as a selection of the appropriate antibiotic or antiviral. The embodiments disclosed herein may also be used to screen environmental samples (air, water, surfaces, food etc.) for the presence of microbial contamination.

Disclosed is a method to identify microbial species, such as bacterial, viral, fungal, yeast, or parasitic species, or the like. Particular embodiments disclosed herein describe methods and systems that will identify and distinguish microbial species within a single sample, or across multiple samples, allowing for recognition of many different microbes. The present methods allow the detection of pathogens and distinguishing between two or more species of one or more organisms, e.g., bacteria, viruses, yeast, protozoa, and fungi or a combination thereof, in a biological or environmental sample, by detecting the presence of a target nucleic acid sequence in the sample. A positive signal obtained from the sample indicates the presence of the microbe. Multiple microbes can be identified simultaneously using the methods and systems of the invention, by employing the use of more than one effector protein, wherein each effector protein targets a specific microbial target sequence. In this way, a multi-level analysis can be performed for a particular subject in which any number of microbes can be detected at once, for example, a subject with unknown respiratory infection, having symptoms of coronavirus, or an individual at risk or having been exposed to coronavirus. In some embodiments, simultaneous detection of multiple microbes may be performed using a set of probes that can identify one or more microbial species.

Microbe Detection

In some embodiments, a method for detecting microbes in samples is provided comprising distributing a sample or set of samples into one or more individual discrete volumes, the individual discrete volumes comprising a CRISPR system as described herein; incubating the sample or set of samples under conditions sufficient to allow binding of the one or more guide RNAs to one or more microbe-specific targets; activating the CRISPR effector protein via binding of the one or more guide RNAs to the one or more target molecules, wherein activating the CRISPR effector protein results in modification of the RNA-based masking construct such that a detectable positive signal is generated; and detecting the detectable positive signal, wherein detection of the detectable positive signal indicates a presence of one or more target molecules in the sample. The one or more target molecules may be mRNA, gDNA (coding or non-coding), trRNA, or rRNA comprising a target nucleotide tide sequence that may be used to distinguish two or more microbial species/strains from one another. The guide RNAs may be designed to detect target sequences. The embodiments disclosed herein may also utilize certain steps to improve hybridization between guide RNA and target RNA sequences. Methods for enhancing ribonucleic acid hybridization are disclosed in WO 2015/085194, entitled "Enhanced Methods of Ribonucleic Acid Hybridization" which is incorporated herein by reference. The microbe-specific target may be RNA or DNA or a protein. If DNA method may further comprise the use of DNA primers that introduce a RNA polymerase promoter as described herein. If the target is a protein than the method will utilized aptamers and steps specific to protein detection described herein.

Detection of Single Nucleotide Variants

In some embodiments, one or more identified target sequences may be detected using guide RNAs that are specific for and bind to the target sequence as described herein. The systems and methods of the present invention can distinguish even between single nucleotide polymorphisms present among different microbial species and therefore, use of multiple guide RNAs in accordance with the invention may further expand on or improve the number of target sequences that may be used to distinguish between species. For example, in some embodiments, the one or more guide RNAs may distinguish between microbes at the species, genus, family, order, class, phylum, kingdom, or phenotype, or a combination thereof.

Detection Based on rRNA Sequences

In certain example embodiments, the devices, systems, and methods disclosed herein may be used to distinguish multiple microbial species in a sample. In certain example embodiments, identification may be based on ribosomal RNA sequences, including the 16S, 23S, and 5S subunits. Methods for identifying relevant rRNA sequences are disclosed in U.S. Patent Application Publication No. 2017/0029872. In certain example embodiments, a set of guide RNA may designed to distinguish each species by a variable region that is unique to each species or strain. Guide RNAs may also be designed to target RNA genes that distinguish microbes at the genus, family, order, class, phylum, kingdom levels, or a combination thereof. In certain example embodiments where amplification is used, a set of amplification primers may be designed to flanking constant regions of the ribosomal RNA sequence and a guide RNA designed to distinguish each species by a variable internal region. In certain example embodiments, the primers and guide RNAs may be designed to conserved and variable regions in the 16S subunit respectfully. Other genes or genomic regions that uniquely variable across species or a subset of species such as the RecA gene family, RNA polymerase $\beta$ subunit, may be used as well. Other suitable phylogenetic markers, and methods for identifying the same, are discussed for example in Wu et al. arXiv:1307.8690 [q-bio.GN].

In certain example embodiments, a method or diagnostic is designed to screen microbes across multiple phylogenetic and/or phenotypic levels at the same time. For example, the method or diagnostic may comprise the use of multiple CRISPR systems with different guide RNAs. A first set of guide RNAs may distinguish, for example, between mycobacteria, gram positive, and gram negative bacteria. These general classes can be even further subdivided. For example, guide RNAs could be designed and used in the method or diagnostic that distinguish enteric and non-enteric within gram negative bacteria. A second set of guide RNA can be designed to distinguish microbes at the genus or species level. Thus a matrix may be produced identifying all mycobacteria, gram positive, gram negative (further divided into enteric and non-enteric) with each genus of species of bacteria identified in a given sample that fall within one of those classes. The foregoing is for example purposes only. Other means for classifying other microbe types are also contemplated and would follow the general structure described above.

Screening for Drug Resistance

In certain example embodiments, the devices, systems and methods disclosed herein may be used to screen for microbial genes of interest, for example antibiotic and/or antiviral resistance genes. Guide RNAs may be designed to distinguish between known genes of interest. Samples, including clinical samples, may then be screened using the embodiments disclosed herein for detection of such genes. The ability to screen for drug resistance at POC would have tremendous benefit in selecting an appropriate treatment regime. In certain example embodiments, the antibiotic resistance genes are carbapenemases including KPC, NDM1, CTX-M15, OXA-48. Other antibiotic resistance genes are known and may be found for example in the Comprehensive Antibiotic Resistance Database (Jia et al. "CARD 2017: expansion and model-centric curation of the Comprehensive Antibiotic Resistance Database." Nucleic Acids Research, 45, D566-573).

Ribavirin is an effective antiviral that hits a number of RNA viruses. Several clinically important viruses have evolved ribavirin resistance including Foot and Mouth Disease Virus doi:10.1128/JVI.03594-13; polio virus (Pfeifer and Kirkegaard. PNAS, 100(12):7289-7294, 2003); and hepatitis C virus (Pfeiffer and Kirkegaard, J. Virol. 79(4): 2346-2355, 2005). A number of other persistent RNA viruses, such as hepatitis and HIV, have evolved resistance to existing antiviral drugs: hepatitis B virus (lamivudine, tenofovir, entecavir) doi:10/1002/hep22900; hepatitis C virus (telaprevir, BILN2061, ITMN-191, SCh6, boceprevir, AG-021541, ACH-806) doi:10.1002/hep.22549; and HIV (many drug resistance mutations) hivb.standford.edu. The embodiments disclosed herein may be used to detect such variants among others.

Aside from drug resistance, there are a number of clinically relevant mutations that could be detected with the embodiments disclosed herein, such as persistent versus acute infection in LCMV (doi:10.1073/pnas.1019304108), and increased infectivity of Ebola (Diehl et al. Cell. 2016, 167(4):1088-1098).

As described herein elsewhere, closely related microbial species (e.g. having only a single nucleotide difference in a given target sequence) may be distinguished by introduction of a synthetic mismatch in the gRNA.

Monitoring Microbe Outbreaks

In some embodiments, a CRISPR system or methods of use thereof as described herein may be used to determine the evolution of a pathogen outbreak. The method may comprise detecting one or more target sequences from a plurality of samples from one or more subjects, wherein the target sequence is a sequence from a microbe causing the outbreaks. Such a method may further comprise determining a pattern of pathogen transmission, or a mechanism involved in a disease outbreak caused by a pathogen.

The pattern of pathogen transmission may comprise continued new transmissions from the natural reservoir of the pathogen or subject-to-subject transmissions (e.g. human-to-human transmission) following a single transmission from the natural reservoir or a mixture of both. In one embodiment, the pathogen transmission may be bacterial or viral transmission, in such case, the target sequence is preferably a microbial genome or fragments thereof. In one embodiment, the pattern of the pathogen transmission is the early pattern of the pathogen transmission, i.e. at the beginning of the pathogen outbreak. Determining the pattern of the pathogen transmission at the beginning of the outbreak increases likelihood of stopping the outbreak at the earliest possible time thereby reducing the possibility of local and international dissemination.

Determining the pattern of the pathogen transmission may comprise detecting a pathogen sequence according to the methods described herein. Determining the pattern of the pathogen transmission may further comprise detecting shared intra-host variations of the pathogen sequence between the subjects and determining whether the shared intra-host variations show temporal patterns. Patterns in observed intrahost and interhost variation provide important insight about transmission and epidemiology (Gire, et al., 2014).

Detection of shared intra-host variations between the subjects that show temporal patterns is an indication of transmission links between subject (in particular between humans) because it can be explained by subject infection from multiple sources (superinfection), sample contamination recurring mutations (with or without balancing selection to reinforce mutations), or co-transmission of slightly divergent viruses that arose by mutation earlier in the transmission chain (Park, et al., *Cell* 161(7):1516-1526, 2015). Detection of shared intra-host variations between subjects may comprise detection of intra-host variants located at common single nucleotide polymorphism (SNP) positions. Positive detection of intra-host variants located at common (SNP) positions is indicative of superinfection and contamination as primary explanations for the intra-host variants. Superinfection and contamination can be parted on the basis of SNP frequency appearing as inter-host variants (Park, et al., 2015). Otherwise superinfection and contamination can be ruled out. In this latter case, detection of shared intra-host variations between subjects may further comprise assessing the frequencies of synonymous and nonsynonymous variants and comparing the frequency of synonymous and nonsynonymous variants to one another. A nonsynonymous mutation is a mutation that alters the amino acid of the protein, likely resulting in a biological change in the microbe that is subject to natural selection. Synonymous substitution does not alter an amino acid sequence. Equal frequency of synonymous and nonsynonymous variants is indicative of the intra-host variants evolving neutrally. If frequencies of synonymous and nonsynonymous variants are divergent, the intra-host variants are likely to be maintained by balancing selection. If frequencies of synonymous and nonsynonymous variants are low, this is indicative of recurrent mutation. If frequencies of synonymous and nonsynonymous variants are high, this is indicative of co-transmission (Park, et al., 2015).

Like Ebola virus, Lassa virus (LASV) can cause hemorrhagic fever with high case fatality rates. Andersen et al. generated a genomic catalog of almost 200 LASV sequences from clinical and rodent reservoir samples (Andersen, et al., Cell Volume 162, Issue 4, p 738-750, 13 Aug. 2015). Andersen et al. show that whereas the 2013-2015 EVD epidemic is fueled by human-to-human transmissions, LASV infections mainly result from reservoir-to-human infections. Andersen et al. elucidated the spread of LASV across West Africa and show that this migration was accompanied by changes in LASV genome abundance, fatality rates, codon adaptation, and translational efficiency. The method may further comprise phylogenetically comparing a first pathogen sequence to a second pathogen sequence, and determining whether there is a phylogenetic link between the first and second pathogen sequences. The second pathogen sequence may be an earlier reference sequence. If there is a phylogenetic link, the method may further comprise rooting the phylogeny of the first pathogen sequence to the second pathogen sequence. Thus, it is possible to construct the lineage of the first pathogen sequence. (Park, et al., 2015).

The method may further comprise determining whether the mutations are deleterious or adaptive. Deleterious mutations are indicative of transmission-impaired viruses and dead-end infections, thus normally only present in an individual subject. Mutations unique to one individual subject are those that occur on the external branches of the phylogenetic tree, whereas internal branch mutations are those present in multiple samples (i.e. in multiple subjects). Higher rate of nonsynonymous substitution is a characteristic of external branches of the phylogenetic tree (Park, et al., 2015).

In internal branches of the phylogenetic tree, selection has had more opportunity to filter out deleterious mutants. Internal branches, by definition, have produced multiple descendent lineages and are thus less likely to include mutations with fitness costs. Thus, lower rate of nonsynonymous substitution is indicative of internal branches (Park, et al., 2015).

Synonymous mutations, which likely have less impact on fitness, occurred at more comparable frequencies on internal and external branches (Park, et al., 2015).

By analyzing the sequenced target sequence, such as viral genomes, it is possible to discover the mechanisms responsible for the severity of the epidemic episode such as during the 2014 Ebola outbreak. For example, Gire et al. made a phylogenetic comparison of the genomes of the 2014 outbreak to all 20 genomes from earlier outbreaks suggests that the 2014 West African virus likely spread from central Africa within the past decade. Rooting the phylogeny using divergence from other ebolavirus genomes was problematic (6, 13). However, rooting the tree on the oldest outbreak revealed a strong correlation between sample date and root-to-tip distance, with a substitution rate of $8 \times 10^{-4}$ per site per year (13). This suggests that the lineages of the three most recent outbreaks all diverged from a common ancestor at roughly the same time, around 2004, which supports the hypothesis that each outbreak represents an independent zoonotic event from the same genetically diverse viral population in its natural reservoir. They also found out that the 2014 EBOV outbreak might be caused by a single transmission from the natural reservoir, followed by human-to-human transmission during the outbreak. Their results also suggested that the epidemic episode in Sierra Leon might stem from the introduction of two genetically distinct viruses from Guinea around the same time (Gire, et al., 2014).

It has been also possible to determine how the Lassa virus spread out from its origin point, in particular thanks to human-to-human transmission and even retrace the history of this spread 400 years back (Andersen, et al., *Cell* 162(4): 738-50, 2015).

In relation to the work needed during the 2013-2015 EBOV outbreak and the difficulties encountered by the medical staff at the site of the outbreak, and more generally, the method of the invention makes it possible to carry out sequencing using fewer selected probes such that sequencing can be accelerated, thus shortening the time needed from sample taking to results procurement. Further, kits and systems can be designed to be usable on the field so that diagnostics of a patient can be readily performed without need to send or ship samples to another part of the country or the world.

In any method described above, sequencing the target sequence or fragment thereof may be used any of the sequencing processes described above. Further, sequencing the target sequence or fragment thereof may be a near-real-time sequencing. Sequencing the target sequence or fragment thereof may be carried out according to previously described methods (Experimental Procedures: Matranga et al., 2014; and Gire, et al., 2014). Sequencing the target sequence or fragment thereof may comprise parallel sequencing of a plurality of target sequences. Sequencing the target sequence or fragment thereof may comprise Illumina sequencing.

Analyzing the target sequence or fragment thereof that hybridizes to one or more of the selected probes may be an identifying analysis, wherein hybridization of a selected probe to the target sequence or a fragment thereof indicates the presence of the target sequence within the sample.

Currently, primary diagnostics are based on the symptoms a patient has. However, various diseases may share identical symptoms so that diagnostics rely much on statistics. For example, malaria triggers flu-like symptoms: headache, fever, shivering, joint pain, vomiting, hemolytic anemia, jaundice, hemoglobin in the urine, retinal damage, and convulsions. These symptoms are also common for septicemia, gastroenteritis, and viral diseases. Amongst the latter, Ebola hemorrhagic fever has the following symptoms fever, sore throat, muscular pain, headaches, vomiting, diarrhea, rash, decreased function of the liver and kidneys, internal and external hemorrhage.

When a patient is presented to a medical unit, for example in tropical Africa, basic diagnostics will conclude to malaria because statistically, malaria is the most probable disease within that region of Africa. The patient is consequently treated for malaria although the patient might not actually have contracted the disease and the patient ends up not being correctly treated. This lack of correct treatment can be life-threatening especially when the disease the patient contracted presents a rapid evolution. It might be too late before the medical staff realizes that the treatment given to the patient is ineffective and comes to the correct diagnostics and administers the adequate treatment to the patient.

The method of the invention provides a solution to this situation. Indeed, because the number of guide RNAs can be dramatically reduced, this makes it possible to provide on a single chip selected probes divided into groups, each group being specific to one disease, such that a plurality of diseases, e.g. viral infection, can be diagnosed at the same time. Thanks to the invention, more than 3 diseases can be diagnosed on a single chip, preferably more than 4, 5, 6, 7, 8, 9, 10, 11, 12, 13, 14, 15, 16, 17, 18, 19, 20 diseases at the same time, preferably the diseases that most commonly occur within the population of a given geographical area. Since each group of selected probes is specific to one of the diagnosed diseases, a more accurate diagnosis can be performed, thus diminishing the risk of administering the wrong treatment to the patient.

In other cases, a disease such as a viral infection may occur without any symptoms, or had caused symptoms but they faded out before the patient is presented to the medical staff. In such cases, either the patient does not seek any medical assistance or the diagnostics is complicated due to the absence of symptoms on the day of the presentation.

The present invention may also be used in concert with other methods of diagnosing disease, identifying pathogens and optimizing treatment based upon detection of nucleic acids, such as mRNA in crude, non-purified samples.

The method of the invention also provides a powerful tool to address this situation. Indeed, since a plurality of groups of selected guide RNAs, each group being specific to one of the most common diseases that occur within the population of the given area, are comprised within a single diagnostic, the medical staff only need to contact a biological sample taken from the patient with the chip. Reading the chip reveals the diseases the patient has contracted.

In some cases, the patient is presented to the medical staff for diagnostics of particular symptoms. The method of the invention makes it possible not only to identify which disease causes these symptoms but at the same time determine whether the patient suffers from another disease he was not aware of.

This information might be of utmost importance when searching for the mechanisms of an outbreak. Indeed, groups of patients with identical viruses also show temporal patterns suggesting a subject-to-subject transmission links.

Example Microbes

The embodiment disclosed herein may be used to detect a number of different microbes. The term microbe as used herein includes bacteria, fungus, protozoa, parasites and viruses.

Bacteria

The following provides an example list of the types of microbes that might be detected using the embodiments disclosed herein. In certain example embodiments, the microbe is a bacterium. Examples of bacteria that can be detected in accordance with the disclosed methods include without limitation any one or more of (or any combination of) *Acinetobacter baumanii, Actinobacillus* sp., Actinomycetes, *Actinomyces* sp. (such as *Actinomyces israelii* and *Actinomyces naeslundii*), *Aeromonas* sp. (such as *Aeromonas hydrophila, Aeromonas veronii* biovar *sobria* (*Aeromonas sobria*), and *Aeromonas caviae*), *Anaplasma phagocytophilum, Anaplasma marginate Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtherias, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Epidermophyton floccosum, Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus*), *Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Mannheimia hemolytica, Microsporum canis, Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium paratuberculosis, Mycobacterium intracellulare, Mycobacterium avium, Mycobacterium bovis*, and *Mycobacterium marinum*), *Mycoplasm* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Pityrosporum orbiculare* (*Malassezia furfur*), *Plesiomonas shigelloides*. *Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Trichophyton rubrum, T mentagrophytes, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* sp. (such as *Yersinia enterocolitica, Yersinia pestis*, and *Yersinia pseudotuberculosis*) and *Xanthomonas maltophilia* among others.

Fungi

In certain example embodiments, the microbe is a fungus or a fungal species. Examples of fungi that can be detected in accordance with the disclosed methods include without limitation any one or more of (or any combination of), *Aspergillus, Blastomyces, Candidiasis, Coccidiodomycosis*,

*Cryptococcus neoformans, Cryptococcus gatti*, sp. *Histoplasma* sp. (such as *Histoplasma capsulatum*), *Pneumocystis* sp. (such as *Pneumocystis jirovecii*), *Stachybotrys* (such as *Stachybotrys chartarum*), *Mucroymcosis, Sporothrix*, fungal eye infections ringworm, *Exserohilum, Cladosporium*.

In certain example embodiments, the fungus is a yeast. Examples of yeast that can be detected in accordance with disclosed methods include without limitation one or more of (or any combination of), *Aspergillus* species (such as *Aspergillus fumigatus, Aspergillus flavus* and *Aspergillus clavatus*), *Cryptococcus* sp. (such as *Cryptococcus neoformans, Cryptococcus gattii, Cryptococcus laurentii* and *Cryptococcus albidus*), a *Geotrichum* species, a *Saccharomyces* species, a *Hansenula* species, a *Candida* species (such as *Candida albicans*), a *Kluyveromyces* species, a *Debaryomyces* species, a *Pichia* species, or combination thereof. In certain example embodiments, the fungi is a mold. Example molds include, but are not limited to, a *Penicillium* species, a *Cladosporium* species, a *Byssochlamys* species, or a combination thereof.

Protozoa

In certain example embodiments, the microbe is a protozoa. Examples of protozoa that can be detected in accordance with the disclosed methods and devices include without limitation any one or more of (or any combination of), Euglenozoa, Heterolobosea, Diplomonadida, Amoebozoa, Blastocystic, and Apicomplexa. Example Euglenoza include, but are not limited to, *Trypanosoma cruzi* (Chagas disease), *T. brucei* gambiense, *T. brucei* rhodesiense, *Leishmania braziliensis, L. infantum, L. mexicana, L. major, L. tropica*, and *L. donovani*. Example Heterolobosea include, but are not limited to, *Naegleria fowleri*. Example Diplomonadids include, but are not limited to, *Giardia intestinalis* (*G. lamblia, G. duodenalis*). Example Amoebozoa include, but are not limited to, *Acanthamoeba castellanii, Balamuthia madrillaris, Entamoeba histolytica*. Example Blastocysts include, but are not limited to, Blastocystic *hominis*. Example Apicomplexa include, but are not limited to, *Babesia microti, Cryptosporidium parvum, Cyclospora cayetanensis, Plasmodium falciparum, P. vivax, P. ovale, P. malariae*, and *Toxoplasma gondii*.

Parasites

In certain example embodiments, the microbe is a parasite. Examples of parasites that can be detected in accordance with disclosed methods include without limitation one or more of (or any combination of), an *Onchocerca* species and a *Plasmodium* species.

Viruses

In certain example embodiments, the systems, devices, and methods, disclosed herein are directed to detecting viruses in a sample. The embodiments disclosed herein may be used to detect viral infection (e.g. of a subject or plant), or determination of a viral strain, including viral strains that differ by a single nucleotide polymorphism. The virus may be a DNA virus, a RNA virus, or a retrovirus. Non-limiting example of viruses useful with the present invention include, but are not limited to Ebola, measles, SARS, Chikungunya, hepatitis, Marburg, yellow fever, MERS, Dengue, Lassa, influenza, rhabdovirus or HIV. A hepatitis virus may include hepatitis A, hepatitis B, or hepatitis C. An influenza virus may include, for example, influenza A or influenza B. An HIV may include HIV 1 or HIV 2. In certain example embodiments, the viral sequence may be a human respiratory syncytial virus, Sudan ebola virus, Bundibugyo virus, Tai Forest ebola virus, Reston ebola virus, Achimota, *Aedes* flavivirus, Aguacate virus, Akabane virus, Alethinophid reptarenavirus, Allpahuayo mammarenavirus, Amapari mmarenavirus, Andes virus, Apoi virus, Aravan virus, Aroa virus, Arumwot virus, Atlantic salmon paramyxovirus, Australian bat lyssavirus, Avian bornavirus, Avian metapneumovirus, Avian paramyxoviruses, penguin or Falkland Islandsvirus, BK polyomavirus, Bagaza virus, Banna virus, Bat herpesvirus, Bat sapovirus, Bear Canon mammarenavirus, Beilong virus, Betacoronavirus, Betapapillomavirus 1-6, Bhanja virus, Bokeloh bat lyssavirus, Borna disease virus, Bourbon virus, Bovine hepacivirus, Bovine parainfluenza virus 3, Bovine respiratory syncytial virus, Brazoran virus, Bunyamwera virus, Caliciviridae virus. California encephalitis virus, Candiru virus, Canine distemper virus, Canine pneumovirus, Cedar virus, Cell fusing agent virus, Cetacean morbillivirus, Chandipura virus, Chaoyang virus, Chapare mammarenavirus, Chikungunya virus, Colobus monkey papillomavirus, Colorado tick fever virus, Cowpox virus, Crimean-Congo hemorrhagic fever virus, *Culex* flavivirus, Cupixi mammarenavirus, Dengue virus, Dobrava-Belgrade virus, Donggang virus, Dugbe virus, Duvenhage virus, Eastern equine encephalitis virus, Entebbe bat virus, Enterovirus A-D, European bat lyssavirus 1-2, Eyach virus, Feline morbillivirus, Fer-de-Lance paramyxovirus, Fitzroy River virus, Flaviviridae virus, Flexal mammarenavirus, GB virus C, Gairo virus, Gemycircularvirus, Goose paramyxovirus SF02, Great Island virus, Guanarito mammarenavirus, Hantaan virus, Hantavirus Z10, Heartland virus, Hendra virus, Hepatitis A/B/C/E, Hepatitis delta virus, Human bocavirus, Human coronavirus, Human endogenous retrovirus K, Human enteric coronavirus, Human genital-associated circular DNA virus-1, Human herpesvirus 1-8, Human immunodeficiency virus 1/2, Human mastadenovirus A-G, Human papillomavirus, Human parainfluenza virus 1-4, Human paraechovirus, Human picornavirus, Human smacovirus, Ikoma lyssavirus, Ilheus virus, Influenza A-C, Ippy mammarenavirus, Irkut virus, J-virus, JC polyomavirus, Japanese encephalitis virus, Junin mammarenavirus, KI polyomavirus, Kadipiro virus, Kamiti River virus, Kedougou virus, Khuj and virus, Kokobera virus, Kyasanur forest disease virus, Lagos bat virus, Langat virus, Lassa mammarenavirus, Latino mammarenavirus, Leopards Hill virus, Liao ning virus, Ljungan virus, Lloviu virus, Louping ill virus, Lujo mammarenavirus, Luna mammarenavirus, Lunk virus, Lymphocytic choriomeningitis mammarenavirus, Lyssavirus Ozernoe, MS512\0.225 virus, Machupo mammarenavirus, Mamastrovirus 1, Manzanilla virus, Mapuera virus, Marburg virus, Mayaro virus, Measles virus, Menangle virus, Mercadeo virus, Merkel cell polyomavirus, Middle East respiratory syndrome coronavirus, Mobala mammarenavirus, Modoc virus, Moijang virus, Mokolo virus, Monkeypox virus, Montana *myotis* leukoenchalitis virus, Mopeia lassa virus reassortant 29, Mopeia mammarenavirus, Morogoro virus, Mossman virus, Mumps virus, Murine pneumonia virus, Murray Valley encephalitis virus, Nariva virus, Newcastle disease virus, Nipah virus, Norwalk virus, Norway rat hepacivirus, Ntaya virus, O'nyong-nyong virus, Oliveros mammarenavirus, Omsk hemorrhagic fever virus, Oropouche virus, Parainfluenza virus 5, Parana mammarenavirus, Parramatta River virus, Peste-des-petits-ruminants virus, Pichande mammarenavirus, Picornaviridae virus, Pirital mammarenavirus, Piscihepevirus A, Porcine parainfluenza virus 1, porcine rubulavirus, Powassan virus, Primate T-lymphotropic virus 1-2, Primate erythroparvovirus 1, Punta Toro virus, Puumala virus, Quang Binh virus, Rabies virus, Razdan virus, Reptile bornavirus 1, Rhinovirus A-B, Rift Valley fever virus, Rinderpest virus, Rio Bravo virus, Rodent Torque Teno virus, Rodent hepacivirus, Ross River virus, Rotavirus A-I, Royal Farm virus, Rubella virus, Sabia mammarenavirus, Salem virus, Sandfly fever Naples virus, Sandfly fever Sicilian virus, Sapporo virus, Sathuperi virus, Seal anellovirus, Semliki Forest virus, Sendai virus, Seoul virus, Sepik virus, Severe acute respiratory syndrome-related coronavirus, Severe fever with thrombocytopenia syndrome virus, Shamonda virus, Shimoni bat virus, Shuni virus, Simbu virus, Simian torque teno virus, Simian virus 40-41, Sin Nombre virus, Sindbis virus, Small anellovirus, Sosuga virus, Spanish goat encephalitis virus, Spondweni virus, St. Louis encephalitis virus, Sunshine virus, TTV-like mini virus, Tacaribe mammarenavirus, Taila virus, Tamana bat virus, Tamiami mammarenavirus, Tembusu virus, Thogoto virus, Thottapalayam virus, Tick-borne encephalitis virus, Tioman virus, Togaviridae virus, Torque teno *canis* virus, Torque teno douroucouli virus, Torque teno *felis* virus, Torque teno midi virus, Torque teno sus virus, Torque teno tamarin virus, Torque teno virus, Torque teno *zalophus* virus, Tuhoko virus, Tula virus, Tupaia paramyxovirus, Usutu virus, Uukuniemi virus, Vaccinia virus, Variola virus, Venezuelan equine encephalitis virus, Vesicular stomatitis Indiana virus, WU Polyomavirus, Wesselsbron virus, West Caucasian bat virus, West Nile virus, Western equine encephalitis virus, Whitewater Arroyo mammarenavirus, Yellow fever virus, Yokose virus, Yug Bogdanovac virus, Zaire ebolavirus, Zika virus, or *Zygosaccharomyces bailii* virus Z viral sequence. Examples of RNA viruses that may be detected include one or more of (or any combination of) Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, or a Deltavirus. In certain example embodiments, the virus is Coronavirus, SARS, Poliovirus, Rhinovirus, Hepatitis A, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus.

In certain example embodiments, the virus may be a plant virus selected from the group comprising Tobacco mosaic virus (TMV), Tomato spotted wilt virus (TSWV), Cucumber mosaic virus (CMV), Potato virus Y (PVY), the RT virus Cauliflower mosaic virus (CaMV), Plum pox virus (PPV), Brome mosaic virus (BMV), Potato virus X (PVX), Citrus tristeza virus (CTV), Barley yellow dwarf virus (BYDV), Potato leafroll virus (PLRV), Tomato bushy stunt virus (TBSV), rice tungro spherical virus (RTSV), rice yellow mottle virus (RYMV), rice hoja blanca virus (RHBV), maize rayado fino virus (MRFV), maize dwarf mosaic virus (MDMV), sugarcane mosaic virus (SCMV), Sweet potato feathery mottle virus (SPFMV), sweet potato sunken vein closterovirus (SPSVV), Grapevine fanleaf virus (GFLV), Grapevine virus A (GVA), Grapevine virus B (GVB), Grapevine fleck virus (GFkV), Grapevine leafroll-associated virus-1, -2, and -3, (GLRaV-1, -2, and -3), *Arabis* mosaic virus (ArMV), or *Rupestris* stem pitting-associated virus (RSPaV). In a preferred embodiment, the target RNA molecule is part of said pathogen or transcribed from a DNA molecule of said pathogen. For example, the target sequence may be comprised in the genome of an RNA virus. It is further preferred that CRISPR effector protein hydrolyzes said target RNA molecule of said pathogen in said plant if said pathogen infects or has infected said plant. It is thus preferred that the CRISPR system is capable of cleaving the target RNA molecule from the plant pathogen both when the CRISPR system (or parts needed for its completion) is applied therapeutically, i.e. after infection has occurred or prophylactically, i.e. before infection has occurred.

In certain example embodiments, the virus may be a retrovirus. Example retroviruses that may be detected using the embodiments disclosed herein include one or more of or any combination of viruses of the Genus Alpharetrovirus, Betaretrovirus, Gammaretrovirus, Deltaretrovirus, Epsilonretrovirus, Lentivirus, Spumavirus, or the Family Metaviridae, Pseudoviridae, and Retroviridae (including HIV), Hepadnaviridae (including Hepatitis B virus), and Caulimoviridae (including Cauliflower mosaic virus).

In certain example embodiments, the virus is a DNA virus. Example DNA viruses that may be detected using the embodiments disclosed herein include one or more of (or any combination of) viruses from the Family Myoviridae, Podoviridae, Siphoviridae, Alloherpesviridae, Herpesviridae (including human herpes virus, and Varicella Zorter virus), Malocoherpesviridae, Lipothrixviridae, Rudiviridae, Adenoviridae, Ampullaviridae, Ascoviridae, Asfarviridae (including African swine fever virus), Baculoviridae, Cicaudaviridae, Clavaviridae, Corticoviridae, Fuselloviridae, Globuloviridae, Guttaviridae, Hytrosaviridae, Iridoviridae, Maseilleviridae, Mimiviridae, Nudiviridae, Nimaviridae, Pandoraviridae, Papillomaviridae, Phycodnaviridae, Plasmaviridae, Polydnaviruses, Polyomaviridae (including Simian virus 40, JC virus, BK virus), Poxviridae (including Cowpox and smallpox), Sphaerolipoviridae, Tectiviridae, Turriviridae, Dinodnavirus, Salterprovirus, Rhizidovirus, among others. In some embodiments, a method of diagnosing a species-specific bacterial infection in a subject suspected of having a bacterial infection is described as obtaining a sample comprising bacterial ribosomal ribonucleic acid from the subject; contacting the sample with one or more of the probes described, and detecting hybridization between the bacterial ribosomal ribonucleic acid sequence present in the sample and the probe, wherein the detection of hybridization indicates that the subject is infected with *Escherichia coli, Klebsiella pneumoniae, Pseudomonas aeruginosa, Staphylococcus aureus, Acinetobacter baumannii, Candida albicans, Enterobacter cloacae, Enterococcus faecalis, Enterococcus faecium, Proteus mirabilis, Staphylococcus agalactiae*, or *Staphylococcus maltophilia* or a combination thereof.

Coronavirus

Systems and methods of the presently disclosed invention are designed to detect coronavirus, in an aspect, the target sequence is the 2019-nCoV, also referred to herein as SARS-CoV-2, which causes COVID-19. The coronavirus is a positive-sense single stranded RNA family of viruses, infecting a variety of animals and humans. SARS-CoV is one type of coronavirus infection, as well as MERS-CoV. Detection of one or more coronaviruses are envisioned, including the SARS-CoV-2 detected in Wuhan City. Sequences of the sARS-CoV-2 are available at GISAID accession no. EPI_ISL_402124 and EPI_ISL_402127-402130, and described in DOI: 10.1101/2020.01.22.914952. Further deposits of the SARS-CoV2 are deposited in the GISAID platform include EP_ISL_402119-402121 and EP_ISL_402123-402124; see also GenBank Accession No. MN908947.3. In an aspect, one may use known SARS and SARS-related coronaviruses or other viruses from one or more hosts to generate a non-redundant alignment. Related viruses can be found, for example in bats.

In certain embodiments, the systems are designed to comprise at least one highly active guide polynucleotide which is designed according to the methods disclosed herein. In a preferred embodiment, the guide polynucleotide binds to at least one target sequence that is a unique coronavirus genomic sequence, thereby identifying the presence of coronavirus to the exclusion of other viruses. The systems and methods can be designed to detect a plurality of respiratory infections or viral infections, including coronavirus.

In an aspect the at least one guide polynucleotide binds to a coronavirus sequence encoding a polypeptide that is immunostimulatory to a host immune system. Immunostimulatory polypeptides have the ability to enhance, stimulate, or increase response of the immune system, typically by inducing the activation or activity of a components of the immune system (e.g. an immune cell). In embodiments, the immunostimulatory polypeptide contributes to immune-mediated disease in the host. In an aspect, the host is a mammal, for example, a human, a bat, or a pangolin, that may be infected by a coronavirus. Cyranoski, D. Did pangolins spread the China coronavirus to people? Nature, 7 Feb. 2020. In certain embodiments, the guide polynucleotide can be designed to detect SARS-CoV-2 or a variant thereof in meat, live animals and humans so that testing can be performed, for example at markets and other public places where sources of contamination can arise.

Gene targets may comprise ORF1ab, N protein, RNA-dependent RNA polymerase (RdRP), E protein, ORF1b-nsp14, Spike glycoprotein (S), or pancorona targets. Molecular assays have been under development and can be used as a starting point to develop guide molecules for the methods and systems described herein. See, "Diagnostic detection of 2019-nCoV by real-time RT-PCR" Charité, Berlin Germany (17 Jan. 2020)' Detection of 2019 novel coronavirus (2019-nCoV) in suspected human cases by RT-PCR—Hong Kong University (23 Jan. 2020); PCR and sequencing protocol for 2019-nCoV—Department of Medical Sciences, Ministry of Public Health, Thailand (updated 28 Jan. 2020); PCR and sequencing protocols for 2019-nCoV-National Institute of Infectious Diseases Japan (24 Jan. 2020); US CDC panel primer and probes—U.S. CDC, USAV—U.S. CDC, USA (28 Jan. 2020); China CDC Primers and probes for detection 2019-nCoV (24 Jan. 2020), incorporated in their entirety by reference. Further, the guide molecule design may exploit differences or similarities with SARS-CoV. Researchers have recently identified simialrities and fifrferences between 2019-nCoV and SARS-CoV. "Coronavirus Genome Annotation Reveals Amino Acid Differences with Other SARS Viruses," genomeweb, Feb. 10, 2020. For example, guide molecules based on the 8a protein, which was present in SARS-CoV but absent in SARS-CoV-2, can be utilized to differentiate between the viruses. Similarly, the 8b and 3b proteins have different lengths in SARS-CoV and sARS-CoV-2 and can be utilized to design guide molecules to detect non-overlapping proteins of nucleotides encoding in the two viruses. Wu et al., Genome Composition and Divergence of the Novel Coronavirus (2019-nCoV) Originating in China, Cell Host & Microbe (2020), DOI: 10.1016/j.chom.2020.02.001, incorporated herein by reference, including all supplemental information, in particular Table 51.

The systems and methods of detection can be used to identify single nucleotide variants, detection based on rRNA sequences, screening for drug resistance, monitoring microbe outbreaks, genetic perturbations, and screening of environmental samples, as described in PCT/US2018/054472 filed Oct. 22, 2018 at [0183]—[0327], incorporated herein by reference.

In certain example embodiments, the systems, devices, and methods disclosed herein may be used for biomarker detection. For example, the systems, devices and method disclosed herein may be used for SNP detection and/or genotyping. The systems, devices and methods disclosed herein may be also used for the detection of any disease state or disorder characterized by aberrant gene expression. Aberrant gene expression includes aberration in the gene expressed, location of expression and level of expression. Multiple transcripts or protein markers related to cardiovascular, immune disorders, and cancer among other diseases may be detected. In certain example embodiments, the embodiments disclosed herein may be used for cell free DNA detection of diseases that involve lysis. In certain example embodiments, the embodiments could be utilized for faster and more portable detection for pre-natal testing of cell-free DNA. The embodiments disclosed herein may be used for screening panels of different SNPs associated with, among others, different coronaviruses, evolving SARS-CoV2, and other related respiratory viral infections. As described herein elsewhere, closely related genotypes/alleles or biomarkers (e.g. having only a single nucleotide difference in a given target sequence) may be distinguished by introduction of a synthetic mismatch in the gRNA.

In an aspect, the invention relates to a method for detecting target nucleic acids in samples, comprising:

distributing a sample or set of samples into one or more individual discrete volumes, the individual discrete volumes comprising a CRISPR system according to the invention as described herein;

incubating the sample or set of samples under conditions sufficient to allow binding of the one or more guide RNAs to one or more target molecules;

activating the CRISPR effector protein via binding of the one or more guide RNAs to the one or more target molecules, wherein activating the CRISPR effector protein results in modification of the RNA-based masking construct such that a detectable positive signal is generated; and detecting the detectable positive signal, wherein detection of the detectable positive signal indicates a presence of one or more target molecules in the sample.

The sensitivity of the assays described herein are well suited for detection of target nucleic acids in a wide variety of biological sample types, including sample types in which the target nucleic acid is dilute or for which sample material is limited. Methods for field deployable and rapid diagnostic assays can be optimized for the type of sample material utilized. See, e.g. Myhrvold et al., 2018. Biomarker screening may be carried out on a number of sample types including, but not limited to, saliva, urine, blood, feces, sputum, and cerebrospinal fluid. The embodiments disclosed herein may also be used to detect up- and/or down-regulation of genes. For example, a sample may be serially diluted such that only over-expressed genes remain above the detection limit threshold of the assay.

In certain embodiments, the present invention provides steps of obtaining a sample of biological fluid (e.g., urine, blood plasma or serum, sputum, cerebral spinal fluid), and extracting the DNA or RNA. The mutant nucleotide sequence to be detected, may be a fraction of a larger molecule or can be present initially as a discrete molecule.

In certain embodiments, DNA is isolated from plasma/serum of a cancer patient. For comparison, DNA samples isolated from neoplastic tissue and a second sample may be isolated from non-neoplastic tissue from the same patient (control), for example, lymphocytes. The non-neoplastic tissue can be of the same type as the neoplastic tissue or from a different organ source. In certain embodiments, blood samples are collected and plasma immediately separated from the blood cells by centrifugation. Serum may be filtered and stored frozen until DNA/RNA extraction.

In an aspect, sample preparation can comprise methods as disclosed herein to circumvent other RNA extraction methods and can be used with standard amplification techniques such as RT-PCR as well as the CRISPR-Cas detection methods disclosed herein. In an aspect, the method may comprise a one-step extraction-free RNA preparation method that can be used with samples tested for coronavirus, which may be, in an aspect, a RT-qPCR testing method, a lateral flow detection method or other CRISPR-Cas detection method disclosed herein. Advantageously, the RNA extraction method can be utilized directly with other testing protocols. In an aspect, the method comprises use of a nasopharyngeal swab, nasal saline lavage, or other nasal sample or nucleic acid sample such as saliva with extraction-free polynucleotide isolation solution, for example, Quick Extract™ DNA Extraction Solution (QE09050), Lucigen. In an aspect, the sample is diluted 2:1, 1:1 or 1:2 sample:extraction-free polynucleotide isolation solution. The sample:extraction mix is incubated at about 90° C. to about 98° C., preferably about 95° C. The incubation period can be about 2, 3, 4, 5, 6, 7, 8, 9, or 10 minutes, preferably about 4 to 6 minutes, or about 5 minutes. Incubation time and temperature may vary depending on sample size and quality. Current CDC Real-Time RT-PCR Diagnostic Panel are as described at fda.gov/media/134922/download, "CDC 2019-Novel Coronavirus (2019-nCoV) Real-Time RT-PCR Diagnostic Panel." In certain embodiments, the extraction-free polynucleotide isolation solution can remain with the sample subsequent to incubation and be utilized in the next steps for detection methods. In an aspect, the detection method is an RT-qPCR reaction and the extraction solution is kept at a concentration of less than 10%, 9%, 8%, 7%, 6%, 5%, 4%, 3% of the reaction mixture, where the reaction mixture comprises the detection reaction reagents, sample and extraction solution.

In certain embodiments, a bead is utilized with particular embodiments of the invention and may be included with the extraction-free polynucleotide isolation solution. The bead may be used to capture, concentrate or otherwise enrich for particular material. The bead may be magnetic, and may be provided to capture nucleic acid material. In another aspect, the bead is a silica bead. Beads may be utilized in an extraction step of the methods disclosed herein. Beads can be optionally used with the methods described herein, including with the one-pot methods that allow for concentration of viral nucleic acids from large volume samples, such as saliva or swab samples to allow for a single one-pot reaction method. Concentration of desired target molecules can be increased by about 10-fold, 50-fold, 100-fold, 200-fold, 500-fold, 800-fold, 1000-fold, 1500-fold, 2000-fold, 2500-fold, 3000-fold, or more.

Magnetic beads in a PEG and salt solution are preferred in an aspect, and in embodiments bind to viral RNA and/or DNA which allows for concentration and lysis concurrently. Silica beads can be used in another aspect. Capture moieties such as oligonucleotide functionalized beads are envisioned for use. The beads may be using with the extraction reagents, allowed to incubate with a sample and the lysis/extraction-free polynucleotide isolation solution, thereby concentrating target molecules on the beads. When used with a cartridge device detailed elsewhere herein, a magnet can be activated and the beads collected, with optional flushing of the extraction-free polynucleotide isolation solution and one or more washes performed. Advantageously, the beads can be used in the one-pot methods and systems without additional washings of the beads, allowing for a more efficient process without increased risks of contamination in multi-step processes. Beads can be utilized with the isothermal amplifications detailed herein, and the beads can flow into an amplification chamber of the cartridge or be maintained in the pot for the amplification step. Upon heating, nucleic acid can be released off the beads.

In certain example embodiments, target nucleic acids are detected directly from a crude or unprocessed sample, such as blood, serum, saliva, cebrospinal fluid, sputum, or urine. In certain example embodiments, the target nucleic acid is cell free DNA.

EXAMPLES

Example 1—Coronavirus Assay Development

Systems and methods can be designed for the detection and diagnosis of viruses and viral infections, including Covid-2019, optionally with acute respiratory infections using the disclosure detailed herein. The systems can comprise two or more CRISPR Cas systems to multiplex, for example, detection of Covid-2019, and other coronaviruses such as SARS-CoV and MERS-CoV. Sequences of the 2019-nCoV are available at GISAID accession no. EPI_ISL_402124 and EPI_ISL_402127-402130, and described in DOI: 10.1101/2020.01.22.914952. Further deposits of the Wuhan coronavirus deposited in the GISAID platform include EP_ISL_402119-402121 and EP_ISL_402123-402124; see also GenBank Accession No. MN908947, and guide design can be predicated on genome sequences disclosed therein and in Tian et al, "Potent binding of 2019 novel coronavirus spike protein by a SARS coronavirus-specific human monoclonal antibody"; doi: 10.1101/2020.01.28.923011, incorporated by reference, which details human monoclonal antibody, CR3022 binding of the 2019-nCoV RBD (KD of 6.3 nM). Guide design can target unique viral genomic regions of the 2019-nCoV or conserved genomic regions across one or more viruses of the coronavirus family. Gene targets may comprise ORF1ab, N protein, RNA-dependent RNA polymerase (RdRP), E protein, ORF1b-nsp14, Spike glycoprotein (S), or pancorona targets, including guide molecules based on the 8a protein, which was present in SARS-CoV but absent in 2019-nCoV, utilized to differentiate between the viruses. Similarly, the 8b and 3b proteins have different lengths in SARS-CoV and 2019-nCoV and can be utilized to design guide molecules to detect non-overlapping proteins of nucleotides encoding in the two viruses. Wu et al., Genome Composition and Divergence of the Novel Coronavirus (2019-nCoV) Originating in China, Cell Host & Microbe (2020), DOI: 10.1016/j.chom.2020.02.001, incorporated herein by reference, including all supplemental information, in particular Table 51. Molecular assays have been under development and can be used as a starting point to develop guide molecules for the methods and systems described herein.

Detection of respiratory viruses such as coronavirus may include a thermostable CRISPR-Cas protein as described herein, which may be a Cas13a ortholog. As described elsewhere herein, one or more Cas13a orthologs may be utilized in a multiplex design, including the thermostable Cas13a orthologs described herein, where such thermostability confers further rapidity to the diagnostic and detections platforms and methods disclosed herein.

Coronavirus detection can comprise two or more detection systems utilizing RNA targeting Cas effector proteins; DNA targeting Cas effector proteins, or a combination thereof. The RNA-targeting effector proteins may be a Cas13 protein, such as Cas13a, Cas13b, or Cas13c, including one of the thermostable Cas13a proteins described herein. The DNA-targeting effector protein may be a Type V protein, e.g. Cas12 protein such as Cpf1 and C2c1. Multiplexing systems can be designed such that different Cas proteins with different sequence specificities or other motif cutting preferences can be used, including, in certain embodiments, at least one Cas13a thermostable protein described herein. See International Publication WO 2019/126577. Type VI and Type V Cas proteins are known to possess different cutting motif preferences. See Gootenberg et al. "Multiplexed and portable nucleic acid detection platform with Cas13b, Cas12a, and Csm6." Science. Apr. 27, 2018, 360:439-444; International Publication WO 2019/051318. Thus, embodiments disclosed herein may further comprise multiplex embodiments comprising two or more Type VI Cas proteins with different cutting preferences, or one or more Type VI Cas proteins and one or more Type V case proteins.

In certain example embodiments, the coronavirus assay comprises a Type VI Cas protein disclosed herein and guide molecule comprising a guide sequence configured to direct binding of the CRISPR-Cas complex to a target molecule and a labeled detection molecule ("RNA-based masking construct"). A multiplex embodiment can be designed to track one or more variants of coronavirus or one or more variants of coronavirus, including the 2019-nCoV, in combination with other viruses, for example, Human respiratory syncytial virus, Middle East respiratory syndrome (MERS) coronavirus, Severe acute respiratory syndrome-related (SARS) coronavirus, and influenza.

In certain embodiments, the detection assay can be provided on a lateral flow device, as described herein. The lateral flow device may comprise a flexible substrate, such as a paper substrate or a flexible polymer-based substrate, which can include freeze-dried reagents for detection assays with a visual readout of the assay results. See, WO 2019/071051 at [0145]-[0151] and Example 2, specifically incorporated herein by reference. Accordingly, the assay can be adapted for field diagnostics, including use of visual readout on a lateral flow device, rapid, sensitive detection and can be deployed for early and direct detection.

Example 2—Lateral Flow Cornavirus Detection

Figures 2A, 2B:
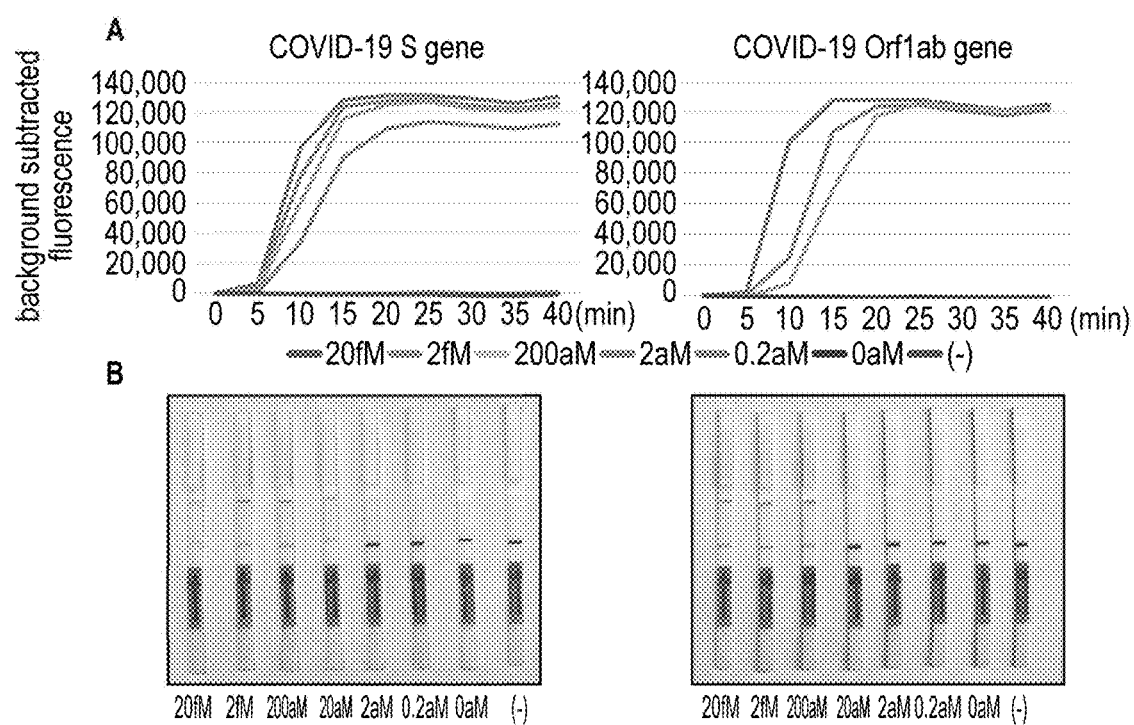
FIG. 2A-2B FIG. 2A—Detection of synthetic COVID-19 sequences using a two-step SHERLOCK reaction (25 min RPA). Readout using fluorescence RNaseAlert reporter.
Figures 3A, 3B:
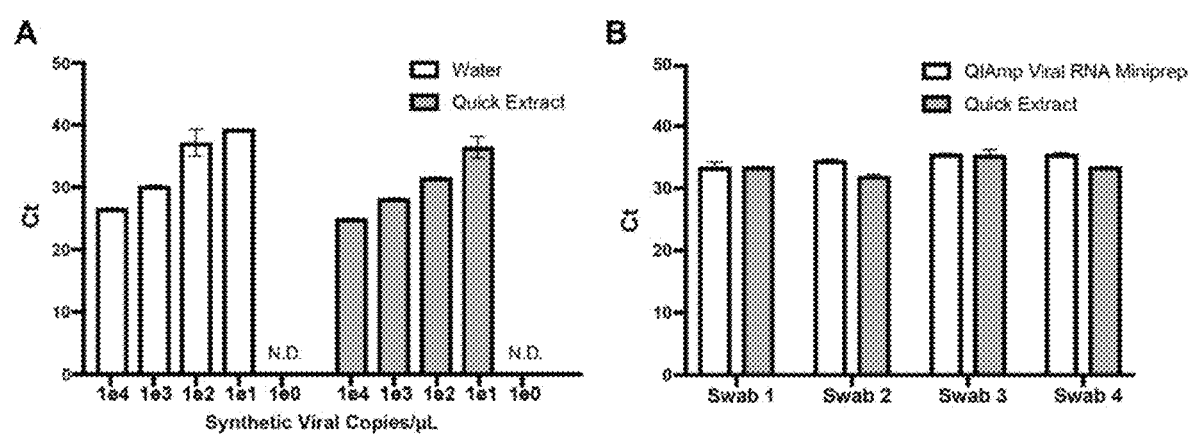
FIG. 3A-3B.

Detection of coronavirus targets was performed using RPA amplification for 25 minutes followed by a 30 minute Cas 13 reaction using the following primers and guides:
S gene RPA GAAATTAATACGACTCACTATAGG-GAGGTTTCAAACTTTACTTGCTTTA Forward CATAGA (SEQ ID NO: 61977)
S gene RPA TCCTAGGTTGAAGATAACCCACAT-AATAAG (SEQ ID NO: 61978) Reverse
S gene GAUUUAGACUACCC-CAAAAACGAAGGGGAC-UAAAACGCAGCACCAGC LwCas13a UGUC-CAACCUGAAGAAG (SEQ ID NO: 61979)
crRNA
Orflab GAAATTAATACGACTCAC-TATAGGGCGAAGTTGTAGGAGACATTATAC RPA TTAAACC (SEQ ID NO: 61980)
Forward Orflab TAGTAAGACTAGAATTGTCTACAT-AAGCAGC (SEQ ID NO: 61981)
RPA Reverse
Orflab GAUUUAGACUACCC-CAAAAACGAAGGGGACUAAAACCCAACCUC-UUC LwCas13a UGUAAUUUUUAAACUAU (SEQ ID NO: 61982)
crRNA Results are provided in FIG. 1, with S gene detection shown on the left and Orflab on the right, and FIG. 2B. The assay has been further validated by fluorescence in FIG. 2A.

Example 3. RNA Preparation for COVID-19 Detection

One of the major bottlenecks for COVID-19 diagnosis is the limited availability of RNA extraction kits for preparing virus RNA from patient samples and the low-throughput nature of the extraction procedure. Here, Applicants describe a one-step extraction-free RNA preparation method that can be carried out in 5 minutes and the reaction can be used directly with the CDC COVID-19 RT-qPCR testing protocol, thus increasing throughput, and alleviating supply chain issues.

Materials and Reagents

Quick Extract DNA Extraction Solution (QE09050), Lucigen Protocol

Step 1. Dilute nasopharyngeal swab stored in Viral Transport Medium or Human Specimen Control (HSC) 1:1 with Quick Extract™ DNA Extraction Solution. For example, in a fresh PCR tube, mix 20 ul of swab sample with 20 ul of Quick Extract.

Step 2. Incubate swab-Quick Extract mix at 95° C. for 5 minutes. Allow reaction to cool on ice before proceeding.

Step 3. Use reaction from step (2) for qRT-PCR. Make sure the amount from step (2) does not exceed 10% of the total qRT-PCR reaction volume. For example, if a RT-qPCR reaction has a total volume of 50 ul, do not use more than 5 ul of the reaction mix from step (2).

Assay Development and Preliminary Validation

Applicants evaluated a number of buffer compositions to identify one that achieved efficient lysis of enveloped virus while preserving the activity of the CDC recommended RT-qPCR reaction (TaqPath™ 1-Step RT-qPCR Master Mix). Of all of the buffers tested, Quick Extract™ DNA Extraction Solution provided satisfactory results.

To confirm that the presence of QE does not interfere with RT-qPCR activity, comparison of RT-qPCR reactions using synthetic SARS-CoV-2 gene fragment (Twist Synthetic SARS-CoV-2 RNA Control 1, SKU:102019) dissolved in either ddH$_2$O or in a 50:50 ddH$_2$O:Quick Extract mixture was performed. Each RT-qPCR reaction was set up with a total volume of 10 ul (1 ul of RNA sample, 0.5 ul of CDC probe N1, 2.5 ul of TaqPath RT-qPCR master mix, and 6 ul of ddH$_2$O). From these reactions, Applicants found that Quick Extract at a final concentration of 5% did not negatively affect the RT-qPCR reaction (FIG. 1A).

Preliminary validation of the Quick Extract RNA preparation procedure was conducted on coronavirus positive nasopharyngeal swabs where it was found that RNA samples prepared using Quick Extract supported similarly sensitive detection of coronavirus as QIAmp Viral RNA Miniprep for all 4 swab samples (FIG. 1B). To simulate low viral load, coronavirus positive swabs were diluted 1:10 in pooled nasopharyngeal swabs from 5 unique, healthy donors (Lee Biosolutions, SKU:991-31-NC-5) prior to purification or Quick Extract treatment. For the QIAmp Viral RNA Miniprep conditions, 100 ul of diluted swab sample was used for extraction and was eluted using 100 ul of ddH$_2$O. 1 ul of the elution was used in a 10 ul RT-qPCR reaction. For the Quick Extract conditions, 1 ul of Quick Extract preparation was used for each 10 ul RT-qPCR reaction.

Example 4. Development of a One Pot RT-LAMP Cas12b SHERLOCK Reaction

Applicants developed a research protocol for a SHERLOCK-based COVID-19 coronavirus detection. The basic protocol is outlined in FIG. 16. A nasopharyngeal swab or saliva sample is collected from a patient. The sample is added to a tube containing SHERLOCK reagents. The tube is heated for 60 minutes at 60° C. A SHERLOCK detection lateral flow strip is then dipped into the reaction in the tube and the strip is then analyzed for results. Table 4 shows final reaction parameters for reagents in the tube.

Figure 16:
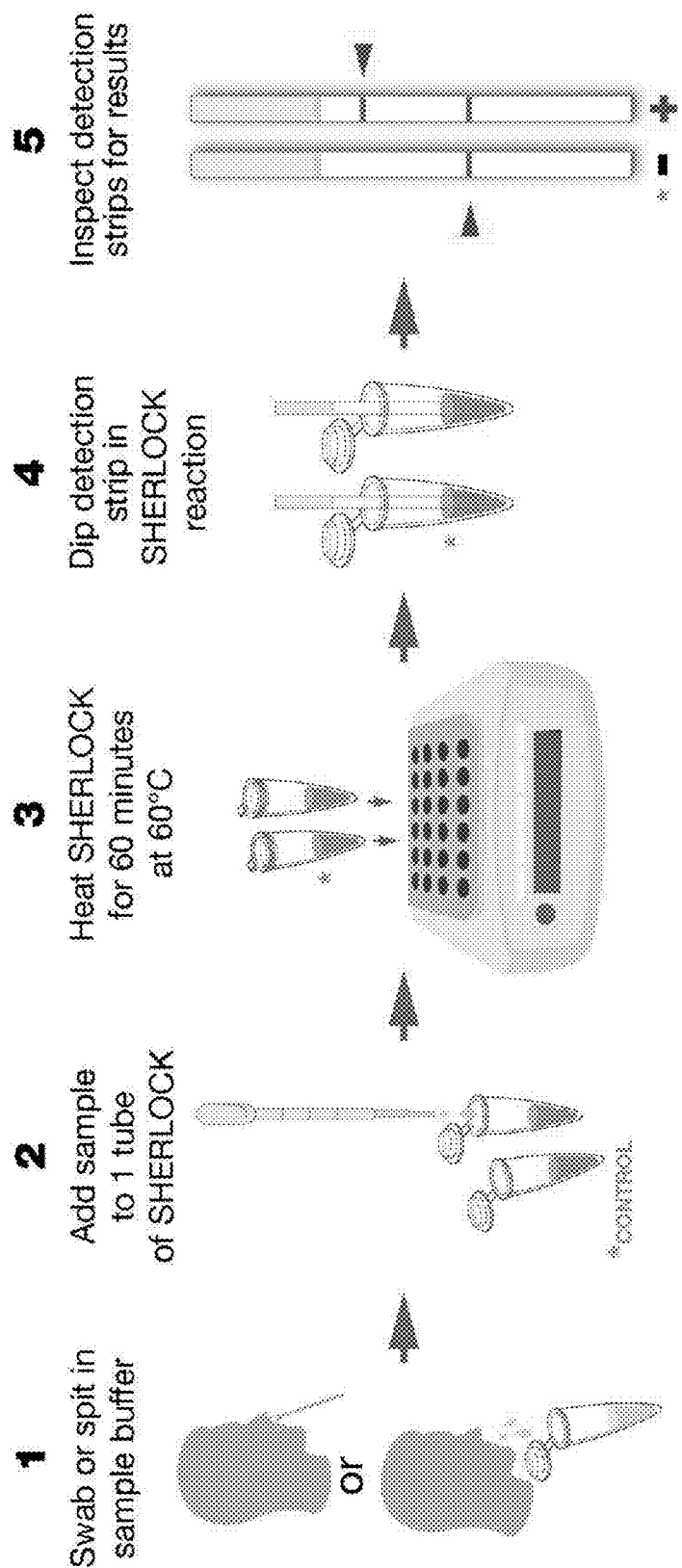
FIG. 16—A schematic for the SHERLOCK diagnostic assay.

The lateral flow strip is inserted directly into this reaction as shown in FIG. 16.

TABLE 4

Final Reaction Parameters

| | Initial Concentration | Final Concentration | Amount (μL) |
|---|---|---|---|
| Isothermal amplification buffer | 10 X | 1 X | 5 |
| dNTPs | 10 mM | 1.4 mM | 7 |
| MgSO4 | 100 mM | 8 mM | 4 |
| Bst 2.0 | 8000 units/mL | 320 units/mL | 2 |
| WS RTx | 15,000 units/mL | 300 units/mL | 1 |
| Aap Cas12b | 2 mg/ml or 15.4 μM | 500 nM | 1.625 |
| Aac Cas12b crRNA | 360 ng/μL or 10 μM | 500 nM | 2.5 |
| WCV332 | 100 μM | 125 nM | 0.0625 |
| Taurine | 500 mM | 50 mM | 5 |
| LAMP primer pool | 10 X | 1 X | 5 |
| Sample | | | 5 |
| H2O | | | 11.8125 |
| Total | | | 50 |

Figure 17:
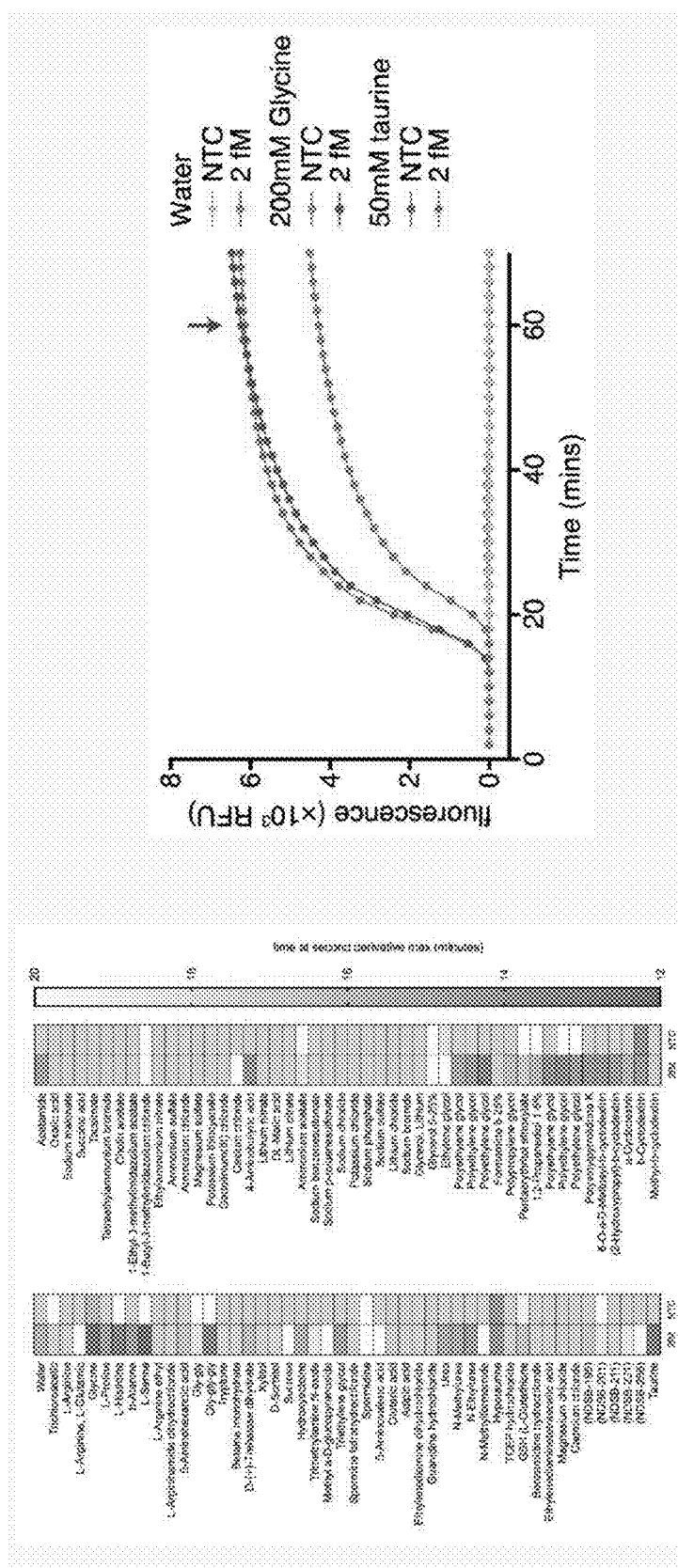
FIG. 17—Shows the different additives that may be used to optimize assay sensitive and/or kinetics.
Figure 18:
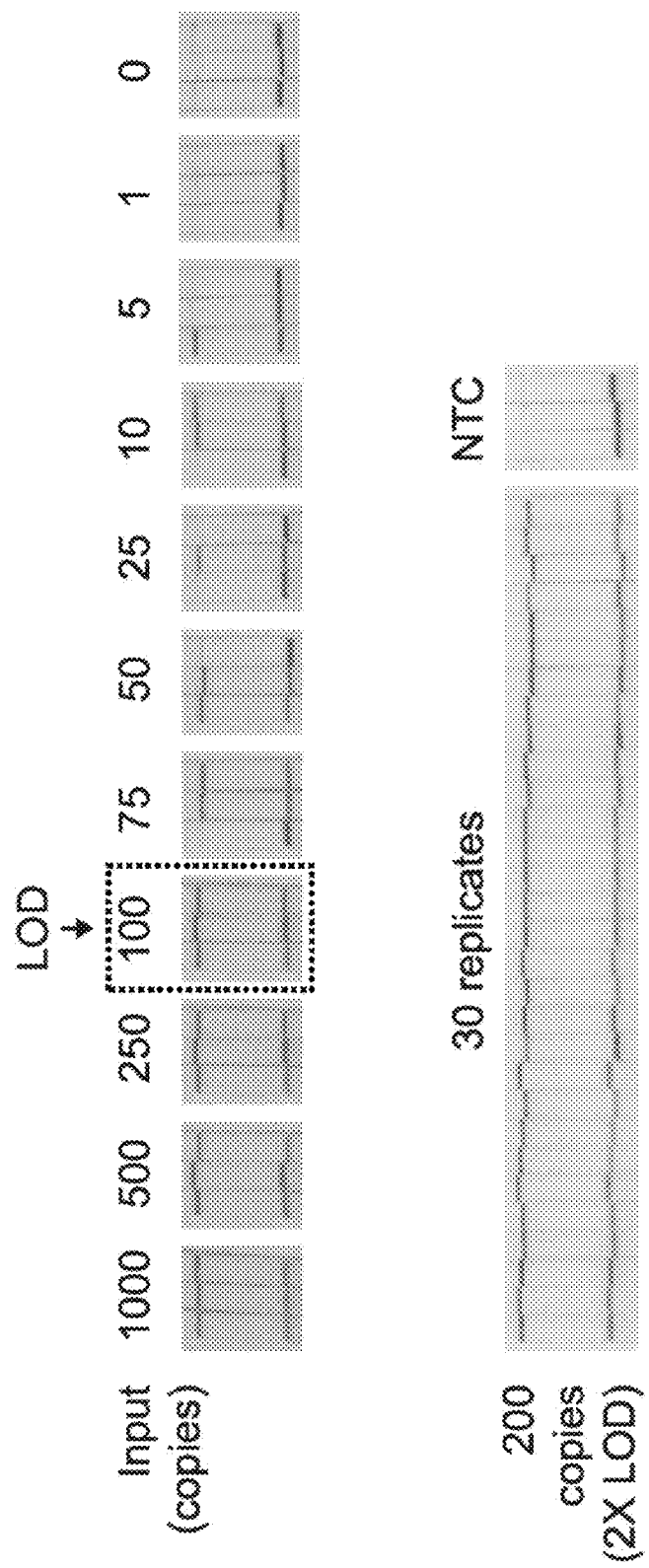
FIG. 18—Shows that the limit of detection is at 100 molecules per reaction.

The different reaction additives that were used to optimize the assay is shown in FIG. 17. FIG. 18 shows results obtained for assessing limit of detection by lateral flow assay at 60° C. for 60 minutes. The limit of detection was 100 molecules per reaction.

Figure 19:
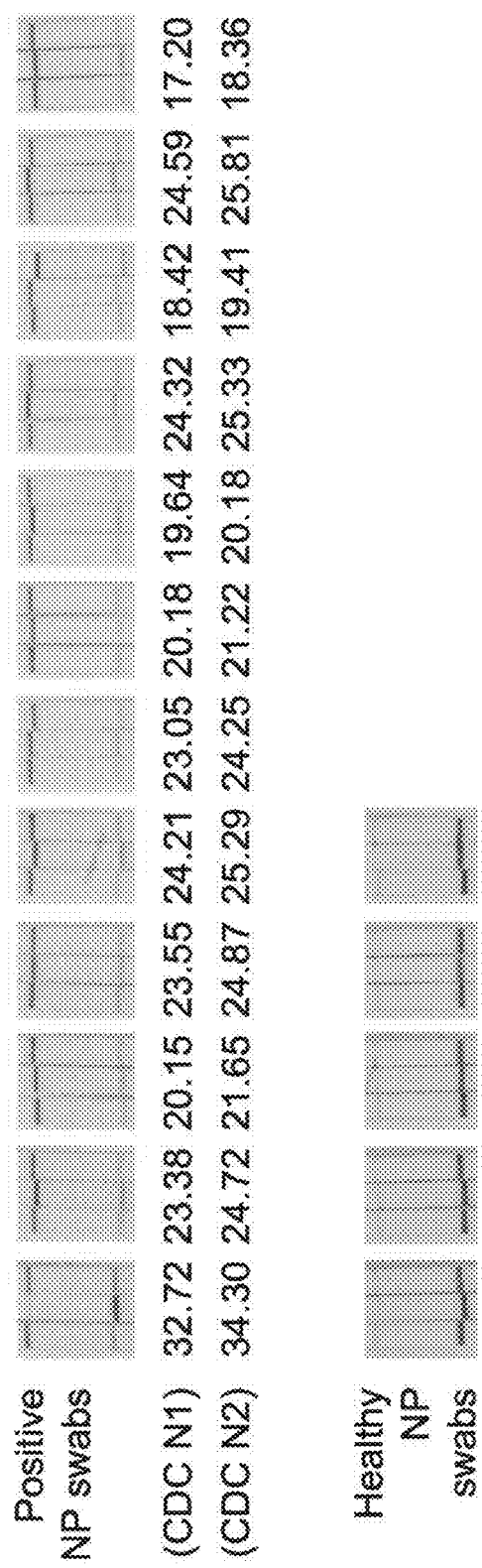
FIG. 19—Shows a comparison of positive SHERLOCK tests to results obtained from qRT-PCR assays.
Figure 20:
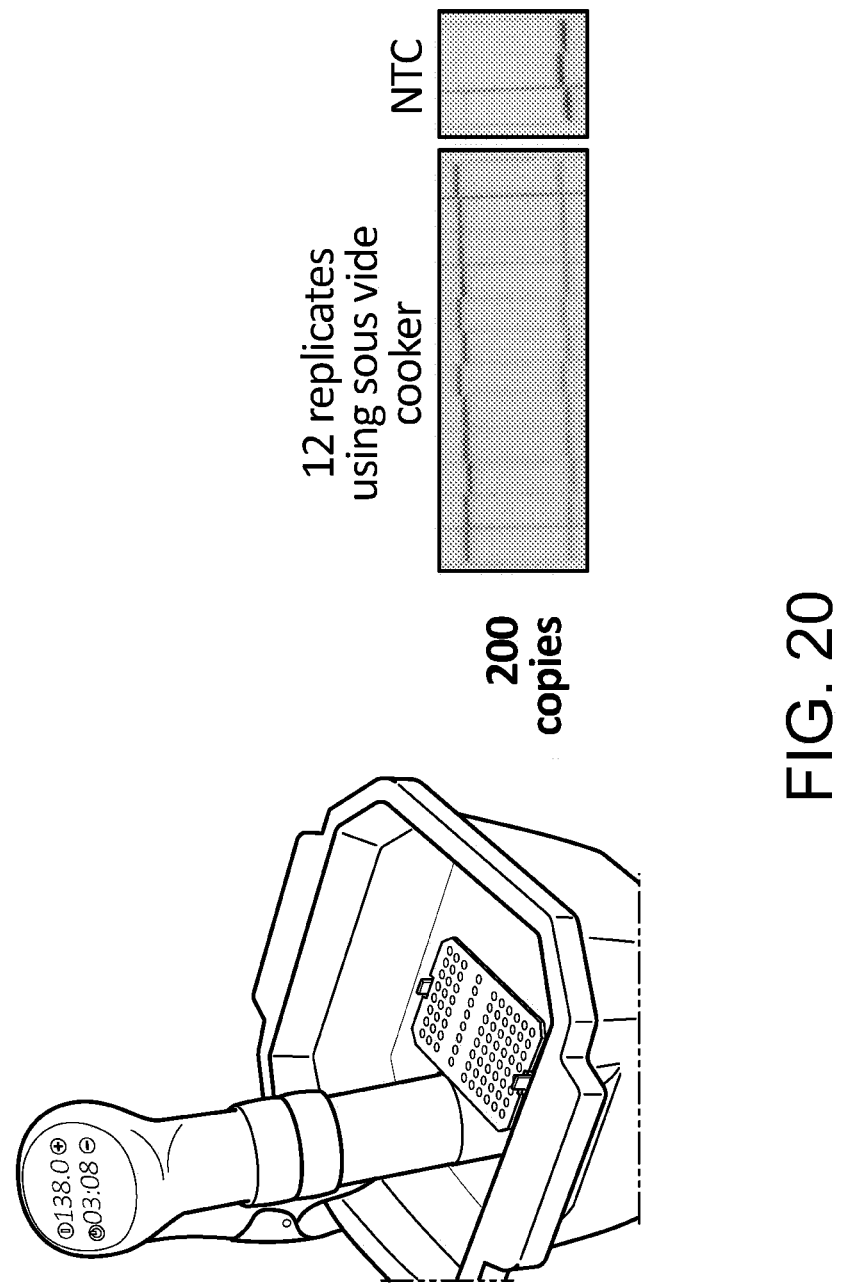
FIG. 20—Illustrates a low cost assay setup using a sous vide cooker.

Results obtained by SHERLOCK assay were compared to results obtained by qRT-PCR, as shown in FIG. 19. The assay can also be performed using a sous vide cooker, as illustrated in FIG. 20, 41.

Example 5. Exemplary Use of Device in Diagnostic Methods

Figure 21:
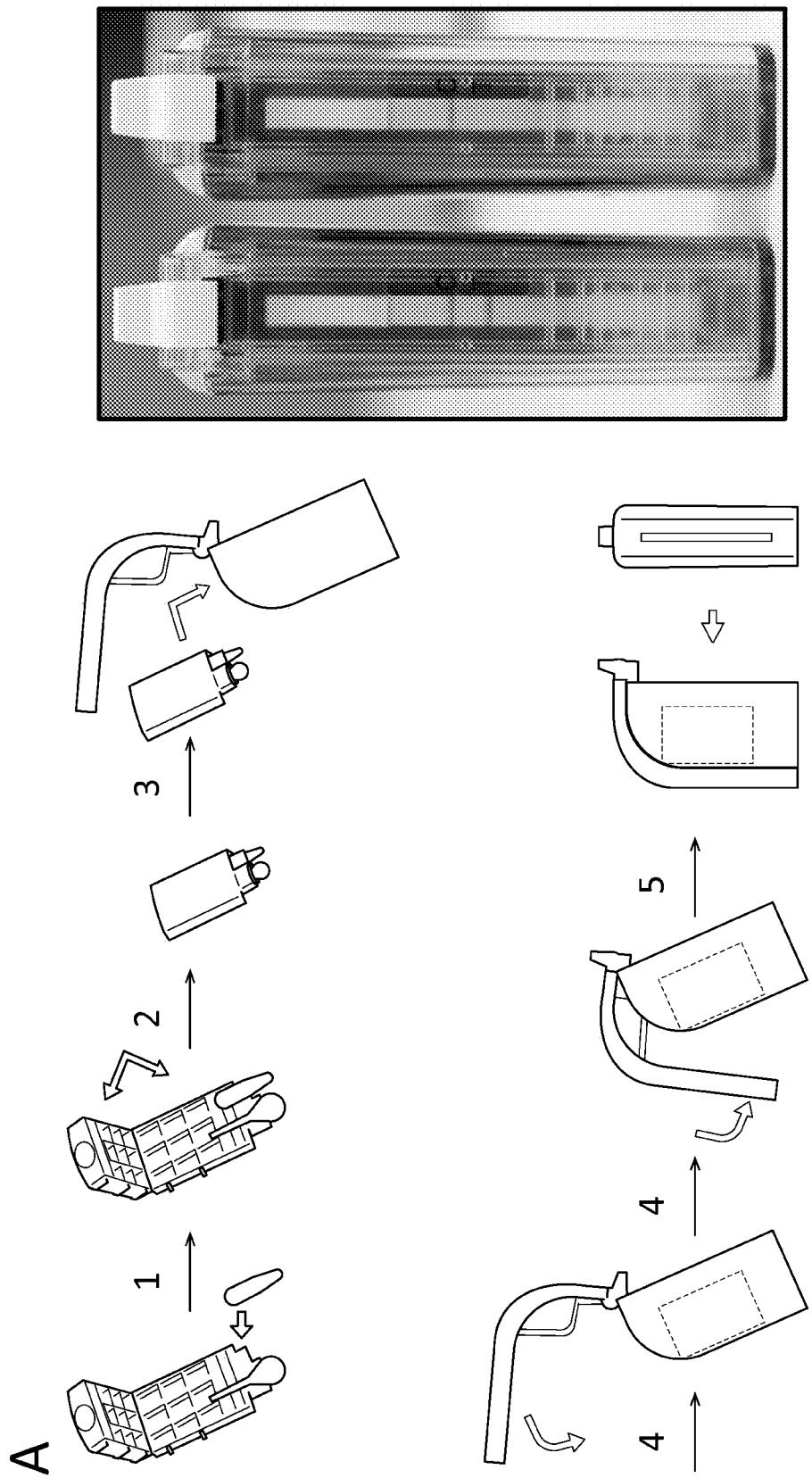
FIG. 21—Shows a point-of-care device that is compatible with SHERLOCK.
Figure 22:
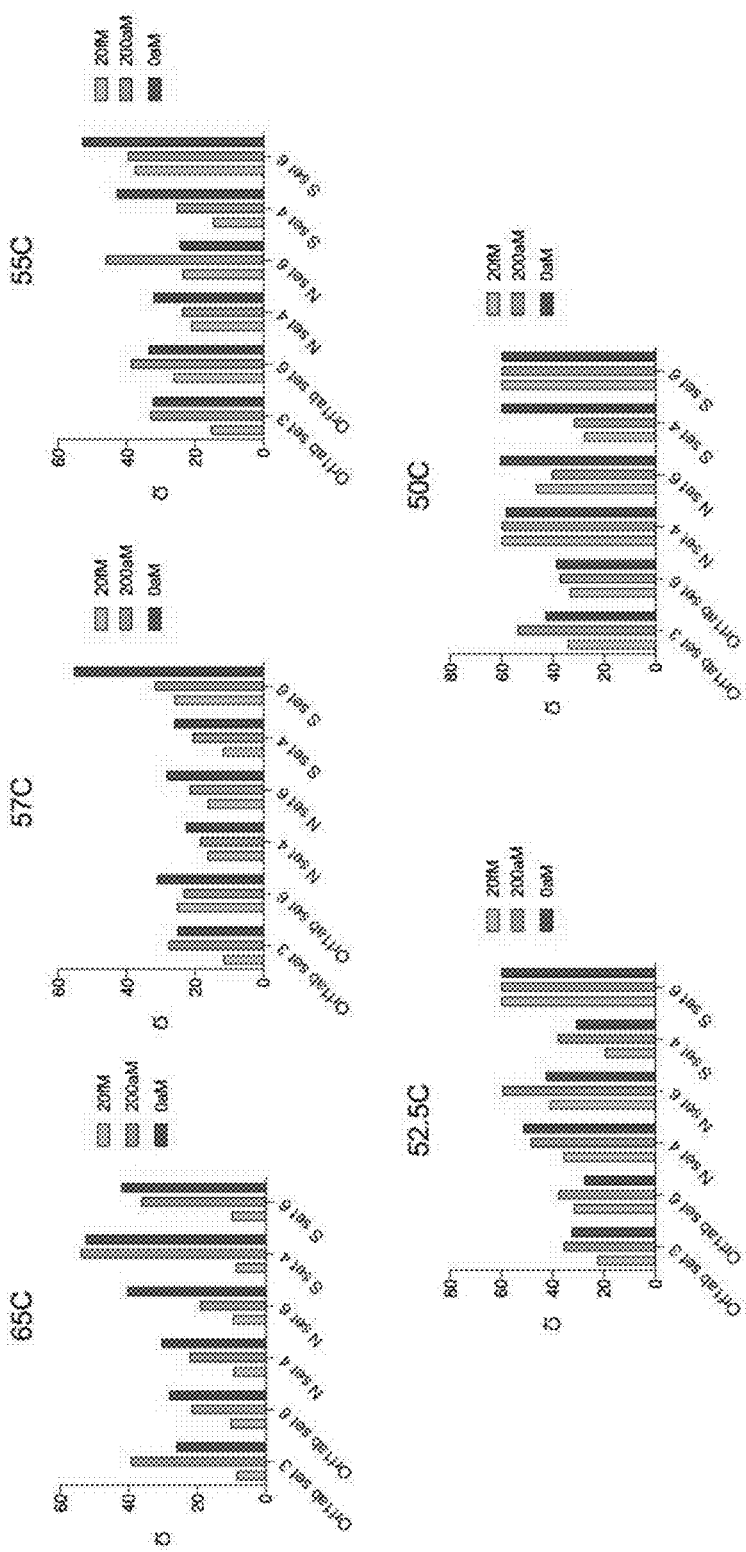
FIG. 22—Demonstrates that LAMP primers are active at lower temperatures.
Figure 23:
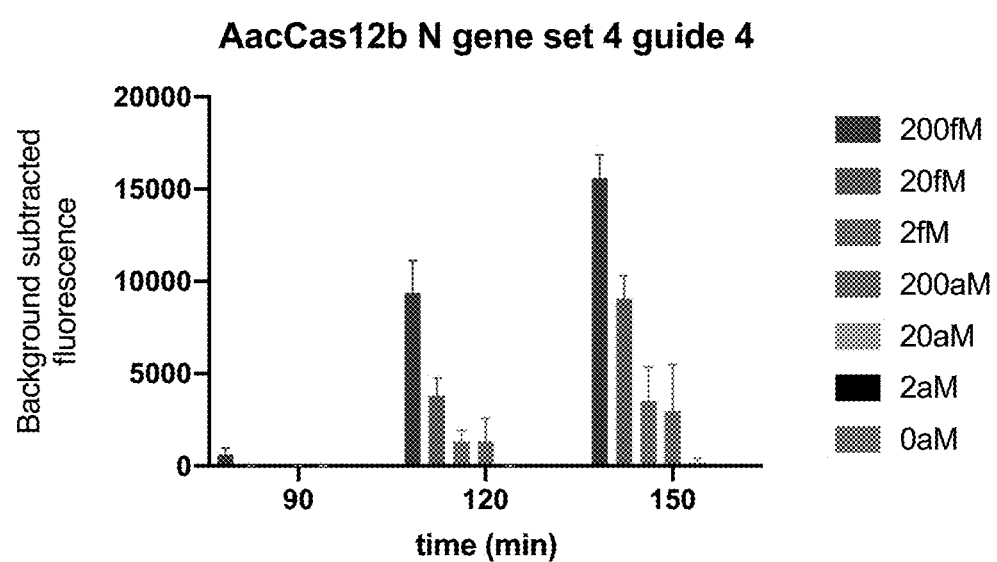
FIG. 23—Demonstrates that combining *Alicyclobacillus acidoterrestris* Cas12b (AacCas12b) with LAMP at 55° C. enables one-pot COVID-19 detection. Input comprised RNA genome of COVID-19 broken into 5 kb fragments.
Figure 24:
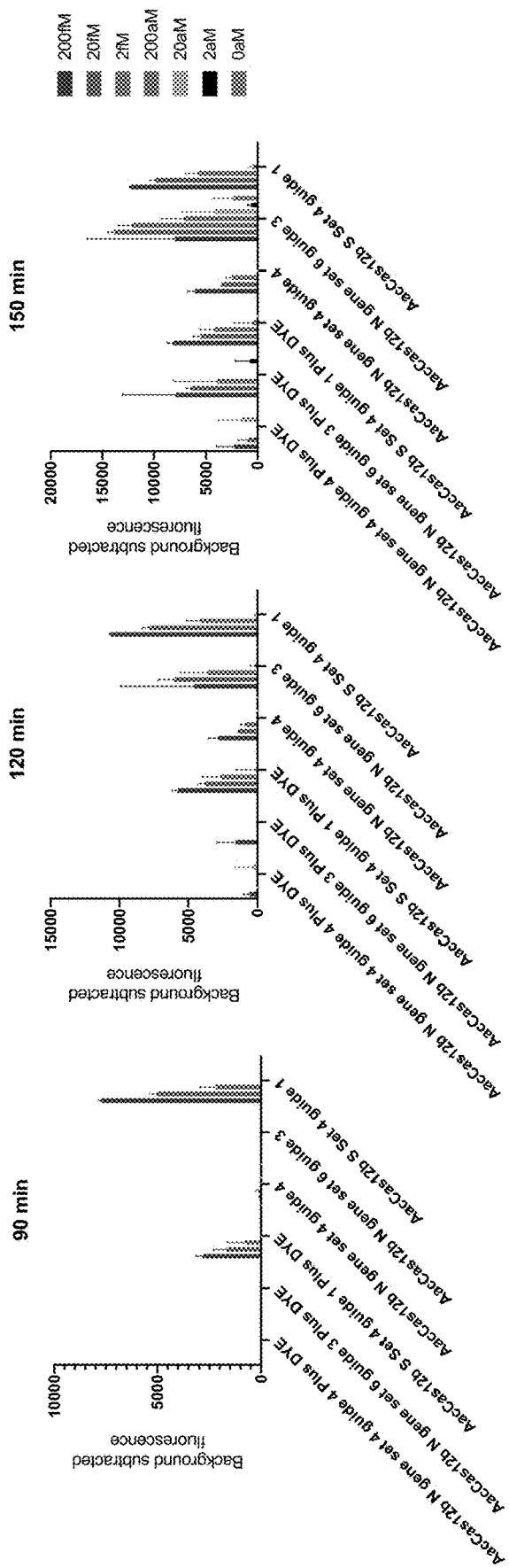
FIG. 24—Demonstrates multiple primer-set and guide combination work targeting different COVID-19 genes. 200 aM detection limit was achieve by 150 minutes. Input comprised RNA genome of COVID-19 broken into 5 kb fragments.

One exemplary device that can be utilized at point of care, in home environments, and/or for distribution as a take home device is shown in FIG. 21. The device can advantageously be disposable and can offer rapid instrument-free visualization of the nucleic acid amplification products of the methods disclosed herein. In an exemplary embodiment, the disposable device is compatible with nucleic acid amplification technologies, including LAMP. The device comprises an ampule which can contain the lateral flow buffer for the lateral flow readout of the amplification result. A sample can be loaded into a container which may comprise the reagents for the SHERLOCK reaction, including amplification reagents and CRISPR-Cas protein and guide molecules, which may optionally be stored in the container as lyophilized reagents. (See FIG. 21 at step 1). The device can further comprise a container for the contents of the SHERLOCK reaction, including LAMP amplification reagents and CRISPR-Cas protein and guide molecules. The device can also be configured to comprise the lateral flow strip, such that after the reaction is conducted, a lateral flow readout is provided in the device utilizing an instrument-free method for the visualization of the reaction products without cross-contamination.

Example 6. Point-of-Care Testing for COVID-19 Using SHERLOCK Diagnostics

Rapid point-of-care (POC) tests capable of being run in any low-resource setting, including at home, are needed to adequately combat the COVID-19 pandemic and re-open society. Applicants previously described a protocol for using the CRISPR-based SHERLOCK (Specific High Sensitivity Enzymatic Reporter UnLOCKing) technique (Gootenberg et al., 2017, 2018) for the detection of SARS-CoV-2. SHERLOCK achieves sensitive detection of SARS-CoV-2 through two consecutive reactions: (1) amplification of the virus RNA using an isothermal amplification reaction, and (2) detection of the resulting amplicon using CRISPR-mediated collateral reporter unlocking. Additional CRISPR-based tests have also been recently developed (Broughton et al., 2020; Ding et al., 2020; Guo et al., 2020; Lucia et al., 2020), but these all rely on two separate reaction steps, which requires liquid handling and opening of tubes. These steps add complexity and can lead to contamination, prohibiting their use outside laboratory environments and precluding use by lay individuals. Other POC tests for COVID-19 have been authorized by the U.S. Food and Drug Administration (FDA), including the Abbott ID NOW and Cepheid Genexpert, but these require complex and expensive instrumentation, limiting use to complex labs and hospitals by trained professionals. Some isothermal pre-amplification methods, such as Loop-mediated Isothermal Amplification (LAMP), have been developed as POC tests (Zhang et al., 2020), but these rely on amplification that can be nonspecific.

Currently, the only tests readily available for at-home or low-resource settings are serology paper-based tests (Whitman et al., 2020). However, these are not adequate for diagnosing live infection as antibodies take 1-2 weeks to become detectable in blood and only signify previous exposure. Therefore, Applicants sought to create a POC COVID-19 nucleic acid test that can be run in any setting. Through a series of optimizations, Applicants developed a streamlined, 1-hour SHERLOCK based test that requires no sample extraction and can be performed at one temperature in a single reaction with minimal fluid handling and visual colorimetric readout (FIG. 16).

The one-pot SHERLOCK SARS-CoV-2 detection protocol works in the following three steps, without requiring separate virus RNA extraction:
  Step (1) 5 mins at 95° C. lysis of virus-containing patient sample using QuickExtract to release virus RNA;
  Step (2) 1 hr at 60° C. detection of virus RNA using one-step SHERLOCK reaction;
  Step (3) 2 mins at room temp visual read out of the detection result by eye using a commercially-available paper dipstick.

In order to integrate the isothermal amplification step with the CRISPR-mediated detection step, Applicants sought to establish a common reaction condition capable of supporting both steps. Due to the supply chain constraints for the commercially-available recombinase polymerase amplification (RPA) reagents and difficulties in producing a rapid one-pot RPA test for sensitive RNA detection, Applicants chose loop-mediated isothermal amplification (LAMP) reaction for amplifying the virus RNA. The requisite enzymes for LAMP are more readily available from a number of commercial suppliers and the LAMP buffers are simpler and more amenable to systematic optimization with Cas enzymes.

Figure 25:
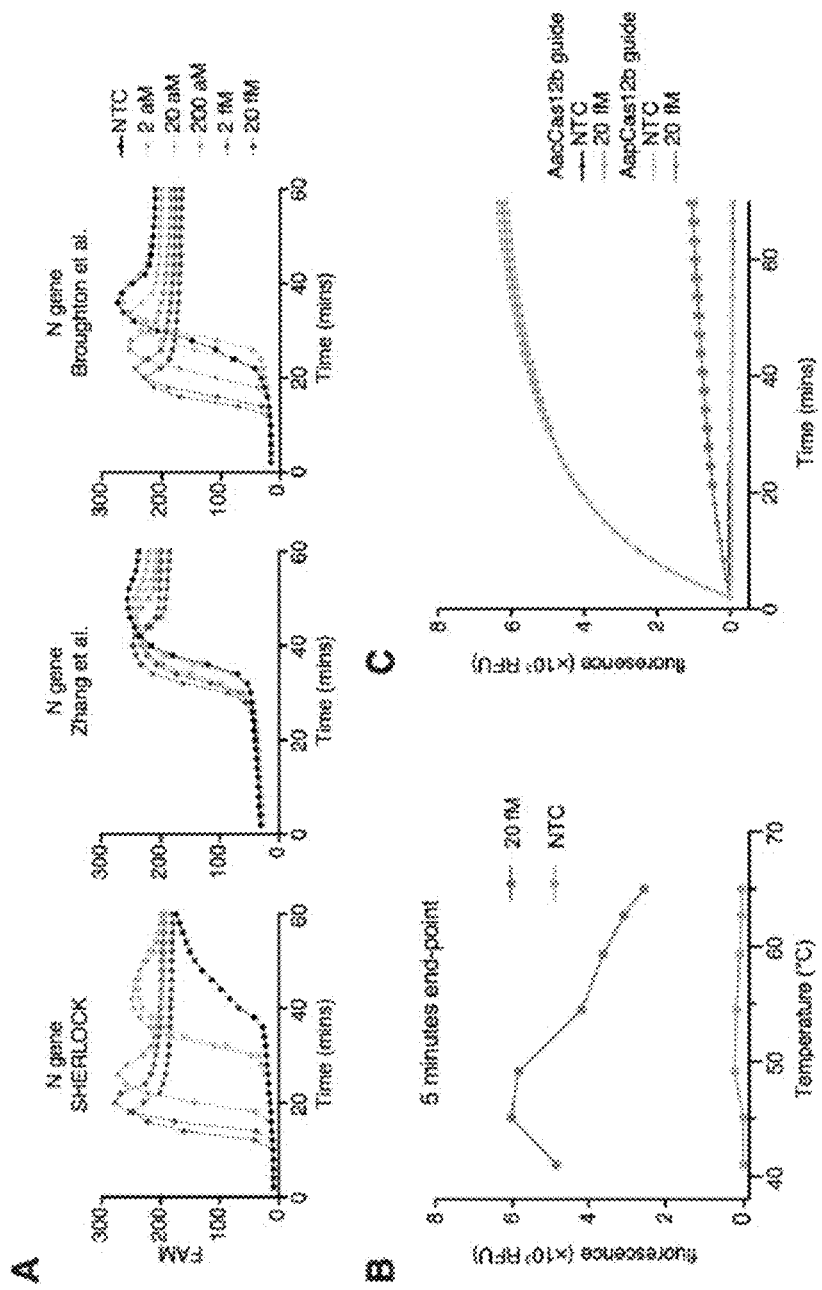
FIG. 25—Development of POC-SHERLOCK using RT-LAMP and thermophilic AapCas12b. (25A) Comparison of the POC-SHERLOCK N gene LAMP primer set to two established LAMP primer sets measured by real-time fluorescence at varying levels of SARS-CoV-2 standard genomes. (25B) Temperature comparison of AapCas12b collateral activity activated by RT-LAMP amplified inputs, including 20 fM SARS-CoV-2 standards and NTC controls. (25C) AapCas12b collateral activity when incubated with AapCas12b or AacCas12b crRNAs and RT-LAMP amplified 20 fM SARS-CoV-2 standards or NTC. (25D) AapCas12b collateral activity measured using different guides for RT-LAMP amplified 20 fM SARS-CoV-2 standards or NTC. (25E) POC-SHERLOCK (One-pot Cas12b and RT-LAMP) results when using AapCas12b or AacCas12b and varying amounts of SARS-CoV-2 inputs or NTC. (25F) POC-SHERLOCK real-time fluorescence performance measured with glycine or taurine additives at 2 fM SARS-CoV-2 input or NTC.
Figure 25:
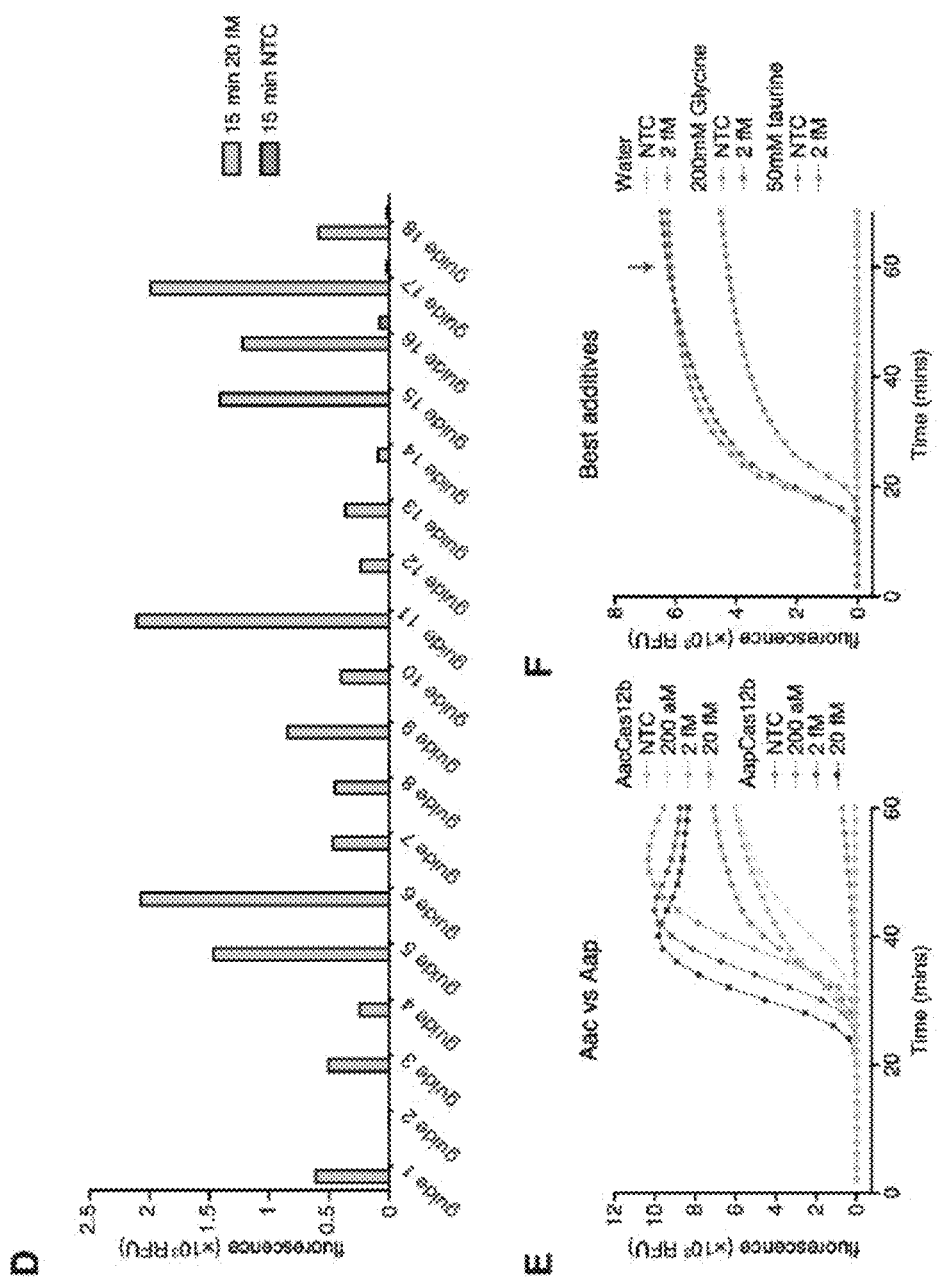

To determine the optimal combination of LAMP primers and guides, Applicants designed 29 sets of LAMP primers targeting different regions of the SARS-CoV-2 genome and identified the best primer set for amplifying gene N (FIG. 25A). As LAMP operates at a higher temperature than RPA (55-65° C. compared to 42° C.), a one-pot reaction demands a Cas enzyme with collateral activity that is thermostable. Of the various Cas proteins Applicants explored, Cas12b from *Alicyclobacillus acidiphilus* (AapCas12b) (Teng et al., 2018) maintained sufficient activity in the same temperature range as LAMP (FIG. 25B). However, because the AapCas12b locus did not contain a CRISPR array, the published single guide RNA (sgRNA) for AapCas12b used a direct repeat (DR) sequence from *Alicyclobacillus macrosporangiidus* Cas12b, which could impede activity. To remedy this, Applicants searched for alternative orthologs with similar protein sequences to AapCas12b and found that *Alicyclobacillus acidoterrestris* Cas12b (AacCas12b) shared a 95% sequence homology (Shmakov et al., 2015). Additionally, the AacCas12b tracrRNA and predicted AapCas12b tracrRNA are 97% identical. Given the high degree of similarity between AapCas12b and AacCas12b protein and tracrRNA, Applicants surmised that the sgRNA for AacCas12b should closely match the cognate AapCas12b DR-tracrRNA hybrid. Indeed, reactions combining AapCas12b enzyme with AacCas12b sgRNA produced more robust and specific nuclease activity compared to the published AapCas12b sgRNA (FIG. 25C).

For the best LAMP amplicon, Applicants tested 18 sgRNAs to identify the optimal combination of primers and guide sequence (FIG. 25D). Using this combination in a one pot reaction, Applicants found that AapCas12b generated faster and higher collateral activity than AacCas12b protein (FIG. 25E). Applicants further optimized one-pot reaction components by screening 94 additives to improve thermal stability, finding that addition of taurine significantly improved reaction kinetics (FIG. 25F).

Figure 6:
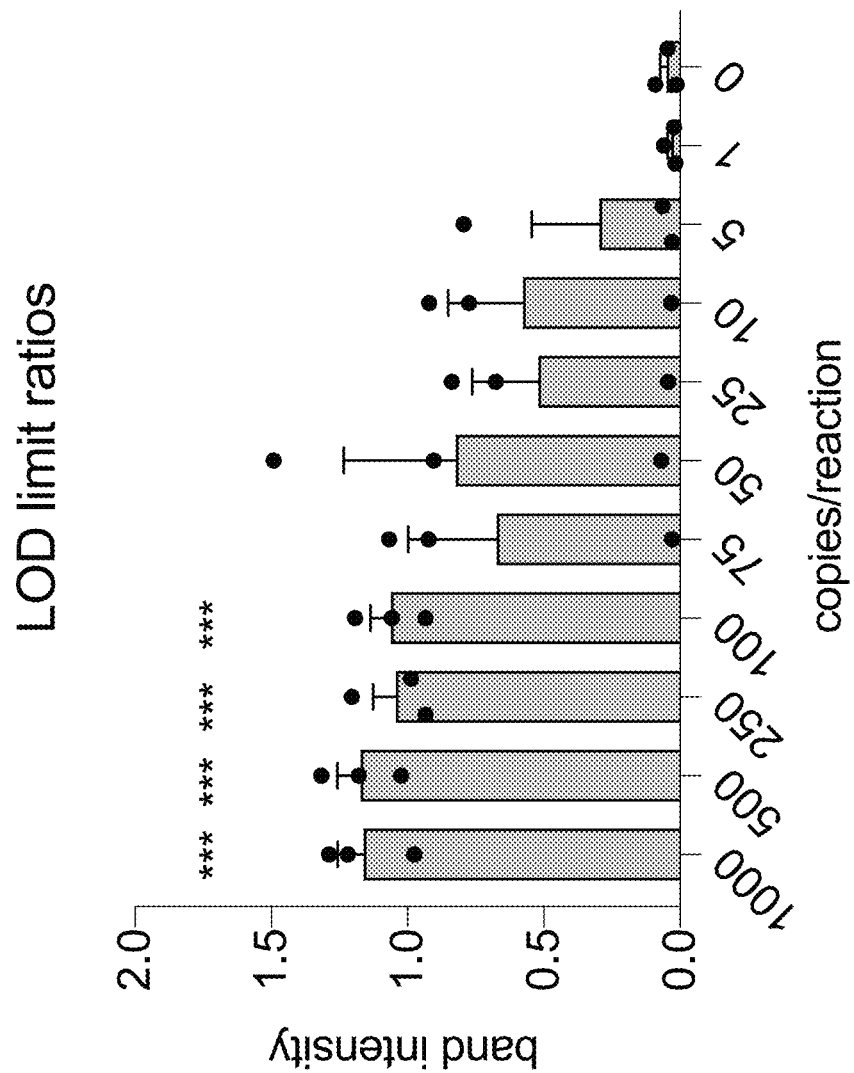
FIG. 6—Graph shows quantification of lateral flow assay from FIG. 5. The bar graph represents quantification of top band intensity/bottom band intensity.
Figure 7:
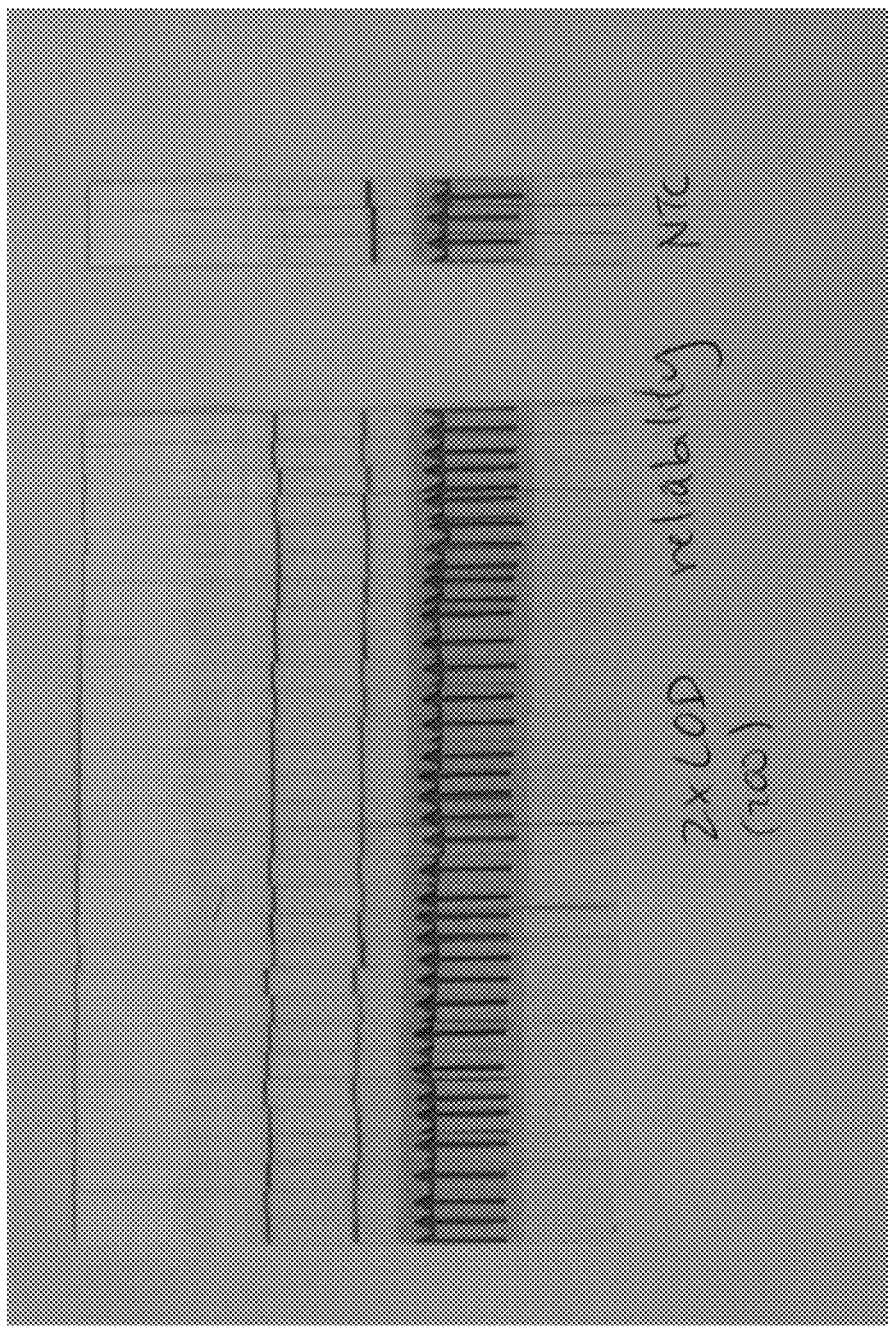
FIG. 7—Shows that SHERLOCK can reliably perform at 2× the limit of detection.
Figure 8:
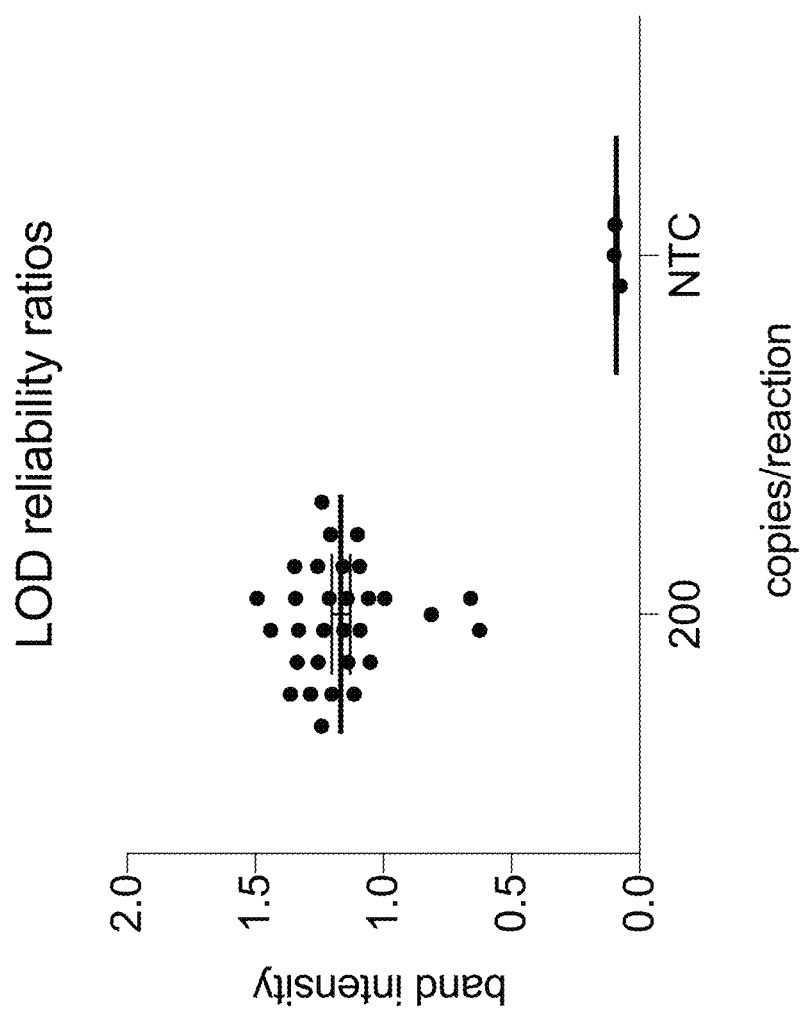
FIG. 8—Graph showing that SHERLOCK can reliably perform at 2× the limit of detection. The graph represents quantification of top band intensity/bottom band intensity of lateral flow assays from FIG. 7.
Figure 9:
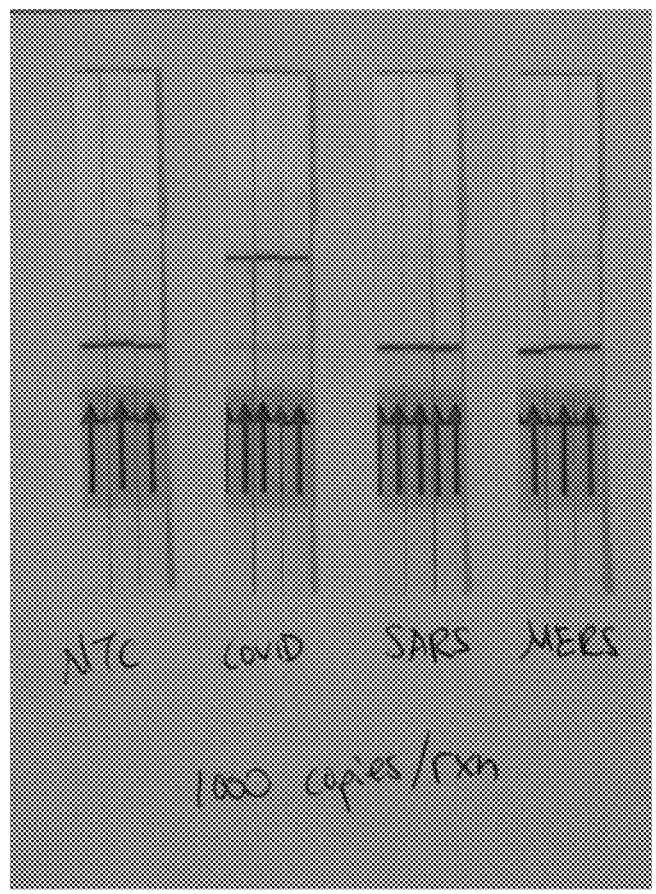
FIG. 9—Shows that the SHERLOCK assay has no cross-reactivity with SARS-CoV or MERS-CoV.
Figure 10:
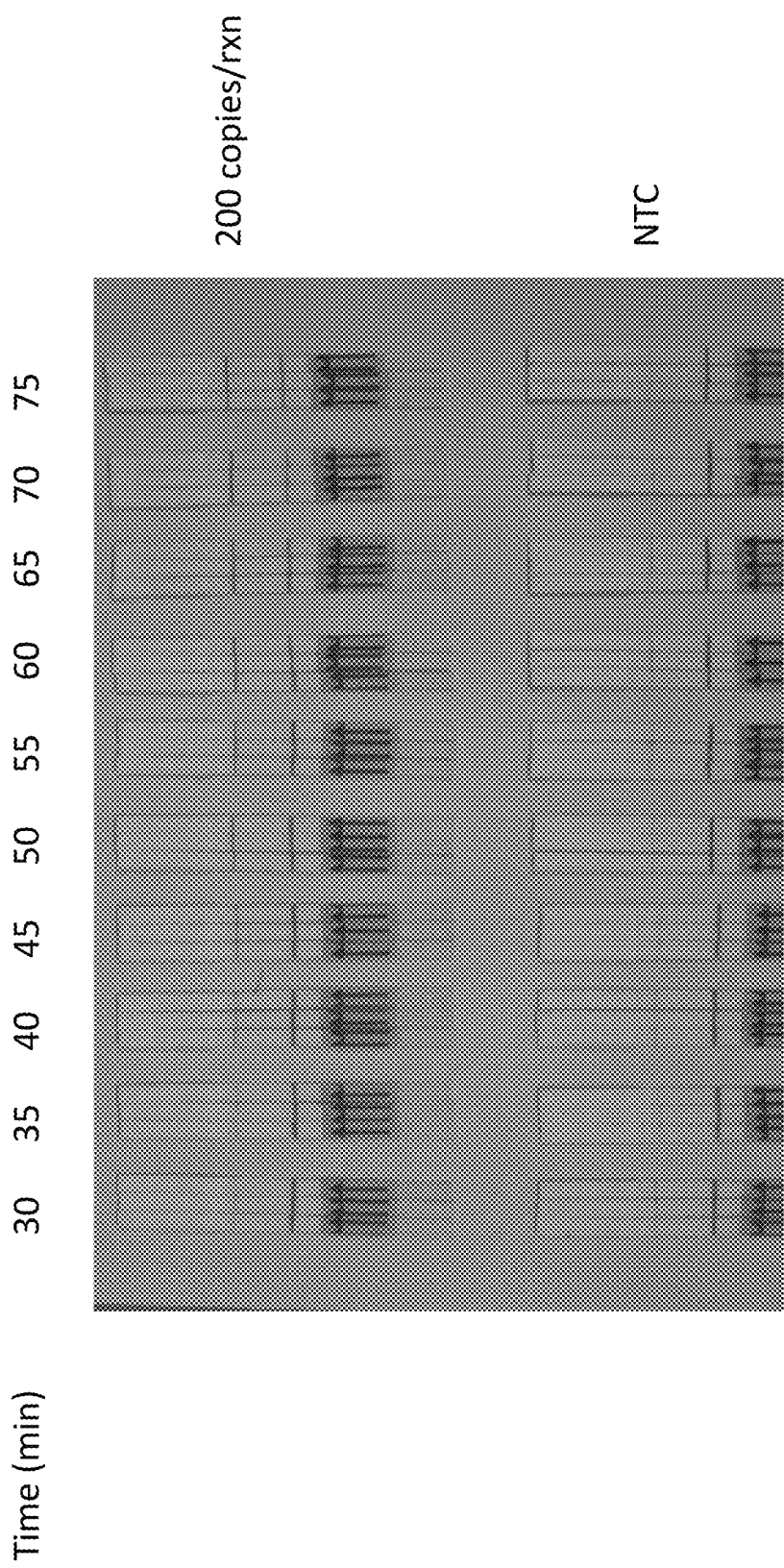
FIG. 10—Shows that a 50 minute incubation is sufficient to reach reaction saturation at 2× limit of detection.
Figure 11:
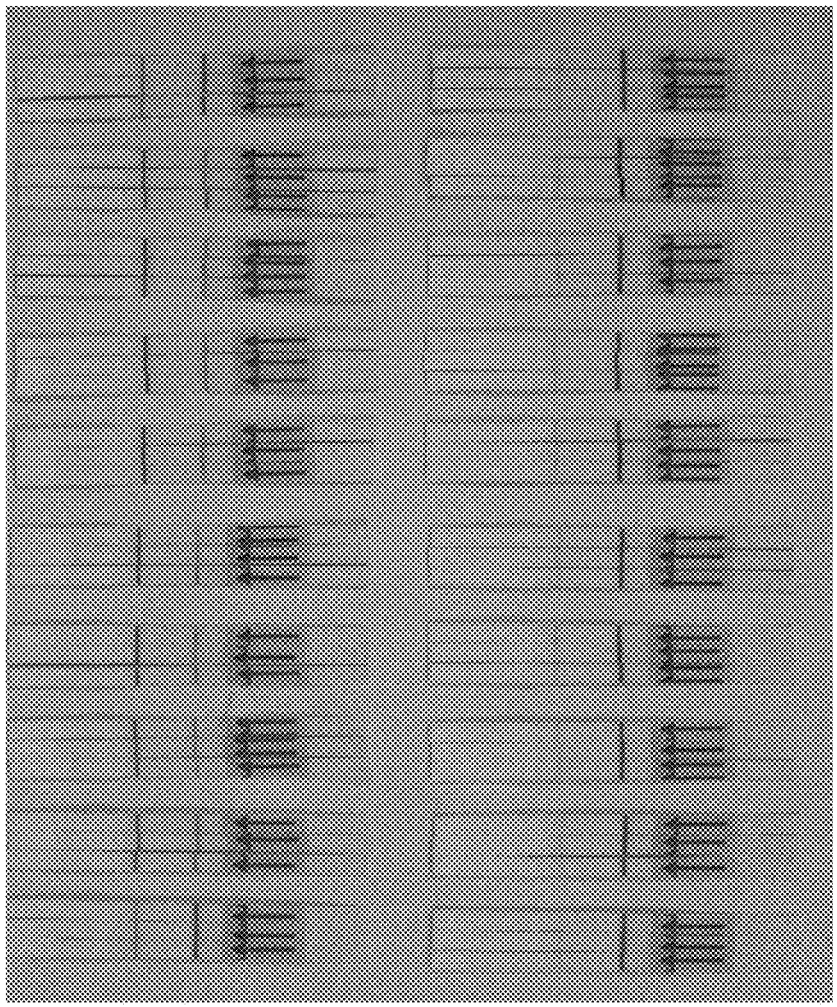
FIG. 11—Shows that SHERLOCK is robust across a 10° C. window.
Figure 12:
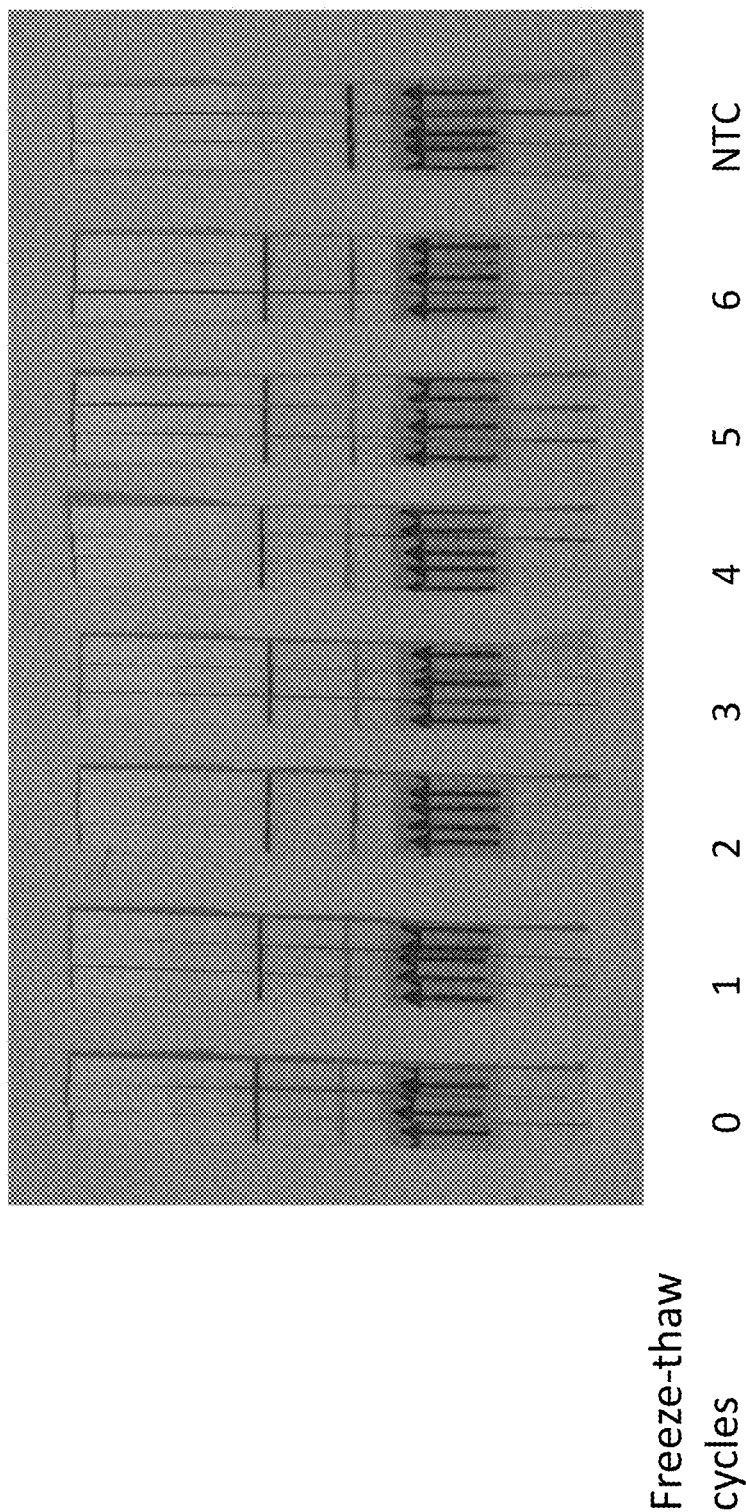
FIG. 12—Shows that SHERLOCK can be master mixed and freeze-thawed for six freeze-thaw cycles or more.
Figure 26:
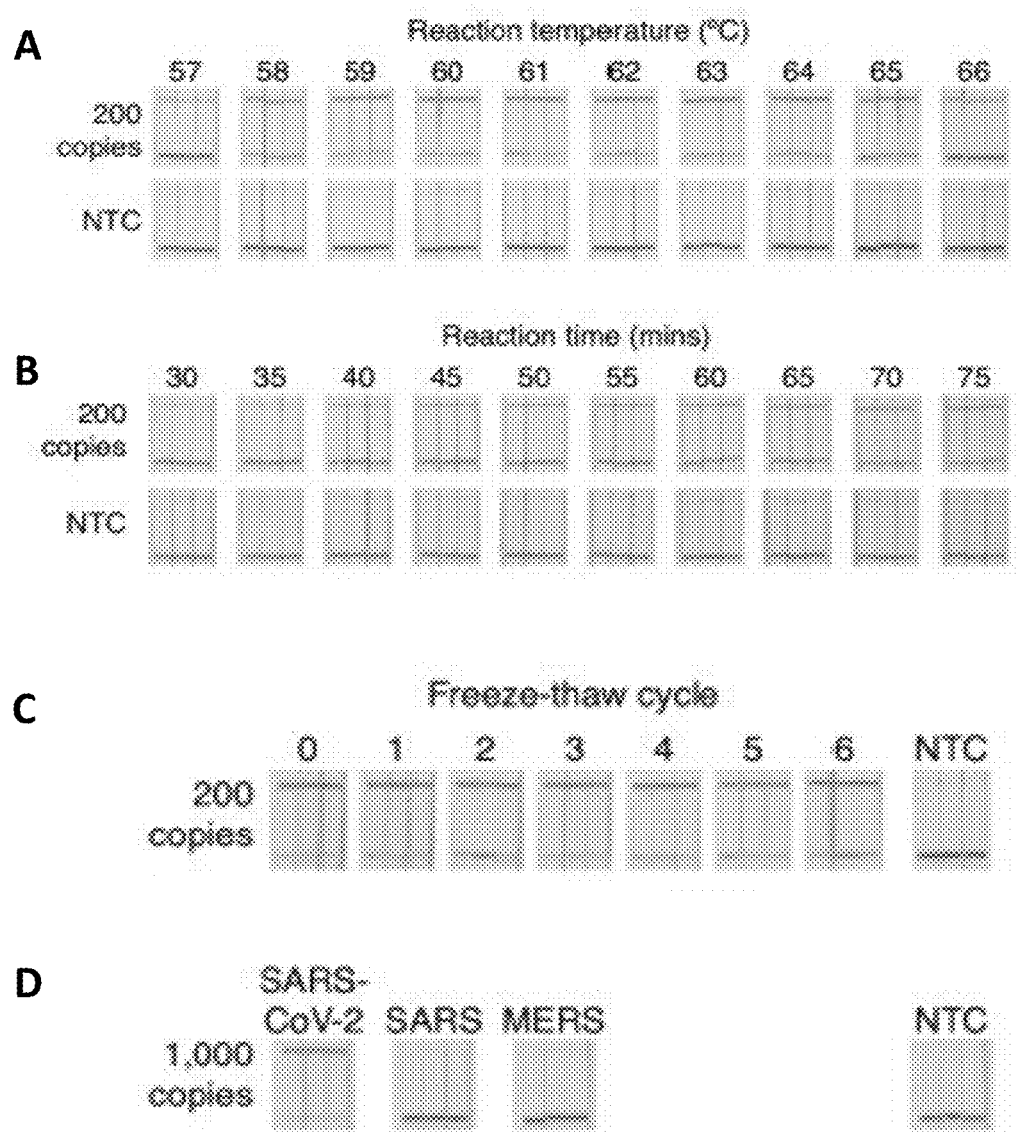
FIG. 26—POC-SHERLOCK performance on lateral flow strips. (26A) Effect of reaction temperature on POC-SHERLOCK lateral flow detection for 200 SARS-CoV-2 copies per reaction and NTC. (26B) Effect of reaction incubation time on POC-SHERLOCK lateral flow detection for 100 SARS-CoV-2 copies per reaction and NTC. (26C) Effect of master mix freeze-thaw cycles on POC-SHERLOCK lateral flow detection for 200 SARS-CoV-2 copies per reaction and NTC. (26D) Measurement of cross-reactivity for COVID-19 POC-SHERLOCK lateral flow test for SARS and MERS N genes compared to NTC. All inputs were at 1,000 copies per reaction.

Applicants profiled the optimized reaction with a lateral flow readout and an RNA extraction-free input using SARS-CoV-2 genome standards spiked into nasopharyngeal (NP) swab to determine limit of detection (LOD), ideal incubation temperature, readout time, and robustness. Applicants found that the LOD of the reaction was 100 copies of SARS-CoV-2 (FIG. 18). This LOD was reliable and reproducible over 30 replicates (FIG. 6). At twice the LOD, the ideal incubation parameters were 60° C. for at least 50 minutes (FIG. 26A, 26B). The reaction components could be formulated as a mastermix and maintained functionality after 6 freeze-thaw cycles (FIG. 26C). The assay exhibited no cross-reactivity with the SARS or MERS coronavirus genomes (FIG. 26D). The reaction could be performed using either a standard heat block or via a water bath maintained by a commercially-available low-cost (under $40 USD) sous-vide cooker (FIG. 20).

Figure 29:
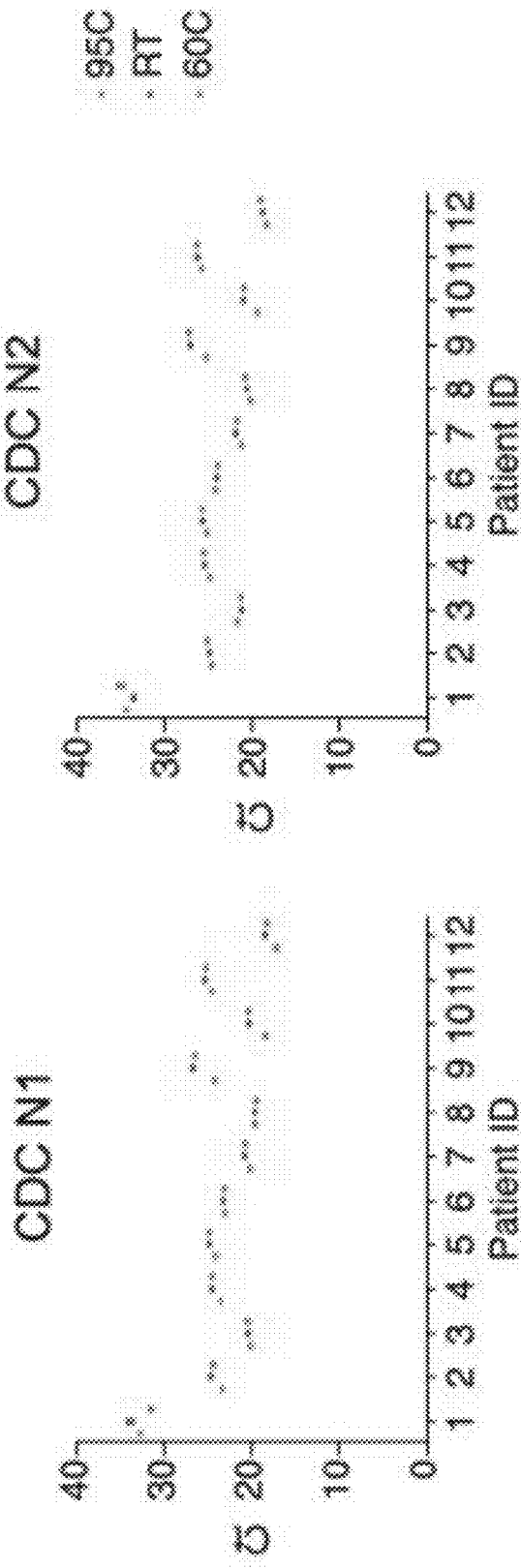
FIG. 29—Comparison of different lysis temperatures for SARS-CoV-2 positive patient nasopharyngeal swab extraction as measured by Ct values from RT-PCR using the CDC N1 and N2 assays. For patients 9 and 10, due to the low volume of samples provided, samples tested with 22° C. and 60° C. lysis conditions were diluted 1:2 prior to POC-SHERLOCK and RT-qPCR.
Figure 42A:
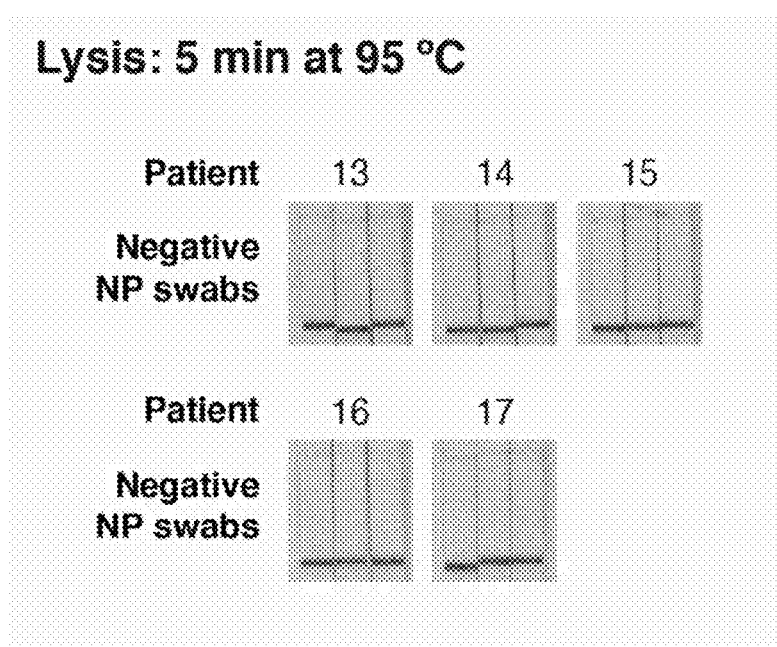
Figure 42B:

Finally, Applicants evaluated the one-pot SHERLOCK detection on 12 positive and 5 negative patient NP swabs. Applicants' assay correctly identified 35/36 positive patient replicates and 15/15 negative patient replicates, resulting in a sensitivity of 97% and specificity of 100% (FIGS. 19 and 27, 42A). To further simplify the assay workflow, Applicants tested whether lysis using QuickExtract at room temperature (22° C.) or the one-pot incubation temperature (60° C.) for 10 mins would be sufficient for detection. As QuickExtract contains Proteinase K that inhibits SHERLOCK without heat inactivation at 95° C., Applicants added Proteinase K Inhibitor to the SHERLOCK reaction. In both cases, Applicants could identify 33/36 positive patient replicates (FIGS. 28A, 28B). Comparison of RT-qPCR Ct values between the lysis methods suggested that both lysis methods are viable alternatives for streamlining the assay workflow, though with a slight decrease (0.2/0.4 Ct at 60° C. and 0.4/0.7 Ct for 22° C. for CDC N1/N2) in sensitivity (FIG. 29).

Materials and Methods

Design of LAMP and SHERLOCK Reactions.

Applicants designed LAMP amplification primers and SHERLOCK AapCas12b guide RNAs to target the N gene of SARS-CoV-2. The N gene is known to be present at higher copy numbers than other segments of the SARS-CoV-2 genome, which helps to increase the detection sensitivity. Below are the LAMP primer sequences and SHERLOCK AapCas12b guide RNAs:

TABLE 5

| LAMP Primers and Cas Guide | |
|---|---|
| F3: | 5'-GCTGCTGAGGCTTCTAAG-3' (SEQ ID NO: 61983) |
| B3: | 5'-GCGTCAATATGCTTATTCAGC-3' (SEQ ID NO: 61984) |
| FIP: | 5'-GCGGCCAATGTTTGTAATCAGTAGACGTGGTCCAGAACAA-3' (SEQ ID NO: 61985) |
| BIP: | 5'-TCAGCGTTCTTCGGAATGTCGCTGTGTAGGTCAACCACG-3' (SEQ ID NO: 61986) |
| Loop Forward: | 5'-CCTTGTCTGATTAGTTCCTGGT-3' (SEQ ID NO: 61987) |
| Loop Reverse: | 5'-TGGCATGGAAGTCACACC-3' (SEQ ID NO: 61988) |
| AapCas12b Guide RNA targeting SARS-CoV-2 N gene: | 5'-GUCUAGAGGACAGAAUUUUCAACGGGUGUGCCAAUGGCCACUUUCCAGGUGG CAAAGCCCGUUGAGCUUCUCAAAUCUGAGAAGUGGCA CCGAAGAACGCUGAAGC GCUG-3' (The spacer matching N gene is underlined.) (SEQ ID NO: 61989) |

AapCas12b Protein Sequence:

| AapCas12b Protein Sequence: |
|---|
| MAVKSMKVKLRLDNMPEIRAGLWKLHTEVNAGVRYYTEWLSLLRQENLY |
| RRSPNGDGEQECYKTAEECKAELLERLRARQVENGHCGPAGSDDELLQL |
| ARQLYELLVPQAIGAKGDAQQIARKFLSPLADKDAVGGLGIAKAGNKPR |
| WVRMREAGEPGWEEEKAKAEARKSTDRTADVLRALADFGLKPLMRVYTD |

```
AapCas12b Protein Sequence:

SDMSSVQWKPLRKGQAVRTWDRDMFQQAIERMMSWESWNQRVGEAYAKL

VEQKSRFEQKNFVGQEHLVQLVNQLQQDMKEASHGLESKEQTAHYLTGR

ALRGSDKVFEKWEKLDPDAPFDLYDTEIKNVQRRNTRRFGSHDLFAKLA

EPKYQALWREDASFLTRYAVYNSIVRKLNHAKMFATFTLPDATAHPIWT

RFDKLGGNLHQYTFLFNEFGEGRHAIRFQKLLTVEDGVAKEVDDVTVPI

SMSAQLDDLLPRDPHELVALYFQDYGAEQHLAGEFGGAKIQYRRDQLNH

LHARRGARDVYLNLSVRVQSQSEARGERRPPYAAVFRLVGDNHRAFVHF

DKLSDYLAEHPDDGKLGSEGLLSGLRVMSVDLGLRTSASISVFRVARKD

ELKPNSEGRVPFCFPIEGNENLVAVHERSQLLKLPGETESKDLRAIREE

RQRTLRQLRTQLAYLRLLVRCGSEDVGRRERSWAKLIEQPMDANQMTPD

WREAFEDELQKLKSLYGICGDREWTEAVYESVRRVWRHMGKQVRDWRKD

VRSGERPKIRGYQKDVVGGNSIEQIEYLERQYKFLKSWSFFGKVSGQVI

RAEKGSRFAITLREHIDHAKEDRLKKLADRIIMEALGYVYALDDERGKG

KWVAKYPPCQLILLEELSEYQFNNDRPPSENNQLMQWSHRGVFQELLNQ

AQVHDLLVGTMYAAFSSRFDARTGAPGIRCRRVPARCAREQNPEPFPWW

LNKFVAEHKLDGCPLRADDLIPTGEGEFFVSPFSAEEGDFHQIHADLNA

AQNLQRRLWSDFDISQIRLRCDWGEVDGEPVLIPRTTGKRTADSYGNKV

FYTKTGVTYYERERGKKRRKVFAQEELSEEEAELLVEADEAREKSVVLM

RDPSGIINRGDWTRQKEFWSMVNQRIEGYLVKQIRSRVRLQESACENTG

DI*
```

Specimen and Nucleic Acid Extraction.

Two types of patient samples have been tested for compatibility with one-pot SHERLOCK. All samples should be collected and processed according to the appropriate biosafety procedure.

a. RNA Extracted from Patient Samples: The patient sample should be collected according to the appropriate biosafety procedures. Please reference the 2020 CDC COVID-19 test protocol for details on specimen collection and subsequent nucleic acid extraction. The input for this protocol, beginning with Step (1), can be the same extracted nucleic acid as used in qRT-PCR assays.

b. Nasopharyngeal (NP) Swabs: NP swabs dissolved in viral transport media (VTM) or TE can be directly used.

Reagents.

For Step (1)—lysis of viral sample:
  QuickExtract DNA Extraction Solution (QE09050), Lucigen. Once thawed, aliquot and store at −20° C. to avoid >3 freeze-thaw cycles.

For Step (2)—one-pot SHERLOCK detection reaction:
  Bst 2.0 WarmStart® DNA Polymerase (M0538L), New England BioLabs
  WarmStart® RTx Reverse Transcriptase (M0380L), New England BioLabs
  10× Isothermal Amplification Buffer (B0374S), New England BioLabs, supplied with M0538L and M0380L
  100 mM MgSO4 (B1003S), New England BioLabs, supplied with M0538L and M0380L
  10 mM Deoxynucleotide (dNTP) Solution Mix (N0447L), New England BioLabs
  Taurine (86329-100G), Millipore Sigma
  AapCas12b protein purified according to Kellner et al., Nature Protocols 2019, stored as 10 µL aliquots at 2 mg/mL.
  Guide RNA for detecting N gene can be ordered from Synthego
  Reporter DNA for lateral flow read out (Lateral Flow Reporter: /56-FAM/TTTTTTT/3Bio/), can be ordered from IDT
  (Optional) Proteinase K Inhibitor (539470-10MG), Millipore Sigma. Resuspend 10 mg of Proteinase K Inhibitor with 150 µL of DMSO to make the stock solution. Dilute stock solution 1:100 with ddH2O to make working aliquots. Store both stock and working solutions at −20° C.

10×LAMP Primer Mix:

TABLE 6

LAMP Primer Mix.

| LAMP Primer (100 µM) | Amount (µL) |
| --- | --- |
| F3 | 2 |
| B3 | 2 |
| FIP | 16 |
| BIP | 16 |
| Loop F | 4 |
| Loop B | 4 |
| ddH₂O | 56 |
| Total | 100 |

A Sherlock mastermix can be prepared as follows:

TABLE 7

| | Initial concentration | Final concentration | Amount (µL) |
| --- | --- | --- | --- |
| Isothermal amplification buffer | 10 X | 1 X | 5 |
| dNTPs | 10 mM | 1.4 mM | 7 |
| MgSO4 | 100 mM | 8 mM | 4 |
| WS Bst 2.0 | 8000 units/mL | 320 units/mL | 2 |
| WS RTx | 15,000 units/mL | 300 units/mL | 1 |
| Aap Cas12b | 2 mg/mL or 15.4 uM | 500 nM | 1.625 |
| Aac Cas12b | 360 ng/uL or | 500 nM | 2.5 |
| crRNA | 10 uM | | |
| Lateral Flow Reporter | 100 uM | 125 nM | 0.0625 |
| Taurine | 500 mM | 50 mM | 5 |
| LAMP primer mix | 10 X | 1 v | 5 |
| ddH₂O | | | 11.8125 |
| Total | | | 45 |

If lysing samples at 22° C. or 60° C. instead of 95° C., replace 2 uL of ddH2O with 2 uL of Proteinase K Inhibitor working solution.

For Step (3) reading out using lateral flow dipstick:
  HybriDetect Dipstick (MGHD 1), Milenia Biotec GmbH
  Positive Control Sequences
  SARS-CoV-2 RNA control (102019), Twist Bioscience
Equipment.
  95° C. heat block or water bath
  60° C. heat block or water bath Alternative: a sous vide immersion cooker capable of supporting the temperature range of 55° C. to 95° C. can also be used (example).

One-Step SHERLOCK Protocol for SARS-CoV-2 Detection

***IMPORTANT NOTE: To prevent sample contamination from confounding detection result, two different work areas should be used for performing Steps (1)/(2) and (3). Steps (1)/(2) should be performed in a pre-amplification area and is especially sensitive to contamination. Amplified samples should not be opened in the work area for Steps (1)/(2). A separate area for post-amplification reactions should be used for performing Step (3) of the protocol. After incubation, reactions from Step (2) should be thoroughly spun down after incubation before opening in the post-amplification area to carry out Step (3).

Step (1)—Lysis of Patients Sample. *Performed in the Pre-Amplification Area*

NP swab sample should be lysed using the QuickExtract lysis buffer (extraction-free polynucleotide isolation solution).

Mix 10 μL of NP swab sample with 10 μL of Quick Extract in an eppendorf tube.

Incubate the sample-QuickExtract mixture at 95° C. for 5 minutes (or at room temperature or 60° C. for 10 mins) and proceed to Step (2).

Step (2)—One Pot SHERLOCK Detection. *Performed in the Pre-Amplification Area*

For each sample, set up one reaction as follows. In addition, a positive control can be set up using the SARS-CoV-2 control RNA. A negative control with Isothermal Amplification Buffer, MgSO4, dNTPs, Lateral Flow Reporter, and sample should also be set up to control for DNAse contamination that may produce false positive results.

TABLE 8

| Reagent | Amount (μL) |
|---|---|
| Sherlock mastermix | 45 |
| Lysed sample | 5 |
| Total | 50 |

Mix thoroughly and incubate each reaction at 60° C. for 1 hour. Spin down the reaction in a centrifuge at maximum speed. Transfer the reaction tubes to the post-amplification area before proceeding to Step (3).

Step (3)—Visual Readout of Detection Result Via Lateral Flow Strip. *Performed in the Post-Amplification Area*

Before opening each tube, spin down each reaction tube in a centrifuge at maximum speed to prevent aerosol contamination. Place a HybriDetect Dipstick into each reaction tube and wait for the reaction to flow through the dipstick.

Positive control samples should show the top line and a faint bottom line. Negative control samples should show the bottom line.

For each test sample, check to see the top line appears, indicating positive SARS-CoV-2 detection.

Additional Information

A detailed general protocol for setting up SHERLOCK-based detection can be found in the following reference: SHERLOCK: nucleic acid detection with CRISPR nucleases. Kellner M J, Koob J G, Gootenberg J S, Abudayyeh O O, and Zhang F. Nature Protocols. 2019 October; 14(10): 2986-3012. doi: 10.1038/s41596-019-0210-2.

Conclusions

Applicants' one-pot SHERLOCK detection method is capable of rapid, point-of-care diagnosis of COVID-19. With 97% sensitivity and 100% specificity on patient samples, Applicants were able to detect presence of SARS-CoV-2 down to 100 molecules of viral genome per reaction in a simplified format that any user could perform in a non-laboratory setting. Because of the rapid speed and lack of instrumentation, we envision that this protocol could be used in low resource clinics, workplaces, and even at home. While Applicants tested on nasopharyngeal swabs, saliva samples have similar viral loads and would be a simpler alternative sample source. Future versions of the protocol could benefit from an all-in-one integrated device that could heat the reaction and transfer the reaction to a paper strip to reduce amplicon spread and streamline the workflow.

TABLE 9

Methods Comparison.

| | SHERLOCKv2, RT-LAMP/AapCas12b | SHERLOCKv1, RPA-Cas13 | SARS-Cov2 DETECTR | CDC SARS-Cov2 qRT-PCR |
|---|---|---|---|---|
| Reference | This study | (Zhang et al. 2020) | Broughton et al., 2020) | (CDC) |
| Target | N gene | N gene and S gene | E gene and N gene | N gene |
| LoD (per 50 ul reaction) | 100 copies | 50-500 copies | 50 copies | 5-15 copies |
| Assay reaction time | 60 min | 55 min | 40 min | 120 min |
| Assay sample-to-result time | 70 min | 90 min (including RNA extraction) | 75 min (including RNA extraction) | 4 h (including RNA extraction) |
| Assay results | Visual | Visual | Visual | Fluorescent |
| Laboratory instrumentation required | None | Centrifuges, water baths | Centrifuges, water baths | Centrifuges, qPCR machine |

TABLE 9-continued

Methods Comparison.

| | SHERLOCKv2, RT-LAMP/AapCas12b | SHERLOCKv1, RPA-Cas13 | SARS-Cov2 DETECTR | CDC SARS-Cov2 qRT-PCR |
|---|---|---|---|---|
| Sample extraction required | None | Yes | Yes | Yes |
| Liquid transfer steps | 1 | 3 | 3 | 1 |

References

Broughton, J. P., Deng, X., Yu, G., Fasching, C. L., Servellita, V., Singh, J., Miao, X., Streithorst, J. A., Granados, A., Sotomayor-Gonzalez, A., et al. (2020). CRISPR-Cas12-based detection of SARS-CoV-2. Nat. Biotechnol.

Ding, X., Yin, K., Li, Z., and Liu, C. (2020). All-in-One Dual CRISPR-Cas12a (AIOD-CRISPR) Assay: A Case for Rapid, Ultrasensitive and Visual Detection of Novel Coronavirus SARS-CoV-2 and HIV virus.

Gootenberg, J. S., Abudayyeh, O. O., Lee, J. W., Essletzbichler, P., Dy, A. J., Joung, J., Verdine, V., Donghia, N., Daringer, N. M., Freije, C. A., et al. (2017). Nucleic acid detection with CRISPR-Cas13a/C2c2. Science 356, 438-442.

Gootenberg, J. S., Abudayyeh, O. O., Kellner, M. J., Joung, J., Collins, J. J., and Zhang, F. (2018). Multiplexed and portable nucleic acid detection platform with Cas13, Cas12a, and Csm6. Science 360, 439-444.

Guo, L., Sun, X., Wang, X., Liang, C., Jiang, H., Gao, Q., Dai, M., Qu, B., Fang, S., Mao, Y., et al. (2020). SARS-CoV-2 detection with CRISPR diagnostics.

Lucia, C., Federico, P.-B., and Alejandra, G. C. (2020). An ultrasensitive, rapid, and portable coronavirus SARS-CoV-2 sequence detection method based on CRISPR-Cas12.

Shmakov, S., Abudayyeh, O. O., Makarova, K. S., Wolf, Y. I., Gootenberg, J. S., Semenova, E., Minakhin, L., Joung, J., Konermann, S., Severinov, K., et al. (2015). Discovery and Functional Characterization of Diverse Class 2 CRISPR-Cas Systems. Mol. Cell 60, 385-397.

Teng, F., Cui, T., Feng, G., Guo, L., Xu, K., Gao, Q., Li, T., Li, J., Zhou, Q., and Li, W. (2018). Repurposing CRISPR-Cas12b for mammalian genome engineering. Cell Discov 4, 63.

Whitman, J. D., Hiatt, J., Mowery, C. T., Shy, B. R., Yu, R., Yamamoto, T. N., Rathore, U., Goldgof, G. M., Whitty, C., Woo, J. M., et al. (2020). Test performance evaluation of SARS-CoV-2 serological assays. medRxiv 2020.04.25.20074856.

Zhang, Y., Odiwuor, N., Xiong, J., Sun, L., Nyaruaba, R. O., Wei, H., and Tanner, N. A. (2020). Rapid Molecular Detection of SARS-CoV-2 (COVID-19) Virus RNA Using Colorimetric LAMP. medRxiv 2020.02.26.20028373.

Example 7—Optimization and Enhancement of Detection Methods

Rather than a multi-step process for the extraction and washing when using beads as is explained in previous prior art methods, the present disclosure improves upon the methods:

A bead and extraction-free polynucleotide isolation solution mix is added to the sample, for about 5 to 10 minutes. At this time, the virus is lysed and bound to the beads. Sample with beads is placed upon magxit, after separation, supernatant is aspirated and reaction buffer mix is added and sample can be subjected in pPCR. Thus, lysis and bead preparation steps are merged rather than multi-steps, and elimination of washes and elution steps are eliminated, with elution merged with the addition of reaction buffer mix.

The bead mix can include potassium chloride, with the typical amount of potassium chloride being reduced or eliminated from the reaction buffer mix. Additionally, the extraction-free polynucleotide isolation solution according to methods as provided herein can comprise proteinase K. Without the typical wash steps utilized after lysis, proteinase K carries over from the lysis step in the current methods, and proteinase K inhibitor is added to the reaction buffer mix.

Beads can be optionally used with the methods described herein, including with the one-pot methods that allow for concentration of viral nucleic acids from large volume samples, such as saliva or swab samples to allow for a single one-pot reaction method.

An exemplary method of making the beads are as follows:

Reagents 500 mL 5M NaCl
1M Tris-HCl, pH 8.0
500 mM EDTA, pH 8.0
Dry Poly-Ethylene Glycol 8000, PEG-8000 (Fisher, P/N BP233-1)
Carboxy-Modified Sera-Mag Speed Beads (Fisher, P/N 09-981-124)

Protocol

Vortex the Sera-Mag speedbeads bottle for 1 minutes.

Add 0.1% (w/v) of your intended production amount, which is 10 mL of the Sera-Mag Speedbeads solution to a 50 mL conical tube.

Using a 50 mL magnetic separator, pellet the magnetic beads.

Aspirate the supernatant and discard.

The beads contain residual azide. Wash them twice with 10 mL of DI water, resuspending the pellet each time by vortexing for 30 seconds.

Pellet the beads for the last time.

Prepare the bead buffer by mixing orderly the following in a 500 mL reagent bottle.

| Component | Volume |
|---|---|
| 5M NaCl | 100 mL |
| 1M Tris-HCl | 5 mL |
| 500mM EDTA | 1 mL |
| PEG-8000 | 90 g |

Invert mix 10 times and fill with DI water until it reaches the 500 mL mark.

Filter using a vacuum filtration unit according to the manufacturer's instructions and store filtered buffer in container of filtration unit until needed.

Remove the final wash fluid on the beads and add 10 mL of the sterile bead buffer to the beads.

Vortex for 30 seconds to resuspend the beads.

Add the bead slurry to the 500 mL bottle containing the remainder of the sterile buffer.

Twirl the bottle to homogenize the beads with the buffer.

The beads can now be aliquoted and stored at −20° C.

Optimization of Reagents

For ease of reference, optimization is described using LAMP amplification, but the design paradigm is applicable to any other isothermal amplification approach detailed herein. Further optimization of the methods as disclosed herein can include first screening primers to identify one or more sets of primers that work well for a particular target, Cas protein and/or reaction. Once the primers have been screened, titration of Magnesium concentration can be performed to identify an optimal magnesium concentration for higher signal to noise. Once an optimum magnesium concentration is identified, additional additives are screened at around 20-25% of the reaction, and once additives are identified, these additives, such as those components identified in FIG. 17, can be evaluated and varied in concentration to identify optimal reaction kinetics for specific reaction parameters, for example, specific primers, target, Cas protein, temperature, and other additive concentrations within the reaction. As described herein, a change form NaCl to KCl allows for the bead and extraction-free polynucleotide isolation solution mix to reduce carryover and optimize reactions, allowing for merger of bead preparation, and washing/elution steps. Additionally, optimization of salt types and concentrations may further aid one-pot reactions

* * *

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

SEQUENCE LISTING

The patent contains a lengthy sequence listing. A copy of the sequence listing is available in electronic form from the USPTO web site (https://seqdata.uspto.gov/?pageRequest=docDetail&DocID=US11851702B2). An electronic copy of the sequence listing will also be available from the USPTO upon request and payment of the fee set forth in 37 CFR 1.19(b)(3).

What is claimed is:

1. A cartridge comprising at least a first and second ampoule, a lysis chamber, an amplification chamber, and a sample receiving chamber, wherein the first ampoule comprises DNA isolation solution capable of isolating a target RNA from a crude or unprocessed sample comprising a cell or virus containing the target RNA and the second ampoule comprises a loop-mediated isothermal amplification (LAMP) composition for detecting the presence of the target RNA in a sample, comprising optimized LAMP primers consisting of SEQ ID NOs: 61983-61988 and amplification reagents for single amplification and glycine or taurine, or a combination thereof for amplifying the target RNA in less than one hour.

2. The cartridge of claim 1, configured to fit in a system comprising a heating means, an optic means, a means for releasing reagents on the cartridge, and a means for readout of assay result.

3. The cartridge of claim 1, wherein the contents of the first ampoule and/or second ampoule are lyophilized.

4. A device designed to receive one or more cartridges of claim 2 and further comprising one or more motors connected to a plunger for rupturing of the first and second ampoule of the cartridge and configured within the device to align with the first and second ampoule of the inserted cartridge, a heating element configured to align with the amplification chamber of the inserted cartridge, an optical detector configured to align with the amplification chamber of the inserted cartridge, and a display.

5. The device of claim 4, further comprising a graphical user interface for programming the device and/or readout of the results of the assay.

6. A system comprising a docking station and two or more devices of claim 5, wherein the docking station is configured to receive the two or more devices.

7. The cartridge of claim 1, wherein the second ampoule comprises isothermal amplification reagents and a CRISPR-Cas collateral detection system for amplifying and detecting a target RNA.

8. The cartridge of claim 7, wherein the target RNA is a coronavirus.

9. The cartridge of claim 1, wherein the DNA isolation solution and/or the lysis well comprises RNA binding beads.

10. The cartridge of claim 1, wherein the DNA isolation solution comprises a protease.

11. The cartridge of claim 10, wherein the protease is proteinase K.

12. The cartridge of claim 1, wherein the amplification reagents comprise reverse transcriptase.

13. The cartridge of claim 1, wherein the first ampoule comprises isolation solution in an amount to provide a ratio from 2:1 to 1:2 isolation solution:crude or unprocessed sample.

14. The cartridge of claim 1, wherein the LAMP composition further comprises colorimetric or fluorescent detection reagents.

* * * * *